United States Patent
Kanda

(10) Patent No.: US 7,781,469 B2
(45) Date of Patent: *Aug. 24, 2010

(54) ARYLACETATE DERIVATIVES HAVING ISOXAZOLE SKELETON

(75) Inventor: Yasuhiko Kanda, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 328 days.

This patent is subject to a terminal disclaimer.

(21) Appl. No.: 11/920,999

(22) PCT Filed: May 23, 2006

(86) PCT No.: PCT/JP2006/310198
§ 371 (c)(1),
(2), (4) Date: Nov. 26, 2007

(87) PCT Pub. No.: WO2006/126514
PCT Pub. Date: Nov. 30, 2006

(65) Prior Publication Data
US 2009/0062531 A1    Mar. 5, 2009

(30) Foreign Application Priority Data
May 27, 2005  (JP) .............................. 2005-155803
Nov. 11, 2005  (JP) .............................. 2005-327171

(51) Int. Cl.
*C07D 261/04*    (2006.01)
*A61K 31/42*    (2006.01)

(52) U.S. Cl. ...................................... 514/378; 548/247

(58) Field of Classification Search ................ 548/247; 514/378
See application file for complete search history.

(56) References Cited

U.S. PATENT DOCUMENTS

| | | | |
|---|---|---|---|
| 2003/0153579 | A1 | 8/2003 | Tajima et al. |
| 2004/0058965 | A1 | 3/2004 | Momose et al. |
| 2004/0171835 | A1 | 9/2004 | Tajima et al. |
| 2007/0054902 | A1 | 3/2007 | Fukui et al. |

FOREIGN PATENT DOCUMENTS

| | | |
|---|---|---|
| EP | 0 558 062 | 5/1997 |
| WO | 99/11255 | 3/1999 |
| WO | 99/46232 | 9/1999 |
| WO | 99/58510 | 11/1999 |
| WO | 01/00603 | 1/2001 |
| WO | 02/053547 | 7/2002 |
| WO | 02/102780 | 12/2002 |
| WO | 03/099793 | 12/2003 |
| WO | 2004/063166 | 7/2004 |
| WO | 2004/091604 | 10/2004 |
| WO | 2005/054213 | 6/2005 |
| WO | 2006/045554 | 5/2006 |

OTHER PUBLICATIONS

B. G. Shearer et al., "Recent Advances in Peroxisome Proliferator-Activated Receptor Science", Current Medical Chemistry, vol. 10, pp. 267-280, 2003.

*Primary Examiner*—Kahsay T Habte
(74) *Attorney, Agent, or Firm*—Wenderoth, Lind & Ponack, L.L.P.

(57) ABSTRACT

A compound of the formula (I):

pharmaceutically acceptable salt or solvate thereof, wherein
Y is a group of the formula:

wherein Ring A is optionally substituted aryl or optionally substituted heteroaryl, $X^3$ is $COOR^{17}$ or the like
Y is not optionally substituted phenyl which is substituted with the formula: $-CR^9R^{10}X^3$ at the para position,
$R^1$ to $R^{10}$ are each independently halogen, hydroxy, optionally substituted lower alkyl, optionally substituted aryl or the like,
$X^1$ is $-O-$, $-S-$ or the like.

18 Claims, No Drawings

ARYLACETATE DERIVATIVES HAVING ISOXAZOLE SKELETON

This application is a U.S. national stage of International Application No. PCT/JP2006/310198 filed May 23, 2006.

FIELD OF THE INVENTION

The present invention relates to new compounds which have an agonistic activity of a peroxisome proliferator-activated receptor (referred to below as PPAR) and which are useful as a medicine.

BACKGROUND ART

Peroxisome proliferators which proliferate an intracellular granule, peroxisome, are thought as important controlling elements of lipid metabolism. A nuclear receptor, PPAR, which is activated by the peroxisome proliferator has turned out to be a multifunctional receptor concerning incretion, metabolism, inflammation or the like. Therefore, the ligand is thought to be able to apply as various medicines and the number of researches is recently increasing.

The subtype genes of PPARs are found from various animal organs and formed a family. In mammals, PPARs are classified into three subtypes of PPARα, PPARδ (also referred to as PPARβ) and PPARγ.

The drugs of the fibrate group used as an antihyperlipemic drug are thought to show the activity by PPARα activation-mediated transcriptional enhancement of the gene group which improves serum lipid. Additionally, it is suggested that PPARα may relate to bone metabolism and expression of the activity of non-steroidal anti-inflammatory drugs.

The thiazolidindion compounds, which are improving drugs for insulin resistance, are ligands of PPARγ. As these compounds show hypoglycemic action, hypolipidemic action, adipocyte differentiation-inducing action or the like, PPARγ agonists are expected to develop as therapeutic agents for diabetes, hyperlipidemia, obesity or the like. Furthermore, PPARγ agonists are expected to be therapeutic agents for chronic pancreatitis, inflammatory colitis, glomerulosclerosis, Alzheimer's disease, psoriasis, parkinsonism, Basedow's disease, chronic rheumatoid arthritis, cancer (breast cancer, colonic cancer, prostatic cancer or the like), sterility or the like.

It was reported that transgenic mice in which PPARδ is overexpressed specifically in adipocyte were difficult to get fat or the like. Therefore, PPARδ agonists can be used as an antiobestic drug or an antidiabetic drug. Additionally, PPARδ agonists are suggested the possibility as therapeutic agents for colonic cancer, osteoporosis, sterility, psoriasis, multiple sclerosis or the like.

Based on these findings, PPAR agonists are expected to be useful for treatment or prevention of hyperlipidemia, diabetes, hyperglycosemia, insulin resistance, obesity, arteriosclerosis, atherosclerosis, hypertension, syndrome X, inflammation, allergic disease (inflammatory colitis, chronic rheumatoid arthritis, chronic pancreatitis, multiple sclerosis, glomerulosclerosis, psoriasis or the like), osteoporosis, sterility, cancer, Alzheimer's disease, parkinsonism, Basedow's disease or the like (Non-Patent Document 1).

Patent Document 1 and Patent Document 2 disclosed various compounds having PPAR agonistic activity, for example, isoxazole compounds. However, compounds of the present invention were not disclosed. Furthermore, isoxazole compounds in Patent Document 2 have substituents on isoxazole in the different position compared to compounds of the present invention. Additionally, although PPARα and (or) PPARγ agonistic activity of the compounds were recognized, no data of PPARδ agonistic activity was disclosed. Furthermore, there was no data of isoxazole compounds even about PPARα or γ agonistic activity. In a word, the PPAR agonistic activity was not recognized.

Although Patent Document 3 disclosed isoxazole compounds, the compounds have substituents on isoxazole in the different position compared to compounds of the present invention. Furthermore, it was disclosed that the compounds are useful for hypercholesterolemia or hyperlipidemia. However, the PPAR agonistic activity was not disclosed.

Although Patent Document 4, 5 and 6 disclosed thiazole, oxazole and pyrazole compounds with PPARδ agonistic activity. However, isoxazole compounds were not suggested.

Patent Document 7, 8 and 9 disclosed isoxazole compounds. However, compounds of this invention were not disclosed.

[Patent Document 1] WO 99/11255
[Patent Document 2] WO 99/58510
[Patent Document 3] EP 0558062
[Patent Document 4] WO 01/00603
[Patent Document 5] WO 99/46232
[Patent Document 6] WO 04/063166
[Patent Document 7] WO 02/053547
[Patent Document 8] WO 03/099793
[Patent Document 9] WO 04/091604
[Non-patent Document 1]
Current Medicinal Chemistry, 2003, Vol. 10, p.p. 267-280

DISCLOSURE OF INVENTION

Problems to be solved by the Invention

The objection of the present invention is to provide good PPAR agonists.

Means for Solving the Problem

The present inventors have intensively studied to synthesize new good PPAR agonists as below. Compounds which have hydrogen at the 4 position of isoxazole and phenylacetic acid at the terminal are disclosed in Patent Document 8. However, the present inventors found that PPAR transcription activity of compounds, of which the hydrogen at the 4 position is substituted for the other substituent such as methyl, is greatly improved compared to the compounds before substitution. Furthermore, the inventors found that compounds of the present invention are less toxic and thought to be safe enough for pharmaceutical use.

The present invention is the followings.

(1) A compound of the formula (I):

[Formula 1]

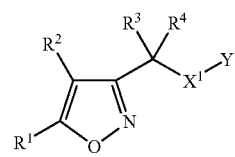

(I)

pharmaceutically acceptable salt or solvate thereof,
wherein
Y is a group of the formula:

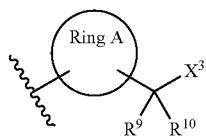

[Formula 2]

wherein Ring A is optionally substituted aryl or optionally substituted heteroaryl, $R^9$ and $R^{10}$ are each independently hydrogen, halogen, cyano, optionally substituted lower alkyl, optionally substituted lower alkoxy, optionally substituted amino or optionally substituted aryl, $X^3$ is $COOR^{17}$, $C(=NR^{17})NR^{18}OR^{19}$ or a group of the formula:

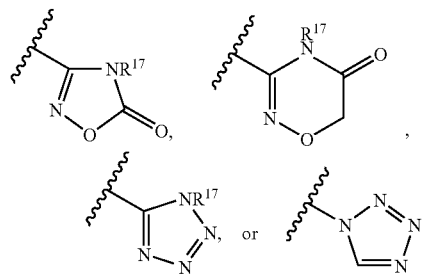

[Formula 3]

wherein $R^{17}$ to $R^{19}$ are each independently hydrogen or optionally substituted lower alkyl, provided that Y is not optionally substituted phenyl which is substituted with a group of the formula:
—$CR^9R^{10}X^3$ at the para position, $R^1$ is halogen, hydroxy, optionally substituted lower alkyl, optionally substituted lower alkenyl, optionally substituted lower alkynyl, optionally substituted lower alkoxy, carboxy, optionally substituted lower alkoxycarbonyl, optionally substituted lower alkylthio, optionally substituted acyl, optionally substituted amino, optionally substituted carbamoyl, optionally substituted thiocarbamoyl, optionally substituted carbamoyloxy, optionally substituted thiocarbamoyloxy, optionally substituted hydrazinocarbonyl, optionally substituted lower alkylsulfonyloxy, optionally substituted arylsulfonyloxy, optionally substituted aryl, optionally substituted aryloxy, optionally substituted arylthio or optionally substituted heterocycle, $R^2$ is hydrogen, halogen, hydroxy, optionally substituted lower alkyl, optionally substituted lower alkenyl, optionally substituted lower alkynyl, optionally substituted lower alkoxy, carboxy, optionally substituted lower alkoxycarbonyl, optionally substituted lower alkylthio, optionally substituted acyl, optionally substituted amino, optionally substituted carbamoyl, optionally substituted thiocarbamoyl, optionally substituted carbamoyloxy, optionally substituted thiocarbamoyloxy, optionally substituted hydrazinocarbonyl, optionally substituted lower alkylsulfonyloxy, optionally substituted arylsulfonyloxy, optionally substituted aryl, optionally substituted aryloxy, optionally substituted arylthio or optionally substituted heterocycle, $R^3$ and $R^4$ are each independently hydrogen, halogen, optionally substituted lower alkyl, optionally substituted lower alkenyl, optionally substituted lower alkynyl, optionally substituted aryl or optionally substituted heterocycle, and $X^1$ is —O—, —S—, —$NR^{11}$- wherein $R^{11}$ is hydrogen, optionally substituted lower alkyl, optionally substituted acyl, optionally substituted lower alkylsulfonyl or optionally substituted arylsulfony, —$CR^{12}R^{13}CO$—, —$(CR^{12}R^{13})mO$—, —$(CR^{12}R^{13})mS$—, —$O(CR^{12}R^{13})$m- wherein $R^{12}$ and R13 are each independently hydrogen or optionally substituted lower alkyl, and m is an integer between 1 and 3, —$ON=CR^{14}$- wherein $R^{14}$ is hydrogen or optionally substituted lower alkyl, or a group of the formula:

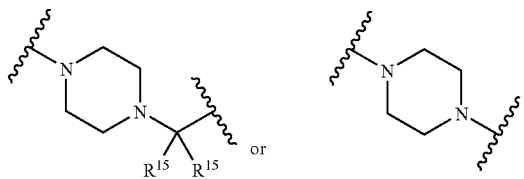

[Formula 4]

wherein $R^{15}$ and $R^{16}$ are each independently hydrogen or optionally substituted lower alkyl.

(2) The compound, pharmaceutically acceptable salt or solvate thereof according to (1), wherein Y is a group of the formula:

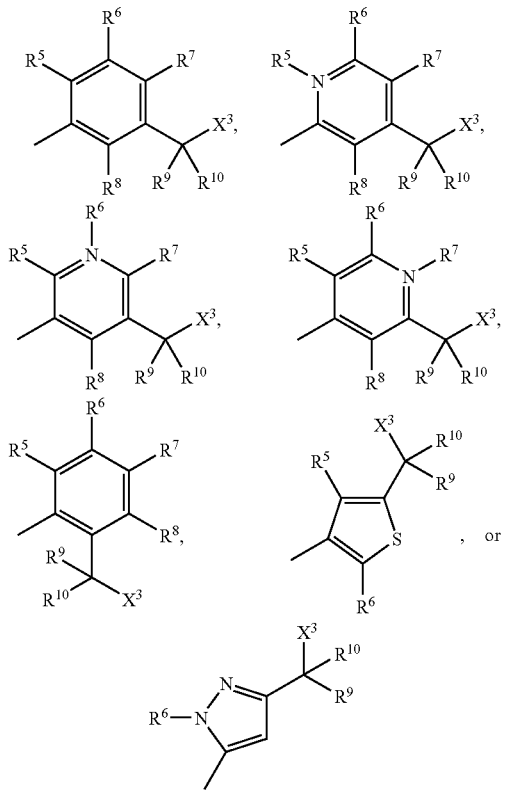

[Formula 5]

wherein
$R^5$, $R^6$, $R^7$ and $R^8$ are each independently hydrogen, halogen, hydroxy, cyano, optionally substituted lower alkyl, optionally substituted lower alkenyl, optionally substituted lower alkynyl, optionally substituted lower alkoxy, optionally substituted lower alkylthio, optionally substituted acyl, optionally substituted amino, optionally substituted aryl, optionally substituted aryloxy, optionally substituted arylthio or optionally substituted heterocycle, and
$R^9$, $R^{10}$ and $X^3$ have the same meaning as defined in (1).

(3) The compound, pharmaceutically acceptable salt or solvate thereof according to (1), wherein $R^1$ is optionally substituted aryl or heterocycle.

(4) The compound, pharmaceutically acceptable salt or solvate thereof according to (1), wherein $R^2$ is optionally substituted lower alkyl.

(5) The compound, pharmaceutically acceptable salt or solvate thereof according to (1), wherein $R^3$ and $R^4$ are hydrogen.

(6) The compound, pharmaceutically acceptable salt or solvate thereof according to (2), wherein $R^5$, $R^6$, $R^7$ and $R^8$ are each independently hydrogen, halogen, optionally substituted lower alkyl or optionally substituted lower alkoxy.

(7) The compound, pharmaceutically acceptable salt or solvate thereof according to (1), wherein $R^9$ and $R^{10}$ are each independently hydrogen or halogen.

(8) The compound, pharmaceutically acceptable salt or solvate thereof according to (1), wherein $X^1$ is O, S or —ON=$CR^{14}$-wherein $R^{14}$ is hydrogen.

(9) The compound, pharmaceutically acceptable salt or solvate thereof according to (1), wherein $X^3$ is $COOR^{17}$ wherein $R^{17}$ is hydrogen or optionally substituted lower alkyl.

(10) The compound, pharmaceutically acceptable salt or solvate thereof according to (2), wherein $R^1$ is optionally substituted aryl or heterocycle,
the substituent(s) of said aryl of $R^1$ is/are selected from a group consisting of halogen, optionally substituted lower alkyl and optionally substituted lower alkoxy,
$R^2$ is optionally substituted lower alkyl,
the substituent(s) of said lower alkyl of $R^2$ is/are selected from a group consisting of optionally substituted lower alkoxy, lower alkylamino, optionally substituted imino, optionally substituted iminooxy, lower alkylsulfonyl, cycloalkyloxy, optionally substituted aryl and optionally substituted heterocycle,
$R^3$ and $R^4$ are hydrogen,
$R^5$, $R^6$, $R^7$ and $R^8$ are each independently, hydrogen, halogen, lower alkyl or lower alkoxy,
$R^9$ and $R^{10}$ are each independently hydrogen or halogen,
$X^1$ is O, S or —ON=$CR^{14}$- wherein $R^{14}$ is hydrogen, and $X^3$ is $COOR^{17}$ wherein $R^{17}$ is hydrogen or lower alkyl.

(11) A pharmaceutical composition comprising the compound, pharmaceutically acceptable salt or solvate thereof according to any one of (1) to (10) as an active ingredient.

(12) A pharmaceutical composition for prevention and/or treatment for a disease concerning peroxisome proliferator-activated receptor(s), which comprises the compound, pharmaceutically acceptable salt or solvate thereof according to any one of (1) to (10) as active ingredient.

Furthermore, the present invention provides a process for PPAR activation characterized by administrating the above compound, a pharmaceutically acceptable salt or a solvate thereof. In details, it is the treatment process and/or prevention process for hyperlipidemia, diabetes, obesity, arteriosclerosis, atherosclerosis, hyperglycemia and/or syndrome X.

As the other embodiment, the present invention provides use of the above compound, pharmaceutically acceptable salt or solvate thereof to produce medicines for PPAR activation, for example, medicines for treatment and/or prevention for hyperlipidemia, diabetes, obesity, arteriosclerosis, atherosclerosis, hyperglycemia and/or syndrome X.

EFFECT OF THE INVENTION

As the following test results show, compounds of the present invention have PPAR agonistic activity and are very useful as medicine and especially medicine for treatment and/or prevention for hyperlipidemia, diabetes, obesity, arteriosclerosis, atherosclerosis, hyperglycemia and/or syndrome X.

BEST MODE FOR CARRYING OUT THE INVENTION

The term "halogen" in the present specification means fluorine, chlorine, bromine or iodine. Especially, fluorine or chlorine is preferable.

The term "lower alkyl" means a C1 to C10, preferably C1 to C6 and more preferably C1 to C3 straight or branched alkyl group. Examples include methyl, ethyl, n-propyl, isopropyl, n-butyl, isobutyl, sec-buthyl, tert-butyl, n-pentyl, isopentyl, neopentyl, hexyl, isohexyl, n-heptyl, isoheptyl, n-octyl, isooctyl, n-nonyl, n-decyl and the like.

The term "lower alkenyl" means C2 to C10, preferably C2 to C6 and more preferably C2 to C4 straight or branched alkenyl having one or more double bond(s) at any position(s). Examples include vinyl, propenyl, isopropenyl, butenyl, isobutenyl, prenyl, butadienyl, pentenyl, isopentenyl, pentadienyl, hexenyl, isohexenyl, hexadienyl, heptenyl, octenyl, nonenyl, decenyl and the like.

The term "lower alkynyl" means C2 to C10, preferably C2 to C6 and more preferably C2 to C4 straight or branched alkynyl. Examples include ethynyl, propynyl, butynyl, pentynyl, hexynyl, heptynyl, octynyl, nonynyl, decenyl and the like. These have one or more triple bond(s) at any position(s) and can have double bond(s).

A substituent of "optionally substituted lower alkyl", "optionally substituted lower alkenyl" or "optionally substituted lower alkynyl" is halogen, hydroxy, optionally substituted lower alkoxy, lower alkynyloxy, optionally substituted amino (e.g., lower alkylamino, arylamino, heterocycleamino, acylamino, lower alkoxycarbonylamino, lower alkylsulfonylamino or arylsulfonylamino), mercapto, lower alkylthio, acyl, acyloxy, optionally substituted imino, optionally substituted iminooxy, carboxy, lower alkoxycarbonyl, carbamoyl, lower alkyl carbamoyl, thiocarbamoyl, lower alkylthiocarbamoyl, carbamoyloxy, lower alkylcarbamoyloxy, thiocarbamoyloxy, lower alkylthiocarbamoyloxy, sulfamoyl, lower alkylsulfamoyl, lower alkylsulfonyl, lower alkylsulfonyloxy, cyano, nitro, optionally substituted cycloalkyl, cycloalkyloxy, optionally substituted aryl, optionally substituted aryloxy, optionally substituted arylthio, optionally substituted aryl lower alkoxy, optionally substituted arylsulfonyl, optionally substituted arylsulfonyloxy, optionally substituted heterocycle (wherein a substituent is halogen, hydroxy, lower alkyl, oxo, halogeno lower alkyl, hydroxy lower alkyl, lower alkenyl, lower alkoxy, aryl lower alkoxy, halogeno lower alkoxy, carboxy, lower alkoxycarbonyl, carbamoyl, lower alkylcarbamoyl, arylcarbamoyl, acylamino, mercapto, lower alkylthio, amino, lower alkylamino, acyl, acyloxy, cyano, nitro, phenyl, heterocycle or the like) or optionally substituted heterocycleoxy (wherein a substituent is halogen, hydroxy, lower alkyl, oxo, halogeno lower alkyl, hydroxy lower alkyl, lower alkenyl, lower alkoxy, aryl lower alkoxy, halogeno lower alkoxy, carboxy, lower alkoxycarbonyl, carbamoyl, lower alkyl carbamoyl, aryl carbamoyl, acyl amino, mercapto, lower alkylthio, amino, lower alkylamino, acyl, acyloxy, cyano, nitro, phenyl, heterocycle or the like). They can be substituted at any position(s) with one or more substituent(s) selected from the above.

A substituent of "optionally substituted lower alkyl", "optionally substituted lower alkenyl", "optionally substituted lower alkynyl" or the like is preferably morpholino, piperidino, piperazino, furyl, thienyl or pyridyl.

A lower alkyl part of "halogeno lower alkyl", "hydroxy lower alkyl", "lower alkoxy", "halogeno lower alkoxy", "aryl lower alkoxy", "hydroxy lower alkoxy", "lower alkylamino", "lower alkylthio", "lower alkylsulfonyl", "lower alkylsulfonyloxy", "lower alkylsulfonyl amino", "lower alkyl carbamoyl", "lower alkylthio carbamoyl", "lower alkyl carbamoyloxy", "lower alkylthio carbamoyloxy", "lower alkyl sulfamoyl", "lower alkoxycarbonyl" or "lower alkoxycarbonyl amino" is same as the above "lower alkyl".

A lower alkynyl part of "lower alkynyloxy" is same as the above "lower alkynyl".

A substituent of "optionally substituted lower alkoxy", "optionally substituted lower alkoxycarbonyl", "optionally substituted lower alkylthio" or "optionally substituted lower alkylsulfonyloxy" is same as a substituent of the above "optionally substituted lower alkyl".

The term "imino" means a group of —NH— or =NH in an organic compound. A substituent of "optionally substituted imino" or "optionally substituted iminooxy" is same as a substituent of the above "optionally substituted lower alkyl". Especially preferable example of the substituent "optionally substituted imino" is optionally substituted alkoxy.

The term "acyl" includes (a) C1-C10, more preferably C1 to C6 and most preferably C1 to C3 straight or branched alkylcarbonyl or alkenyl carbonyl, (b) C4 to C9 and preferably C4 to C7 cycloalkylcarbonyl, (c) C7 to C11 arylcarbonyl or (d) formyl. Examples are formyl, acetyl, propionyl, butyryl, isobutyryl, valeryl, pivaloyl, hexanoyl, acryloyl, propioloyl, methacryloyl, crotonoyl, cyclopropylcarbonyl, cyclohexylcarbonyl, cyclooctylcarbonyl, benzoyl and the like.

An acyl part of "acyl amino" or "acyloxy" is same as the above "acyl".

A substituent of "optionally substituted acyl" is same as a substituent of the above "optionally substituted lower alkyl". Furthermore, cycloalkyl carbonyl and aryl carbonyl can be substituted with lower alkyl, halogeno lower alkyl, hydroxy lower alkyl, lower alkenyl, halogeno lower alkenyl and/or hydroxy lower alkenyl.

A substituent of "optionally substituted amino" is same as the above "optionally substituted lower alkyl". Furthermore, "optionally substituted amino" can be substituted with lower alkyl, halogeno lower alkyl, hydroxy lower alkyl, lower alkenyl, halogeno lower alkenyl and/or hydroxy lower alkenyl.

A substituent of "optionally substituted carbamoyl", "optionally substituted thiocarbamoyl", "optionally substituted carbamoyloxy", "optionally substituted thiocarbamoyloxy" or "optionally substituted hydrazinocarbonyl" is same as the above "optionally substituted lower alkyl".

The term "cycloalkyl" includes C3 to C8 and preferably C5 or C6 cyclic alkyl. For example, it is cyclopropyl, cyclobutyl, cyclopentyl, cyclohexyl, cycloheptyl, cyclooctyl or the like.

The term "aryl" includes phenyl, naphthyl, anthryl, phenanthryl or the like. Additionally, it includes aryl, which is condensed with the other non-aromatic hydrocarbon ring, for example, indanyl, indenyl, biphenylyl, acenaphthenyl, fluorenyl or the like. In case that aryl is condensed with the other non-aromatic hydrocarbon ring, bonds can be attached to any of the rings. The preferable example of aryl is phenyl.

A substituent of "optionally substituted cycloalkyl" or "optionally substituted aryl" is same as a substituent of the above "optionally substituted lower alkyl" as long as there is not a special provision. Furthermore, it can be substituted with lower alkyl, halogeno lower alkyl, hydroxy lower alkyl, lower alkenyl, halogeno lower alkenyl, hydroxy lower alkenyl, alkylenedioxy and/or oxo.

An aryl part of "aryloxy", "arylthio", "aryl lower alkoxy", "aryl amino" "arylsulfonyl", "arylsulfonyloxy" or "arylsulfonylamino" is same as the above "aryl".

A substituent of "optionally substituted aryl lower alkoxy", "optionally substituted aryloxy", "optionally substituted arylthio" "optionally substituted arylsulfonyl" or "optionally substituted arylsulfonyloxy" is same as a substituent of the above "optionally substituted aryl" as long as there is not a special provision.

The term "heterocycle" and "optionally substituted heteroaryl" includes heterocycle having 1 or more hetero atom(s) selected from O, S and N in a ring, for example, 5- to 6-membered heteroaryl such as pyrrolyl, imidazolyl, pyrazolyl, pyridyl, pyridazinyl, pyrimidinyl, pyradinyl, triazolyl, triazinyl, tetrazolyl, isoxazolyl, oxazolyl, oxadiazolyl, isothiazolyl, thiazolyl, thiadiazolyl, furyl, thienyl or the like; bicyclic condensed heterocycle such as indolyl, isoindolyl, indazolyl, indolizinyl, quinolyl, isoquinolyl, cinnolinyl, phthalazinyl, quinazolinyl, naphthyridinyl, quinoxalinyl, prinyl, pteridinyl, benzopyranyl, benzimidazolyl, benzisoxazolyl, benzoxazolyl, benzoxadiazolyl, benzoisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyradino pyridazinyl, quinazolinyl, tetrahydroquinolyl, tetrahydrobenzothienyl or the like; tricyclic condensed heterocycle such as carbazolyl, acridinyl, xanthenyl, phenothiazinyl, phenoxathiinyl, phenoxazinyl, dibenzofuryl or the like; non-aromatic heterocycle such as indolinyl, dioxanyl, thiiranyl, oxyranyl, oxathiolanyl, azetidinyl, thianyl, pyrrolidinyl, pyrrolinyl, imidazolidinyl, imidazolinyl, pyrazolidinyl, pyrazolinyl, piperidyl, piperidino, piperazinyl, piperidino, morpholinyl, morpholino, oxadiadinyl, dihydropyridyl or the like. In case that heterocycle is a condensed ring, the bonds can be attached to any of the rings.

As "heterocycle" for $R^1$ and $R^2$, pyridyl, benzofuryl, morpholino or piperazino or piperidino is preferred.

A substituent of "optionally substituted heterocycle" or "optionally substituted heteroaryl" is same as the above "optionally substituted aryl".

A heterocycle part of "heterocycleamino" or "heterocycleoxy" is same as the above "heterocycle".

Ring A is optionally substituted aryl or optionally substituted heteroaryl (provided that Y is not optionally substituted phenyl which is substituted with a group of the formula: —$CR^9R^{10}X^3$ at the para position). "Optionally substituted aryl" or "optionally substituted heteroaryl" for Ring A may be substituted with substituent(s) other than the group of the formula: —$CR^9R^{10}X^3$. The substituent is the same as the above "optionally substituted aryl". Especially preferable examples of Ring A are optionally substituted phenyl which is substituted with a group of the formula: —$CR^9R^{10}X^3$ at the meta or ortho position (the substituent is hydrogen, halogen, optionally substituted lower alkyl or optionally substituted lower alkoxy), optionally substituted pyridine which is substituted with a group of the formula: —$CR^9R^{10}X^3$ at the meta position, pyrane, furan, thiophene or pyrrole (the substituent is hydrogen, halogen, optionally substituted lower alkyl or optionally substituted lower alkoxy). Furthermore, groups of the following formula are preferable.

[Formula 6]

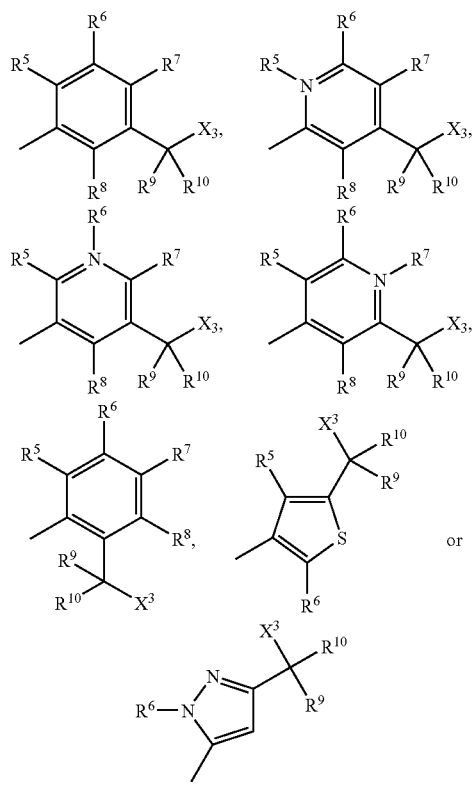

$R^1$ is halogen, hydroxy, optionally substituted lower alkyl, optionally substituted lower alkenyl, optionally substituted lower alkynyl, optionally substituted lower alkoxy, carboxy, optionally substituted lower alkoxycarbonyl, optionally substituted lower alkylthio, optionally substituted acyl, optionally substituted amino, optionally substituted carbamoyl, optionally substituted thiocarbamoyl, optionally substituted carbamoyloxy, optionally substituted thiocarbamoyloxy, optionally substituted hydrazinocarbonyl, optionally substituted lower alkylsulfonyloxy, optionally substituted arylsulfonyloxy, optionally substituted aryl, optionally substituted aryloxy, optionally substituted arylthio or optionally substituted heterocycle. Optionally substituted aryl or heterocycle is especially preferable. Optionally substituted aryl (the substituent is halogen, optionally substituted lower alkoxy or optionally substituted lower alkyl) is more preferable.

$R^2$ is hydrogen, halogen, hydroxy, optionally substituted lower alkyl, optionally substituted lower alkenyl, optionally substituted lower alkynyl, optionally substituted lower alkoxy, carboxy, optionally substituted lower alkoxycarbonyl, optionally substituted lower alkylthio, optionally substituted acyl, optionally substituted amino, optionally substituted carbamoyl, optionally substituted thiocarbamoyl, optionally substituted carbamoyloxy, optionally substituted thiocarbamoyloxy, optionally substituted hydrazinocarbonyl, optionally substituted lower alkylsulfonyloxy, optionally substituted arylsulfonyloxy, optionally substituted aryl, optionally substituted aryloxy, optionally substituted arylthio or optionally substituted heterocycle. Optionally substituted lower alkyl is especially preferable. Optionally substituted lower alkyl (the substituent is halogen, lower alkoxy, lower alkylamino, optionally substituted imino, optionally substituted iminooxy, lower alkylsulfonyl, cycloalkyloxy, optionally substituted aryl or optionally substituted heterocycle) is more preferable.

When $R^2$ is optionally substituted lower alkyl, the preferable substituent(s) is optionally substituted imino, cycloalkyloxy, optionally substituted lower alkoxy (the substituent is cycloalkyl, optionally substituted heterocycle (the substituent is oxo or lower alkyl) or optionally substituted amino (the substituent is lower alkylsulfonyl or arylsulfonyl)), optionally substituted heterocycleoxy (the substituent is oxo or lower alkyl) or optionally substituted iminooxy (the substituent is lower alkyl or cycloalkyl).

When $R^2$ is optionally substituted lower alkyl and the substituent is optionally substituted imino, the preferable substituent(s) of imino is hydroxy, optionally substituted lower alkoxy (the substituent is optionally substituted heterocycle (the substituent is oxo or lower alkyl) or optionally substituted amino (the substituent is lower alkylsulfonyl or arylsulfonyl)), cycloalkyloxy, optionally substituted alkyl (the substituent is cycloalkyl) or optionally substituted heterocycleoxy (the substituent is oxo and lower alkyl).

$R^3$ and $R^4$ are each independently, hydrogen, halogen, optionally substituted lower alkyl, optionally substituted lower alkenyl, optionally substituted lower alkynyl, optionally substituted aryl or optionally substituted heterocycle. Hydrogen is especially preferable.

$R^5$, $R^6$, $R^7$ and $R^8$ are each independently hydrogen, halogen, hydroxy, cyano, optionally substituted lower alkyl, optionally substituted lower alkenyl, optionally substituted lower alkynyl, optionally substituted lower alkoxy, optionally substituted lower alkylthio, optionally substituted acyl, optionally substituted amino, optionally substituted aryl, optionally substituted aryloxy, optionally substituted arylthio or optionally substituted heterocycle. Hydrogen, halogen, optionally substituted lower alkyl or optionally substituted lower alkoxy is especially preferable. Hydrogen, halogen, lower alkyl or lower alkoxy is more preferable.

$R^9$ and $R^{10}$ are each independently hydrogen, halogen, cyano, optionally substituted lower alkyl, optionally substituted lower alkoxy, optionally substituted amino or optionally substituted aryl. Hydrogen or halogen is especially preferable.

$X^1$ is —O—, —S—, —NR$^{11}$— wherein R$^{11}$ is hydrogen, optionally substituted lower alkyl, optionally substituted acyl, optionally substituted lower alkylsulfonyl or optionally substituted arylsulfonyl, —CR$^{12}$R$^{13}$CO—, —(CR$^{12}$R$^{13}$) mO—, —(CR$^{12}$R$^{13}$)mS—, —O(CR$^{12}$R$^{13}$)m- wherein R$^{12}$ and R$^{13}$ are each independently hydrogen or optionally substituted lower alkyl, and m is an integer between 1 and 3, —ON=CR$^{14}$— wherein R$^{14}$ is hydrogen or optionally substituted lower alkyl, or a group of the formula:

[Formula 7]

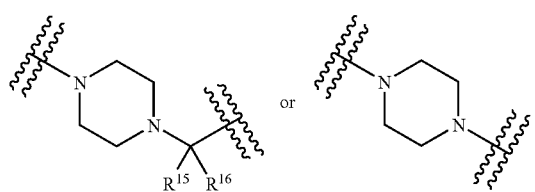

wherein $R^{15}$ and $R^{16}$ are each independently hydrogen or optionally substituted lower alkyl. —O—, —S— or —ON=CR$^{14}$— wherein $R^{14}$ is hydrogen is especially preferable. —S— is more preferable.

$X^3$ is COOR$^{17}$, C(=NR$^{17}$)NR$^{18}$OR$^{19}$, or a group of the formula:

[Formula 8]

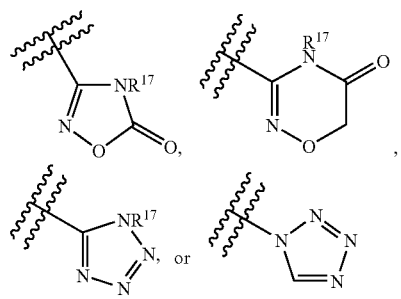

wherein $R^{17}$ to $R^{19}$ are each independently hydrogen or optionally substituted lower alkyl. COOR$^{17}$ ($R^{17}$ is hydrogen or optionally substituted lower alkyl) is especially preferable. COOR$^{17}$ ($R^{17}$ is hydrogen) is more preferable.

A compound of the present invention includes pharmaceutically acceptable salts, which can produce each compound. "A pharmaceutically acceptable salt" includes for example, salts of inorganic acid such as hydrochloric acid, sulfuric acid, nitric acid, phosphoric acid or the like; salts of organic acid such as paratoluenesulfonic acid, methanesulfonic acid, oxalic acid, citric acid or the like; salts of organic salt group such as ammonium, trimethylammonium or triethylammonium; salts of alkali metal such as sodium or potassium; alkaline-earth metal salts such as calcium, magnesium or the like.

A compound of the present invention includes a solvate thereof and can be coordinate any number of solvent molecules to Compound (I). Preferred is hydrate.

When Compound (I) of the present invention has an asymmetric carbon atom, it contained racemic body and all stereoisomers (a diastereoisomer, an antipode or the like). When Compound (I) of the present invention has a double bond and there is geometrical isomer at a substituent position of double bond, it includes both type of the isomers.

Compound (I) of the present invention can be synthesized, for example, by the following processes.

(Process 1) Synthesis of Compound (Ia) ($X^1$=O, (CR$^{12}$R$^{13}$)mO, O(CR$^{12}$R$^{13}$)m)

[Formula 9]

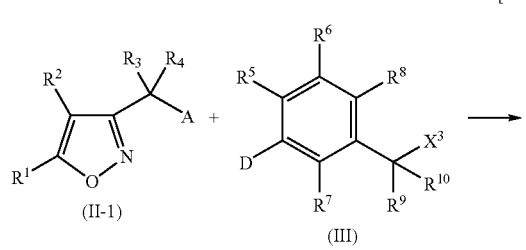

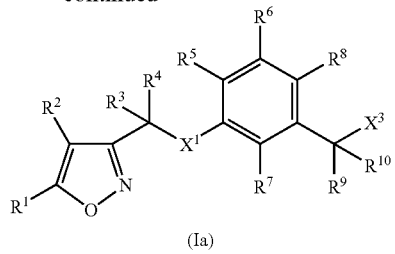

(Ia)

wherein the one of A and D is OH and another is (CR$^{12}$R$^{13}$)mOH or both A and D are OH, and the other signs are the same meanings as the above.

Compound (II-1) and Compound (III) are subject to Mitsunobu reaction to obtain Compound (Ia). Mitsunobu reaction can be performed by a well-known process and preferably performed in a solvent of N,N-dimethyl formamide, dimethyl sulfoxide, aromatic hydrocarbon group (e.g., toluene, benzene, xylene or the like), saturated hydrocarbon group (e.g., cyelohexane, hexane or the like), halogenated hydrocarbon group (e.g., dichloromethane, 1,2-dichloroethane or the like), ether group (e.g., tetrahydrofuran, dioxane or the like), ketone group (e.g., acetone, methyl ethylketone or the like), nitryl group (e.g., acetonitrile or the like), water, a mixed solvent thereof or the like under the presence of azodicarboxylate, amide (diethylazodicarboxylate or the like) or phosphine group such as triphenylphosphine or the like at −30° C. to 150° C. and preferably at 0° C. to 100° C. for 0.5 to 90 hours.

As Compound (II-1) and Compound (III), well known compounds and compounds, which are lead from well-known compounds by usual processes, can be used.

(Process 2) Synthesis of Compound (Ib) ($X^1$=O, S or NR$^{11}$)

[Formula 10]

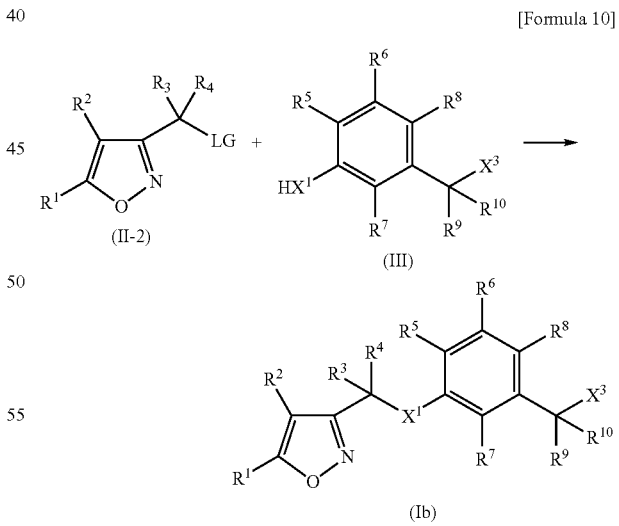

wherein LG is a leaving group such as halogen, lower alkylsulfonyloxy or the like and the other signs are the same meanings as the above.

Compound (Ib) can be synthesized by reacting Compound (II-2) and Compound (III). The reaction can be performed in an appropriate solvent under the presence of base at −10 to 180° C. and preferably at 0 to 150° C. for 0.5 to 90 hours. As the solvent, the same solvent described in the above process 1 can be used. The base is, for example, metal hydride (e.g., sodium hydride, potassium hydride or the like), metal hydroxide (e.g., sodium hydroxide, potassium hydroxide, calcium hydroxide, barium hydroxide or the like), metal carbonate (e.g., sodium carbonate, potassium carbonate, calcium carbonate, cesium carbonate or the like), metal alkoxide (e.g., sodium methoxide, sodium ethoxide, Potassium tert-butoxide or the like), sodium hydrogen carbonate, metallic sodium, organic amine (triethylamine, DBU or the like) or the like.

As Compound (II-2) and Compound (III), well known compounds and compounds, which is lead from well-known compounds by usual processes, can be used.

(Process 3) Synthesis of Compound (Ic) ($X^1$=$CR^{12}ON$=CH)

Compound (Ic) can be synthesized by the following route.

[Formula 11]

(II-3)

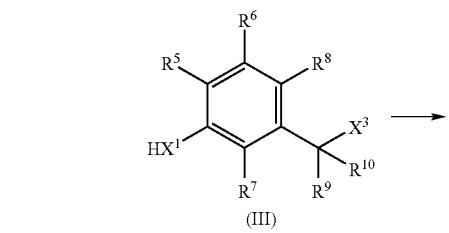
(III)

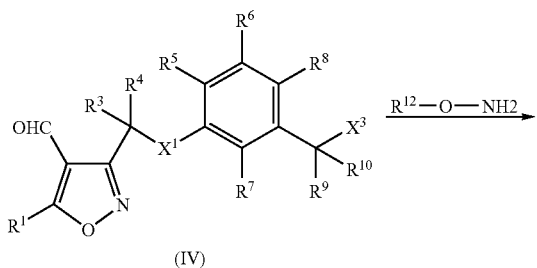
(IV)

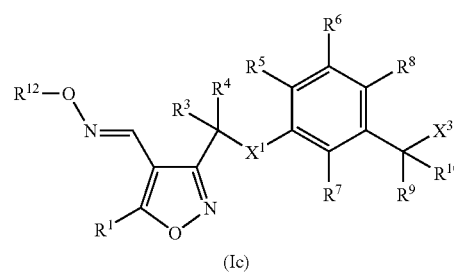
(Ic)

wherein LG is a leaving group such as halogen, lower alkylsulfonyl or the like, Hal is halogen and the other signs have the same meanings as the above.

Compound (II-3) and Compound (III) are subject to addition reaction to give Compound (IV). The reaction can be performed preferably in an appropriate solvent under the presence of base at −50° C. to 150° C. and preferably at −20° C. to 100° C. for 0.5 to 60 hours. The solvent described in the above process 1 can be used as the solvent. The base described in the above process 2 can be used as the base.

Compound (IV) is reacted with hydroxylamine of R12NH2 or the hydrochloric acid salt to give Compound (Ic). The reaction can be performed preferably in an appropriate solvent at −10° C. to 180° C. and preferably at −0° C. to 150° C. for 0.5 to 90 hours. The solvent described in the above process 1 can be used as the solvent.

(Process 4) Synthesis of Compound (Id) ($X^3$=C(=NH)NHOH)

Compound (Id) is synthesized by the following process.

[Formula 12]

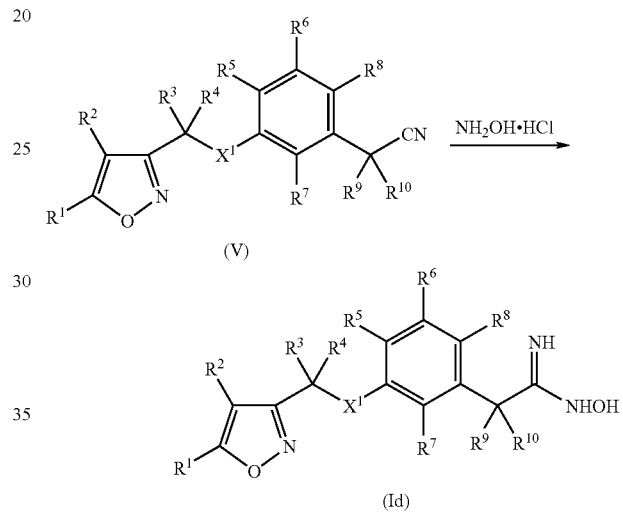

wherein each sign has the same meanings as the above.

Compound (V) is reacted with hydroxylamine to give a target Compound (Id). The reaction can be performed in an appropriate solvent at 0° C. to 150° C. and preferably at 20° C. to 100° C. for 0.5 to 90 hours. The solvent described in the above process 1 can be used as the solvent. The base described in the above process 2 can be used as the base.

As Compound (V), well known compounds and compounds, which is lead from well-known compounds by usual methods, can be used.

(Process 5) Synthesis of Compound (Ie) ($X^3$=oxadiazolon)

[Formula 13]

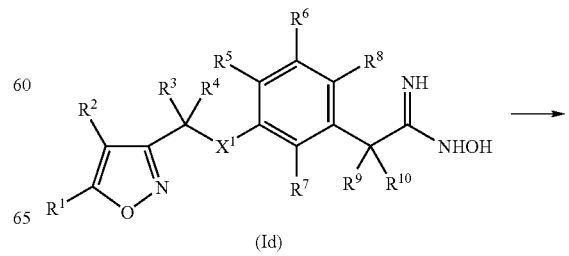
(Id)

-continued

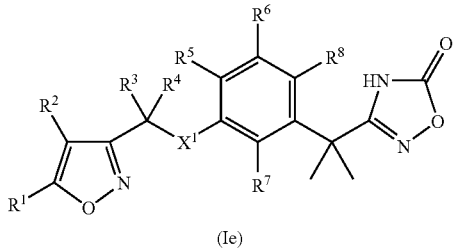

(Ie)

wherein each sign has the same meanings as the above.

Compound (Id) obtained in the above process 4 is reacted with CDI, phosgene, triphosgene or the like to give a target Compound (Ie). The reaction can be performed in an appropriate solvent at −30° C. to 150° C. and preferably at 0° C. to 100° C. for 0.5 to 90 hours. The solvent described in the above process 1 can be used as a solvent. The base described in the above process 2 can be used as the base.

The target oxadiazolon Compound (Ie) substituted with $R^{17}$ is obtained by following process. A compound wherein $R^{17}$ is H is synthesized by the above process, followed by introducing an appropriate subsistent by the usual process to give target compound.

(Process 6) Synthesis of compound (If) ($X^3$=oxadiadinon)

[Formula 14]

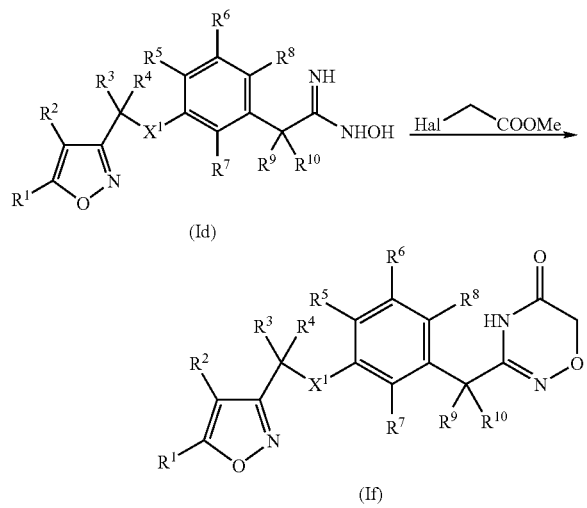

wherein each sign has the same meanings as the above.

Compound (Id) obtained in the above process 4 and a halogen compound are reacted to give target compound (If). The reaction can be performed in an appropriate solvent at −30° C. to 150° C. and preferably at 0° C. to 100° C. for 0.5 to 90 hours reaction. The solvent described in the above process 1 can be used as the solvent. The base described in the above process 2 can be used as the base.

When the compound obtained by the above any process is ester, i.e. $X^3$=COOR$^{17}$, this compound is hydrolyze by the usual process to give carboxylic acid, i.e. $X^3$=COOH.

If necessary, at an appropriate step in the above process for producing, any substituent can be transform to a different substituent by the well-known organic synthesized reaction.

For example, when the compound has halogen, it is reacted with alcohol in a solvent such as DMF, tetrahydrofuran or the like under the presence of base such as sodium hydride, potassium hydride or the like and deacid reagent such as alkali metal hydroxide, alkali metal hydrogencarbonate, alkali metal carbonate, organic base or the like at −20° C. to 100° C. to give compound whose substituent is transformed to lower alkoxy.

When the compound has hydroxy, it is reacted with oxidizing agent such as pyridinium dichromate, Jones reagent, manganese dioxide, potassium permanganate, ruthenium tetroxide or the like in a solvent such as dimethyl formamide, tetrahydrofuran, dichloromethane, benzene, acetone or the like to give a compound whose substituent is transformed to carboxy.

If necessary, after amino or hydroxy of a compound is protected by the usual process at an appropriate step, it is subjected to the reaction and then deprotected by treatment with acid or base at an appropriate step.

As an amino protecting group, phthalimide, lower alkoxycarbonyl, lower alkenyloxy carbonyl, halogeno alkoxycarbonyl, aryl lower alkoxycarbonyl, trialkyl silyl, lower alkylsulfonyl, halogeno lower alkylsulfonyl, arylsulfonyl, lower alkylcarbonyl, arylcarbonyl or the like can be used.

As a hydroxy protecting group, alkyl (t-butyl or the like), aralkyl (triphenylmethyl or benzyl), trialkyl silyl (t-butyldimethylsilyl, triisopropyl silyl or the like), alkyldiarylsilyl (t-butyldiphenylsilyl or the like), triaralkylsilyl (tribenzylsilyl or the like), alkoxyalkyl (methoxymethyl, 1-ethoxyethyl, 1-methyl 1-methoxyethyl or the like), alkoxyalkoxyalkyl (methoxyethoxymethyl or the like), alkylthioalkyl (methylthiomethyl or the like), tetrahydropyranyl (tetrahydropyran-2-yl, 4-methoxytetrahydropyran-4-yl or the like), tetrahydrothiopyranyl (tetrahydrothiopyran-2-yl or the like), tetrahydrofuranyl (tetrahydrofuran-2-yl or the like), tetrahydrothio furanyl (tetrahydrothio furan-2-yl or the like), aralkyloxyalkyl (benzyloxymethyl or the like) alkylsulfonyl, acyl, p-toluenesulfonyl or the like can be used.

Deprotection reaction is accomplished in a solvent such as tetrahydrofuran, dimethylformamide, diethylether, dichloromethane, toluene, benzene, xylene, cyelohexane, hexane, chloroform, ethyl acetate, butyl acetate, pentane, heptane, dioxane, acetone, acetonitrile or a mixed solvent thereof, by using base such as hydrazine, pyridine, sodium hydroxide, potassium hydroxide or the like or acid such as hydrochloric acid, trifluoroacetic acid, hydrofluoric acid or the like.

Preferable compounds in compounds of the present invention are followings.

In the tables, "=CPh" and "C=CPh" has the same meaning, —C≡C-Ph.

1) A compound wherein the part (Part A) of the formula:

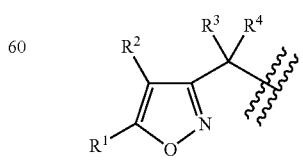

is the one of the followings.

TABLE 1

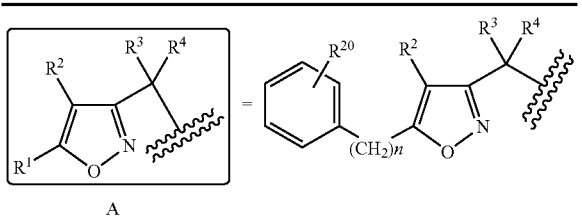

A

| Part A No. | R20 | n | R2 | R3, R4 |
|---|---|---|---|---|
| A1 | 4-Cl | 0 | H | H, H |
| A2 | 4-Cl | 0 | H | Me, Me |
| A3 | 4-Cl | 0 | H | Et, Et |
| A4 | 4-Cl | 0 | H | H, Et |
| A5 | 4-Cl | 0 | H | H, Ph |
| A6 | 4-Cl | 0 | H | H, C6H4-4-F |
| A7 | 4-Cl | 0 | Me | H, H |
| A8 | 4-Cl | 0 | Me | Me, Me |
| A9 | 4-Cl | 0 | Me | Et, Et |
| A10 | 4-Cl | 0 | Me | H, Et |
| A11 | 4-Cl | 0 | Me | H, Ph |
| A12 | 4-Cl | 0 | Me | H, C6H4-4-F |
| A13 | 4-Cl | 0 | OMe | H, H |
| A14 | 4-Cl | 0 | OMe | Me, Me |
| A15 | 4-Cl | 0 | OMe | Et, Et |
| A16 | 4-Cl | 0 | OMe | H, Et |
| A17 | 4-Cl | 0 | OMe | H, Ph |
| A18 | 4-Cl | 0 | OMe | H, C6H4-4-F |
| A19 | 4-Cl | 0 | CH2OH | H, H |
| A20 | 4-Cl | 0 | CH2OH | H, C6H4-4-F |
| A21 | 4-Cl | 0 | CH2OMe | H, H |
| A22 | 4-Cl | 0 | CH2OMe | Me, Me |
| A23 | 4-Cl | 0 | CH2OMe | Et, Et |
| A24 | 4-Cl | 0 | CH2OMe | H, Et |
| A25 | 4-Cl | 0 | CH2OMe | H, Ph |
| A26 | 4-Cl | 0 | CH2OMe | H, C6H4-4-F |
| A27 | 4-Cl | 0 | CF3 | H, H |
| A28 | 4-Cl | 0 | CF3 | Me, Me |
| A29 | 4-Cl | 0 | CF3 | Et, Et |
| A30 | 4-Cl | 0 | CF3 | H, Et |
| A31 | 4-Cl | 0 | CF3 | H, Ph |
| A32 | 4-Cl | 0 | CF3 | H, C6H4-4-F |
| A33 | 4-Cl | 0 | CH2OPh | H, H |
| A34 | 4-Cl | 0 | CH2OPh | H, C6H4-4-F |
| A35 | 4-Cl | 0 | CH2OCH2Ph | H, H |
| A36 | 4-Cl | 0 | CH2OCH2Ph | H, C6H4-4-F |
| A37 | 4-Cl | 0 | CH2-morpholino | H, H |

TABLE 2

| Part A No. | R20 | n | R2 | R3, R4 |
|---|---|---|---|---|
| A38 | 4-Cl | 0 | CH2-morpholino | Me, Me |
| A39 | 4-Cl | 0 | CH2-morpholino | Et, Et |
| A40 | 4-Cl | 0 | CH2-morpholino | H, Et |
| A41 | 4-Cl | 0 | CH2-morpholino | H, Ph |
| A42 | 4-Cl | 0 | CH2-morpholino | H, C6H4-4-F |
| A43 | 4-Cl | 0 | CH2NHBu | H, H |
| A44 | 4-Cl | 0 | CH2NHBu | H, C6H4-4-F |
| A45 | 4-Cl | 0 | C≡CPh | H, H |
| A46 | 4-Cl | 0 | C≡CPh | H, C6H4-4-F |
| A47 | 4-Cl | 0 | Ph | H, H |
| A48 | 4-Cl | 0 | Ph | H, C6H4-4-F |
| A49 | 4-Cl | 0 | C6H4-4-CF3 | H, H |
| A50 | 4-Cl | 0 | C6H4-4-CF3 | H, C6H4-4-F |
| A51 | 4-Cl | 0 | C6H4-3-CF3 | H, H |
| A52 | 4-Cl | 0 | C6H4-3-CF3 | H, C6H4-4-F |
| A53 | 4-Cl | 0 | C6H4-4-OH | H, H |
| A54 | 4-Cl | 0 | C6H4-4-OH | H, C6H4-4-F |
| A55 | 4-Cl | 0 | CH2Ph | H, H |
| A56 | 4-Cl | 0 | CH2Ph | H, C6H4-4-F |
| A57 | 4-Cl | 0 | CH2C6H4-4-CF3 | H, H |
| A58 | 4-Cl | 0 | CH2C6H4-4-CF3 | Me, Me |
| A59 | 4-Cl | 0 | CH2C6H4-4-CF3 | Et, Et |
| A60 | 4-Cl | 0 | CH2C6H4-4-CF3 | H, Et |
| A61 | 4-Cl | 0 | CH2C6H4-4-CF3 | H, Ph |
| A62 | 4-Cl | 0 | CH2C6H4-4-CF3 | H, C6H4-4-F |
| A63 | 4-Cl | 0 | CH2C6H4-4-OCF3 | H, H |
| A64 | 4-Cl | 0 | CH2C6H4-4-OCF3 | H, C6H4-4-F |
| A65 | 4-Cl | 0 | CH2C6H4-4-Ph | H, H |
| A66 | 4-Cl | 0 | CH2C6H4-4-Ph | H, C6H4-4-F |
| A67 | 4-Cl | 0 | CH2C6H4-2-Cl | H, H |
| A68 | 4-Cl | 0 | CH2C6H4-2-Cl | H, C6H4-4-F |
| A69 | 4-Cl | 0 | (CH2)2Ph | H, H |
| A70 | 4-Cl | 0 | (CH2)2Ph | H, C6H4-4-F |
| A71 | 4-Cl | 0 | SPh | H, H |
| A72 | 4-Cl | 0 | SPh | H, C6H4-4-F |
| A73 | 4-Cl | 0 | NH2 | H, H |
| A74 | 4-Cl | 0 | NH2 | H, C6H4-4-F |
| A75 | 4-Cl | 0 | NHMe | H, H |
| A76 | 4-Cl | 0 | NHMe | H, C6H4-4-F |
| A77 | 4-Cl | 0 | CH2-piperazino-Ph | H, H |
| A78 | 4-Cl | 0 | CH2-piperazino-Ph | H, C6H4-4-F |
| A79 | 4-Cl | 0 | CH2-piperidino | H, H |
| A80 | 4-Cl | 0 | CH2-piperidino | H, C6H4-4-F |
| A81 | 4-Cl | 0 | OCH2Ph | H, H |
| A82 | 4-Cl | 0 | OCH2Ph | H, C6H4-4-F |
| A83 | 4-Cl | 0 | Ac | H, H |
| A84 | 4-Cl | 0 | Ac | H, C6H4-4-F |
| A85 | 4-Cl | 0 | CONH2 | H, H |

TABLE 3

| Part A No. | R20 | n | R2 | R3, R4 |
|---|---|---|---|---|
| A86 | 4-Cl | 0 | CONH2 | H, C6H4-4-F |
| A87 | 4-Cl | 0 | CSNH2 | H, H |
| A88 | 4-Cl | 0 | CSNH2 | H, C6H4-4-F |
| A89 | 4-Cl | 0 | OCONH2 | H, H |
| A90 | 4-Cl | 0 | OCONH2 | H, C6H4-4-F |
| A91 | 4-Cl | 0 | OCSNH2 | H, H |
| A92 | 4-Cl | 0 | OCSNH2 | H, C6H4-4-F |
| A93 | 4-Cl | 0 | OSO2Me | H, H |
| A94 | 4-Cl | 0 | OSO2Me | H, C6H4-4-F |
| A95 | 4-Cl | 0 | OSO2Ph | H, H |
| A96 | 4-Cl | 0 | OSO2Ph | H, C6H4-4-F |
| A97 | 4-Cl | 0 | I | H, H |
| A98 | 4-Cl | 0 | I | H, C6H4-4-F |
| A99 | 4-Cl | 1 | H | H, H |
| A100 | 4-Cl | 1 | H | Me, Me |
| A101 | 4-Cl | 1 | H | Et, Et |
| A102 | 4-Cl | 1 | H | H, Et |
| A103 | 4-Cl | 1 | H | H, Ph |
| A104 | 4-Cl | 1 | H | H, C6H4-4-F |
| A105 | 4-Cl | 1 | Me | H, H |
| A106 | 4-Cl | 1 | Me | Me, Me |
| A107 | 4-Cl | 1 | Me | Et, Et |
| A108 | 4-Cl | 1 | Me | H, Et |
| A109 | 4-Cl | 1 | Me | H, Ph |
| A110 | 4-Cl | 1 | Me | H, C6H4-4-F |
| A111 | 4-Cl | 1 | OMe | H, H |
| A112 | 4-Cl | 1 | OMe | Me, Me |
| A113 | 4-Cl | 1 | OMe | Et, Et |
| A114 | 4-Cl | 1 | OMe | H, Et |
| A115 | 4-Cl | 1 | OMe | H, Ph |
| A116 | 4-Cl | 1 | OMe | H, C6H4-4-F |
| A117 | 4-Cl | 1 | CH2OH | H, H |
| A118 | 4-Cl | 1 | CH2OH | H, C6H4-4-F |
| A119 | 4-Cl | 1 | CH2OMe | H, H |
| A120 | 4-Cl | 1 | CH2OMe | Me, Me |
| A121 | 4-Cl | 1 | CH2OMe | Et, Et |
| A122 | 4-Cl | 1 | CH2OMe | H, Et |
| A123 | 4-Cl | 1 | CH2OMe | H, Ph |
| A124 | 4-Cl | 1 | CH2OMe | H, C6H4-4-F |
| A125 | 4-Cl | 1 | CF3 | H, H |
| A126 | 4-Cl | 1 | CF3 | Me, Me |
| A127 | 4-Cl | 1 | CF3 | Et, Et |

TABLE 3-continued

| Part A No. | R20 | n | R2 | R3, R4 |
|---|---|---|---|---|
| A128 | 4-Cl | 1 | CF3 | H, Et |
| A129 | 4-Cl | 1 | CF3 | H, Ph |
| A130 | 4-Cl | 1 | CF3 | H, C6H4-4-F |
| A131 | 4-Cl | 1 | CH2OPh | H, H |
| A132 | 4-Cl | 1 | CH2OPh | H, C6H4-4-F |
| A133 | 4-Cl | 1 | CH2OCH2Ph | H, H |

TABLE 4

| Part A No. | R20 | n | R2 | R3, R4 |
|---|---|---|---|---|
| A134 | 4-Cl | 1 | CH2OCH2Ph | H, C6H4-4-F |
| A135 | 4-Cl | 1 | CH2-morpholino | H, H |
| A136 | 4-Cl | 1 | CH2-morpholino | Me, Me |
| A137 | 4-Cl | 1 | CH2-morpholino | Et, Et |
| A138 | 4-Cl | 1 | CH2-morpholino | H, Et |
| A139 | 4-Cl | 1 | CH2-morpholino | H, Ph |
| A140 | 4-Cl | 1 | CH2-morpholino | H, C6H4-4-F |
| A141 | 4-Cl | 1 | CH2NHBu | H, H |
| A142 | 4-Cl | 1 | CH2NHBu | H, C6H4-4-F |
| A143 | 4-Cl | 1 | C≡CPh | H, H |
| A144 | 4-Cl | 1 | C≡CPh | H, C6H4-4-F |
| A145 | 4-Cl | 1 | Ph | H, H |
| A146 | 4-Cl | 1 | Ph | H, C6H4-4-F |
| A147 | 4-Cl | 1 | C6H4-4-CF3 | H, H |
| A148 | 4-Cl | 1 | C6H4-4-CF3 | H, C6H4-4-F |
| A149 | 4-Cl | 1 | C6H4-3-CF3 | H, H |
| A150 | 4-Cl | 1 | C6H4-3-CF3 | H, C6H4-4-F |
| A151 | 4-Cl | 1 | C6H4-4-OH | H, H |
| A152 | 4-Cl | 1 | C6H4-4-OH | H, C6H4-4-F |
| A153 | 4-Cl | 1 | CH2Ph | H, H |
| A154 | 4-Cl | 1 | CH2Ph | H, C6H4-4-F |
| A155 | 4-Cl | 1 | CH2C6H4-4-CF3 | H, H |
| A156 | 4-Cl | 1 | CH2C6H4-4-CF3 | Me, Me |
| A157 | 4-Cl | 1 | CH2C6H4-4-CF3 | Et, Et |
| A158 | 4-Cl | 1 | CH2C6H4-4-CF3 | H, Et |
| A159 | 4-Cl | 1 | CH2C6H4-4-CF3 | H, Ph |
| A160 | 4-Cl | 1 | CH2C6H4-4-CF3 | H, C6H4-4-F |
| A161 | 4-Cl | 1 | CH2C6H4-4-OCF3 | H, H |
| A162 | 4-Cl | 1 | CH2C6H4-4-OCF3 | H, C6H4-4-F |
| A163 | 4-Cl | 1 | CH2C6H4-4-Ph | H, H |
| A164 | 4-Cl | 1 | CH2C6H4-4-Ph | H, C6H4-4-F |
| A165 | 4-Cl | 1 | CH2C6H4-2-Cl | H, H |
| A166 | 4-Cl | 1 | CH2C6H4-2-Cl | H, C6H4-4-F |
| A167 | 4-Cl | 1 | (CH2)2Ph | H, H |
| A168 | 4-Cl | 1 | (CH2)2Ph | H, C6H4-4-F |
| A169 | 4-Cl | 1 | SPh | H, H |
| A170 | 4-Cl | 1 | SPh | H, C6H4-4-F |
| A171 | 4-Cl | 1 | NH2 | H, H |
| A172 | 4-Cl | 1 | NH2 | H, C6H4-4-F |
| A173 | 4-Cl | 1 | NHMe | H, H |
| A174 | 4-Cl | 1 | NHMe | H, C6H4-4-F |
| A175 | 4-Cl | 1 | CH2-piperazino-Ph | H, H |
| A176 | 4-Cl | 1 | CH2-piperazino-Ph | H, C6H4-4-F |
| A177 | 4-Cl | 1 | CH2-piperidino | H, H |
| A178 | 4-Cl | 1 | CH2-piperidino | H, C6H4-4-F |
| A179 | 4-Cl | 1 | OCH2Ph | H, H |
| A180 | 4-Cl | 1 | OCH2Ph | H, C6H4-4-F |
| A181 | 4-Cl | 1 | Ac | H, H |

TABLE 5

| Part A No. | R20 | n | R2 | R3, R4 |
|---|---|---|---|---|
| A182 | 4-Cl | 1 | Ac | H, C6H4-4-F |
| A183 | 4-Cl | 1 | CONH2 | H, H |
| A184 | 4-Cl | 1 | CONH2 | H, C6H4-4-F |
| A185 | 4-Cl | 1 | CSNH2 | H, H |
| A186 | 4-Cl | 1 | CSNH2 | H, C6H4-4-F |
| A187 | 4-Cl | 1 | OCONH2 | H, H |
| A188 | 4-Cl | 1 | OCONH2 | H, C6H4-4-F |
| A189 | 4-Cl | 1 | OCSNH2 | H, H |

TABLE 5-continued

| Part A No. | R20 | n | R2 | R3, R4 |
|---|---|---|---|---|
| A190 | 4-Cl | 1 | OCSNH2 | H, C6H4-4-F |
| A191 | 4-Cl | 1 | OSO2Me | H, H |
| A192 | 4-Cl | 1 | OSO2Me | H, C6H4-4-F |
| A193 | 4-Cl | 1 | OSO2Ph | H, H |
| A194 | 4-Cl | 1 | OSO2Ph | H, C6H4-4-F |
| A195 | 4-Cl | 1 | I | H, H |
| A196 | 4-Cl | 1 | I | H, C6H4-4-F |
| A197 | 4-Cl | 2 | H | H, H |
| A198 | 4-Cl | 2 | H | Me, Me |
| A199 | 4-Cl | 2 | H | Et, Et |
| A200 | 4-Cl | 2 | H | H, Et |
| A201 | 4-Cl | 2 | H | H, Ph |
| A202 | 4-Cl | 2 | H | H, C6H4-4-F |
| A203 | 4-Cl | 2 | Me | H, H |
| A204 | 4-Cl | 2 | Me | Me, Me |
| A205 | 4-Cl | 2 | Me | Et, Et |
| A206 | 4-Cl | 2 | Me | H, Et |
| A207 | 4-Cl | 2 | Me | H, Ph |
| A208 | 4-Cl | 2 | Me | H, C6H4-4-F |
| A209 | 4-Cl | 2 | OMe | H, H |
| A210 | 4-Cl | 2 | OMe | Me, Me |
| A211 | 4-Cl | 2 | OMe | Et, Et |
| A212 | 4-Cl | 2 | OMe | H, Et |
| A213 | 4-Cl | 2 | OMe | H, Ph |
| A214 | 4-Cl | 2 | OMe | H, C6H4-4-F |
| A215 | 4-Cl | 2 | CH2OH | H, H |
| A216 | 4-Cl | 2 | CH2OH | H, C6H4-4-F |
| A217 | 4-Cl | 2 | CH2OMe | H, H |
| A218 | 4-Cl | 2 | CH2OMe | Me, Me |
| A219 | 4-Cl | 2 | CH2OMe | Et, Et |
| A220 | 4-Cl | 2 | CH2OMe | H, Et |
| A221 | 4-Cl | 2 | CH2OMe | H, Ph |
| A222 | 4-Cl | 2 | CH2OMe | H, C6H4-4-F |
| A223 | 4-Cl | 2 | CF3 | H, H |
| A224 | 4-Cl | 2 | CF3 | Me, Me |
| A225 | 4-Cl | 2 | CF3 | Et, Et |
| A226 | 4-Cl | 2 | CF3 | H, Et |
| A227 | 4-Cl | 2 | CF3 | H, Ph |
| A228 | 4-Cl | 2 | CF3 | H, C6H4-4-F |
| A229 | 4-Cl | 2 | CH2OPh | H, H |

TABLE 6

| Part A No. | R20 | n | R2 | R3, R4 |
|---|---|---|---|---|
| A230 | 4-Cl | 2 | CH2OPh | H, C6H4-4-F |
| A231 | 4-Cl | 2 | CH2OCH2Ph | H, H |
| A232 | 4-Cl | 2 | CH2OCH2Ph | H, C6H4-4-F |
| A233 | 4-Cl | 2 | CH2-morpholino | H, H |
| A234 | 4-Cl | 2 | CH2-morpholino | Me, Me |
| A235 | 4-Cl | 2 | CH2-morpholino | Et, Et |
| A236 | 4-Cl | 2 | CH2-morpholino | H, Et |
| A237 | 4-Cl | 2 | CH2-morpholino | H, Ph |
| A238 | 4-Cl | 2 | CH2-morpholino | H, C6H4-4-F |
| A239 | 4-Cl | 2 | CH2NHBu | H, H |
| A240 | 4-Cl | 2 | CH2NHBu | H, C6H4-4-F |
| A241 | 4-Cl | 2 | C≡CPh | H, H |
| A242 | 4-Cl | 2 | C≡CPh | H, C6H4-4-F |
| A243 | 4-Cl | 2 | Ph | H, H |
| A244 | 4-Cl | 2 | Ph | H, C6H4-4-F |
| A245 | 4-Cl | 2 | C6H4-4-CF3 | H, H |
| A246 | 4-Cl | 2 | C6H4-4-CF3 | H, C6H4-4-F |
| A247 | 4-Cl | 2 | C6H4-3-CF3 | H, H |
| A248 | 4-Cl | 2 | C6H4-3-CF3 | H, C6H4-4-F |
| A249 | 4-Cl | 2 | C6H4-4-OH | H, H |
| A250 | 4-Cl | 2 | C6H4-4-OH | H, C6H4-4-F |
| A251 | 4-Cl | 2 | CH2Ph | H, H |
| A252 | 4-Cl | 2 | CH2Ph | H, C6H4-4-F |
| A253 | 4-Cl | 2 | CH2C6H4-4-CF3 | H, H |
| A254 | 4-Cl | 2 | CH2C6H4-4-CF3 | Me, Me |
| A255 | 4-Cl | 2 | CH2C6H4-4-CF3 | Et, Et |
| A256 | 4-Cl | 2 | CH2C6H4-4-CF3 | H, Et |
| A257 | 4-Cl | 2 | CH2C6H4-4-CF3 | H, Ph |
| A258 | 4-Cl | 2 | CH2C6H4-4-CF3 | H, C6H4-4-F |

TABLE 6-continued

| Part A No. | R20 | n | R2 | R3, R4 |
|---|---|---|---|---|
| A259 | 4-Cl | 2 | CH2C6H4-4-OCF3 | H, H |
| A260 | 4-Cl | 2 | CH2C6H4-4-OCF3 | H, C6H4-4-F |
| A261 | 4-Cl | 2 | CH2C6H4-4-Ph | H, H |
| A262 | 4-Cl | 2 | CH2C6H4-4-Ph | H, C6H4-4-F |
| A263 | 4-Cl | 2 | CH2C6H4-2-Cl | H, H |
| A264 | 4-Cl | 2 | CH2C6H4-2-Cl | H, C6H4-4-F |
| A265 | 4-Cl | 2 | (CH2)2Ph | H, H |
| A266 | 4-Cl | 2 | (CH2)2Ph | H, C6H4-4-F |
| A267 | 4-Cl | 2 | SPh | H, H |
| A268 | 4-Cl | 2 | SPh | H, C6H4-4-F |
| A269 | 4-Cl | 2 | NH2 | H, H |
| A270 | 4-Cl | 2 | NH2 | H, C6H4-4-F |
| A271 | 4-Cl | 2 | NHMe | H, H |
| A272 | 4-Cl | 2 | NHMe | H, C6H4-4-F |
| A273 | 4-Cl | 2 | CH2-piperazino-Ph | H, H |
| A274 | 4-Cl | 2 | CH2-piperazino-Ph | H, C6H4-4-F |
| A275 | 4-Cl | 2 | CH2-piperidino | H, H |
| A276 | 4-Cl | 2 | CH2-piperidino | H, C6H4-4-F |
| A277 | 4-Cl | 2 | OCH2Ph | H, H |

TABLE 7

| Part A No. | R20 | n | R2 | R3, R4 |
|---|---|---|---|---|
| A278 | 4-Cl | 2 | OCH2Ph | H, C6H4-4-F |
| A279 | 4-Cl | 2 | Ac | H, H |
| A280 | 4-Cl | 2 | Ac | H, C6H4-4-F |
| A281 | 4-Cl | 2 | CONH2 | H, H |
| A282 | 4-Cl | 2 | CONH2 | H, C6H4-4-F |
| A283 | 4-Cl | 2 | CSNH2 | H, H |
| A284 | 4-Cl | 2 | CSNH2 | H, C6H4-4-F |
| A285 | 4-Cl | 2 | OCONH2 | H, H |
| A286 | 4-Cl | 2 | OCONH2 | H, C6H4-4-F |
| A287 | 4-Cl | 2 | OCSNH2 | H, H |
| A288 | 4-Cl | 2 | OCSNH2 | H, C6H4-4-F |
| A289 | 4-Cl | 2 | OSO2Me | H, H |
| A290 | 4-Cl | 2 | OSO2Me | H, C6H4-4-F |
| A291 | 4-Cl | 2 | OSO2Ph | H, H |
| A292 | 4-Cl | 2 | OSO2Ph | H, C6H4-4-F |
| A293 | 4-Cl | 2 | I | H, H |
| A294 | 4-Cl | 2 | I | H, C6H4-4-F |
| A295 | 4-CF3 | 0 | H | H, H |
| A296 | 4-CF3 | 0 | H | Me, Me |
| A297 | 4-CF3 | 0 | H | Et, Et |
| A298 | 4-CF3 | 0 | H | H, Et |
| A299 | 4-CF3 | 0 | H | H, Ph |
| A300 | 4-CF3 | 0 | H | H, C6H4-4-F |
| A301 | 4-CF3 | 0 | Me | H, H |
| A302 | 4-CF3 | 0 | Me | Me, Me |
| A303 | 4-CF3 | 0 | Me | Et, Et |
| A304 | 4-CF3 | 0 | Me | H, Et |
| A305 | 4-CF3 | 0 | Me | H, Ph |
| A306 | 4-CF3 | 0 | Me | H, C6H4-4-F |
| A307 | 4-CF3 | 0 | OMe | H, H |
| A308 | 4-CF3 | 0 | OMe | Me, Me |
| A309 | 4-CF3 | 0 | OMe | Et, Et |
| A310 | 4-CF3 | 0 | OMe | H, Et |
| A311 | 4-CF3 | 0 | OMe | H, Ph |
| A312 | 4-CF3 | 0 | OMe | H, C6H4-4-F |
| A313 | 4-CF3 | 0 | CH2OH | H, H |
| A314 | 4-CF3 | 0 | CH2OH | H, C6H4-4-F |
| A315 | 4-CF3 | 0 | CH2OMe | H, H |
| A316 | 4-CF3 | 0 | CH2OMe | Me, Me |
| A317 | 4-CF3 | 0 | CH2OMe | Et, Et |
| A318 | 4-CF3 | 0 | CH2OMe | H, Et |
| A319 | 4-CF3 | 0 | CH2OMe | H, Ph |
| A320 | 4-CF3 | 0 | CH2OMe | H, C6H4-4-F |
| A321 | 4-CF3 | 0 | CF3 | H, H |
| A322 | 4-CF3 | 0 | CF3 | Me, Me |
| A323 | 4-CF3 | 0 | CF3 | Et, Et |
| A324 | 4-CF3 | 0 | CF3 | H, Et |
| A325 | 4-CF3 | 0 | CF3 | H, Ph |

TABLE 8

| Part A No. | R20 | n | R2 | R3, R4 |
|---|---|---|---|---|
| A326 | 4-CF3 | 0 | CF3 | H, C6H4-4-F |
| A327 | 4-CF3 | 0 | CH2OPh | H, H |
| A328 | 4-CF3 | 0 | CH2OPh | H, C6H4-4-F |
| A329 | 4-CF3 | 0 | CH2OCH2Ph | H, H |
| A330 | 4-CF3 | 0 | CH2OCH2Ph | H, C6H4-4-F |
| A331 | 4-CF3 | 0 | CH2-morpholino | H, H |
| A332 | 4-CF3 | 0 | CH2-morpholino | Me, Me |
| A333 | 4-CF3 | 0 | CH2-morpholino | Et, Et |
| A334 | 4-CF3 | 0 | CH2-morpholino | H, Et |
| A335 | 4-CF3 | 0 | CH2-morpholino | H, Ph |
| A336 | 4-CF3 | 0 | CH2-morpholino | H, C6H4-4-F |
| A337 | 4-CF3 | 0 | CH2NHBu | H, H |
| A338 | 4-CF3 | 0 | CH2NHBu | H, C6H4-4-F |
| A339 | 4-CF3 | 0 | C≡CPh | H, H |
| A340 | 4-CF3 | 0 | C≡CPh | H, C6H4-4-F |
| A341 | 4-CF3 | 0 | Ph | H, H |
| A342 | 4-CF3 | 0 | Ph | H, C6H4-4-F |
| A343 | 4-CF3 | 0 | C6H4-4-CF3 | H, H |
| A344 | 4-CF3 | 0 | C6H4-4-CF3 | H, C6H4-4-F |
| A345 | 4-CF3 | 0 | C6H4-3-CF3 | H, H |
| A346 | 4-CF3 | 0 | C6H4-3-CF3 | H, C6H4-4-F |
| A347 | 4-CF3 | 0 | C6H4-4-OH | H, H |
| A348 | 4-CF3 | 0 | C6H4-4-OH | H, C6H4-4-F |
| A349 | 4-CF3 | 0 | CH2Ph | H, H |
| A350 | 4-CF3 | 0 | CH2Ph | H, C6H4-4-F |
| A351 | 4-CF3 | 0 | CH2C6H4-4-CF3 | H, H |
| A352 | 4-CF3 | 0 | CH2C6H4-4-CF3 | Me, Me |
| A353 | 4-CF3 | 0 | CH2C6H4-4-CF3 | Et, Et |
| A354 | 4-CF3 | 0 | CH2C6H4-4-CF3 | H, Et |
| A355 | 4-CF3 | 0 | CH2C6H4-4-CF3 | H, Ph |
| A356 | 4-CF3 | 0 | CH2C6H4-4-CF3 | H, C6H4-4-F |
| A357 | 4-CF3 | 0 | CH2C6H4-4-OCF3 | H, H |
| A358 | 4-CF3 | 0 | CH2C6H4-4-OCF3 | H, C6H4-4-F |
| A359 | 4-CF3 | 0 | CH2C6H4-4-Ph | H, H |
| A360 | 4-CF3 | 0 | CH2C6H4-4-Ph | H, C6H4-4-F |
| A361 | 4-CF3 | 0 | CH2C6H4-2-Cl | H, H |
| A362 | 4-CF3 | 0 | CH2C6H4-2-Cl | H, C6H4-4-F |
| A363 | 4-CF3 | 0 | (CH2)2Ph | H, H |
| A364 | 4-CF3 | 0 | (CH2)2Ph | H, C6H4-4-F |
| A365 | 4-CF3 | 0 | SPh | H, H |
| A366 | 4-CF3 | 0 | SPh | H, C6H4-4-F |
| A367 | 4-CF3 | 0 | NH2 | H, H |
| A368 | 4-CF3 | 0 | NH2 | H, C6H4-4-F |
| A369 | 4-CF3 | 0 | NHMe | H, H |
| A370 | 4-CF3 | 0 | NHMe | H, C6H4-4-F |
| A371 | 4-CF3 | 0 | CH2-piperazino-Ph | H, H |
| A372 | 4-CF3 | 0 | CH2-piperazino-Ph | H, C6H4-4-F |
| A373 | 4-CF3 | 0 | CH2-piperidino | H, H |

TABLE 9

| Part A No. | R20 | n | R2 | R3, R4 |
|---|---|---|---|---|
| A374 | 4-CF3 | 0 | CH2-piperidino | H, C6H4-4-F |
| A375 | 4-CF3 | 0 | OCH2Ph | H, H |
| A376 | 4-CF3 | 0 | OCH2Ph | H, C6H4-4-F |
| A377 | 4-CF3 | 0 | Ac | H, H |
| A378 | 4-CF3 | 0 | Ac | H, C6H4-4-F |
| A379 | 4-CF3 | 0 | CONH2 | H, H |
| A380 | 4-CF3 | 0 | CONH2 | H, C6H4-4-F |
| A381 | 4-CF3 | 0 | CSNH2 | H, H |
| A382 | 4-CF3 | 0 | CSNH2 | H, C6H4-4-F |
| A383 | 4-CF3 | 0 | OCONH2 | H, H |
| A384 | 4-CF3 | 0 | OCONH2 | H, C6H4-4-F |
| A385 | 4-CF3 | 0 | OCSNH2 | H, H |
| A386 | 4-CF3 | 0 | OCSNH2 | H, C6H4-4-F |
| A387 | 4-CF3 | 0 | OSO2Me | H, H |
| A388 | 4-CF3 | 0 | OSO2Me | H, C6H4-4-F |
| A389 | 4-CF3 | 0 | OSO2Ph | H, H |
| A390 | 4-CF3 | 0 | OSO2Ph | H, C6H4-4-F |
| A391 | 4-CF3 | 0 | I | H, H |
| A392 | 4-CF3 | 0 | I | H, C6H4-4-F |
| A393 | 4-CF3 | 1 | H | H, H |
| A394 | 4-CF3 | 1 | H | Me, Me |

TABLE 9-continued

| Part A No. | R20 | n | R2 | R3, R4 |
|---|---|---|---|---|
| A395 | 4-CF3 | 1 | H | Et, Et |
| A396 | 4-CF3 | 1 | H | H, Et |
| A397 | 4-CF3 | 1 | H | H, Ph |
| A398 | 4-CF3 | 1 | H | H, C6H4-4-F |
| A399 | 4-CF3 | 1 | Me | H, H |
| A400 | 4-CF3 | 1 | Me | Me, Me |
| A401 | 4-CF3 | 1 | Me | Et, Et |
| A402 | 4-CF3 | 1 | Me | H, Et |
| A403 | 4-CF3 | 1 | Me | H, Ph |
| A404 | 4-CF3 | 1 | Me | H, C6H4-4-F |
| A405 | 4-CF3 | 1 | OMe | H, H |
| A406 | 4-CF3 | 1 | OMe | Me, Me |
| A407 | 4-CF3 | 1 | OMe | Et, Et |
| A408 | 4-CF3 | 1 | OMe | H, Et |
| A409 | 4-CF3 | 1 | OMe | H, Ph |
| A410 | 4-CF3 | 1 | OMe | H, C6H4-4-F |
| A411 | 4-CF3 | 1 | CH2OH | H, H |
| A412 | 4-CF3 | 1 | CH2OH | H, C6H4-4-F |
| A413 | 4-CF3 | 1 | CH2OMe | H, H |
| A414 | 4-CF3 | 1 | CH2OMe | Me, Me |
| A415 | 4-CF3 | 1 | CH2OMe | Et, Et |
| A416 | 4-CF3 | 1 | CH2OMe | H, Et |
| A417 | 4-CF3 | 1 | CH2OMe | H, Ph |
| A418 | 4-CF3 | 1 | CH2OMe | H, C6H4-4-F |
| A419 | 4-CF3 | 1 | CF3 | H, H |
| A420 | 4-CF3 | 1 | CF3 | Me, Me |
| A421 | 4-CF3 | 1 | CF3 | Et, Et |

TABLE 10

| Part A No. | R20 | n | R2 | R3, R4 |
|---|---|---|---|---|
| A422 | 4-CF3 | 1 | CF3 | H, Et |
| A423 | 4-CF3 | 1 | CF3 | H, Ph |
| A424 | 4-CF3 | 1 | CF3 | H, C6H4-4-F |
| A425 | 4-CF3 | 1 | CH2OPh | H, H |
| A426 | 4-CF3 | 1 | CH2OPh | H, C6H4-4-F |
| A427 | 4-CF3 | 1 | CH2OCH2Ph | H, H |
| A428 | 4-CF3 | 1 | CH2OCH2Ph | H, C6H4-4-F |
| A429 | 4-CF3 | 1 | CH2-morpholino | H, H |
| A430 | 4-CF3 | 1 | CH2-morpholino | Me, Me |
| A431 | 4-CF3 | 1 | CH2-morpholino | Et, Et |
| A432 | 4-CF3 | 1 | CH2-morpholino | H, Et |
| A433 | 4-CF3 | 1 | CH2-morpholino | H, Ph |
| A434 | 4-CF3 | 1 | CH2-morpholino | H, C6H4-4-F |
| A435 | 4-CF3 | 1 | CH2NHBu | H, H |
| A436 | 4-CF3 | 1 | CH2NHBu | H, C6H4-4-F |
| A437 | 4-CF3 | 1 | C≡CPh | H, H |
| A438 | 4-CF3 | 1 | C≡CPh | H, C6H4-4-F |
| A439 | 4-CF3 | 1 | Ph | H, H |
| A440 | 4-CF3 | 1 | Ph | H, C6H4-4-F |
| A441 | 4-CF3 | 1 | C6H4-4-CF3 | H, H |
| A442 | 4-CF3 | 1 | C6H4-4-CF3 | H, C6H4-4-F |
| A443 | 4-CF3 | 1 | C6H4-3-CF3 | H, H |
| A444 | 4-CF3 | 1 | C6H4-3-CF3 | H, C6H4-4-F |
| A445 | 4-CF3 | 1 | C6H4-4-OH | H, H |
| A446 | 4-CF3 | 1 | C6H4-4-OH | H, C6H4-4-F |
| A447 | 4-CF3 | 1 | CH2Ph | H, H |
| A448 | 4-CF3 | 1 | CH2Ph | H, C6H4-4-F |
| A449 | 4-CF3 | 1 | CH2C6H4-4-CF3 | H, H |
| A450 | 4-CF3 | 1 | CH2C6H4-4-CF3 | Me, Me |
| A451 | 4-CF3 | 1 | CH2C6H4-4-CF3 | Et, Et |
| A452 | 4-CF3 | 1 | CH2C6H4-4-CF3 | H, Et |
| A453 | 4-CF3 | 1 | CH2C6H4-4-CF3 | H, Ph |
| A454 | 4-CF3 | 1 | CH2C6H4-4-CF3 | H, C6H4-4-F |
| A455 | 4-CF3 | 1 | CH2C6H4-4-OCF3 | H, H |
| A456 | 4-CF3 | 1 | CH2C6H4-4-OCF3 | H, C6H4-4-F |
| A457 | 4-CF3 | 1 | CH2C6H4-4-Ph | H, H |
| A458 | 4-CF3 | 1 | CH2C6H4-4-Ph | H, C6H4-4-F |
| A459 | 4-CF3 | 1 | CH2C6H4-2-Cl | H, H |
| A460 | 4-CF3 | 1 | CH2C6H4-2-Cl | H, C6H4-4-F |
| A461 | 4-CF3 | 1 | (CH2)2Ph | H, H |
| A462 | 4-CF3 | 1 | (CH2)2Ph | H, C6H4-4-F |
| A463 | 4-CF3 | 1 | SPh | H, H |

TABLE 10-continued

| Part A No. | R20 | n | R2 | R3, R4 |
|---|---|---|---|---|
| A464 | 4-CF3 | 1 | SPh | H, C6H4-4-F |
| A465 | 4-CF3 | 1 | NH2 | H, H |
| A466 | 4-CF3 | 1 | NH2 | H, C6H4-4-F |
| A467 | 4-CF3 | 1 | NHMe | H, H |
| A468 | 4-CF3 | 1 | NHMe | H, C6H4-4-F |
| A469 | 4-CF3 | 1 | CH2-piperazino-Ph | H, H |

TABLE 11

| Part A No. | R20 | n | R2 | R3, R4 |
|---|---|---|---|---|
| A470 | 4-CF3 | 1 | CH2-piperazino-Ph | H, C6H4-4-F |
| A471 | 4-CF3 | 1 | CH2-piperidino | H, H |
| A472 | 4-CF3 | 1 | CH2-piperidino | H, C6H4-4-F |
| A473 | 4-CF3 | 1 | OCH2Ph | H, H |
| A474 | 4-CF3 | 1 | OCH2Ph | H, C6H4-4-F |
| A475 | 4-CF3 | 1 | Ac | H, H |
| A476 | 4-CF3 | 1 | Ac | H, C6H4-4-F |
| A477 | 4-CF3 | 1 | CONH2 | H, H |
| A478 | 4-CF3 | 1 | CONH2 | H, C6H4-4-F |
| A479 | 4-CF3 | 1 | CSNH2 | H, H |
| A480 | 4-CF3 | 1 | CSNH2 | H, C6H4-4-F |
| A481 | 4-CF3 | 1 | OCONH2 | H, H |
| A482 | 4-CF3 | 1 | OCONH2 | H, C6H4-4-F |
| A483 | 4-CF3 | 1 | OCSNH2 | H, H |
| A484 | 4-CF3 | 1 | OCSNH2 | H, C6H4-4-F |
| A485 | 4-CF3 | 1 | OSO2Me | H, H |
| A486 | 4-CF3 | 1 | OSO2Me | H, C6H4-4-F |
| A487 | 4-CF3 | 1 | OSO2Ph | H, H |
| A488 | 4-CF3 | 1 | OSO2Ph | H, C6H4-4-F |
| A489 | 4-CF3 | 1 | I | H, H |
| A490 | 4-CF3 | 1 | I | H, C6H4-4-F |
| A491 | 4-CF3 | 2 | H | H, H |
| A492 | 4-CF3 | 2 | H | Me, Me |
| A493 | 4-CF3 | 2 | H | Et, Et |
| A494 | 4-CF3 | 2 | H | H, Et |
| A495 | 4-CF3 | 2 | H | H, Ph |
| A496 | 4-CF3 | 2 | H | H, C6H4-4-F |
| A497 | 4-CF3 | 2 | Me | H, H |
| A498 | 4-CF3 | 2 | Me | Me, Me |
| A499 | 4-CF3 | 2 | Me | Et, Et |
| A500 | 4-CF3 | 2 | Me | H, Et |
| A501 | 4-CF3 | 2 | Me | H, Ph |
| A502 | 4-CF3 | 2 | Me | H, C6H4-4-F |
| A503 | 4-CF3 | 2 | OMe | H, H |
| A504 | 4-CF3 | 2 | OMe | Me, Me |
| A505 | 4-CF3 | 2 | OMe | Et, Et |
| A506 | 4-CF3 | 2 | OMe | H, Et |
| A507 | 4-CF3 | 2 | OMe | H, Ph |
| A508 | 4-CF3 | 2 | OMe | H, C6H4-4-F |
| A509 | 4-CF3 | 2 | CH2OH | H, H |
| A510 | 4-CF3 | 2 | CH2OH | H, C6H4-4-F |
| A511 | 4-CF3 | 2 | CH2OMe | H, H |
| A512 | 4-CF3 | 2 | CH2OMe | Me, Me |
| A513 | 4-CF3 | 2 | CH2OMe | Et, Et |
| A514 | 4-CF3 | 2 | CH2OMe | H, Et |
| A515 | 4-CF3 | 2 | CH2OMe | H, Ph |
| A516 | 4-CF3 | 2 | CH2OMe | H, C6H4-4-F |
| A517 | 4-CF3 | 2 | CF3 | H, H |

TABLE 12

| Part A No. | R20 | n | R2 | R3, R4 |
|---|---|---|---|---|
| A518 | 4-CF3 | 2 | CF3 | Me, Me |
| A519 | 4-CF3 | 2 | CF3 | Et, Et |
| A520 | 4-CF3 | 2 | CF3 | H, Et |
| A521 | 4-CF3 | 2 | CF3 | H, Ph |
| A522 | 4-CF3 | 2 | CF3 | H, C6H4-4-F |
| A523 | 4-CF3 | 2 | CH2OPh | H, H |
| A524 | 4-CF3 | 2 | CH2OPh | H, C6H4-4-F |
| A525 | 4-CF3 | 2 | CH2OCH2Ph | H, H |

TABLE 12-continued

| Part A No. | R20 | n | R2 | R3, R4 |
|---|---|---|---|---|
| A526 | 4-CF3 | 2 | CH2OCH2Ph | H, C6H4-4-F |
| A527 | 4-CF3 | 2 | CH2-morpholino | H, H |
| A528 | 4-CF3 | 2 | CH2-morpholino | Me, Me |
| A529 | 4-CF3 | 2 | CH2-morpholino | Et, Et |
| A530 | 4-CF3 | 2 | CH2-morpholino | H, Et |
| A531 | 4-CF3 | 2 | CH2-morpholino | H, Ph |
| A532 | 4-CF3 | 2 | CH2-morpholino | H, C6H4-4-F |
| A533 | 4-CF3 | 2 | CH2NHBu | H, H |
| A534 | 4-CF3 | 2 | CH2NHBu | H, C6H4-4-F |
| A535 | 4-CF3 | 2 | C≡CPh | H, H |
| A536 | 4-CF3 | 2 | C≡CPh | H, C6H4-4-F |
| A537 | 4-CF3 | 2 | Ph | H, H |
| A538 | 4-CF3 | 2 | Ph | H, C6H4-4-F |
| A539 | 4-CF3 | 2 | C6H4-4-CF3 | H, H |
| A540 | 4-CF3 | 2 | C6H4-4-CF3 | H, C6H4-4-F |
| A541 | 4-CF3 | 2 | C6H4-3-CF3 | H, H |
| A542 | 4-CF3 | 2 | C6H4-3-CF3 | H, C6H4-4-F |
| A543 | 4-CF3 | 2 | C6H4-4-OH | H, H |
| A544 | 4-CF3 | 2 | C6H4-4-OH | H, C6H4-4-F |
| A545 | 4-CF3 | 2 | CH2Ph | H, H |
| A546 | 4-CF3 | 2 | CH2Ph | H, C6H4-4-F |
| A547 | 4-CF3 | 2 | CH2C6H4-4-CF3 | H, H |
| A548 | 4-CF3 | 2 | CH2C6H4-4-CF3 | Me, Me |
| A549 | 4-CF3 | 2 | CH2C6H4-4-CF3 | Et, Et |
| A550 | 4-CF3 | 2 | CH2C6H4-4-CF3 | H, Et |
| A551 | 4-CF3 | 2 | CH2C6H4-4-CF3 | H, Ph |
| A552 | 4-CF3 | 2 | CH2C6H4-4-CF3 | H, C6H4-4-F |
| A553 | 4-CF3 | 2 | CH2C6H4-4-OCF3 | H, H |
| A554 | 4-CF3 | 2 | CH2C6H4-4-OCF3 | H, C6H4-4-F |
| A555 | 4-CF3 | 2 | CH2C6H4-4-Ph | H, H |
| A556 | 4-CF3 | 2 | CH2C6H4-4-Ph | H, C6H4-4-F |
| A557 | 4-CF3 | 2 | CH2C6H4-2-Cl | H, H |
| A558 | 4-CF3 | 2 | CH2C6H4-2-Cl | H, C6H4-4-F |
| A559 | 4-CF3 | 2 | (CH2)2Ph | H, H |
| A560 | 4-CF3 | 2 | (CH2)2Ph | H, C6H4-4-F |
| A561 | 4-CF3 | 2 | SPh | H, H |
| A562 | 4-CF3 | 2 | SPh | H, C6H4-4-F |
| A563 | 4-CF3 | 2 | NH2 | H, H |
| A564 | 4-CF3 | 2 | NH2 | H, C6H4-4-F |
| A565 | 4-CF3 | 2 | NHMe | H, H |

TABLE 13

| Part A No. | R20 | n | R2 | R3, R4 |
|---|---|---|---|---|
| A566 | 4-CF3 | 2 | NHMe | H, C6H4-4-F |
| A567 | 4-CF3 | 2 | CH2-piperazino-Ph | H, H |
| A568 | 4-CF3 | 2 | CH2-piperazino-Ph | H, C6H4-4-F |
| A569 | 4-CF3 | 2 | CH2-piperidino | H, H |
| A570 | 4-CF3 | 2 | CH2-piperidino | H, C6H4-4-F |
| A571 | 4-CF3 | 2 | OCH2Ph | H, H |
| A572 | 4-CF3 | 2 | OCH2Ph | H, C6H4-4-F |
| A573 | 4-CF3 | 2 | Ac | H, H |
| A574 | 4-CF3 | 2 | Ac | H, C6H4-4-F |
| A575 | 4-CF3 | 2 | CONH2 | H, H |
| A576 | 4-CF3 | 2 | CONH2 | H, C6H4-4-F |
| A577 | 4-CF3 | 2 | CSNH2 | H, H |
| A578 | 4-CF3 | 2 | CSNH2 | H, C6H4-4-F |
| A579 | 4-CF3 | 2 | OCONH2 | H, H |
| A580 | 4-CF3 | 2 | OCONH2 | H, C6H4-4-F |
| A581 | 4-CF3 | 2 | OCSNH2 | H, H |
| A582 | 4-CF3 | 2 | OCSNH2 | H, C6H4-4-F |
| A583 | 4-CF3 | 2 | OSO2Me | H, H |
| A584 | 4-CF3 | 2 | OSO2Me | H, C6H4-4-F |
| A585 | 4-CF3 | 2 | OSO2Ph | H, H |
| A586 | 4-CF3 | 2 | OSO2Ph | H, C6H4-4-F |
| A587 | 4-CF3 | 2 | I | H, H |
| A588 | 4-CF3 | 2 | I | H, C6H4-4-F |
| A589 | H | 0 | H | H, H |
| A590 | 3-F | 0 | H | Me, Me |
| A591 | 2-Me | 0 | H | Et, Et |
| A592 | 3-OMe | 0 | H | H, Et |
| A593 | 4-OH | 0 | H | H, Ph |
| A594 | 4-OMe | 0 | H | H, C6H4-4-F |

TABLE 13-continued

| Part A No. | R20 | n | R2 | R3, R4 |
|---|---|---|---|---|
| A595 | 2-Ac | 0 | Me | H, H |
| A596 | 4-CH=CH2 | 0 | Me | Me, Me |
| A597 | 4-CF3, 3-F | 0 | Me | Et, Et |
| A598 | 4-OCF3 | 0 | Me | H, Et |
| A599 | 4-SMe | 0 | Me | H, Ph |
| A600 | 3,5-difluoro | 0 | Me | H, C6H4-4-F |
| A601 | H | 0 | OMe | H, H |
| A602 | 3-F | 0 | OMe | Me, Me |
| A603 | 2-Me | 0 | OMe | Et, Et |
| A604 | 3-OMe | 0 | OMe | H, Et |
| A605 | 4-OH | 0 | OMe | H, Ph |
| A606 | 4-OMe | 0 | OMe | H, C6H4-4-F |
| A607 | 2-Ac | 0 | CH2OH | H, H |
| A608 | 4-CH=CH2 | 0 | CH2OH | H, C6H4-4-F |
| A609 | 4-CF3, 3-F | 0 | CH2OMe | H, H |
| A610 | 4-OCF3 | 0 | CH2OMe | Me, Me |
| A611 | 4-SMe | 0 | CH2OMe | Et, Et |
| A612 | 3,5-difluoro | 0 | CH2OMe | H, Et |
| A613 | H | 0 | CH2OMe | H, Ph |
| A614 | 3-F | 0 | CH2OMe | H, C6H4-4-F |
| A615 | 2-Me | 0 | CF3 | H, H |
| A616 | 3-OMe | 0 | CF3 | Me, Me |

TABLE 14

| Part A No. | R20 | n | R2 | R3, R4 |
|---|---|---|---|---|
| A617 | 4-OH | 0 | CF3 | Et, Et |
| A618 | 4-OMe | 0 | CF3 | H, Et |
| A619 | 2-Ac | 0 | CF3 | H, Ph |
| A620 | 4-CH=CH2 | 0 | CF3 | H, C6H4-4-F |
| A621 | 4-CF3, 3-F | 0 | CH2OPh | H, H |
| A622 | 4-OCF3 | 0 | CH2OPh | H, C6H4-4-F |
| A623 | 4-SMe | 0 | CH2OCH2Ph | H, H |
| A624 | 3,5-difluoro | 0 | CH2OCH2Ph | H, C6H4-4-F |
| A625 | H | 0 | CH2-morpholino | H, H |
| A626 | 3-F | 0 | CH2-morpholino | Me, Me |
| A627 | 2-Me | 0 | CH2-morpholino | Et, Et |
| A628 | 3-OMe | 0 | CH2-morpholino | H, Et |
| A629 | 4-OH | 0 | CH2-morpholino | H, Ph |
| A630 | 4-OMe | 0 | CH2-morpholino | H, C6H4-4-F |
| A631 | 2-Ac | 0 | CH2NHBu | H, H |
| A632 | 4-CH=CH2 | 0 | CH2NHBu | H, C6H4-4-F |
| A633 | 4-CF3, 3-F | 0 | C≡CPh | H, H |
| A634 | 4-OCF3 | 0 | C≡CPh | H, C6H4-4-F |
| A635 | 4-SMe | 0 | Ph | H, H |
| A636 | 3,5-difluoro | 0 | Ph | H, C6H4-4-F |
| A637 | H | 0 | C6H4-4-CF3 | H, H |
| A638 | 3-F | 0 | C6H4-4-CF3 | H, C6H4-4-F |
| A639 | 2-Me | 0 | C6H4-3-CF3 | H, H |
| A640 | 3-OMe | 0 | C6H4-3-CF3 | H, C6H4-4-F |
| A641 | 4-OH | 0 | C6H4-4-OH | H, H |
| A642 | 4-OMe | 0 | C6H4-4-OH | H, C6H4-4-F |
| A643 | 2-Ac | 0 | CH2Ph | H, H |
| A644 | 4-CH=CH2 | 0 | CH2Ph | H, C6H4-4-F |
| A645 | 4-CF3, 3-F | 0 | CH2C6H4-4-CF3 | H, H |
| A646 | 4-OCF3 | 0 | CH2C6H4-4-CF3 | Me, Me |
| A647 | 4-SMe | 0 | CH2C6H4-4-CF3 | Et, Et |
| A648 | 3,5-difluoro | 0 | CH2C6H4-4-CF3 | H, Et |
| A649 | H | 0 | CH2C6H4-4-CF3 | H, Ph |
| A650 | 3-F | 0 | CH2C6H4-4-CF3 | H, C6H4-4-F |
| A651 | 2-Me | 0 | CH2C6H4-4-OCF3 | H, H |
| A652 | 3-OMe | 0 | CH2C6H4-4-OCF3 | H, C6H4-4-F |
| A653 | 4-OH | 0 | CH2C6H4-4-Ph | H, H |
| A654 | 4-OMe | 0 | CH2C6H4-4-Ph | H, C6H4-4-F |
| A655 | 2-Ac | 0 | CH2C6H4-2-Cl | H, H |
| A656 | 4-CH=CH2 | 0 | CH2C6H4-2-Cl | H, C6H4-4-F |
| A657 | 4-CF3, 3-F | 0 | (CH2)2Ph | H, H |
| A658 | 4-OCF3 | 0 | (CH2)2Ph | H, C6H4-4-F |
| A659 | 4-SMe | 0 | SPh | H, H |
| A660 | 3,5-difluoro | 0 | SPh | H, C6H4-4-F |
| A661 | H | 0 | NH2 | H, H |
| A662 | 3-F | 0 | NH2 | H, C6H4-4-F |
| A663 | 2-Me | 0 | NHMe | H, H |

TABLE 14-continued

| Part A No. | R20 | n | R2 | R3, R4 |
|---|---|---|---|---|
| A664 | 3-OMe | 0 | NHMe | H, C6H4-4-F |
| A665 | 4-OH | 0 | CH2-piperazino-Ph | H, H |
| A666 | 4-OMe | 0 | CH2-piperazino-Ph | H, C6H4-4-F |
| A667 | 2-Ac | 0 | CH2-piperidino | H, H |

TABLE 15

| Part A No. | R20 | n | R2 | R3, R4 |
|---|---|---|---|---|
| A668 | 4-CH=CH2 | 0 | CH2-piperidino | H, C6H4-4-F |
| A669 | 4-CF3, 3-F | 0 | OCH2Ph | H, H |
| A670 | 4-OCF3 | 0 | OCH2Ph | H, C6H4-4-F |
| A671 | 4-SMe | 0 | Ac | H, H |
| A672 | 3,5-difluoro | 0 | Ac | H, C6H4-4-F |
| A673 | H | 0 | CONH2 | H, H |
| A674 | 3-F | 0 | CONH2 | H, C6H4-4-F |
| A675 | 2-Me | 0 | CSNH2 | H, H |
| A676 | 3-OMe | 0 | CSNH2 | H, C6H4-4-F |
| A677 | 4-OH | 0 | OCONH2 | H, H |
| A678 | 4-OMe | 0 | OCONH2 | H, C6H4-4-F |
| A679 | 2-Ac | 0 | OCSNH2 | H, H |
| A680 | 4-CH=CH2 | 0 | OCSNH2 | H, C6H4-4-F |
| A681 | 4-CF3, 3-F | 0 | OSO2Me | H, H |
| A682 | 4-OCF3 | 0 | OSO2Me | H, C6H4-4-F |
| A683 | 4-SMe | 0 | OSO2Ph | H, H |
| A684 | 3,5-difluoro | 0 | OSO2Ph | H, C6H4-4-F |
| A685 | H | 0 | I | H, H |
| A686 | 3-F | 0 | I | H, C6H4-4-F |
| A687 | H | 1 | H | H, H |
| A688 | 3-F | 1 | H | Me, Me |
| A689 | 2-Me | 1 | H | Et, Et |
| A690 | 3-OMe | 1 | H | H, Et |
| A691 | 4-OH | 1 | H | H, Ph |
| A692 | 4-OMe | 1 | H | H, C6H4-4-F |
| A693 | 2-Ac | 1 | Me | H, H |
| A694 | 4-CH=CH2 | 1 | Me | Me, Me |
| A695 | 4-CF3, 3-F | 1 | Me | Et, Et |
| A696 | 4-OCF3 | 1 | Me | H, Et |
| A697 | 4-SMe | 1 | Me | H, Ph |
| A698 | 3,5-difluoro | 1 | Me | H, C6H4-4-F |
| A699 | H | 1 | OMe | H, H |
| A700 | 3-F | 1 | OMe | Me, Me |
| A701 | 2-Me | 1 | OMe | Et, Et |
| A702 | 3-OMe | 1 | OMe | H, Et |
| A703 | 4-OH | 1 | OMe | H, Ph |
| A704 | 4-OMe | 1 | OMe | H, C6H4-4-F |
| A705 | 2-Ac | 1 | CH2OH | H, H |
| A706 | 4-CH=CH2 | 1 | CH2OH | H, C6H4-4-F |
| A707 | 4-CF3, 3-F | 1 | CH2OMe | H, H |
| A708 | 4-OCF3 | 1 | CH2OMe | Me, Me |
| A709 | 4-SMe | 1 | CH2OMe | Et, Et |
| A710 | 3,5-difluoro | 1 | CH2OMe | H, Et |
| A711 | H | 1 | CH2OMe | H, Ph |
| A712 | 3-F | 1 | CH2OMe | H, C6H4-4-F |
| A713 | 2-Me | 1 | CF3 | H, H |
| A714 | 3-OMe | 1 | CF3 | Me, Me |
| A715 | 4-OH | 1 | CF3 | Et, Et |
| A716 | 4-OMe | 1 | CF3 | H, Et |
| A717 | 2-Ac | 1 | CF3 | H, Ph |
| A718 | 4-CH=CH2 | 1 | CF3 | H, C6H4-4-F |

TABLE 16

| Part A No. | R20 | n | R2 | R3, R4 |
|---|---|---|---|---|
| A719 | 4-CF3, 3-F | 1 | CH2OPh | H, H |
| A720 | 4-OCF3 | 1 | CH2OPh | H, C6H4-4-F |
| A721 | 4-SMe | 1 | CH2OCH2Ph | H, H |
| A722 | 3,5-difluoro | 1 | CH2OCH2Ph | H, C6H4-4-F |
| A723 | H | 1 | CH2-morpholino | H, H |
| A724 | 3-F | 1 | CH2-morpholino | Me, Me |
| A725 | 2-Me | 1 | CH2-morpholino | Et, Et |
| A726 | 3-OMe | 1 | CH2-morpholino | H, Et |
| A727 | 4-OH | 1 | CH2-morpholino | H, Ph |
| A728 | 4-OMe | 1 | CH2-morpholino | H, C6H4-4-F |
| A729 | 2-Ac | 1 | CH2NHBu | H, H |
| A730 | 4-CH=CH2 | 1 | CH2NHBu | H, C6H4-4-F |
| A731 | 4-CF3, 3-F | 1 | C≡CPh | H, H |
| A732 | 4-OCF3 | 1 | C≡CPh | H, C6H4-4-F |
| A733 | 4-SMe | 1 | Ph | H, H |
| A734 | 3,5-difluoro | 1 | Ph | H, C6H4-4-F |
| A735 | H | 2 | C6H4-4-CF3 | H, H |
| A736 | 3-F | 2 | C6H4-4-CF3 | H, C6H4-4-F |
| A737 | 2-Me | 2 | C6H4-3-CF3 | H, H |
| A738 | 3-OMe | 2 | C6H4-3-CF3 | H, C6H4-4-F |
| A739 | 4-OH | 2 | C6H4-4-OH | H, H |
| A740 | 4-OMe | 2 | C6H4-4-OH | H, C6H4-4-F |
| A741 | 2-Ac | 2 | CH2Ph | H, H |
| A742 | 4-CH=CH2 | 2 | CH2Ph | H, C6H4-4-F |
| A743 | 4-CF3, 3-F | 2 | CH2C6H4-4-CF3 | H, H |
| A744 | 4-OCF3 | 2 | CH2C6H4-4-CF3 | Me, Me |
| A745 | 4-SMe | 2 | CH2C6H4-4-CF3 | Et, Et |
| A746 | 3,5-difluoro | 2 | CH2C6H4-4-CF3 | H, Et |
| A747 | H | 2 | CH2C6H4-4-CF3 | H, Ph |
| A748 | 3-F | 2 | CH2C6H4-4-CF3 | H, C6H4-4-F |
| A749 | 2-Me | 2 | CH2C6H4-4-OCF3 | H, H |
| A750 | 3-OMe | 2 | CH2C6H4-4-OCF3 | H, C6H4-4-F |
| A751 | 4-OH | 2 | CH2C6H4-4-Ph | H, H |
| A752 | 4-OMe | 2 | CH2C6H4-4-Ph | H, C6H4-4-F |
| A753 | 2-Ac | 2 | CH2C6H4-2-Cl | H, H |
| A754 | 4-CH=CH2 | 2 | CH2C6H4-2-Cl | H, C6H4-4-F |
| A755 | 4-CF3, 3-F | 2 | (CH2)2Ph | H, H |
| A756 | 4-OCF3 | 2 | (CH2)2Ph | H, C6H4-4-F |
| A757 | 4-SMe | 2 | SPh | H, H |
| A758 | 3,5-difluoro | 2 | SPh | H, C6H4-4-F |
| A759 | H | 2 | NH2 | H, H |
| A760 | 3-F | 2 | NH2 | H, C6H4-4-F |
| A761 | 2-Me | 2 | NHMe | H, H |
| A762 | 3-OMe | 2 | NHMe | H, C6H4-4-F |
| A763 | 4-OH | 2 | CH2-piperazino-Ph | H, H |
| A764 | 4-OMe | 2 | CH2-piperazino-Ph | H, C6H4-4-F |
| A765 | 2-Ac | 2 | CH2-piperidino | H, H |
| A766 | 4-CH=CH2 | 2 | CH2-piperidino | H, C6H4-4-F |
| A767 | 4-CF3, 3-F | 2 | OCH2Ph | H, H |
| A768 | 4-OCF3 | 2 | OCH2Ph | H, C6H4-4-F |
| A769 | 4-SMe | 2 | Ac | H, H |

TABLE 17

| Part A No. | R20 | n | R2 | R3, R4 |
|---|---|---|---|---|
| A770 | 3,5-difluoro | 2 | Ac | H, C6H4-4-F |
| A771 | H | 2 | CONH2 | H, H |
| A772 | 3-F | 2 | CONH2 | H, C6H4-4-F |
| A773 | 2-Me | 2 | CSNH2 | H, H |
| A774 | 3-OMe | 2 | CSNH2 | H, C6H4-4-F |
| A775 | 4-OH | 2 | OCONH2 | H, H |
| A776 | 4-OMe | 2 | OCONH2 | H, C6H4-4-F |
| A777 | 2-Ac | 2 | OCSNH2 | H, H |
| A778 | 4-CH=CH2 | 2 | OCSNH2 | H, C6H4-4-F |
| A779 | 4-CF3, 3-F | 2 | OSO2Me | H, H |
| A780 | 4-OCF3 | 2 | OSO2Me | H, C6H4-4-F |
| A781 | 4-SMe | 2 | OSO2Ph | H, H |
| A782 | 3,5-difluoro | 2 | OSO2Ph | H, C6H4-4-F |
| A783 | H | 2 | I | H, H |
| A784 | 3-F | 2 | I | H, C6H4-4-F |
| A785 | 4-CF3 | 0 | CH=NOH | H, H |
| A786 | 4-CF3 | 0 | CH=NOMe | H, H |
| A787 | 4-CF3 | 0 | CH=NOEt | H, H |
| A788 | 4-CF3 | 0 | CH=NOnPr | H, H |
| A789 | 4-CF3 | 0 | CH=NOiPr | H, H |
| A790 | 4-CF3 | 0 | CH=NOcPy | H, H |
| A791 | 4-CF3 | 0 | CH=NOnBu | H, H |
| A792 | 4-CF3 | 0 | CH=NOcBu | H, H |

TABLE 17-continued

| Part A No. | R20 | n | R2 | R3, R4 |
|---|---|---|---|---|
| A793 | 4-CF3 | 0 | CH=NOnPen | H, H |
| A794 | 4-CF3 | 0 | CH=NOcPen | H, H |
| A795 | 4-CF3 | 0 | CH=NOcHex | H, H |
| A796 | 4-CF3 | 0 | CH=NOcHex | H, H |
| A797 | 4-CF3 | 0 | CH=NOCH2iPr | H, H |
| A798 | 4-CF3 | 0 | CH=NOCH2cPr | H, H |
| A799 | 4-CF3 | 0 | CH=NOCH2cBu | H, H |
| A800 | 4-CF3 | 0 | CH=NOCH2cPen | H, H |
| A801 | 4-CF3 | 0 | CH=NOCH2cHex | H, H |
| A802 | 4-CF3 | 0 | CH=NO(CH2)2iPr | H, H |
| A803 | 4-CF3 | 0 | CH=NO(CH2)2cPr | H, H |
| A804 | 4-CF3 | 0 | CH=NO(CH2)2cBu | H, H |
| A805 | 4-CF3 | 0 | CH=NO(CH2)2cPen | H, H |
| A806 | 4-CF3 | 0 | CH=NO(CH2)2cHex | H, H |
| A807 | 4-CF3 | 0 | CH=NO(CH2)3iPr | H, H |
| A808 | 4-CF3 | 0 | CH=NO(CH2)3cPr | H, H |
| A809 | 4-CF3 | 0 | CH=NO(CH2)3cBu | H, H |
| A810 | 4-CF3 | 0 | CH=NO(CH2)3cPen | H, H |
| A811 | 4-CF3 | 0 | CH=NO(CH2)3cHex | H, H |
| A812 | 4-CF3 | 0 | —HC=NO-(tetrahydrofuran-3-yl) | H, H |
| A813 | 4-CF3 | 0 | —HC=NO-(tetrahydrothiophen-3-yl) | H, H |
| A814 | 4-CF3 | 0 | —HC=NO-(tetrahydrothiophen-3-yl, SO2) | H, H |

TABLE 18

| Part A No. | R20 | n | R2 | R3, R4 |
|---|---|---|---|---|
| A815 | 4-CF3 | 0 | —HC=NO-(pyrrolidin-3-yl, NH) | H, H |
| A816 | 4-CF3 | 0 | —HC=NO-(pyrrolidin-3-yl, NMe) | H, H |
| A817 | 4-CF3 | 0 | —HC=NO-(pyrrolidin-3-yl, NEt) | H, H |
| A818 | 4-CF3 | 0 | —HC=NO-(pyrrolidin-3-yl, NnPr) | H, H |
| A819 | 4-CF3 | 0 | —HC=NO-(tetrahydropyran-4-yl) | H, H |
| A820 | 4-CF3 | 0 | —HC=NO-(tetrahydrothiopyran-4-yl) | H, H |
| A821 | 4-CF3 | 0 | —HC=NO-(tetrahydrothiopyran-4-yl, SO2) | H, H |
| A822 | 4-CF3 | 0 | —HC=NO-(piperidin-4-yl, NH) | H, H |
| A823 | 4-CF3 | 0 | —HC=NO-(piperidin-4-yl, NMe) | H, H |
| A824 | 4-CF3 | 0 | —HC=NO-(piperidin-4-yl, NEt) | H, H |
| A825 | 4-CF3 | 0 | —HC=NO-(piperidin-4-yl, NnPr) | H, H |
| A826 | 4-CF3 | 0 | —HC=NOCH2-(tetrahydrofuran-3-yl) | H, H |
| A827 | 4-CF3 | 0 | —HC=NOCH2-(tetrahydrothiophen-3-yl) | H, H |
| A828 | 4-CF3 | 0 | —HC=NOCH2-(tetrahydrothiophen-3-yl, SO2) | H, H |
| A829 | 4-CF3 | 0 | —HC=NOCH2-(pyrrolidin-3-yl, NH) | H, H |
| A830 | 4-CF3 | 0 | —HC=NOCH2-(pyrrolidin-3-yl, NMe) | H, H |
| A831 | 4-CF3 | 0 | —HC=NOCH2-(pyrrolidin-3-yl, NnPr) | H, H |
| A832 | 4-CF3 | 0 | —HC=NOCH2-(pyrrolidin-3-yl, NEt) | H, H |
| A833 | 4-CF3 | 0 | —HC=NOCH2-(tetrahydropyran-4-yl) | H, H |
| A834 | 4-CF3 | 0 | —HC=NOCH2-(tetrahydrothiopyran-4-yl) | H, H |
| A835 | 4-CF3 | 0 | —HC=NOCH2-(tetrahydrothiopyran-4-yl, SO2) | H, H |

TABLE 18-continued

| Part A No. | R20 | n | R2 | R3, R4 |
|---|---|---|---|---|
| A836 | 4-CF3 | 0 | 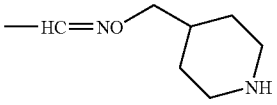 —HC=NO-CH2-(piperidine-NH) | H, H |
| A837 | 4-CF3 | 0 | 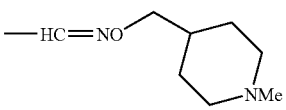 —HC=NO-CH2-(piperidine-NMe) | H, H |
| A838 | 4-CF3 | 0 | 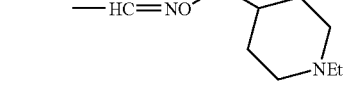 —HC=NO-CH2-(piperidine-NEt) | H, H |
| A839 | 4-CF3 | 0 | 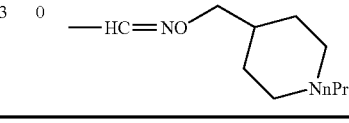 —HC=NO-CH2-(piperidine-NnPr) | H, H |

TABLE 19

| Part A No. | R20 | n | R2 | R3, R4 |
|---|---|---|---|---|
| A840 | 4-CF3 | 0 | 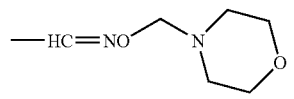 —HC=NO-CH2-(morpholine) | H, H |
| A841 | 4-CF3 | 0 | 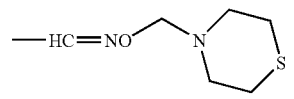 —HC=NO-CH2-(thiomorpholine) | H, H |
| A842 | 4-CF3 | 0 | 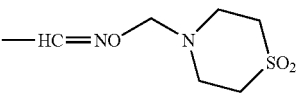 —HC=NO-CH2-(thiomorpholine-SO2) | H, H |
| A843 | 4-CF3 | 0 | 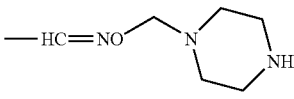 —HC=NO-CH2-(piperazine-NH) | H, H |
| A844 | 4-CF3 | 0 | 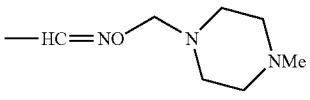 —HC=NO-CH2-(piperazine-NMe) | H, H |
| A845 | 4-CF3 | 0 | 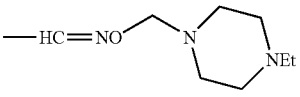 —HC=NO-CH2-(piperazine-NEt) | H, H |
| A846 | 4-CF3 | 0 | 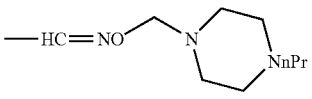 —HC=NO-CH2-(piperazine-NnPr) | H, H |
| A847 | 4-CF3 | 0 | 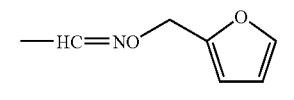 —HC=NO-CH2-(furan-2-yl) | H, H |
| A848 | 4-CF3 | 0 |  —HC=NO-CH2-(furan-3-yl) | H, H |
| A849 | 4-CF3 | 0 | 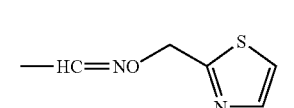 —HC=NO-CH2-(thiazol-2-yl) | H, H |

TABLE 19-continued

| Part A No. | R20 | n | R2 | R3, R4 |
|---|---|---|---|---|
| A850 | 4-CF3 | 0 | —HC=NO—CH2-(2-thienyl) | H, H |
| A851 | 4-CF3 | 0 | —HC=NO—CH2-(3-thienyl) | H, H |
| A852 | 4-CF3 | 0 | —HC=NO—CH2-(3-pyridyl) | H, H |
| A853 | 4-CF3 | 0 | —HC=NO—CH2-(4-pyridyl) | H, H |
| A854 | 4-CF3 | 0 | —HC=NO—CH2CH2—NHSO2Me | H, H |
| A855 | 4-CF3 | 0 | —HC=NO—CH2CH2—NHSO2Et | H, H |
| A856 | 4-CF3 | 0 | —HC=NO—CH2CH2—NHSO2nPr | H, H |
| A857 | 4-CF3 | 0 | —HC=NO—CH2CH2—NHSO2Ph | H, H |
| A858 | 4-CF3 | 0 | —HC=NO—(CH2)3—NHSO2Me | H, H |
| A859 | 4-CF3 | 0 | —HC=NO—(CH2)3—NHSO2Et | H, H |
| A860 | 4-CF3 | 0 | —HC=NO—(CH2)3—NHSO2nPr | H, H |
| A861 | 4-CF3 | 0 | —HC=NO—(CH2)3—NHSO2Ph | H, H |
| A862 | 4-CF3 | 0 | CH2OcPr | H, H |
| A863 | 4-CF3 | 0 | CH2OcBu | H, H |
| A864 | 4-CF3 | 0 | CH2OcPen | H, H |
| A865 | 4-CF3 | 0 | CH2OcHex | H, H |
| A866 | 4-CF3 | 0 | CH2OCH2cPr | H, H |
| A867 | 4-CF3 | 0 | CH2OCH2cBu | H, H |
| A868 | 4-CF3 | 0 | CH2OCH2cPen | H, H |
| A869 | 4-CF3 | 0 | CH2OCH2cHex | H, H |
| A870 | 4-CF3 | 0 | CH2O(CH2)2cPr | H, H |
| A871 | 4-CF3 | 0 | CH2O(CH2)2cBu | H, H |

TABLE 20

| Part A No. | R20 | n | R2 | R3, R4 |
|---|---|---|---|---|
| A872 | 4-CF3 | 0 | CH2O(CH2)2cPen | H, H |
| A873 | 4-CF3 | 0 | CH2O(CH2)2cHex | H, H |
| A874 | 4-CF3 | 0 | CH2O(CH2)3cPr | H, H |
| A875 | 4-CF3 | 0 | CH2O(CH2)3cBu | H, H |
| A876 | 4-CF3 | 0 | CH2O(CH2)3cPen | H, H |
| A877 | 4-CF3 | 0 | CH2O(CH2)3cHex | H, H |
| A878 | 4-CF3 | 0 | CH2O-(tetrahydrofuran-3-yl) | H, H |
| A879 | 4-CF3 | 0 | CH2O-(tetrahydrothiophen-3-yl) | H, H |

TABLE 20-continued
| Part A No. | R20 | n | R2 | R3, R4 |
|---|---|---|---|---|
| A880 | 4-CF3 | 0 | 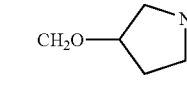 | H, H |
| A881 | 4-CF3 | 0 | | H, H |
| A882 | 4-CF3 | 0 | | H, H |
| A883 | 4-CF3 | 0 | | H, H |
| A884 | 4-CF3 | 0 | | H, H |
| A885 | 4-CF3 | 0 | | H, H |
| A886 | 4-CF3 | 0 | | H, H |
| A887 | 4-CF3 | 0 | | H, H |
| A888 | 4-CF3 | 0 | | H, H |
| A889 | 4-CF3 | 0 | | H, H |
| A890 | 4-CF3 | 0 | | H, H |
| A891 | 4-CF3 | 0 | | H, H |
| A892 | 4-CF3 | 0 | | H, H |
| A893 | 4-CF3 | 0 | | H, H |
| A894 | 4-CF3 | 0 | | H, H |
| A895 | 4-CF3 | 0 | | H, H |
TABLE 20-continued
| Part A No. | R20 | n | R2 | R3, R4 |
|---|---|---|---|---|
| A896 | 4-CF3 | 0 | 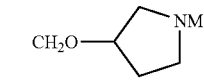 | H, H |
| A897 | 4-CF3 | 0 | | H, H |
| A898 | 4-CF3 | 0 | | H, H |
| A899 | 4-CF3 | 0 | | H, H |
| A900 | 4-CF3 | 0 | | H, H |
TABLE 21
| Part A No. | R20 | n | R2 | R3, R4 |
|---|---|---|---|---|
| A901 | 4-CF3 | 0 |  | H, H |
| A902 | 4-CF3 | 0 | | H, H |
| A903 | 4-CF3 | 0 | | H, H |
| A904 | 4-CF3 | 0 | | H, H |
| A905 | 4-CF3 | 0 | | H, H |
| A906 | 4-CF3 | 0 | | H, H |
| A907 | 4-CF3 | 0 | | H, H |

TABLE 21-continued

| Part A No. | R20 | n | R2 | R3, R4 |
|---|---|---|---|---|
| A908 | 4-CF3 | 0 | CH2O-CH2-(thiomorpholine-1,1-dioxide) | H, H |
| A909 | 4-CF3 | 0 | CH2O-CH2-(piperazine-NH) | H, H |
| A910 | 4-CF3 | 0 | CH2O-CH2-(piperazine-NMe) | H, H |
| A911 | 4-CF3 | 0 | CH2O-CH2-(piperazine-NEt) | H, H |
| A912 | 4-CF3 | 0 | CH2O-CH2-(piperazine-NnPr) | H, H |
| A913 | 4-CF3 | 0 | CH2O-CH2-(2-furyl) | H, H |
| A914 | 4-CF3 | 0 | CH2O-CH2CH2-(2-furyl) | H, H |
| A915 | 4-CF3 | 0 | CH2O-CH2-(2-thiazolyl) | H, H |
| A916 | 4-CF3 | 0 | CH2O-CH2-(2-thienyl) | H, H |
| A917 | 4-CF3 | 0 | CH2O-CH2-(3-thienyl) | H, H |
| A918 | 4-CF3 | 0 | CH2O-CH2-(3-pyridyl) | H, H |
| A919 | 4-CF3 | 0 | CH2O-CH2-(4-pyridyl) | H, H |
| A920 | 4-CF3 | 0 | CH2O-CH2CH2-NHSO2Me | H, H |
| A921 | 4-CF3 | 0 | CH2O-CH2CH2-NHSO2Et | H, H |
| A922 | 4-CF3 | 0 | CH2O-CH2CH2-NHSO2nPr | H, H |
| A923 | 4-CF3 | 0 | CH2O-CH2CH2-NHSO2Ph | H, H |
| A924 | 4-CF3 | 0 | CH2O-CH2CH2CH2-NHSO2Me | H, H |
| A925 | 4-CF3 | 0 | CH2O-CH2CH2CH2-NHSO2Et | H, H |
| A926 | 4-CF3 | 0 | CH2O-CH2CH2CH2-NHSO2nPr | H, H |
| A927 | 4-CF3 | 0 | CH2O-CH2CH2CH2-NHSO2Ph | H, H |
| A928 | 4-CF3 | 0 | CH2ON=CHCH3 | H, H |

TABLE 22

| Part A No. | R20 | n | R2 | R3, R4 |
|---|---|---|---|---|
| A929 | 4-CF3 | 0 | CH2ON=CH(CH3)2 | H, H |
| A930 | 4-CF3 | 0 | CH2O-N=cyclopentylidene | H, H |
| A931 | 4-CF3 | 0 | CH2O-N=cyclohexylidene | H, H |
| A932 | 4-Cl | 0 | CH=NOH | H, H |
| A933 | 4-Cl | 0 | CH=NOMe | H, H |
| A934 | 4-Cl | 0 | CH=NOEt | H, H |
| A935 | 4-Cl | 0 | CH=NOnPr | H, H |
| A936 | 4-Cl | 0 | CH=NOiPr | H, H |
| A937 | 4-Cl | 0 | CH=NocPr | H, H |
| A938 | 4-Cl | 0 | CH=NonBu | H, H |
| A939 | 4-Cl | 0 | CH=NOCH2CH(CH3)2 | H, H |
| A940 | 4-Cl | 0 | CH=NocBu | H, H |
| A941 | 4-Cl | 0 | CH=NonPen | H, H |
| A942 | 4-Cl | 0 | CH=NocPen | H, H |
| A943 | 4-Cl | 0 | CH=NonHex | H, H |
| A944 | 4-Cl | 0 | CH=NocHex | H, H |
| A945 | 4-Cl | 0 | CH=NOH | H, H |
| A946 | 4-Cl | 0 | CH=NOCH2iPr | H, H |
| A947 | 4-Cl | 0 | CH=NOCH2cPr | H, H |
| A948 | 4-Cl | 0 | CH=NOCH2cBu | H, H |
| A949 | 4-Cl | 0 | CH=NOCH2cPen | H, H |
| A950 | 4-Cl | 0 | CH=NOCH2cHex | H, H |
| A951 | 4-Cl | 0 | CH=NO(CH2)2iPr | H, H |
| A952 | 4-Cl | 0 | CH=NO(CH2)2cPr | H, H |
| A953 | 4-Cl | 0 | CH=NO(CH2)2cBu | H, H |
| A954 | 4-Cl | 0 | CH=NO(CH2)2cPen | H, H |
| A955 | 4-Cl | 0 | CH=NO(CH2)2cHex | H, H |
| A956 | 4-Cl | 0 | CH=NO(CH2)3iPr | H, H |
| A957 | 4-Cl | 0 | CH=NO(CH2)3cPr | H, H |
| A958 | 4-Cl | 0 | CH=NO(CH2)3cBu | H, H |
| A959 | 4-Cl | 0 | CH=NO(CH2)3cPen | H, H |
| A960 | 4-Cl | 0 | CH=NO(CH2)3cHex | H, H |
| A961 | 4-Cl | 0 | —HC=NO-(tetrahydrofuran-3-yl) | H, H |
| A962 | 4-Cl | 0 | —HC=NO-(tetrahydrothiophen-3-yl) | H, H |

TABLE 22-continued

| Part A No. | R20 | n | R2 | R3, R4 |
|---|---|---|---|---|
| A963 | 4-Cl | 0 | —HC=NO-(tetrahydrothiophene-SO₂)- | H, H |
| A964 | 4-Cl | 0 | —HC=NO-(pyrrolidine-NH)- | H, H |
| A965 | 4-Cl | 0 | —HC=NO-(pyrrolidine-NMe)- | H, H |
| A966 | 4-Cl | 0 | —HC=NO-(pyrrolidine-NEt)- | H, H |

TABLE 23

| Part A No. | R20 | n | R2 | R3, R4 |
|---|---|---|---|---|
| A967 | 4-Cl | 0 | —HC=NO-(pyrrolidine-NnPr)- | H, H |
| A968 | 4-Cl | 0 | —HC=NO-(tetrahydropyran)- | H, H |
| A969 | 4-Cl | 0 | —HC=NO-(tetrahydrothiopyran)- | H, H |
| A970 | 4-Cl | 0 | —HC=NO-(tetrahydrothiopyran-SO₂)- | H, H |
| A971 | 4-Cl | 0 | —HC=NO-(piperidine-NH)- | H, H |
| A972 | 4-Cl | 0 | —HC=NO-(piperidine-NMe)- | H, H |
| A973 | 4-Cl | 0 | —HC=NO-(piperidine-NEt)- | H, H |
| A974 | 4-Cl | 0 | —HC=NO-(piperidine-NnPr)- | H, H |
| A975 | 4-Cl | 0 | —HC=NO-CH₂-(tetrahydrofuran)- | H, H |
| A976 | 4-Cl | 0 | —HC=NO-CH₂-(tetrahydrothiophene)- | H, H |

TABLE 23-continued

| Part A No. | R20 | n | R2 | R3, R4 |
|---|---|---|---|---|
| A977 | 4-Cl | 0 | —HC=NO-CH₂-(tetrahydrothiophene-SO₂)- | H, H |
| A978 | 4-Cl | 0 | —HC=NO-CH₂-(pyrrolidine-NH)- | H, H |
| A979 | 4-Cl | 0 | —HC=NO-CH₂-(pyrrolidine-NMe)- | H, H |
| A980 | 4-Cl | 0 | —HC=NO-CH₂-(pyrrolidine-NnPr)- | H, H |
| A981 | 4-Cl | 0 | —HC=NO-CH₂-(pyrrolidine-NEt)- | H, H |
| A982 | 4-Cl | 0 | —HC=NO-CH₂-(tetrahydropyran)- | H, H |
| A983 | 4-Cl | 0 | —HC=NO-CH₂-(tetrahydrothiopyran)- | H, H |
| A984 | 4-Cl | 0 | —HC=NO-CH₂-(tetrahydrothiopyran-SO₂)- | H, H |
| A985 | 4-Cl | 0 | —HC=NO-CH₂-(piperidine-NH)- | H, H |
| A986 | 4-Cl | 0 | —HC=NO-CH₂-(piperidine-NMe)- | H, H |
| A987 | 4-Cl | 0 | —HC=NO-CH₂-(piperidine-NEt)- | H, H |
| A988 | 4-Cl | 0 | —HC=NO-CH₂-(piperidine-NnPr)- | H, H |
| A989 | 4-Cl | 0 | —HC=NO-CH₂-(morpholine)- | H, H |

TABLE 23-continued

| Part A No. | R20 | n | R2 | R3, R4 |
|---|---|---|---|---|
| A990 | 4-Cl | 0 | —HC=NO-CH2-(thiomorpholine) | H, H |

TABLE 24

| Part A No. | R20 | n | R2 | R3, R4 |
|---|---|---|---|---|
| A991 | 4-Cl | 0 | —HC=NO-CH2-(thiomorpholine-1,1-dioxide) | H, H |
| A992 | 4-Cl | 0 | —HC=NO-CH2-(piperazine-NH) | H, H |
| A993 | 4-Cl | 0 | —HC=NO-CH2-(piperazine-NMe) | H, H |
| A994 | 4-Cl | 0 | —HC=NO-CH2-(piperazine-NEt) | H, H |
| A995 | 4-Cl | 0 | —HC=NO-CH2-(piperazine-NnPr) | H, H |
| A996 | 4-Cl | 0 | —HC=NO-CH2-(2-furyl) | H, H |
| A997 | 4-Cl | 0 | —HC=NO-CH2-(3-furyl) | H, H |
| A998 | 4-Cl | 0 | —HC=NO-CH2-(2-thiazolyl) | H, H |
| A999 | 4-Cl | 0 | —HC=NO-CH2-(2-thienyl) | H, H |
| A1000 | 4-Cl | 0 | —HC=NO-CH2-(3-thienyl) | H, H |
| A1001 | 4-Cl | 0 | —HC=NO-CH2-(3-pyridyl) | H, H |
| A1002 | 4-Cl | 0 | —HC=NO-CH2-(4-pyridyl) | H, H |
| A1003 | 4-Cl | 0 | —HC=NO-CH2CH2-NHSO2Me | H, H |
| A1004 | 4-Cl | 0 | —HC=NO-CH2CH2-NHSO2Et | H, H |
| A1005 | 4-Cl | 0 | —HC=NO-CH2CH2-NHSO2nPr | H, H |
| A1006 | 4-Cl | 0 | —HC=NO-CH2CH2-NHSO2Ph | H, H |
| A1007 | 4-Cl | 0 | —HC=NO-(CH2)3-NHSO2Me | H, H |
| A1008 | 4-Cl | 0 | —HC=NO-(CH2)3-NHSO2Et | H, H |
| A1009 | 4-Cl | 0 | —HC=NO-(CH2)3-NHSO2nPr | H, H |
| A1010 | 4-Cl | 0 | —HC=NO-(CH2)3-NHSO2Ph | H, H |
| A1011 | 4-Cl | 0 | CH2OcPr | H, H |
| A1012 | 4-Cl | 0 | CH2OcBu | H, H |
| A1013 | 4-Cl | 0 | CH2OcPen | H, H |
| A1014 | 4-Cl | 0 | CH2OcHex | H, H |
| A1015 | 4-Cl | 0 | CH2OCH2cPr | H, H |
| A1016 | 4-Cl | 0 | CH2OCH2cBu | H, H |
| A1017 | 4-Cl | 0 | CH2OCH2cPen | H, H |
| A1018 | 4-Cl | 0 | CH2OCH2cHex | H, H |
| A1019 | 4-Cl | 0 | CH2O(CH2)2cPr | H, H |
| A1020 | 4-Cl | 0 | CH2O(CH2)2cBu | H, H |
| A1021 | 4-Cl | 0 | CH2O(CH2)2cPen | H, H |
| A1022 | 4-Cl | 0 | CH2O(CH2)2cHex | H, H |

TABLE 25

| Part A No. | R20 | n | R2 | R3, R4 |
|---|---|---|---|---|
| A1023 | 4-Cl | 0 | CH2O(CH2)3cPr | H, H |
| A1024 | 4-Cl | 0 | CH2O(CH2)3cBu | H, H |
| A1025 | 4-Cl | 0 | CH2O(CH2)3cPen | H, H |
| A1026 | 4-Cl | 0 | CH2O(CH2)3cHex | H, H |
| A1027 | 4-Cl | 0 | CH2O-(tetrahydrofuran-3-yl) | H, H |
| A1028 | 4-Cl | 0 | CH2O-(tetrahydrothiophen-3-yl) | H, H |
| A1029 | 4-Cl | 0 | CH2O-(tetrahydrothiophene-1,1-dioxide-3-yl) | H, H |
| A1030 | 4-Cl | 0 | CH2O-(pyrrolidin-3-yl, NH) | H, H |

TABLE 25-continued

| Part A No. | R20 | n | R2 | R3, R4 |
|---|---|---|---|---|
| A1031 | 4-Cl | 0 | CH2O-pyrrolidine-NMe | H, H |
| A1032 | 4-Cl | 0 | CH2O-pyrrolidine-NEt | H, H |
| A1033 | 4-Cl | 0 | CH2O-pyrrolidine-NnPr | H, H |
| A1034 | 4-Cl | 0 | CH2O-tetrahydropyran (O) | H, H |
| A1035 | 4-Cl | 0 | CH2O-tetrahydrothiopyran (S) | H, H |
| A1036 | 4-Cl | 0 | CH2O-thiopyran-SO2 | H, H |
| A1037 | 4-Cl | 0 | CH2O-piperidine-NH | H, H |
| A1038 | 4-Cl | 0 | CH2O-piperidine-NMe | H, H |
| A1039 | 4-Cl | 0 | CH2O-piperidine-NEt | H, H |
| A1040 | 4-Cl | 0 | CH2O-piperidine-NnPr | H, H |
| A1041 | 4-Cl | 0 | CH2O-CH2-tetrahydrofuran (O) | H, H |
| A1042 | 4-Cl | 0 | CH2O-CH2-tetrahydrothiophene (S) | H, H |
| A1043 | 4-Cl | 0 | CH2O-CH2-thiolane-SO2 | H, H |
| A1044 | 4-Cl | 0 | CH2O-CH2-pyrrolidine-NH | H, H |
| A1045 | 4-Cl | 0 | CH2O-CH2-pyrrolidine-NMe | H, H |
| A1046 | 4-Cl | 0 | CH2O-CH2-pyrrolidine-NnPr | H, H |
| A1047 | 4-Cl | 0 | CH2O-CH2-pyrrolidine-NEt | H, H |
| A1048 | 4-Cl | 0 | CH2O-CH2-tetrahydropyran (O) | H, H |
| A1049 | 4-Cl | 0 | CH2O-CH2-tetrahydrothiopyran (S) | H, H |

TABLE 26

| Part A No. | R20 | n | R2 | R3, R4 |
|---|---|---|---|---|
| A1050 | 4-Cl | 0 | CH2O-CH2-thiopyran-SO2 | H, H |
| A1051 | 4-Cl | 0 | CH2O-CH2-piperidine-NH | H, H |
| A1052 | 4-Cl | 0 | CH2O-CH2-piperidine-NMe | H, H |
| A1053 | 4-Cl | 0 | CH2O-CH2-piperidine-NEt | H, H |
| A1054 | 4-Cl | 0 | CH2O-CH2-piperidine-NnPr | H, H |
| A1055 | 4-Cl | 0 | CH2O-CH2-morpholine (N,O) | H, H |
| A1056 | 4-Cl | 0 | CH2O-CH2-thiomorpholine (N,S) | H, H |
| A1057 | 4-Cl | 0 | CH2O-CH2-thiomorpholine-SO2 | H, H |

TABLE 26-continued

| Part A No. | R20 | n | R2 | R3, R4 |
|---|---|---|---|---|
| A1058 | 4-Cl | 0 | CH₂O-piperazine-NH | H, H |
| A1059 | 4-Cl | 0 | CH₂O-piperazine-NMe | H, H |
| A1060 | 4-Cl | 0 | CH₂O-piperazine-NEt | H, H |
| A1061 | 4-Cl | 0 | CH₂O-piperazine-NnPr | H, H |
| A1062 | 4-Cl | 0 | CH₂O-CH₂-(2-furyl) | H, H |
| A1063 | 4-Cl | 0 | CH₂O-CH₂CH₂-(2-furyl) | H, H |
| A1064 | 4-Cl | 0 | CH₂O-CH₂-(2-thiazolyl) | H, H |
| A1065 | 4-Cl | 0 | CH₂O-CH₂-(2-thienyl) | H, H |
| A1066 | 4-Cl | 0 | CH₂O-CH₂-(3-thienyl) | H, H |
| A1067 | 4-Cl | 0 | CH₂O-CH₂-(3-pyridyl) | H, H |
| A1068 | 4-Cl | 0 | CH₂O-CH₂-(4-pyridyl) | H, H |
| A1069 | 4-Cl | 0 | CH₂O-CH₂CH₂-NHSO₂Me | H, H |
| A1070 | 4-Cl | 0 | CH₂O-CH₂CH₂-NHSO₂Et | H, H |
| A1071 | 4-Cl | 0 | CH₂O-CH₂CH₂-NHSO₂nPr | H, H |
| A1072 | 4-Cl | 0 | CH₂O-CH₂CH₂-NHSO₂Ph | H, H |
| A1073 | 4-Cl | 0 | CH₂O-(CH₂)₃-NHSO₂Me | H, H |
| A1074 | 4-Cl | 0 | CH₂O-(CH₂)₃-NHSO₂Et | H, H |
| A1075 | 4-Cl | 0 | CH₂O-(CH₂)₃-NHSO₂nPr | H, H |

TABLE 27

| Part A No. | R20 | n | R2 | R3, R4 |
|---|---|---|---|---|
| A1076 | 4-Cl | 0 | CH₂O-(CH₂)₃-NHSO₂Ph | H, H |
| A1077 | 4-Cl | 0 | CH2ON=CHCH3 | H, H |
| A1078 | 4-Cl | 0 | CH2ON=CH(CH3)2 | H, H |
| A1079 | 4-Cl | 0 | CH₂O—N=cyclopentylidene | H, H |
| A1080 | 4-Cl | 0 | CH₂O—N=cyclohexylidene | H, H |
| A1081 | 4-OCF3 | 0 | CH=NOH | H, H |
| A1082 | 4-OCF3 | 0 | CH=NOMe | H, H |
| A1083 | 4-OCF3 | 0 | CH=NOEt | H, H |
| A1084 | 4-OCF3 | 0 | CH=NOnPr | H, H |
| A1085 | 4-OCF3 | 0 | CH=NOiPr | H, H |
| A1086 | 4-OCF3 | 0 | CH=NOcPr | H, H |
| A1087 | 4-OCF3 | 0 | CH=NOnBu | H, H |
| A1088 | 4-OCF3 | 0 | CH=NOCH2CH(CH3)2 | H, H |
| A1089 | 4-OCF3 | 0 | CH=NOcBu | H, H |
| A1090 | 4-OCF3 | 0 | CH=NOnPen | H, H |
| A1091 | 4-OCF3 | 0 | CH=NOcPen | H, H |
| A1092 | 4-OCF3 | 0 | CH=NOnHex | H, H |
| A1093 | 4-OCF3 | 0 | CH=NOcHex | H, H |
| A1094 | 4-OCF3 | 0 | CH=NOH | H, H |
| A1095 | 4-OCF3 | 0 | CH=NOCH2iPr | H, H |
| A1096 | 4-OCF3 | 0 | CH=NOCH2cPr | H, H |
| A1097 | 4-OCF3 | 0 | CH=NOCH2cBu | H, H |
| A1098 | 4-OCF3 | 0 | CH=NOCH2cPen | H, H |
| A1099 | 4-OCF3 | 0 | CH=NOCH2cHex | H, H |
| A1100 | 4-OCF3 | 0 | CH=NO(CH2)2iPr | H, H |
| A1101 | 4-OCF3 | 0 | CH=NO(CH2)2cPr | H, H |
| A1102 | 4-OCF3 | 0 | CH=NO(CH2)2cBu | H, H |
| A1103 | 4-OCF3 | 0 | CH=NO(CH2)2cPen | H, H |
| A1104 | 4-OCF3 | 0 | CH=NO(CH2)2cHex | H, H |
| A1105 | 4-OCF3 | 0 | CH=NO(CH2)3iPr | H, H |
| A1106 | 4-OCF3 | 0 | CH=NO(CH2)3cPr | H, H |
| A1107 | 4-OCF3 | 0 | CH=NO(CH2)3cBu | H, H |
| A1108 | 4-OCF3 | 0 | CH=NO(CH2)3cPen | H, H |
| A1109 | 4-OCF3 | 0 | CH=NO(CH2)3cHex | H, H |
| A1110 | 4-OCF3 | 0 | —HC=NO-(3-tetrahydrofuryl) | H, H |
| A1111 | 4-OCF3 | 0 | —HC=NO-(3-tetrahydrothienyl) | H, H |
| A1112 | 4-OCF3 | 0 | —HC=NO-(3-tetrahydrothienyl-SO₂) | H, H |

TABLE 27-continued

| Part A No. | R20 | n | R2 | R3, R4 |
|---|---|---|---|---|
| A1113 | 4-OCF3 | 0 | —HC=NO-(3-pyrrolidinyl, NH) | H, H |

TABLE 28

| Part A No. | R20 | n | R2 | R3, R4 |
|---|---|---|---|---|
| A1114 | 4-OCF3 | 0 | —HC=NO-(3-pyrrolidinyl, NMe) | H, H |
| A1115 | 4-OCF3 | 0 | —HC=NO-(3-pyrrolidinyl, NEt) | H, H |
| A1116 | 4-OCF3 | 0 | —HC=NO-(3-pyrrolidinyl, NnPr) | H, H |
| A1117 | 4-OCF3 | 0 | —HC=NO-(tetrahydropyran-4-yl, O) | H, H |
| A1118 | 4-OCF3 | 0 | —HC=NO-(tetrahydrothiopyran-4-yl, S) | H, H |
| A1119 | 4-OCF3 | 0 | —HC=NO-(tetrahydrothiopyran-4-yl, SO2) | H, H |
| A1120 | 4-OCF3 | 0 | —HC=NO-(piperidin-4-yl, NH) | H, H |
| A1121 | 4-OCF3 | 0 | —HC=NO-(piperidin-4-yl, NMe) | H, H |
| A1122 | 4-OCF3 | 0 | —HC=NO-(piperidin-4-yl, NEt) | H, H |
| A1123 | 4-OCF3 | 0 | —HC=NO-(piperidin-4-yl, NnPr) | H, H |
| A1124 | 4-OCF3 | 0 | —HC=NO-CH2-(tetrahydrofuran-3-yl, O) | H, H |
| A1125 | 4-OCF3 | 0 | —HC=NO-CH2-(tetrahydrothiophen-3-yl, S) | H, H |
| A1126 | 4-OCF3 | 0 | —HC=NO-CH2-(tetrahydrothiophen-3-yl, SO2) | H, H |
| A1127 | 4-OCF3 | 0 | —HC=NO-CH2-(pyrrolidin-3-yl, NH) | H, H |
| A1128 | 4-OCF3 | 0 | —HC=NO-CH2-(pyrrolidin-3-yl, NMe) | H, H |
| A1129 | 4-OCF3 | 0 | —HC=NO-CH2-(pyrrolidin-3-yl, NnPr) | H, H |
| A1130 | 4-OCF3 | 0 | —HC=NO-CH2-(pyrrolidin-3-yl, NEt) | H, H |
| A1131 | 4-OCF3 | 0 | —HC=NO-CH2-(tetrahydropyran-4-yl, O) | H, H |
| A1132 | 4-OCF3 | 0 | —HC=NO-CH2-(tetrahydrothiopyran-4-yl, S) | H, H |
| A1133 | 4-OCF3 | 0 | —HC=NO-CH2-(tetrahydrothiopyran-4-yl, SO2) | H, H |
| A1134 | 4-OCF3 | 0 | —HC=NO-CH2-(piperidin-4-yl, NH) | H, H |
| A1135 | 4-OCF3 | 0 | —HC=NO-CH2-(piperidin-4-yl, NMe) | H, H |
| A1136 | 4-OCF3 | 0 | —HC=NO-CH2-(piperidin-4-yl, NEt) | H, H |
| A1137 | 4-OCF3 | 0 | —HC=NO-CH2-(piperidin-4-yl, NnPr) | H, H |

TABLE 29

| Part A No. | R20 | n | R2 | R3, R4 |
|---|---|---|---|---|
| A1138 | 4-OCF3 | 0 | —HC=NOCH2-morpholinyl(N) | H, H |
| A1139 | 4-OCF3 | 0 | —HC=NOCH2-thiomorpholinyl(N) | H, H |
| A1140 | 4-OCF3 | 0 | —HC=NOCH2-thiomorpholinyl(N)-S,S-dioxide | H, H |
| A1141 | 4-OCF3 | 0 | —HC=NOCH2-piperazinyl(N)-NH | H, H |
| A1142 | 4-OCF3 | 0 | —HC=NOCH2-piperazinyl(N)-NMe | H, H |
| A1143 | 4-OCF3 | 0 | —HC=NOCH2-piperazinyl(N)-NEt | H, H |
| A1144 | 4-OCF3 | 0 | —HC=NOCH2-piperazinyl(N)-NnPr | H, H |
| A1145 | 4-OCF3 | 0 | —HC=NOCH2-(2-furyl) | H, H |
| A1146 | 4-OCF3 | 0 | —HC=NOCH2-(3-furyl) | H, H |
| A1147 | 4-OCF3 | 0 | —HC=NOCH2-(2-thiazolyl) | H, H |
| A1148 | 4-OCF3 | 0 | —HC=NOCH2-(2-thienyl) | H, H |
| A1149 | 4-OCF3 | 0 | —HC=NOCH2-(3-thienyl) | H, H |
| A1150 | 4-OCF3 | 0 | —HC=NOCH2-(3-pyridyl) | H, H |
| A1151 | 4-OCF3 | 0 | —HC=NOCH2-(4-pyridyl) | H, H |

TABLE 29-continued

| Part A No. | R20 | n | R2 | R3, R4 |
|---|---|---|---|---|
| A1152 | 4-OCF3 | 0 | —HC=NO–CH2CH2–NHSO2Me | H, H |
| A1153 | 4-OCF3 | 0 | —HC=NO–CH2CH2–NHSO2Et | H, H |
| A1154 | 4-OCF3 | 0 | —HC=NO–CH2CH2–NHSO2nPr | H, H |
| A1155 | 4-OCF3 | 0 | —HC=NO–CH2CH2–NHSO2Ph | H, H |
| A1156 | 4-OCF3 | 0 | —HC=NO–(CH2)3–NHSO2Me | H, H |
| A1157 | 4-OCF3 | 0 | —HC=NO–(CH2)3–NHSO2Et | H, H |
| A1158 | 4-OCF3 | 0 | —HC=NO–(CH2)3–NHSO2nPr | H, H |
| A1159 | 4-OCF3 | 0 | —HC=NO–(CH2)3–NHSO2Ph | H, H |
| A1160 | 4-OCF3 | 0 | CH2OcPr | H, H |
| A1161 | 4-OCF3 | 0 | CH2OcBu | H, H |
| A1162 | 4-OCF3 | 0 | CH2OcPen | H, H |
| A1163 | 4-OCF3 | 0 | CH2OcHex | H, H |
| A1164 | 4-OCF3 | 0 | CH2OCH2cPr | H, H |
| A1165 | 4-OCF3 | 0 | CH2OCH2cBu | H, H |
| A1166 | 4-OCF3 | 0 | CH2OCH2cPen | H, H |
| A1167 | 4-OCF3 | 0 | CH2OCH2cHex | H, H |
| A1168 | 4-OCF3 | 0 | CH2O(CH2)2cPr | H, H |

TABLE 30

| Part A No. | R20 | n | R2 | R3, R4 |
|---|---|---|---|---|
| A1169 | 4-OCF3 | 0 | CH2O(CH2)2cBu | H, H |
| A1170 | 4-OCF3 | 0 | CH2O(CH2)2cPen | H, H |
| A1171 | 4-OCF3 | 0 | CH2O(CH2)2cHex | H, H |
| A1172 | 4-OCF3 | 0 | CH2O(CH2)3cPr | H, H |
| A1173 | 4-OCF3 | 0 | CH2O(CH2)3cBu | H, H |
| A1174 | 4-OCF3 | 0 | CH2O(CH2)3cPen | H, H |
| A1175 | 4-OCF3 | 0 | CH2O(CH2)3cHex | H, H |
| A1176 | 4-OCF3 | 0 | CH2O-tetrahydrofuran-3-yl | H, H |
| A1177 | 4-OCF3 | 0 | CH2O-tetrahydrothiophen-3-yl | H, H |
| A1178 | 4-OCF3 | 0 | CH2O-(tetrahydrothiophen-3-yl-1,1-dioxide) | H, H |
| A1179 | 4-OCF3 | 0 | CH2O-pyrrolidin-3-yl (NH) | H, H |
| A1180 | 4-OCF3 | 0 | CH2O-pyrrolidin-3-yl (NMe) | H, H |
| A1181 | 4-OCF3 | 0 | CH2O-pyrrolidin-3-yl (NEt) | H, H |
| A1182 | 4-OCF3 | 0 | CH2O-pyrrolidin-3-yl (NnPr) | H, H |
| A1183 | 4-OCF3 | 0 | CH2O-tetrahydropyran-4-yl | H, H |
| A1184 | 4-OCF3 | 0 | CH2O-tetrahydrothiopyran-4-yl | H, H |
| A1185 | 4-OCF3 | 0 | CH2O-(tetrahydrothiopyran-4-yl-1,1-dioxide) | H, H |
| A1186 | 4-OCF3 | 0 | CH2O-piperidin-4-yl (NH) | H, H |
| A1187 | 4-OCF3 | 0 | CH2O-piperidin-4-yl (NMe) | H, H |

TABLE 30-continued

| Part A No. | R20 | n | R2 | R3, R4 |
|---|---|---|---|---|
| A1188 | 4-OCF3 | 0 | CH2O-(piperidine-NEt) | H, H |
| A1189 | 4-OCF3 | 0 | CH2O-(piperidine-NnPr) | H, H |
| A1190 | 4-OCF3 | 0 | CH2O-(tetrahydrofuran-3-yl) | H, H |
| A1191 | 4-OCF3 | 0 | CH2O-(tetrahydrothiophen-3-yl) | H, H |
| A1192 | 4-OCF3 | 0 | CH2O-(tetrahydrothiophene-SO2-3-yl) | H, H |
| A1193 | 4-OCF3 | 0 | CH2O-(pyrrolidin-3-yl NH) | H, H |
| A1194 | 4-OCF3 | 0 | CH2O-(pyrrolidin-3-yl NMe) | H, H |
| A1195 | 4-OCF3 | 0 | CH2O-(pyrrolidin-3-yl NnPr) | H, H |
| A1196 | 4-OCF3 | 0 | CH2O-(pyrrolidin-3-yl NEt) | H, H |
| A1197 | 4-OCF3 | 0 | CH2O-CH2-(tetrahydropyran-4-yl) | H, H |

TABLE 31

| Part A No. | R20 | n | R2 | R3, R4 |
|---|---|---|---|---|
| A1198 | 4-OCF3 | 0 | CH2O-CH2-(tetrahydrothiopyran-4-yl) | H, H |
| A1199 | 4-OCF3 | 0 | CH2O-CH2-(tetrahydrothiopyran-SO2-4-yl) | H, H |
| A1200 | 4-OCF3 | 0 | CH2O-CH2-(piperidin-4-yl NH) | H, H |
| A1201 | 4-OCF3 | 0 | CH2O-CH2-(piperidin-4-yl NMe) | H, H |
| A1202 | 4-OCF3 | 0 | CH2O-CH2-(piperidin-4-yl NEt) | H, H |
| A1203 | 4-OCF3 | 0 | CH2O-CH2-(piperidin-4-yl NnPr) | H, H |
| A1204 | 4-OCF3 | 0 | CH2O-CH2-morpholinyl | H, H |
| A1205 | 4-OCF3 | 0 | CH2O-CH2-thiomorpholinyl | H, H |
| A1206 | 4-OCF3 | 0 | CH2O-CH2-thiomorpholinyl-SO2 | H, H |
| A1207 | 4-OCF3 | 0 | CH2O-CH2-piperazinyl NH | H, H |
| A1208 | 4-OCF3 | 0 | CH2O-CH2-piperazinyl NMe | H, H |
| A1209 | 4-OCF3 | 0 | CH2O-CH2-piperazinyl NEt | H, H |
| A1210 | 4-OCF3 | 0 | CH2O-CH2-piperazinyl NnPr | H, H |
| A1211 | 4-OCF3 | 0 | CH2O-CH2-furan-2-yl | H, H |
| A1212 | 4-OCF3 | 0 | CH2O-CH2CH2-furan-2-yl | H, H |
| A1213 | 4-OCF3 | 0 | CH2O-CH2-thiazol-2-yl | H, H |
| A1214 | 4-OCF3 | 0 | CH2O-CH2-thiophen-2-yl | H, H |

TABLE 31-continued

| Part A No. | R20 | n | R2 | R3, R4 |
|---|---|---|---|---|
| A1215 | 4-OCF3 | 0 | 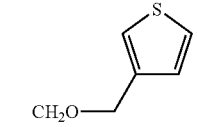 | H, H |
| A1216 | 4-OCF3 | 0 | 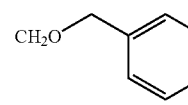 | H, H |
| A1217 | 4-OCF3 | 0 | 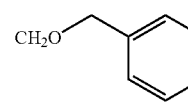 | H, H |
| A1218 | 4-OCF3 | 0 | 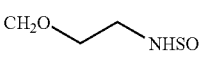 | H, H |
| A1219 | 4-OCF3 | 0 | 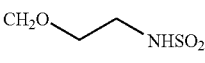 | H, H |
| A1220 | 4-OCF3 | 0 | 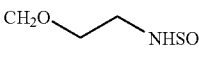 | H, H |
| A1221 | 4-OCF3 | 0 | 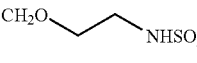 | H, H |
| A1222 | 4-OCF3 | 0 | 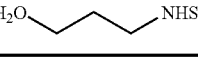 | H, H |

TABLE 32

| Part A No. | R20 | n | R2 | R3, R4 |
|---|---|---|---|---|
| A1223 | 4-OCF3 | 0 | 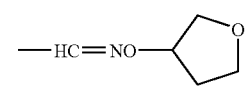 | H, H |
| A1224 | 4-OCF3 | 0 | 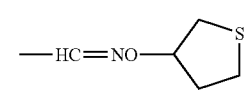 | H, H |
| A1225 | 4-OCF3 | 0 | 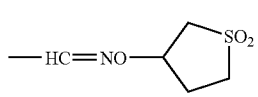 | H, H |
| A1226 | 4-OCF3 | 0 | CH2ON=CHCH3 | H, H |
| A1227 | 4-OCF3 | 0 | CH2ON=CH(CH3)2 | H, H |
| A1228 | 4-OCF3 | 0 | 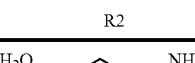 | H, H |
| A1229 | 4-OCF3 | 0 |  | H, H |
| A1230 | 2-Cl, 4-Cl | 0 | CH=NOH | H, H |
| A1231 | 2-Cl, 4-Cl | 0 | CH=NOMe | H, H |
| A1232 | 2-Cl, 4-Cl | 0 | CH=NOEt | H, H |
| A1233 | 2-Cl, 4-Cl | 0 | CH=NOnPr | H, H |
| A1234 | 2-Cl, 4-Cl | 0 | CH=NOiPr | H, H |
| A1235 | 2-Cl, 4-Cl | 0 | CH=NocPr | H, H |
| A1236 | 2-Cl, 4-Cl | 0 | CH=NonBu | H, H |
| A1237 | 2-Cl, 4-Cl | 0 | CH=NOCH2CH(CH3)2 | H, H |
| A1238 | 2-Cl, 4-Cl | 0 | CH=NocBu | H, H |
| A1239 | 2-Cl, 4-Cl | 0 | CH=NonPen | H, H |
| A1240 | 2-Cl, 4-Cl | 0 | CH=NocPen | H, H |

TABLE 32-continued

| Part A No. | R20 | n | R2 | R3, R4 |
|---|---|---|---|---|
| A1241 | 2-Cl, 4-Cl | 0 | CH=NonHex | H, H |
| A1242 | 2-Cl, 4-Cl | 0 | CH=NocHex | H, H |
| A1243 | 2-Cl, 4-Cl | 0 | CH=NOH | H, H |
| A1244 | 2-Cl, 4-Cl | 0 | CH=NOCH2iPr | H, H |
| A1245 | 2-Cl, 4-Cl | 0 | CH=NOCH2cPr | H, H |
| A1246 | 2-Cl, 4-Cl | 0 | CH=NOCH2cBu | H, H |
| A1247 | 2-Cl, 4-Cl | 0 | CH=NOCH2cPen | H, H |
| A1248 | 2-Cl, 4-Cl | 0 | CH=NOCH2cHex | H, H |
| A1249 | 2-Cl, 4-Cl | 0 | CH=NO(CH2)2iPr | H, H |
| A1250 | 2-Cl, 4-Cl | 0 | CH=NO(CH2)2cPr | H, H |
| A1251 | 2-Cl, 4-Cl | 0 | CH=NO(CH2)2cBu | H, H |
| A1252 | 2-Cl, 4-Cl | 0 | CH=NO(CH2)2cPen | H, H |
| A1253 | 2-Cl, 4-Cl | 0 | CH=NO(CH2)2cHex | H, H |
| A1254 | 2-Cl, 4-Cl | 0 | CH=NO(CH2)3iPr | H, H |
| A1255 | 2-Cl, 4-Cl | 0 | CH=NO(CH2)3cPr | H, H |
| A1256 | 2-Cl, 4-Cl | 0 | CH=NO(CH2)3cBu | H, H |
| A1257 | 2-Cl, 4-Cl | 0 | CH=NO(CH2)3cPen | H, H |
| A1258 | 2-Cl, 4-Cl | 0 | CH=NO(CH2)3cHex | H, H |
| A1259 | 2-Cl, 4-Cl | 0 | 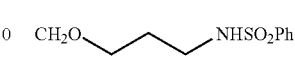 | H, H |
| A1260 | 2-Cl, 4-Cl | 0 | 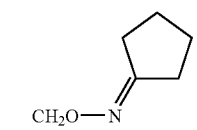 | H, H |
| A1261 | 2-Cl, 4-Cl | 0 | 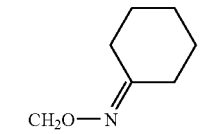 | H, H |

TABLE 33

| Part A No. | R20 | n | R2 | R3, R4 |
|---|---|---|---|---|
| A1262 | 2-Cl, 4-Cl | 0 | 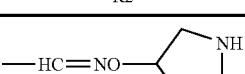 | H, H |
| A1263 | 2-Cl, 4-Cl | 0 | 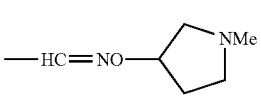 | H, H |
| A1264 | 2-Cl, 4-Cl | 0 | 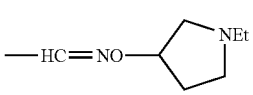 | H, H |
| A1265 | 2-Cl, 4-Cl | 0 | 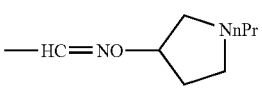 | H, H |
| A1266 | 2-Cl, 4-Cl | 0 | 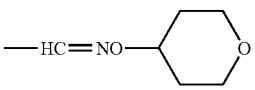 | H, H |
| A1267 | 2-Cl, 4-Cl | 0 | 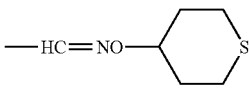 | H, H |
| A1268 | 2-Cl, 4-Cl | 0 | 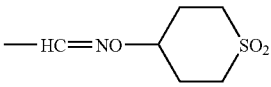 | H, H |

TABLE 33-continued

| Part A No. | R20 | n | R2 | R3, R4 |
|---|---|---|---|---|
| A1269 | 2-Cl, 4-Cl | 0 | —HC=NO-(piperidine-NH) | H, H |
| A1270 | 2-Cl, 4-Cl | 0 | —HC=NO-(piperidine-NMe) | H, H |
| A1271 | 2-Cl, 4-Cl | 0 | —HC=NO-(piperidine-NEt) | H, H |
| A1272 | 2-Cl, 4-Cl | 0 | —HC=NO-(piperidine-NnPr) | H, H |
| A1273 | 2-Cl, 4-Cl | 0 | —HC=NO-CH2-(tetrahydrofuran-O) | H, H |
| A1274 | 2-Cl, 4-Cl | 0 | —HC=NO-CH2-(tetrahydrothiophene-S) | H, H |
| A1275 | 2-Cl, 4-Cl | 0 | —HC=NO-CH2-(tetrahydrothiophene-SO2) | H, H |
| A1276 | 2-Cl, 4-Cl | 0 | —HC=NO-CH2-(pyrrolidine-NH) | H, H |
| A1277 | 2-Cl, 4-Cl | 0 | —HC=NO-CH2-(pyrrolidine-NMe) | H, H |
| A1278 | 2-Cl, 4-Cl | 0 | —HC=NO-CH2-(pyrrolidine-NnPr) | H, H |
| A1279 | 2-Cl, 4-Cl | 0 | —HC=NO-CH2-(pyrrolidine-NEt) | H, H |
| A1280 | 2-Cl, 4-Cl | 0 | —HC=NO-CH2-(tetrahydropyran-O) | H, H |
| A1281 | 2-Cl, 4-Cl | 0 | —HC=NO-CH2-(tetrahydrothiopyran-S) | H, H |
| A1282 | 2-Cl, 4-Cl | 0 | —HC=NO-CH2-(tetrahydrothiopyran-SO2) | H, H |
| A1283 | 2-Cl, 4-Cl | 0 | —HC=NO-CH2-(piperidine-NH) | H, H |
| A1284 | 2-Cl, 4-Cl | 0 | —HC=NO-CH2-(piperidine-NMe) | H, H |
| A1285 | 2-Cl, 4-Cl | 0 | —HC=NO-CH2-(piperidine-NEt) | H, H |
| A1286 | 2-Cl, 4-Cl | 0 | —HC=NO-CH2-(piperidine-NnPr) | H, H |

TABLE 34

| Part A No. | R20 | n | R2 | R3, R4 |
|---|---|---|---|---|
| A1287 | 2-Cl, 4-Cl | 0 | —HC=NO-CH2-(morpholine) | H, H |
| A1288 | 2-Cl, 4-Cl | 0 | —HC=NO-CH2-(thiomorpholine) | H, H |
| A1289 | 2-Cl, 4-Cl | 0 | —HC=NO-CH2-(thiomorpholine-SO2) | H, H |

TABLE 34-continued

| Part A No. | R20 | n | R2 | R3, R4 |
|---|---|---|---|---|
| A1290 | 2-Cl, 4-Cl | 0 | —HC=NO-CH2-piperazine-NH | H, H |
| A1291 | 2-Cl, 4-Cl | 0 | —HC=NO-CH2-piperazine-NMe | H, H |
| A1292 | 2-Cl, 4-Cl | 0 | —HC=NO-CH2-piperazine-NEt | H, H |
| A1293 | 2-Cl, 4-Cl | 0 | —HC=NO-CH2-piperazine-NnPr | H, H |
| A1294 | 2-Cl, 4-Cl | 0 | —HC=NO-CH2-(2-furyl) | H, H |
| A1295 | 2-Cl, 4-Cl | 0 | —HC=NO-CH2-(3-furyl) | H, H |
| A1296 | 2-Cl, 4-Cl | 0 | —HC=NO-CH2-(2-thiazolyl) | H, H |
| A1297 | 2-Cl, 4-Cl | 0 | —HC=NO-CH2-(2-thienyl) | H, H |
| A1298 | 2-Cl, 4-Cl | 0 | —HC=NO-CH2-(3-thienyl) | H, H |
| A1299 | 2-Cl, 4-Cl | 0 | —HC=NO-CH2-(3-pyridyl) | H, H |
| A1300 | 2-Cl, 4-Cl | 0 | —HC=NO-CH2-(4-pyridyl) | H, H |
| A1301 | 2-Cl, 4-Cl | 0 | —HC=NO-CH2CH2-NHSO$_2$Me | H, H |
| A1302 | 2-Cl, 4-Cl | 0 | —HC=NO-CH2CH2-NHSO$_2$Et | H, H |
| A1303 | 2-Cl, 4-Cl | 0 | —HC=NO-CH2CH2-NHSO$_2$nPr | H, H |
| A1304 | 2-Cl, 4-Cl | 0 | —HC=NO-CH2CH2-NHSO$_2$Ph | H, H |
| A1305 | 2-Cl, 4-Cl | 0 | —HC=NO-CH2CH2CH2-NHSO$_2$Me | H, H |

TABLE 34-continued

| Part A No. | R20 | n | R2 | R3, R4 |
|---|---|---|---|---|
| A1306 | 2-Cl, 4-Cl | 0 | —HC=NO—(CH2)—NHSO2Et | H, H |
| A1307 | 2-Cl, 4-Cl | 0 | —HC=NO—(CH2)—NHSO2nPr | H, H |
| A1308 | 2-Cl, 4-Cl | 0 | —HC=NO—(CH2)—NHSO2Ph | H, H |
| A1309 | 2-Cl, 4-Cl | 0 | CH2OcPr | H, H |
| A1310 | 2-Cl, 4-Cl | 0 | CH2OcBu | H, H |
| A1311 | 2-Cl, 4-Cl | 0 | CH2OcPen | H, H |
| A1312 | 2-Cl, 4-Cl | 0 | CH2OcHex | H, H |
| A1313 | 2-Cl, 4-Cl | 0 | CH2OCH2cPr | H, H |
| A1314 | 2-Cl, 4-Cl | 0 | CH2OCH2cBu | H, H |
| A1315 | 2-Cl, 4-Cl | 0 | CH2OCH2cPen | H, H |
| A1316 | 2-Cl, 4-Cl | 0 | CH2OCH2cHex | H, H |
| A1317 | 2-Cl, 4-Cl | 0 | CH2O(CH2)2cPr | H, H |

TABLE 35

| Part A No. | R20 | n | R2 | R3, R4 |
|---|---|---|---|---|
| A1318 | 2-Cl, 4-Cl | 0 | CH2O(CH2)2cBu | H, H |
| A1319 | 2-Cl, 4-Cl | 0 | CH2O(CH2)2cPen | H, H |
| A1320 | 2-Cl, 4-Cl | 0 | CH2O(CH2)2cHex | H, H |
| A1321 | 2-Cl, 4-Cl | 0 | CH2O(CH2)3cPr | H, H |
| A1322 | 2-Cl, 4-Cl | 0 | CH2O(CH2)3cBu | H, H |
| A1323 | 2-Cl, 4-Cl | 0 | CH2O(CH2)3cPen | H, H |
| A1324 | 2-Cl, 4-Cl | 0 | CH2O(CH2)3cHex | H, H |
| A1325 | 2-Cl, 4-Cl | 0 | CH2O-(tetrahydrofuran-3-yl) | H, H |
| A1326 | 2-Cl, 4-Cl | 0 | CH2O-(tetrahydrothiophen-3-yl) | H, H |
| A1327 | 2-Cl, 4-Cl | 0 | CH2O-(1,1-dioxo-tetrahydrothiophen-3-yl) | H, H |
| A1328 | 2-Cl, 4-Cl | 0 | CH2O-(pyrrolidin-3-yl) | H, H |
| A1329 | 2-Cl, 4-Cl | 0 | CH2O-(1-methylpyrrolidin-3-yl) | H, H |
| A1330 | 2-Cl, 4-Cl | 0 | CH2O-(1-ethylpyrrolidin-3-yl) | H, H |
| A1331 | 2-Cl, 4-Cl | 0 | CH2O-(1-n-propylpyrrolidin-3-yl) | H, H |
| A1332 | 2-Cl, 4-Cl | 0 | CH2O-(tetrahydropyran-4-yl) | H, H |
| A1333 | 2-Cl, 4-Cl | 0 | CH2O-(tetrahydrothiopyran-4-yl) | H, H |
| A1334 | 2-Cl, 4-Cl | 0 | CH2O-(1,1-dioxo-tetrahydrothiopyran-4-yl) | H, H |
| A1335 | 2-Cl, 4-Cl | 0 | CH2O-(piperidin-4-yl) | H, H |
| A1336 | 2-Cl, 4-Cl | 0 | CH2O-(1-methylpiperidin-4-yl) | H, H |
| A1337 | 2-Cl, 4-Cl | 0 | CH2O-(1-ethylpiperidin-4-yl) | H, H |
| A1338 | 2-Cl, 4-Cl | 0 | CH2O-(1-n-propylpiperidin-4-yl) | H, H |
| A1339 | 2-Cl, 4-Cl | 0 | CH2O-CH2-(tetrahydrofuran-3-yl) | H, H |
| A1340 | 2-Cl, 4-Cl | 0 | CH2O-CH2-(tetrahydrothiophen-3-yl) | H, H |
| A1341 | 2-Cl, 4-Cl | 0 | CH2O-CH2-(1,1-dioxo-tetrahydrothiophen-3-yl) | H, H |
| A1342 | 2-Cl, 4-Cl | 0 | CH2O-CH2-(pyrrolidin-3-yl) | H, H |
| A1343 | 2-Cl, 4-Cl | 0 | CH2O-CH2-(1-methylpyrrolidin-3-yl) | H, H |

TABLE 35-continued

| Part A No. | R20 | n | R2 | R3, R4 |
|---|---|---|---|---|
| A1344 | 2-Cl, 4-Cl | 0 | CH₂O-pyrrolidine-NnPr | H, H |
| A1345 | 2-Cl, 4-Cl | 0 | CH₂O-pyrrolidine-NEt | H, H |
| A1346 | 2-Cl, 4-Cl | 0 | CH₂O-tetrahydropyran | H, H |

TABLE 36

| Part A No. | R20 | n | R2 | R3, R4 |
|---|---|---|---|---|
| A1347 | 2-Cl, 4-Cl | 0 | CH₂O-tetrahydrothiopyran (S) | H, H |
| A1348 | 2-Cl, 4-Cl | 0 | CH₂O-tetrahydrothiopyran (SO₂) | H, H |
| A1349 | 2-Cl, 4-Cl | 0 | CH₂O-piperidine-NH | H, H |
| A1350 | 2-Cl, 4-Cl | 0 | CH₂O-piperidine-NMe | H, H |
| A1351 | 2-Cl, 4-Cl | 0 | CH₂O-piperidine-NEt | H, H |
| A1352 | 2-Cl, 4-Cl | 0 | CH₂O-piperidine-NnPr | H, H |
| A1353 | 2-Cl, 4-Cl | 0 | CH₂O-morpholine | H, H |
| A1354 | 2-Cl, 4-Cl | 0 | CH₂O-thiomorpholine (S) | H, H |
| A1355 | 2-Cl, 4-Cl | 0 | CH₂O-thiomorpholine (SO₂) | H, H |
| A1356 | 2-Cl, 4-Cl | 0 | CH₂O-piperazine-NH | H, H |
| A1357 | 2-Cl, 4-Cl | 0 | CH₂O-piperazine-NMe | H, H |
| A1358 | 2-Cl, 4-Cl | 0 | CH₂O-piperazine-NEt | H, H |
| A1359 | 2-Cl, 4-Cl | 0 | CH₂O-piperazine-NnPr | H, H |
| A1360 | 2-Cl, 4-Cl | 0 | CH₂O-CH₂-furan | H, H |
| A1361 | 2-Cl, 4-Cl | 0 | CH₂O-CH₂CH₂-furan | H, H |
| A1362 | 2-Cl, 4-Cl | 0 | CH₂O-CH₂-thiazole | H, H |
| A1363 | 2-Cl, 4-Cl | 0 | CH₂O-CH₂-thiophene | H, H |
| A1364 | 2-Cl, 4-Cl | 0 | CH₂O-CH₂-thiophene (3-) | H, H |
| A1365 | 2-Cl, 4-Cl | 0 | CH₂O-CH₂-pyridine (3-) | H, H |
| A1366 | 2-Cl, 4-Cl | 0 | CH₂O-CH₂-pyridine (4-) | H, H |
| A1367 | 2-Cl, 4-Cl | 0 | CH₂O-CH₂CH₂-NHSO₂Me | H, H |
| A1368 | 2-Cl, 4-Cl | 0 | CH₂O-CH₂CH₂-NHSO₂Et | H, H |
| A1369 | 2-Cl, 4-Cl | 0 | CH₂O-CH₂CH₂-NHSO₂nPr | H, H |
| A1370 | 2-Cl, 4-Cl | 0 | CH₂O-CH₂CH₂-NHSO₂Ph | H, H |
| A1371 | 2-Cl, 4-Cl | 0 | CH₂O-CH₂CH₂CH₂-NHSO₂Me | H, H |

TABLE 37

| Part A No. | R20 | n | R2 | R3, R4 |
|---|---|---|---|---|
| A1372 | 2-Cl, 4-Cl | 0 | CH₂O~~~NHSO₂Et | H, H |
| A1373 | 2-Cl, 4-Cl | 0 | CH₂O~~~NHSO₂nPr | H, H |
| A1374 | 2-Cl, 4-Cl | 0 | CH₂O~~~NHSO₂Ph | H, H |
| A1375 | 2-Cl, 4-Cl | 0 | CH2ON=CHCH3 | H, H |
| A1376 | 2-Cl, 4-Cl | 0 | CH2ON=CH(CH3)2 | H, H |
| A1377 | 2-Cl, 4-Cl | 0 |  | H, H |
| A1378 | 2-Cl, 4-Cl | 0 |  | H, H |
| A1379 | 4-OMe | 0 | CH=NOH | H, H |
| A1380 | 4-OMe | 0 | CH=NOMe | H, H |
| A1381 | 4-OMe | 0 | CH=NOEt | H, H |
| A1382 | 4-OMe | 0 | CH=NOnPr | H, H |
| A1383 | 4-OMe | 0 | CH=NOiPr | H, H |
| A1384 | 4-OMe | 0 | CH=NOcPr | H, H |
| A1385 | 4-OMe | 0 | CH=NOnBu | H, H |
| A1386 | 4-OMe | 0 | CH=NOCH2CH(CH3)2 | H, H |
| A1387 | 4-OMe | 0 | CH=NOcBu | H, H |
| A1388 | 4-OMe | 0 | CH=NOnPen | H, H |
| A1389 | 4-OMe | 0 | CH=NOcPen | H, H |
| A1390 | 4-OMe | 0 | CH=NOnHex | H, H |
| A1391 | 4-OMe | 0 | CH=NOcHex | H, H |
| A1392 | 4-OMe | 0 | CH=NOH | H, H |
| A1393 | 4-OMe | 0 | CH=NOCH2iPr | H, H |
| A1394 | 4-OMe | 0 | CH=NOCH2cPr | H, H |
| A1395 | 4-OMe | 0 | CH=NOCH2cBu | H, H |
| A1396 | 4-OMe | 0 | CH=NOCH2cPen | H, H |
| A1397 | 4-OMe | 0 | CH=NOCH2cHex | H, H |
| A1398 | 4-OMe | 0 | CH=NO(CH2)2iPr | H, H |
| A1399 | 4-OMe | 0 | CH=NO(CH2)2cPr | H, H |
| A1400 | 4-OMe | 0 | CH=NO(CH2)2cBu | H, H |
| A1401 | 4-OMe | 0 | CH=NO(CH2)2cPen | H, H |
| A1402 | 4-OMe | 0 | CH=NO(CH2)2cHex | H, H |
| A1403 | 4-OMe | 0 | CH=NO(CH2)3iPr | H, H |
| A1404 | 4-OMe | 0 | CH=NO(CH2)3cPr | H, H |
| A1405 | 4-OMe | 0 | CH=NO(CH2)3cBu | H, H |
| A1406 | 4-OMe | 0 | CH=NO(CH2)3cPen | H, H |
| A1407 | 4-OMe | 0 | CH=NO(CH2)3cHex | H, H |
| A1408 | 4-OMe | 0 |  | H, H |
| A1409 | 4-OMe | 0 | 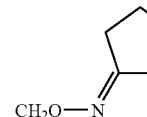 | H, H |
| A1410 | 4-OMe | 0 | 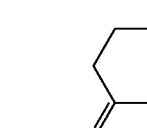 | H, H |

TABLE 38

| Part A No. | R20 | n | R2 | R3, R4 |
|---|---|---|---|---|
| A1411 | 4-OMe | 0 | 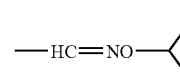 | H, H |
| A1412 | 4-OMe | 0 | 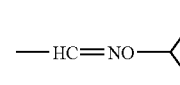 | H, H |
| A1413 | 4-OMe | 0 | 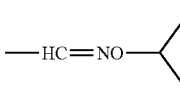 | H, H |
| A1414 | 4-OMe | 0 | 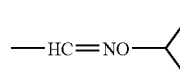 | H, H |
| A1415 | 4-OMe | 0 | 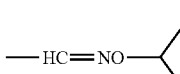 | H, H |
| A1416 | 4-OMe | 0 | 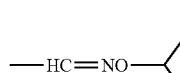 | H, H |
| A1417 | 4-OMe | 0 | 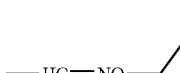 | H, H |
| A1418 | 4-OMe | 0 |  | H, H |
| A1419 | 4-OMe | 0 |  | H, H |
| A1420 | 4-OMe | 0 | 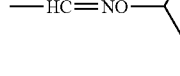 | H, H |
| A1421 | 4-OMe | 0 | 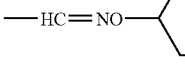 | H, H |
| A1422 | 4-OMe | 0 | 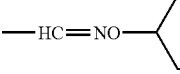 | H, H |
| A1423 | 4-OMe | 0 | 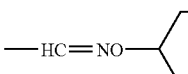 | H, H |
| A1424 | 4-OMe | 0 | 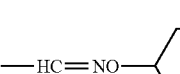 | H, H |
| A1425 | 4-OMe | 0 |  | H, H |

TABLE 38-continued

| Part A No. | R20 | n | R2 | R3, R4 |
|---|---|---|---|---|
| A1426 | 4-OMe | 0 | —HC=NO—CH2-(3-pyrrolidinyl-NMe) | H, H |
| A1427 | 4-OMe | 0 | —HC=NO—CH2-(3-pyrrolidinyl-NnPr) | H, H |
| A1428 | 4-OMe | 0 | —HC=NO—CH2-(3-pyrrolidinyl-NEt) | H, H |
| A1429 | 4-OMe | 0 | —HC=NO—CH2-(4-tetrahydropyranyl) | H, H |
| A1430 | 4-OMe | 0 | —HC=NO—CH2-(4-tetrahydrothiopyranyl) | H, H |
| A1431 | 4-OMe | 0 | —HC=NO—CH2-(4-tetrahydrothiopyranyl-SO2) | H, H |
| A1432 | 4-OMe | 0 | —HC=NO—CH2-(4-piperidinyl-NH) | H, H |
| A1433 | 4-OMe | 0 | —HC=NO—CH2-(4-piperidinyl-NMe) | H, H |
| A1434 | 4-OMe | 0 | —HC=NO—CH2-(4-piperidinyl-NEt) | H, H |
| A1435 | 4-OMe | 0 | —HC=NO—CH2-(4-piperidinyl-NnPr) | H, H |

TABLE 39

| Part A No. | R20 | n | R2 | R3, R4 |
|---|---|---|---|---|
| A1436 | 4-OMe | 0 | —HC=NO—CH2-(morpholin-4-yl) | H, H |
| A1437 | 4-OMe | 0 | —HC=NO—CH2-(thiomorpholin-4-yl) | H, H |
| A1438 | 4-OMe | 0 | —HC=NO—CH2-(thiomorpholin-4-yl-SO2) | H, H |
| A1439 | 4-OMe | 0 | —HC=NO—CH2-(piperazin-1-yl-NH) | H, H |
| A1440 | 4-OMe | 0 | —HC=NO—CH2-(piperazin-1-yl-NMe) | H, H |
| A1441 | 4-OMe | 0 | —HC=NO—CH2-(piperazin-1-yl-NEt) | H, H |
| A1442 | 4-OMe | 0 | —HC=NO—CH2-(piperazin-1-yl-NnPr) | H, H |
| A1443 | 4-OMe | 0 | —HC=NO—CH2-(furan-2-yl) | H, H |
| A1444 | 4-OMe | 0 | —HC=NO—CH2-(furan-3-yl) | H, H |
| A1445 | 4-OMe | 0 | —HC=NO—CH2-(thiazol-2-yl) | H, H |
| A1446 | 4-OMe | 0 | —HC=NO—CH2-(thiophen-2-yl) | H, H |
| A1447 | 4-OMe | 0 | —HC=NO—CH2-(thiophen-3-yl) | H, H |
| A1448 | 4-OMe | 0 | —HC=NO—CH2-(pyridin-3-yl) | H, H |
| A1449 | 4-OMe | 0 | —HC=NO—CH2-(pyridin-4-yl) | H, H |
| A1450 | 4-OMe | 0 | —HC=NO—CH2CH2—NHSO2Me | H, H |
| A1451 | 4-OMe | 0 | —HC=NO—CH2CH2—NHSO2Et | H, H |
| A1452 | 4-OMe | 0 | —HC=NO—CH2CH2—NHSO2nPr | H, H |

TABLE 39-continued

| Part A No. | R20 | n | R2 | R3, R4 |
|---|---|---|---|---|
| A1453 | 4-OMe | 0 | —HC=NO~CH2CH2~NHSO2Ph | H, H |
| A1454 | 4-OMe | 0 | —HC=NO~(CH2)3~NHSO2Me | H, H |
| A1455 | 4-OMe | 0 | —HC=NO~(CH2)3~NHSO2Et | H, H |
| A1456 | 4-OMe | 0 | —HC=NO~(CH2)3~NHSO2nPr | H, H |
| A1457 | 4-OMe | 0 | —HC=NO~(CH2)3~NHSO2Ph | H, H |
| A1458 | 4-OMe | 0 | CH2OcPr | H, H |
| A1459 | 4-OMe | 0 | CH2OcBu | H, H |
| A1460 | 4-OMe | 0 | CH2OcPen | H, H |
| A1461 | 4-OMe | 0 | CH2OcHex | H, H |
| A1462 | 4-OMe | 0 | CH2OCH2cPr | H, H |
| A1463 | 4-OMe | 0 | CH2OCH2cBu | H, H |
| A1464 | 4-OMe | 0 | CH2OCH2cPen | H, H |
| A1465 | 4-OMe | 0 | CH2OCH2cHex | H, H |
| A1466 | 4-OMe | 0 | CH2O(CH2)2cPr | H, H |

TABLE 40

| Part A No. | R20 | n | R2 | R3, R4 |
|---|---|---|---|---|
| A1467 | 4-OMe | 0 | CH2O(CH2)2cBu | H, H |
| A1468 | 4-OMe | 0 | CH2O(CH2)2cPen | H, H |
| A1469 | 4-OMe | 0 | CH2O(CH2)2cHex | H, H |
| A1470 | 4-OMe | 0 | CH2O(CH2)3cPr | H, H |
| A1471 | 4-OMe | 0 | CH2O(CH2)3cBu | H, H |
| A1472 | 4-OMe | 0 | CH2O(CH2)3cPen | H, H |
| A1473 | 4-OMe | 0 | CH2O(CH2)3cHex | H, H |
| A1474 | 4-OMe | 0 | CH2O-(tetrahydrofuran-3-yl) | H, H |
| A1475 | 4-OMe | 0 | CH2O-(tetrahydrothiophen-3-yl) | H, H |
| A1476 | 4-OMe | 0 | CH2O-(tetrahydrothiophene-3-yl 1,1-dioxide) | H, H |
| A1477 | 4-OMe | 0 | CH2O-(pyrrolidin-3-yl, NH) | H, H |
| A1478 | 4-OMe | 0 | CH2O-(pyrrolidin-3-yl, NMe) | H, H |
| A1479 | 4-OMe | 0 | CH2O-(pyrrolidin-3-yl, NEt) | H, H |
| A1480 | 4-OMe | 0 | CH2O-(pyrrolidin-3-yl, NnPr) | H, H |
| A1481 | 4-OMe | 0 | CH2O-(tetrahydropyran-4-yl, O) | H, H |
| A1482 | 4-OMe | 0 | CH2O-(tetrahydrothiopyran-4-yl, S) | H, H |
| A1483 | 4-OMe | 0 | CH2O-(tetrahydrothiopyran-4-yl, SO2) | H, H |
| A1484 | 4-OMe | 0 | CH2O-(piperidin-4-yl, NH) | H, H |
| A1485 | 4-OMe | 0 | CH2O-(piperidin-4-yl, NMe) | H, H |
| A1486 | 4-OMe | 0 | CH2O-(piperidin-4-yl, NEt) | H, H |
| A1487 | 4-OMe | 0 | CH2O-(piperidin-4-yl, NnPr) | H, H |
| A1488 | 4-OMe | 0 | CH2O-CH2-(tetrahydrofuran-3-yl) | H, H |
| A1489 | 4-OMe | 0 | CH2O-CH2-(tetrahydrothiophen-3-yl) | H, H |
| A1490 | 4-OMe | 0 | CH2O-CH2-(tetrahydrothiophene-3-yl 1,1-dioxide) | H, H |
| A1491 | 4-OMe | 0 | CH2O-CH2-(pyrrolidin-3-yl, NH) | H, H |
| A1492 | 4-OMe | 0 | CH2O-CH2-(pyrrolidin-3-yl, NMe) | H, H |
| A1493 | 4-OMe | 0 | CH2O-CH2-(pyrrolidin-3-yl, NnPr) | H, H |
| A1494 | 4-OMe | 0 | CH2O-CH2-(pyrrolidin-3-yl, NEt) | H, H |
| A1495 | 4-OMe | 0 | CH2O-CH2-(tetrahydropyran-4-yl) | H, H |

TABLE 41

| Part A No. | R20 | n | R2 | R3, R4 |
|---|---|---|---|---|
| A1496 | 4-OMe | 0 | CH₂O-(tetrahydrothiopyran-4-yl) | H, H |
| A1497 | 4-OMe | 0 | CH₂O-(1,1-dioxo-tetrahydrothiopyran-4-yl) | H, H |
| A1498 | 4-OMe | 0 | CH₂O-(piperidin-4-yl)NH | H, H |
| A1499 | 4-OMe | 0 | CH₂O-(1-methylpiperidin-4-yl) | H, H |
| A1500 | 4-OMe | 0 | CH₂O-(1-ethylpiperidin-4-yl) | H, H |
| A1501 | 4-OMe | 0 | CH₂O-(1-n-propylpiperidin-4-yl) | H, H |
| A1502 | 4-OMe | 0 | CH₂-morpholinyl | H, H |
| A1503 | 4-OMe | 0 | CH₂-thiomorpholinyl | H, H |
| A1504 | 4-OMe | 0 | CH₂-(1,1-dioxothiomorpholinyl) | H, H |
| A1505 | 4-OMe | 0 | CH₂-piperazinyl-NH | H, H |
| A1506 | 4-OMe | 0 | CH₂-(4-methylpiperazinyl) | H, H |
| A1507 | 4-OMe | 0 | CH₂-(4-ethylpiperazinyl) | H, H |
| A1508 | 4-OMe | 0 | CH₂-(4-n-propylpiperazinyl) | H, H |
| A1509 | 4-OMe | 0 | CH₂O-CH₂-(furan-2-yl) | H, H |
| A1510 | 4-OMe | 0 | CH₂O-CH₂CH₂-(furan-2-yl) | H, H |
| A1511 | 4-OMe | 0 | CH₂O-CH₂-(thiazol-2-yl) | H, H |
| A1512 | 4-OMe | 0 | CH₂O-CH₂-(thiophen-2-yl) | H, H |
| A1513 | 4-OMe | 0 | CH₂O-CH₂-(thiophen-3-yl) | H, H |
| A1514 | 4-OMe | 0 | CH₂O-CH₂-(pyridin-3-yl) | H, H |
| A1515 | 4-OMe | 0 | CH₂O-CH₂-(pyridin-4-yl) | H, H |
| A1516 | 4-OMe | 0 | CH₂O-CH₂CH₂-NHSO₂Me | H, H |
| A1517 | 4-OMe | 0 | CH₂O-CH₂CH₂-NHSO₂Et | H, H |
| A1518 | 4-OMe | 0 | CH₂O-CH₂CH₂-NHSO₂nPr | H, H |
| A1519 | 4-OMe | 0 | CH₂O-CH₂CH₂-NHSO₂Ph | H, H |
| A1520 | 4-OMe | 0 | CH₂O-CH₂CH₂CH₂-NHSO₂Me | H, H |

TABLE 42

| Part A No. | R20 | n | R2 | R3, R4 |
|---|---|---|---|---|
| A1521 | 4-OMe | 0 | CH₂O-CH₂CH₂CH₂-NHSO₂Et | H, H |

TABLE 42-continued

| Part A No. | R20 | n | R2 | R3, R4 |
|---|---|---|---|---|
| A1522 | 4-OMe | 0 | CH₂O~~~NHSO₂nPr | H, H |
| A1523 | 4-OMe | 0 | CH₂O~~~NHSO₂Ph | H, H |
| A1524 | 4-OMe | 0 | CH2ON=CHCH3 | H, H |
| A1525 | 4-OMe | 0 | CH2ON=CH(CH3)2 | H, H |
| A1526 | 4-OMe | 0 | CH₂O—N=cyclopentylidene | H, H |
| A1527 | 4-OMe | 0 | CH₂O—N=cyclohexylidene | H, H |
| A1528 | 4-Cl | 0 | Me | H, 4-pyridyl |
| A1529 | 4-Cl | 0 | CH2OMe | H, CH2CH=CH2 |
| A1530 | 4-Cl | 0 | CH2-morpholino | H, C≡CPh |
| A1531 | 4-CF3 | 0 | CH2C6H4-4-CF3 | H, CH=CH2 |
| A1532 | 4-CF3 | 0 | OMe | H, C6H4-4-Ph |
| A1533 | 4-CF3 | 0 | CF3 | H, CH2C≡CH |
| A1534 | 4-CF3 | 0 | Me | H, CH=CHPh |
| A1535 | 4-CF3 | 0 | CH2OMe | H, 3-furyl |

TABLE 43

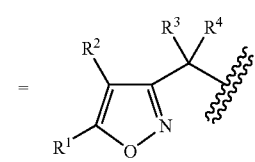 = 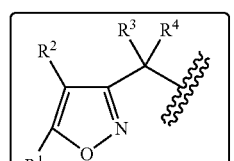

A

| Part A No. | R1 | R2 | R3, R4 |
|---|---|---|---|
| A2353 | Me | H | H, H |
| A2354 | Me | H | Me, Me |
| A2355 | Me | H | Et, Et |
| A2356 | Me | H | H, Et |
| A2357 | Me | H | H, Ph |
| A2358 | Me | H | H, C6H4-4-F |
| A2359 | Me | Me | H, H |
| A2360 | Me | Me | Me, Me |
| A2361 | Me | Me | Et, Et |
| A2362 | Me | Me | H, Et |
| A2363 | Me | Me | H, Ph |
| A2364 | Me | Me | H, C6H4-4-F |
| A2365 | Me | CH2OMe | H, H |
| A2366 | Me | CH2OMe | Me, Me |
| A2367 | Me | CH2OMe | Et, Et |
| A2368 | Me | CH2OMe | H, Et |
| A2369 | Me | CH2OMe | H, Ph |
| A2370 | Me | CH2OMe | H, C6H4-4-F |
| A2371 | Me | CF3 | H, H |
| A2372 | Me | CF3 | Me, Me |
| A2373 | Me | CF3 | Et, Et |
| A2374 | Me | CF3 | H, Et |
| A2375 | Me | CF3 | H, Ph |
| A2376 | Me | CF3 | H, C6H4-4-F |
| A2377 | Me | CH2OH | H, H |
| A2378 | Me | CH2OH | H, C6H4-4-F |
| A2379 | Me | CH2NHBu | H, H |
| A2380 | Me | CH2NHBu | H, C6H4-4-F |
| A2381 | Me | CH2C≡CH | H, H |
| A2382 | Me | CH2C≡CH | H, C6H4-4-F |
| A2383 | Me | OMe | H, H |
| A2384 | Me | OMe | H, C6H4-4-F |
| A2385 | Me | NH2 | H, H |
| A2386 | Me | NH2 | H, C6H4-4-F |

TABLE 44

| Part A No. | R1 | R2 | R3, R4 |
|---|---|---|---|
| A2387 | Me | NHMe | H, H |
| A2388 | Me | NHMe | H, C6H4-4-F |
| A2389 | Me | CH2OPh | H, H |
| A2390 | Me | CH2OPh | H, C6H4-4-F |
| A2391 | Me | CH2OCH2Ph | H, H |
| A2392 | Me | CH2OCH2Ph | H, C6H4-4-F |
| A2393 | Me | CH2-morpholino | H, H |
| A2394 | Me | CH2-morpholino | H, C6H4-4-F |
| A2395 | Me | CH=CH-pyridyl | H, H |
| A2396 | Me | CH=CH-pyridyl | H, C6H4-4-F |
| A2397 | Me | C≡CPh | H, H |
| A2398 | Me | C≡CPh | H, C6H4-4-F |

TABLE 44-continued

| Part A No. | R1 | R2 | R3, R4 |
|---|---|---|---|
| A2399 | Me | Ph | H, H |
| A2400 | Me | Ph | H, C6H4-4-F |
| A2401 | Me | C6H4-4-CF3 | H, H |
| A2402 | Me | C6H4-4-CF3 | Me, Me |
| A2403 | Me | C6H4-4-CF3 | Et, Et |
| A2404 | Me | C6H4-4-CF3 | H, Et |
| A2405 | Me | C6H4-4-CF3 | H, Ph |
| A2406 | Me | C6H4-4-CF3 | H, C6H4-4-F |
| A2407 | Me | C6H4-3-CF3 | H, H |
| A2408 | Me | C6H4-3-CF3 | H, C6H4-4-F |
| A2409 | Me | C6H4-4-OH | H, H |
| A2410 | Me | C6H4-4-OH | H, C6H4-4-F |
| A2411 | Me | CH2Ph | H, H |
| A2412 | Me | CH2Ph | H, C6H4-4-F |
| A2413 | Me | CH2C6H4-4-CF3 | H, H |
| A2414 | Me | CH2C6H4-4-CF3 | Me, Me |
| A2415 | Me | CH2C6H4-4-CF3 | Et, Et |
| A2416 | Me | CH2C6H4-4-CF3 | H, Et |
| A2417 | Me | CH2C6H4-4-CF3 | H, Ph |
| A2418 | Me | CH2C6H4-4-CF3 | H, C6H4-4-F |
| A2419 | Me | CH2C6H4-4-OCF3 | H, H |
| A2420 | Me | CH2C6H4-4-OCF3 | H, C6H4-4-F |
| A2421 | Me | CH2C6H4-4-Ph | H, H |
| A2422 | Me | CH2C6H4-4-Ph | H, C6H4-4-F |
| A2423 | Me | CH2C6H4-2-Cl | H, H |
| A2424 | Me | CH2C6H4-2-Cl | H, C6H4-4-F |
| A2425 | Me | (CH2)2Ph | H, H |
| A2426 | Me | (CH2)2Ph | H, C6H4-4-F |
| A2427 | Me | CH2-piperazino-Ph | H, H |
| A2428 | Me | CH2-piperazino-Ph | Me, Me |
| A2429 | Me | CH2-piperazino-Ph | Et, Et |
| A2430 | Me | CH2-piperazino-Ph | H, Et |

TABLE 45

| Part A No. | R1 | R2 | R3, R4 |
|---|---|---|---|
| A2431 | Me | CH2-piperazino-Ph | H, Ph |
| A2432 | Me | CH2-piperazino-Ph | H, C6H4-4-F |
| A2433 | Me | CH2-piperidino | H, H |
| A2434 | Me | CH2-piperidino | H, C6H4-4-F |
| A2435 | Me | SPh | H, H |
| A2436 | Me | SPh | H, C6H4-4-F |
| A2437 | Me | OCH2Ph | H, H |
| A2438 | Me | OCH2Ph | H, C6H4-4-F |
| A2439 | Me | Ac | H, H |
| A2440 | Me | Ac | H, C6H4-4-F |
| A2441 | Me | CONH2 | H, H |
| A2442 | Me | CONH2 | H, C6H4-4-F |
| A2443 | Me | CSNH2 | H, H |
| A2444 | Me | CSNH2 | H, C6H4-4-F |
| A2445 | Me | OCONH2 | H, H |
| A2446 | Me | OCONH2 | H, C6H4-4-F |
| A2447 | Me | OCSNH2 | H, H |
| A2448 | Me | OCSNH2 | H, C6H4-4-F |
| A2449 | Me | OSO2Me | H, H |
| A2450 | Me | OSO2Me | H, C6H4-4-F |
| A2451 | Me | OSO2Ph | H, H |
| A2452 | Me | OSO2Ph | H, C6H4-4-F |
| A2453 | Me | I | H, H |
| A2454 | Me | I | H, C6H4-4-F |
| A2455 | CF3 | H | H, H |
| A2456 | CF3 | H | Me, Me |
| A2457 | CF3 | H | Et, Et |
| A2458 | CF3 | H | H, Et |
| A2459 | CF3 | H | H, Ph |
| A2460 | CF3 | H | H, C6H4-4-F |
| A2461 | CF3 | Me | H, H |
| A2462 | CF3 | Me | Me, Me |
| A2463 | CF3 | Me | Et, Et |
| A2464 | CF3 | Me | H, Et |
| A2465 | CF3 | Me | H, Ph |
| A2466 | CF3 | Me | H, C6H4-4-F |
| A2467 | CF3 | CH2OMe | H, H |

TABLE 45-continued

| Part A No. | R1 | R2 | R3, R4 |
|---|---|---|---|
| A2468 | CF3 | CH2OMe | Me, Me |
| A2469 | CF3 | CH2OMe | Et, Et |
| A2470 | CF3 | CH2OMe | H, Et |
| A2471 | CF3 | CH2OMe | H, Ph |
| A2472 | CF3 | CH2OMe | H, C6H4-4-F |
| A2473 | CF3 | CF3 | H, H |
| A2474 | CF3 | CF3 | Me, Me |

TABLE 46

| Part A No. | R1 | R2 | R3, R4 |
|---|---|---|---|
| A2475 | CF3 | CF3 | Et, Et |
| A2476 | CF3 | CF3 | H, Et |
| A2477 | CF3 | CF3 | H, Ph |
| A2478 | CF3 | CF3 | H, C6H4-4-F |
| A2479 | CF3 | CH2OH | H, H |
| A2480 | CF3 | CH2OH | H, C6H4-4-F |
| A2481 | CF3 | CH2NHBu | H, H |
| A2482 | CF3 | CH2NHBu | H, C6H4-4-F |
| A2483 | CF3 | CH2C≡CH | H, H |
| A2484 | CF3 | CH2C≡CH | H, C6H4-4-F |
| A2485 | CF3 | OMe | H, H |
| A2486 | CF3 | OMe | H, C6H4-4-F |
| A2487 | CF3 | NH2 | H, H |
| A2488 | CF3 | NH2 | H, C6H4-4-F |
| A2489 | CF3 | NHMe | H, H |
| A2490 | CF3 | NHMe | H, C6H4-4-F |
| A2491 | CF3 | CH2OPh | H, H |
| A2492 | CF3 | CH2OPh | H, C6H4-4-F |
| A2493 | CF3 | CH2OCH2Ph | H, H |
| A2494 | CF3 | CH2OCH2Ph | H, C6H4-4-F |
| A2495 | CF3 | CH2-morpholino | H, H |
| A2496 | CF3 | CH2-morpholino | H, C6H4-4-F |
| A2497 | CF3 | CH═CH-pyridyl | H, H |
| A2498 | CF3 | CH═CH-pyridyl | H, C6H4-4-F |
| A2499 | CF3 | C≡CPh | H, H |
| A2500 | CF3 | C≡CPh | H, C6H4-4-F |
| A2501 | CF3 | Ph | H, H |
| A2502 | CF3 | Ph | H, C6H4-4-F |
| A2503 | CF3 | C6H4-4-CF3 | H, H |
| A2504 | CF3 | C6H4-4-CF3 | Me, Me |
| A2505 | CF3 | C6H4-4-CF3 | Et, Et |
| A2506 | CF3 | C6H4-4-CF3 | H, Et |
| A2507 | CF3 | C6H4-4-CF3 | H, Ph |
| A2508 | CF3 | C6H4-4-CF3 | H, C6H4-4-F |
| A2509 | CF3 | C6H4-3-CF3 | H, H |
| A2510 | CF3 | C6H4-3-CF3 | H, C6H4-4-F |
| A2511 | CF3 | C6H4-4-OH | H, H |
| A2512 | CF3 | C6H4-4-OH | H, C6H4-4-F |
| A2513 | CF3 | CH2Ph | H, H |
| A2514 | CF3 | CH2Ph | H, C6H4-4-F |
| A2515 | CF3 | CH2C6H4-4-CF3 | H, H |
| A2516 | CF3 | CH2C6H4-4-CF3 | Me, Me |
| A2517 | CF3 | CH2C6H4-4-CF3 | Et, Et |
| A2518 | CF3 | CH2C6H4-4-CF3 | H, Et |

TABLE 47

| Part A No. | R1 | R2 | R3, R4 |
|---|---|---|---|
| A2519 | CF3 | CH2C6H4-4-CF3 | H, Ph |
| A2520 | CF3 | CH2C6H4-4-CF3 | H, C6H4-4-F |
| A2521 | CF3 | CH2C6H4-4-OCF3 | H, H |
| A2522 | CF3 | CH2C6H4-4-OCF3 | H, C6H4-4-F |
| A2523 | CF3 | CH2C6H4-4-Ph | H, H |
| A2524 | CF3 | CH2C6H4-4-Ph | H, C6H4-4-F |
| A2525 | CF3 | CH2C6H4-2-Cl | H, H |
| A2526 | CF3 | CH2C6H4-2-Cl | H, C6H4-4-F |
| A2527 | CF3 | (CH2)2Ph | H, H |
| A2528 | CF3 | (CH2)2Ph | H, C6H4-4-F |
| A2529 | CF3 | CH2-piperazino-Ph | H, H |

TABLE 47-continued

| Part A No. | R1 | R2 | R3, R4 |
|---|---|---|---|
| A2530 | CF3 | CH2-piperazino-Ph | Me, Me |
| A2531 | CF3 | CH2-piperazino-Ph | Et, Et |
| A2532 | CF3 | CH2-piperazino-Ph | H, Et |
| A2533 | CF3 | CH2-piperazino-Ph | H, Ph |
| A2534 | CF3 | CH2-piperazino-Ph | H, C6H4-4-F |
| A2535 | CF3 | CH2-piperidino | H, H |
| A2536 | CF3 | CH2-piperidino | H, C6H4-4-F |
| A2537 | CF3 | SPh | H, H |
| A2538 | CF3 | SPh | H, C6H4-4-F |
| A2539 | CF3 | OCH2Ph | H, H |
| A2540 | CF3 | OCH2Ph | H, C6H4-4-F |
| A2541 | CF3 | Ac | H, H |
| A2542 | CF3 | Ac | H, C6H4-4-F |
| A2543 | CF3 | CONH2 | H, H |
| A2544 | CF3 | CONH2 | H, C6H4-4-F |
| A2545 | CF3 | CSNH2 | H, H |
| A2546 | CF3 | CSNH2 | H, C6H4-4-F |
| A2547 | CF3 | OCONH2 | H, H |
| A2548 | CF3 | OCONH2 | H, C6H4-4-F |
| A2549 | CF3 | OCSNH2 | H, H |
| A2550 | CF3 | OCSNH2 | H, C6H4-4-F |
| A2551 | CF3 | OSO2Me | H, H |
| A2552 | CF3 | OSO2Me | H, C6H4-4-F |
| A2553 | CF3 | OSO2Ph | H, H |
| A2554 | CF3 | OSO2Ph | H, C6H4-4-F |
| A2555 | CF3 | I | H, H |
| A2556 | CF3 | I | H, C6H4-4-F |
| A2557 | CH=CHPh | H | H, H |
| A2558 | CH=CHPh | H | Me, Me |
| A2559 | CH=CHPh | H | Et, Et |
| A2560 | CH=CHPh | H | H, Et |
| A2561 | CH=CHPh | H | H, Ph |
| A2562 | CH=CHPh | H | H, C6H4-4-F |

TABLE 48

| Part A No. | R1 | R2 | R3, R4 |
|---|---|---|---|
| A2563 | CH=CHPh | Me | H, H |
| A2564 | CH=CHPh | Me | Me, Me |
| A2565 | CH=CHPh | Me | Et, Et |
| A2566 | CH=CHPh | Me | H, Et |
| A2567 | CH=CHPh | Me | H, Ph |
| A2568 | CH=CHPh | Me | H, C6H4-4-F |
| A2569 | CH=CHPh | CH2OMe | H, H |
| A2570 | CH=CHPh | CH2OMe | Me, Me |
| A2571 | CH=CHPh | CH2OMe | Et, Et |
| A2572 | CH=CHPh | CH2OMe | H, Et |
| A2573 | CH=CHPh | CH2OMe | H, Ph |
| A2574 | CH=CHPh | CH2OMe | H, C6H4-4-F |
| A2575 | CH=CHPh | CF3 | H, H |
| A2576 | CH=CHPh | CF3 | Me, Me |
| A2577 | CH=CHPh | CF3 | Et, Et |
| A2578 | CH=CHPh | CF3 | H, Et |
| A2579 | CH=CHPh | CF3 | H, Ph |
| A2580 | CH=CHPh | CF3 | H, C6H4-4-F |
| A2581 | CH=CHPh | CH2OH | H, H |
| A2582 | CH=CHPh | CH2OH | H, C6H4-4-F |
| A2583 | CH=CHPh | CH2NHBu | H, H |
| A2584 | CH=CHPh | CH2NHBu | H, C6H4-4-F |
| A2585 | CH=CHPh | CH2C≡CH | H, H |
| A2586 | CH=CHPh | CH2C≡CH | H, C6H4-4-F |
| A2587 | CH=CHPh | OMe | H, H |
| A2588 | CH=CHPh | OMe | H, C6H4-4-F |
| A2589 | CH=CHPh | NH2 | H, H |
| A2590 | CH=CHPh | NH2 | H, C6H4-4-F |
| A2591 | CH=CHPh | NHMe | H, H |
| A2592 | CH=CHPh | NHMe | H, C6H4-4-F |
| A2593 | CH=CHPh | CH2OPh | H, H |
| A2594 | CH=CHPh | CH2OPh | H, C6H4-4-F |
| A2595 | CH=CHPh | CH2OCH2Ph | H, H |
| A2596 | CH=CHPh | CH2OCH2Ph | H, C6H4-4-F |
| A2597 | CH=CHPh | CH2-morpholino | H, H |
| A2598 | CH=CHPh | CH2-morpholino | H, C6H4-4-F |

TABLE 48-continued

| Part A No. | R1 | R2 | R3, R4 |
|---|---|---|---|
| A2599 | CH=CHPh | CH=CH-pyridyl | H, H |
| A2600 | CH=CHPh | CH=CH-pyridyl | H, C6H4-4-F |
| A2601 | CH=CHPh | C≡CPh | H, H |
| A2602 | CH=CHPh | C≡CPh | H, C6H4-4-F |
| A2603 | CH=CHPh | Ph | H, H |
| A2604 | CH=CHPh | Ph | H, C6H4-4-F |
| A2605 | CH=CHPh | C6H4-4-CF3 | H, H |
| A2606 | CH=CHPh | C6H4-4-CF3 | Me, Me |

TABLE 49

| Part A No. | R1 | R2 | R3, R4 |
|---|---|---|---|
| A2607 | CH=CHPh | C6H4-4-CF3 | Et, Et |
| A2608 | CH=CHPh | C6H4-4-CF3 | H, Et |
| A2609 | CH=CHPh | C6H4-4-CF3 | H, Ph |
| A2610 | CH=CHPh | C6H4-4-CF3 | H, C6H4-4-F |
| A2611 | CH=CHPh | C6H4-3-CF3 | H, H |
| A2612 | CH=CHPh | C6H4-3-CF3 | H, C6H4-4-F |
| A2613 | CH=CHPh | C6H4-4-OH | H, H |
| A2614 | CH=CHPh | C6H4-4-OH | H, C6H4-4-F |
| A2615 | CH=CHPh | CH2Ph | H, H |
| A2616 | CH=CHPh | CH2Ph | H, C6H4-4-F |
| A2617 | CH=CHPh | CH2C6H4-4-CF3 | H, H |
| A2618 | CH=CHPh | CH2C6H4-4-CF3 | Me, Me |
| A2619 | CH=CHPh | CH2C6H4-4-CF3 | Et, Et |
| A2620 | CH=CHPh | CH2C6H4-4-CF3 | H, Et |
| A2621 | CH=CHPh | CH2C6H4-4-CF3 | H, Ph |
| A2622 | CH=CHPh | CH2C6H4-4-CF3 | H, C6H4-4-F |
| A2623 | CH=CHPh | CH2C6H4-4-OCF3 | H, H |
| A2624 | CH=CHPh | CH2C6H4-4-OCF3 | H, C6H4-4-F |
| A2625 | CH=CHPh | CH2C6H4-4-Ph | H, H |
| A2626 | CH=CHPh | CH2C6H4-4-Ph | H, C6H4-4-F |
| A2627 | CH=CHPh | CH2C6H4-2-Cl | H, H |
| A2628 | CH=CHPh | CH2C6H4-2-Cl | H, C6H4-4-F |
| A2629 | CH=CHPh | (CH2)2Ph | H, H |
| A2630 | CH=CHPh | (CH2)2Ph | H, C6H4-4-F |
| A2631 | CH=CHPh | CH2-piperazino-Ph | H, H |
| A2632 | CH=CHPh | CH2-piperazino-Ph | Me, Me |
| A2633 | CH=CHPh | CH2-piperazino-Ph | Et, Et |
| A2634 | CH=CHPh | CH2-piperazino-Ph | H, Et |
| A2635 | CH=CHPh | CH2-piperazino-Ph | H, Ph |
| A2636 | CH=CHPh | CH2-piperazino-Ph | H, C6H4-4-F |
| A2637 | CH=CHPh | CH2-piperidino | H, H |
| A2638 | CH=CHPh | CH2-piperidino | H, C6H4-4-F |
| A2639 | CH=CHPh | SPh | H, H |
| A2640 | CH=CHPh | SPh | H, C6H4-4-F |
| A2641 | CH=CHPh | OCH2Ph | H, H |
| A2642 | CH=CHPh | OCH2Ph | H, C6H4-4-F |
| A2643 | CH=CHPh | Ac | H, H |
| A2644 | CH=CHPh | Ac | H, C6H4-4-F |
| A2645 | CH=CHPh | CONH2 | H, H |
| A2646 | CH=CHPh | CONH2 | H, C6H4-4-F |
| A2647 | CH=CHPh | CSNH2 | H, H |
| A2648 | CH=CHPh | CSNH2 | H, C6H4-4-F |
| A2649 | CH=CHPh | OCONH2 | H, H |
| A2650 | CH=CHPh | OCONH2 | H, C6H4-4-F |

TABLE 50

| Part A No. | R1 | R2 | R3, R4 |
|---|---|---|---|
| A2651 | CH=CHPh | OCSNH2 | H, H |
| A2652 | CH=CHPh | OCSNH2 | H, C6H4-4-F |
| A2653 | CH=CHPh | OSO2Me | H, H |
| A2654 | CH=CHPh | OSO2Me | H, C6H4-4-F |
| A2655 | CH=CHPh | OSO2Ph | H, H |
| A2656 | CH=CHPh | OSO2Ph | H, C6H4-4-F |
| A2657 | CH=CHPh | I | H, H |
| A2658 | CH=CHPh | I | H, C6H4-4-F |
| A2659 | ≡CPh | H | H, H |
| A2660 | ≡CPh | H | Me, Me |

TABLE 50-continued

| Part A No. | R1 | R2 | R3, R4 |
|---|---|---|---|
| A2661 | =CPh | H | Et, Et |
| A2662 | =CPh | H | H, Et |
| A2663 | =CPh | H | H, Ph |
| A2664 | =CPh | H | H, C6H4-4-F |
| A2665 | =CPh | Me | H, H |
| A2666 | =CPh | Me | Me, Me |
| A2667 | =CPh | Me | Et, Et |
| A2668 | =CPh | Me | H, Et |
| A2669 | =CPh | Me | H, Ph |
| A2670 | =CPh | Me | H, C6H4-4-F |
| A2671 | =CPh | CH2OMe | H, H |
| A2672 | =CPh | CH2OMe | Me, Me |
| A2673 | =CPh | CH2OMe | Et, Et |
| A2674 | =CPh | CH2OMe | H, Et |
| A2675 | =CPh | CH2OMe | H, Ph |
| A2676 | =CPh | CH2OMe | H, C6H4-4-F |
| A2677 | =CPh | CF3 | H, H |
| A2678 | =CPh | CF3 | Me, Me |
| A2679 | =CPh | CF3 | Et, Et |
| A2680 | =CPh | CF3 | H, Et |
| A2681 | =CPh | CF3 | H, Ph |
| A2682 | =CPh | CF3 | H, C6H4-4-F |
| A2683 | =CPh | CH2OH | H, H |
| A2684 | =CPh | CH2OH | H, C6H4-4-F |
| A2685 | =CPh | CH2NHBu | H, H |
| A2686 | =CPh | CH2NHBu | H, C6H4-4-F |
| A2687 | =CPh | CH2C≡CH | H, H |
| A2688 | =CPh | CH2C≡CH | H, C6H4-4-F |
| A2689 | =CPh | OMe | H, H |
| A2690 | =CPh | OMe | H, C6H4-4-F |
| A2691 | =CPh | NH2 | H, H |
| A2692 | =CPh | NH2 | H, C6H4-4-F |
| A2693 | =CPh | NHMe | H, H |
| A2694 | =CPh | NHMe | H, C6H4-4-F |

TABLE 51

| Part A No. | R1 | R2 | R3, R4 |
|---|---|---|---|
| A2695 | =CPh | CH2OPh | H, H |
| A2696 | =CPh | CH2OPh | H, C6H4-4-F |
| A2697 | =CPh | CH2OCH2Ph | H, H |
| A2698 | =CPh | CH2OCH2Ph | H, C6H4-4-F |
| A2699 | =CPh | CH2-morpholino | H, H |
| A2700 | =CPh | CH2-morpholino | H, C6H4-4-F |
| A2701 | =CPh | CH=CH-pyridyl | H, H |
| A2702 | =CPh | CH=CH-pyridyl | H, C6H4-4-F |
| A2703 | =CPh | C≡CPh | H, H |
| A2704 | =CPh | C≡CPh | H, C6H4-4-F |
| A2705 | =CPh | Ph | H, H |
| A2706 | =CPh | Ph | H, C6H4-4-F |
| A2707 | =CPh | C6H4-4-CF3 | H, H |
| A2708 | =CPh | C6H4-4-CF3 | Me, Me |
| A2709 | =CPh | C6H4-4-CF3 | Et, Et |
| A2710 | =CPh | C6H4-4-CF3 | H, Et |
| A2711 | =CPh | C6H4-4-CF3 | H, Ph |
| A2712 | =CPh | C6H4-4-CF3 | H, C6H4-4-F |
| A2713 | =CPh | C6H4-3-CF3 | H, H |
| A2714 | =CPh | C6H4-3-CF3 | H, C6H4-4-F |
| A2715 | =CPh | C6H4-4-OH | H, H |
| A2716 | =CPh | C6H4-4-OH | H, C6H4-4-F |
| A2717 | =CPh | CH2Ph | H, H |
| A2718 | =CPh | CH2Ph | H, C6H4-4-F |
| A2719 | =CPh | CH2C6H4-4-CF3 | H, H |
| A2720 | =CPh | CH2C6H4-4-CF3 | Me, Me |
| A2721 | =CPh | CH2C6H4-4-CF3 | Et, Et |
| A2722 | =CPh | CH2C6H4-4-CF3 | H, Et |
| A2723 | =CPh | CH2C6H4-4-CF3 | H, Ph |
| A2724 | =CPh | CH2C6H4-4-CF3 | H, C6H4-4-F |
| A2725 | =CPh | CH2C6H4-4-OCF3 | H, H |
| A2726 | =CPh | CH2C6H4-4-OCF3 | H, C6H4-4-F |
| A2727 | =CPh | CH2C6H4-4-Ph | H, H |
| A2728 | =CPh | CH2C6H4-4-Ph | H, C6H4-4-F |
| A2729 | =CPh | CH2C6H4-2-Cl | H, H |

TABLE 51-continued

| Part A No. | R1 | R2 | R3, R4 |
|---|---|---|---|
| A2730 | =CPh | CH2C6H4-2-Cl | H, C6H4-4-F |
| A2731 | =CPh | (CH2)2Ph | H, H |
| A2732 | =CPh | (CH2)2Ph | H, C6H4-4-F |
| A2733 | =CPh | CH2-piperazino-Ph | H, H |
| A2734 | =CPh | CH2-piperazino-Ph | Me, Me |
| A2735 | =CPh | CH2-piperazino-Ph | Et, Et |
| A2736 | =CPh | CH2-piperazino-Ph | H, Et |
| A2737 | =CPh | CH2-piperazino-Ph | H, Ph |
| A2738 | =CPh | CH2-piperazino-Ph | H, C6H4-4-F |

TABLE 52

| Part A No. | R1 | R2 | R3, R4 |
|---|---|---|---|
| A2739 | =CPh | CH2-piperidino | H, H |
| A2740 | =CPh | CH2-piperidino | H, C6H4-4-F |
| A2741 | =CPh | SPh | H, H |
| A2742 | =CPh | SPh | H, C6H4-4-F |
| A2743 | =CPh | OCH2Ph | H, H |
| A2744 | =CPh | OCH2Ph | H, C6H4-4-F |
| A2745 | =CPh | Ac | H, H |
| A2746 | =CPh | Ac | H, C6H4-4-F |
| A2747 | =CPh | CONH2 | H, H |
| A2748 | =CPh | CONH2 | H, C6H4-4-F |
| A2749 | =CPh | CSNH2 | H, H |
| A2750 | =CPh | CSNH2 | H, C6H4-4-F |
| A2751 | =CPh | OCONH2 | H, H |
| A2752 | =CPh | OCONH2 | H, C6H4-4-F |
| A2753 | =CPh | OCSNH2 | H, H |
| A2754 | =CPh | OCSNH2 | H, C6H4-4-F |
| A2755 | =CPh | OSO2Me | H, H |
| A2756 | =CPh | OSO2Me | H, C6H4-4-F |
| A2757 | =CPh | OSO2Ph | H, H |
| A2758 | =CPh | OSO2Ph | H, C6H4-4-F |
| A2759 | =CPh | I | H, H |
| A2760 | =CPh | I | H, C6H4-4-F |
| A2762 | F | H | Me, Me |
| A2763 | Et | H | Et, Et |
| A2764 | iBu | H | H, Et |
| A2765 | CH=CHMe | H | H, Ph |
| A2766 | OH | H | H, C6H4-4-F |
| A2767 | OEt | Me | H, H |
| A2768 | COPh | Me | Me, Me |
| A2769 | 4-pyridyl | Me | Et, Et |
| A2770 | morpholino | Me | H, Et |
| A2771 | NHiPr | Me | H, Ph |
| A2773 | F | CH2OMe | H, H |
| A2774 | Et | CH2OMe | Me, Me |
| A2775 | iBu | CH2OMe | Et, Et |
| A2776 | CH=CHMe | CH2OMe | H, Et |
| A2777 | OH | CH2OMe | H, Ph |
| A2778 | OEt | CH2OMe | H, C6H4-4-F |
| A2779 | COPh | CF3 | H, H |
| A2780 | 4-pyridyl | CF3 | Me, Me |
| A2781 | morpholino | CF3 | Et, Et |
| A2782 | NHiPr | CF3 | H, Et |
| A2784 | F | CF3 | H, C6H4-4-F |
| A2785 | Et | CH2OH | H, H |

TABLE 53

| Part A No. | R1 | R2 | R3, R4 |
|---|---|---|---|
| A2786 | iBu | CH2OH | H, C6H4-4-F |
| A2787 | CH=CHMe | CH2NHBu | H, H |
| A2788 | OH | CH2NHBu | H, C6H4-4-F |
| A2789 | OEt | CH2C≡CH | H, H |
| A2790 | COPh | CH2C≡CH | H, C6H4-4-F |
| A2791 | 4-pyridyl | OMe | H, H |
| A2792 | morpholino | OMe | H, C6H4-4-F |
| A2793 | NHiPr | NH2 | H, H |
| A2795 | F | NHMe | H, H |

TABLE 53-continued

| Part A No. | R1 | R2 | R3, R4 |
|---|---|---|---|
| A2796 | Et | NHMe | H, C6H4-4-F |
| A2797 | iBu | CH2OPh | H, H |
| A2798 | CH=CHMe | CH2OPh | H, C6H4-4-F |
| A2799 | OH | CH2OCH2Ph | H, H |
| A2800 | OEt | CH2OCH2Ph | H, C6H4-4-F |
| A2801 | COPh | CH2-morpholino | H, H |
| A2802 | 4-pyridyl | CH2-morpholino | H, C6H4-4-F |
| A2803 | morpholino | CH=CH-pyridyl | H, H |
| A2804 | NHiPr | CH=CH-pyridyl | H, C6H4-4-F |
| A2806 | F | C≡CPh | H, C6H4-4-F |
| A2807 | Et | Ph | H, H |
| A2808 | iBu | Ph | H, C6H4-4-F |
| A2809 | CH=CHMe | C6H4-4-CF3 | H, H |
| A2810 | OH | C6H4-4-CF3 | Me, Me |
| A2811 | OEt | C6H4-4-CF3 | Et, Et |
| A2812 | COPh | C6H4-4-CF3 | H, Et |
| A2813 | 4-pyridyl | C6H4-4-CF3 | H, Ph |
| A2814 | morpholino | C6H4-4-CF3 | H, C6H4-4-F |
| A2815 | NHiPr | C6H4-3-CF3 | H, H |
| A2817 | F | C6H4-4-OH | H, H |
| A2818 | Et | C6H4-4-OH | H, C6H4-4-F |
| A2819 | iBu | CH2Ph | H, H |
| A2820 | CH=CHMe | CH2Ph | H, C6H4-4-F |
| A2821 | OH | CH2C6H4-4-CF3 | H, H |
| A2822 | OEt | CH2C6H4-4-CF3 | Me, Me |
| A2823 | COPh | CH2C6H4-4-CF3 | Et, Et |
| A2824 | 4-pyridyl | CH2C6H4-4-CF3 | H, Et |
| A2825 | morpholino | CH2C6H4-4-CF3 | H, Ph |
| A2826 | NHiPr | CH2C6H4-4-CF3 | H, C6H4-4-F |
| A2828 | F | CH2C6H4-4-OCF3 | H, C6H4-4-F |
| A2829 | Et | CH2C6H4-4-Ph | H, H |
| A2830 | iBu | CH2C6H4-4-Ph | H, C6H4-4-F |
| A2831 | CH=CHMe | CH2C6H4-2-Cl | H, H |
| A2832 | OH | CH2C6H4-2-Cl | H, C6H4-4-F |
| A2833 | OEt | (CH2)2Ph | H, H |

TABLE 54

| Part A No. | R1 | R2 | R3, R4 |
|---|---|---|---|
| A2834 | COPh | (CH2)2Ph | H, C6H4-4-F |
| A2835 | 4-pyridyl | CH2-piperazino-Ph | H, H |
| A2836 | morpholino | CH2-piperazino-Ph | Me, Me |
| A2837 | NHiPr | CH2-piperazino-Ph | Et, Et |
| A2839 | F | CH2-piperazino-Ph | H, Ph |
| A2840 | Et | CH2-piperazino-Ph | H, C6H4-4-F |
| A2841 | iBu | CH2-piperidino | H, H |
| A2842 | CH=CHMe | CH2-piperidino | H, C6H4-4-F |
| A2843 | OH | SPh | H, H |
| A2844 | OEt | SPh | H, C6H4-4-F |
| A2845 | COPh | OCH2Ph | H, H |
| A2846 | 4-pyridyl | OCH2Ph | H, C6H4-4-F |
| A2847 | morpholino | Ac | H, H |
| A2848 | NHiPr | Ac | H, C6H4-4-F |
| A2850 | F | CONH2 | H, C6H4-4-F |
| A2851 | Et | CSNH2 | H, H |
| A2852 | iBu | CSNH2 | H, C6H4-4-F |
| A2853 | CH=CHMe | OCONH2 | H, H |
| A2854 | OH | OCONH2 | H, C6H4-4-F |
| A2855 | OEt | OCSNH2 | H, H |
| A2856 | COPh | OCSNH2 | H, C6H4-4-F |
| A2857 | 4-pyridyl | OSO2Me | H, H |
| A2858 | morpholino | OSO2Me | H, C6H4-4-F |
| A2859 | NHiPr | OSO2Ph | H, H |
| A2861 | F | I | H, H |
| A2862 | Et | I | H, C6H4-4-F |
| A3385 | CH2OMe | Me | H, H |
| A3386 | CH2OMe | Me | Me, Me |
| A3387 | CH2OMe | Me | Et, Et |
| A3388 | CH2OMe | Me | H, Et |
| A3389 | CH2OMe | Me | H, Ph |
| A3390 | CH2OMe | Me | H, C6H4-4-F |
| A3397 | CH2OH | Me | H, H |
| A3552 | CH2-piperazino-Ph | CF3 | H, Et |

TABLE 54-continued

| Part A No. | R1 | R2 | R3, R4 |
|---|---|---|---|
| A3553 | CH2-piperazino-Ph | CF3 | H, Ph |
| A3554 | CH2-piperazino-Ph | CF3 | H, C6H4-4-F |
| A3555 | CH2-piperidino | CF3 | H, H |
| A3556 | CH2-piperidino | CF3 | H, C6H4-4-F |
| A3557 | SPh | CF3 | H, H |
| A3558 | SPh | CF3 | H, C6H4-4-F |
| A3559 | OCH2Ph | CF3 | H, H |
| A3560 | OCH2Ph | CF3 | H, C6H4-4-F |
| A3561 | Ac | CF3 | H, H |
| A3562 | Ac | CF3 | H, C6H4-4-F |

TABLE 55

| Part A No. | R1 | R2 | R3, R4 |
|---|---|---|---|
| A3563 | CONH2 | CF3 | H, H |
| A3564 | CONH2 | CF3 | H, C6H4-4-F |
| A3565 | CSNH2 | CF3 | H, H |
| A3566 | CSNH2 | CF3 | H, C6H4-4-F |
| A3567 | OCONH2 | CF3 | H, H |
| A3568 | OCONH2 | CF3 | H, C6H4-4-F |
| A3569 | OCSNH2 | CF3 | H, H |
| A3570 | OCSNH2 | CF3 | H, C6H4-4-F |
| A3571 | OSO2Me | CF3 | H, H |
| A3572 | OSO2Me | CF3 | H, C6H4-4-F |
| A3573 | OSO2Ph | CF3 | H, H |
| A3574 | OSO2Ph | CF3 | H, C6H4-4-F |
| A3575 | I | CF3 | H, H |
| A3576 | I | CF3 | H, C6H4-4-F |
| A3627 | C6H4-4-CF3 | CH=CHPh | Et, Et |
| A3628 | C6H4-4-CF3 | CH=CHPh | H, Et |
| A3629 | C6H4-4-CF3 | CH=CHPh | H, Ph |
| A3630 | C6H4-4-CF3 | CH=CHPh | H, C6H4-4-F |
| A3631 | C6H4-3-CF3 | CH=CHPh | H, H |
| A3632 | C6H4-3-CF3 | CH=CHPh | H, C6H4-4-F |
| A3633 | C6H4-4-OH | CH=CHPh | H, H |
| A3634 | C6H4-4-OH | CH=CHPh | H, C6H4-4-F |
| A3635 | CH2Ph | CH=CHPh | H, H |
| A3636 | CH2Ph | CH=CHPh | H, C6H4-4-F |
| A3637 | CH2C6H4-4-CF3 | CH=CHPh | H, H |
| A3638 | CH2C6H4-4-CF3 | CH=CHPh | Me, Me |
| A3639 | CH2C6H4-4-CF3 | CH=CHPh | Et, Et |
| A3640 | CH2C6H4-4-CF3 | CH=CHPh | H, Et |
| A3641 | CH2C6H4-4-CF3 | CH=CHPh | H, Ph |
| A3642 | CH2C6H4-4-CF3 | CH=CHPh | H, C6H4-4-F |
| A3643 | CH2C6H4-4-OCF3 | CH=CHPh | H, H |
| A3644 | CH2C6H4-4-OCF3 | CH=CHPh | H, C6H4-4-F |
| A3645 | CH2C6H4-4-Ph | CH=CHPh | H, H |
| A3646 | CH2C6H4-4-Ph | CH=CHPh | H, C6H4-4-F |
| A3647 | CH2C6H4-2-Cl | CH=CHPh | H, H |
| A3648 | CH2C6H4-2-Cl | CH=CHPh | H, C6H4-4-F |
| A3649 | (CH2)2Ph | CH=CHPh | H, H |
| A3650 | (CH2)2Ph | CH=CHPh | H, C6H4-4-F |
| A3651 | CH2-piperazino-Ph | CH=CHPh | H, H |
| A3652 | CH2-piperazino-Ph | CH=CHPh | Me, Me |
| A3704 | CH2OH | ≡CPh | H, C6H4-4-F |
| A3705 | CH2NHBu | ≡CPh | H, H |
| A3706 | CH2NHBu | ≡CPh | H, C6H4-4-F |
| A3707 | CH2C≡CH | ≡CPh | H, H |

TABLE 56

| Part A No. | R1 | R2 | R3, R4 |
|---|---|---|---|
| A3708 | CH2C≡CH | ≡CPh | H, C6H4-4-F |
| A3709 | OMe | ≡CPh | H, H |
| A3710 | OMe | ≡CPh | H, C6H4-4-F |
| A3711 | NH2 | ≡CPh | H, H |
| A3712 | NH2 | ≡CPh | H, C6H4-4-F |
| A3713 | NHMe | ≡CPh | H, H |
| A3714 | NHMe | ≡CPh | H, C6H4-4-F |
| A3715 | CH2OPh | ≡CPh | H, H |

TABLE 56-continued

| Part A No. | R1 | R2 | R3, R4 |
|---|---|---|---|
| A3716 | CH2OPh | =CPh | H, C6H4-4-F |
| A3717 | CH2OCH2Ph | =CPh | H, H |
| A3718 | CH2OCH2Ph | =CPh | H, C6H4-4-F |
| A3719 | CH2-morpholino | =CPh | H, H |
| A3720 | CH2-morpholino | =CPh | H, C6H4-4-F |
| A3721 | CH=CH-pyridyl | =CPh | H, H |
| A3722 | CH=CH-pyridyl | =CPh | H, C6H4-4-F |
| A3723 | C≡CPh | =CPh | H, H |
| A3724 | C≡CPh | =CPh | H, C6H4-4-F |
| A3725 | Ph | =CPh | H, H |
| A3726 | Ph | =CPh | H, C6H4-4-F |
| A3727 | C6H4-4-CF3 | =CPh | H, H |
| A3728 | C6H4-4-CF3 | =CPh | Me, Me |
| A3806 | CH2OH | iBu | H, C6H4-4-F |
| A3807 | CH2NHBu | CH=CHMe | H, H |
| A3808 | CH2NHBu | OH | H, C6H4-4-F |
| A3809 | CH2C≡CH | OEt | H, H |
| A3810 | CH2C≡CH | COPh | H, C6H4-4-F |
| A3811 | OMe | 4-pyridyl | H, H |
| A3812 | OMe | morpholino | H, C6H4-4-F |
| A3813 | NH2 | NHiPr | H, H |
| A3814 | NH2 | H | H, C6H4-4-F |
| A3815 | NHMe | F | H, H |
| A3816 | NHMe | Et | H, C6H4-4-F |
| A3817 | CH2OPh | iBu | H, H |
| A3818 | CH2OPh | CH=CHMe | H, C6H4-4-F |
| A3819 | CH2OCH2Ph | OH | H, H |
| A3820 | CH2OCH2Ph | OEt | H, H |
| A3821 | CH2-morpholino | COPh | H, H |
| A3822 | CH2-morpholino | 4-pyridyl | H, C6H4-4-F |
| A3823 | CH=CH-pyridyl | morpholino | H, H |
| A3824 | CH=CH-pyridyl | NHiPr | H, C6H4-4-F |
| A3825 | C≡CPh | H | H, H |
| A3826 | C≡CPh | F | H, C6H4-4-F |
| A3827 | Ph | Et | H, H |
| A3828 | Ph | iBu | H, C6H4-4-F |

TABLE 57

| Part A No. | R1 | R2 | R3, R4 |
|---|---|---|---|
| A3829 | C6H4-4-CF3 | CH=CHMe | H, H |
| A3830 | C6H4-4-CF3 | OH | Me, Me |
| A3831 | C≡CC4H6-4-CF4 | CH=NOH | H, H |
| A3832 | C≡CC4H6-4-CF4 | CH=NOMe | H, H |
| A3833 | C≡CC4H6-4-CF4 | CH=NOEt | H, H |
| A3834 | C≡CC4H6-4-CF4 | CH=NOnPr | H, H |
| A3835 | C≡CC4H6-4-CF4 | CH=NOiPr | H, H |
| A3836 | C≡CC4H6-4-CF4 | CH=NOcPy | H, H |
| A3837 | C≡CC4H6-4-CF4 | CH=NOnBu | H, H |
| A3838 | C≡CC4H6-4-CF4 | CH=NOcBu | H, H |
| A3839 | C≡CC4H6-4-CF4 | CH=NOnPen | H, H |
| A3840 | C≡CC4H6-4-CF4 | CH=NOcPen | H, H |
| A3841 | C≡CC4H6-4-CF4 | CH=NOnHex | H, H |
| A3842 | C≡CC4H6-4-CF4 | CH=NOcHex | H, H |
| A3843 | C≡CC4H6-4-CF4 | CH=NOCH2iPr | H, H |
| A3844 | C≡CC4H6-4-CF4 | CH=NOCH2cPr | H, H |
| A3845 | C≡CC4H6-4-CF4 | CH=NOCH2cBu | H, H |
| A3846 | C≡CC4H6-4-CF4 | CH=NOCH2cPen | H, H |
| A3847 | C≡CC4H6-4-CF4 | CH=NOCH2cHex | H, H |
| A3848 | C≡CC4H6-4-CF4 | CH=NO(CH2)2iPr | H, H |
| A3849 | C≡CC4H6-4-CF4 | CH=NO(CH2)2cPr | H, H |
| A3850 | C≡CC4H6-4-CF4 | CH=NO(CH2)2cBu | H, H |
| A3851 | C≡CC4H6-4-CF4 | CH=NO(CH2)2cPen | H, H |
| A3852 | C≡CC4H6-4-CF4 | CH=NO(CH2)2cHex | H, H |
| A3853 | C≡CC4H6-4-CF4 | CH=NO(CH2)3iPr | H, H |
| A3854 | C≡CC4H6-4-CF4 | CH=NO(CH2)3cPr | H, H |
| A3855 | C≡CC4H6-4-CF4 | CH=NO(CH2)3cBu | H, H |
| A3856 | C≡CC4H6-4-CF4 | CH=NO(CH2)3cPen | H, H |
| A3857 | C≡CC4H6-4-CF4 | CH=NO(CH2)3cHex | H, H |
| A3858 | C≡CC4H6-4-CF4 | —HC=NO-(tetrahydrofuran-3-yl, O) | H, H |
| A3859 | C≡CC4H6-4-CF4 | —HC=NO-(tetrahydrothiophen-3-yl, S) | H, H |
| A3860 | C≡CC4H6-4-CF4 | —HC=NO-(tetrahydrothiophen-3-yl-SO2) | H, H |
| A3861 | C≡CC4H6-4-CF4 | —HC=NO-(pyrrolidin-3-yl, NH) | H, H |
| A3862 | C≡CC4H6-4-CF4 | —HC=NO-(pyrrolidin-3-yl, NMe) | H, H |
| A3863 | C≡CC4H6-4-CF4 | —HC=NO-(pyrrolidin-3-yl, NEt) | H, H |
| A3864 | C≡CC4H6-4-CF4 | —HC=NO-(pyrrolidin-3-yl, NnPr) | H, H |
| A3865 | C≡CC4H6-4-CF4 | —HC=NO-(tetrahydropyran-4-yl, O) | H, H |
| A3866 | C≡CC4H6-4-CF4 | —HC=NO-(tetrahydrothiopyran-4-yl, S) | H, H |
| A3867 | C≡CC4H6-4-CF4 | —HC=NO-(tetrahydrothiopyran-4-yl-SO2) | H, H |

TABLE 58

| Part A No. | R1 | R2 | R3, R4 |
|---|---|---|---|
| A3868 | C≡CC4H6-4-CF4 | —HC=NO-(piperidin-4-yl, NH) | H, H |

TABLE 58-continued

| Part A No. | R1 | R2 | R3, R4 |
|---|---|---|---|
| A3869 | C≡CC4H6-4-CF4 | —HC=NO-(piperidine-NMe) | H, H |
| A3870 | C≡CC4H6-4-CF4 | —HC=NO-(piperidine-NEt) | H, H |
| A3871 | C≡CC4H6-4-CF4 | —HC=NO-(piperidine-NnPr) | H, H |
| A3872 | C≡CC4H6-4-CF4 | —HC=NO-CH2-(tetrahydrofuran-3-yl, O) | H, H |
| A3873 | C≡CC4H6-4-CF4 | —HC=NO-CH2-(tetrahydrothiophene-3-yl, S) | H, H |
| A3874 | C≡CC4H6-4-CF4 | —HC=NO-CH2-(tetrahydrothiophene-3-yl, SO2) | H, H |
| A3875 | C≡CC4H6-4-CF4 | —HC=NO-CH2-(pyrrolidine-NH) | H, H |
| A3876 | C≡CC4H6-4-CF4 | —HC=NO-CH2-(pyrrolidine-NMe) | H, H |
| A3877 | C≡CC4H6-4-CF4 | —HC=NO-CH2-(pyrrolidine-NnPr) | H, H |
| A3878 | C≡CC4H6-4-CF4 | —HC=NO-CH2-(pyrrolidine-NEt) | H, H |
| A3879 | C≡CC4H6-4-CF4 | —HC=NO-CH2-(tetrahydropyran-4-yl, O) | H, H |
| A3880 | C≡CC4H6-4-CF4 | —HC=NO-CH2-(tetrahydrothiopyran-4-yl, S) | H, H |
| A3881 | C≡CC4H6-4-CF4 | —HC=NO-CH2-(tetrahydrothiopyran-4-yl, SO2) | H, H |
| A3882 | C≡CC4H6-4-CF4 | —HC=NO-CH2-(piperidine-4-yl, NH) | H, H |

TABLE 58-continued

| Part A No. | R1 | R2 | R3, R4 |
|---|---|---|---|
| A3883 | C≡CC4H6-4-CF4 | —HC=NO-CH2-(4-piperidinyl-NMe) 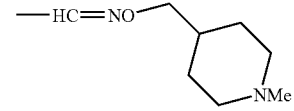 | H, H |
| A3884 | C≡CC4H6-4-CF4 | —HC=NO-CH2-(4-piperidinyl-NEt) 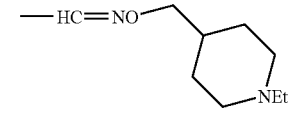 | H, H |
| A3885 | C≡CC4H6-4-CF4 | —HC=NO-CH2-(4-piperidinyl-NnPr) 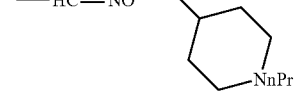 | H, H |
| A3886 | C≡CC4H6-4-CF4 | —HC=NO-CH2-(morpholin-4-yl) 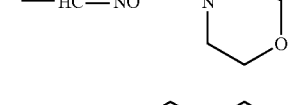 | H, H |
| A3887 | C≡CC4H6-4-CF4 | —HC=NO-CH2-(thiomorpholin-4-yl) 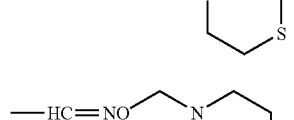 | H, H |
| A3888 | C≡CC4H6-4-CF4 | —HC=NO-CH2-(thiomorpholin-4-yl-S,S-dioxide) 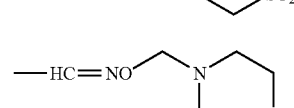 | H, H |
| A3889 | C≡CC4H6-4-CF4 | —HC=NO-CH2-(piperazin-1-yl-NH) 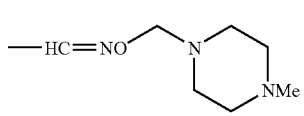 | H, H |
| A3890 | C≡CC4H6-4-CF4 | —HC=NO-CH2-(piperazin-1-yl-NMe) 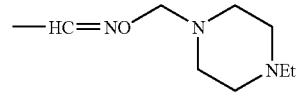 | H, H |
| A3891 | C≡CC4H6-4-CF4 | —HC=NO-CH2-(piperazin-1-yl-NEt) 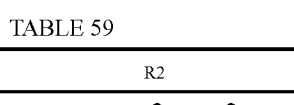 | H, H |

TABLE 59

| Part A No. | R1 | R2 | R3, R4 |
|---|---|---|---|
| A3892 | C≡CC4H6-4-CF4 | —HC=NO-CH2-(piperazin-1-yl-NnPr) 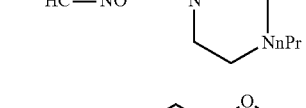 | H, H |
| A3893 | C≡CC4H6-4-CF4 | —HC=NO-CH2-(furan-2-yl)  | H, H |
| A3894 | C≡CC4H6-4-CF4 | —HC=NO-CH2-(furan-3-yl) 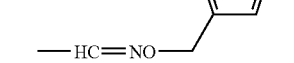 | H, H |

TABLE 59-continued

| Part A No. | R1 | R2 | R3, R4 |
|---|---|---|---|
| A3895 | C≡CC4H6-4-CF4 | —HC=NO-CH2-(thiazol-2-yl) | H, H |
| A3896 | C≡CC4H6-4-CF4 | —HC=NO-CH2-(thien-2-yl) | H, H |
| A3897 | C≡CC4H6-4-CF4 | —HC=NO-CH2-(thien-3-yl) | H, H |
| A3898 | C≡CC4H6-4-CF4 | —HC=NO-CH2-(pyridin-3-yl) | H, H |
| A3899 | C≡CC4H6-4-CF4 | —HC=NO-CH2-(pyridin-4-yl) | H, H |
| A3900 | C≡CC4H6-4-CF4 | —HC=NO-CH2CH2-NHSO$_2$Me | H, H |
| A3901 | C≡CC4H6-4-CF4 | —HC=NO-CH2CH2-NHSO$_2$Et | H, H |
| A3902 | C≡CC4H6-4-CF4 | —HC=NO-CH2CH2-NHSO$_2$nPr | H, H |
| A3903 | C≡CC4H6-4-CF4 | —HC=NO-CH2CH2-NHSO$_2$Ph | H, H |
| A3904 | C≡CC4H6-4-CF4 | —HC=NO-(CH2)3-NHSO$_2$Me | H, H |
| A3905 | C≡CC4H6-4-CF4 | —HC=NO-(CH2)3-NHSO$_2$Et | H, H |
| A3906 | C≡CC4H6-4-CF4 | —HC=NO-(CH2)3-NHSO$_2$Pr | H, H |
| A3907 | C≡CC4H6-4-CF4 | —HC=NO-(CH2)3-NHSO$_2$Ph | H, H |
| A3908 | C≡CC4H6-4-CF4 | CH2OcPr | H, H |
| A3909 | C≡CC4H6-4-CF4 | CH2OcBu | H, H |
| A3910 | C≡CC4H6-4-CF4 | CH2OcPen | H, H |
| A3911 | C≡CC4H6-4-CF4 | CH2OcHex | H, H |
| A3912 | C≡CC4H6-4-CF4 | CH2OCH2cPr | H, H |
| A3913 | C≡CC4H6-4-CF4 | CH2OCH2cBu | H, H |
| A3914 | C≡CC4H6-4-CF4 | CH2OCH2cPen | H, H |
| A3915 | C≡CC4H6-4-CF4 | CH2OCH2cHex | H, H |
| A3916 | C≡CC4H6-4-CF4 | CH2O(CH2)2cPr | H, H |
| A3917 | C≡CC4H6-4-CF4 | CH2O(CH2)2cBu | H, H |
| A3918 | C≡CC4H6-4-CF4 | CH2O(CH2)2cPen | H, H |
| A3919 | C≡CC4H6-4-CF4 | CH2O(CH2)2cHex | H, H |
| A3920 | C≡CC4H6-4-CF4 | CH2O(CH2)3cPr | H, H |
| A3921 | C≡CC4H6-4-CF4 | CH2O(CH2)3cBu | H, H |
| A3922 | C≡CC4H6-4-CF4 | CH2O(CH2)3cPen | H, H |
| A3923 | C≡CC4H6-4-CF4 | CH2O(CH2)3cHex | H, H |
| A3924 | C≡CC4H6-4-CF4 | CH2O-(tetrahydrofuran-3-yl) | H, H |

TABLE 59-continued

| Part A No. | R1 | R2 | R3, R4 |
|---|---|---|---|
| A3925 | C≡CC4H6-4-CF4 | 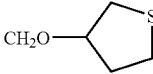 | H, H |

TABLE 60

| Part A No. | R1 | R2 | R3, R4 |
|---|---|---|---|
| A3926 | C≡CC4H6-4-CF4 | CH₂O-pyrrolidine-NH | H, H |
| A3927 | C≡CC4H6-4-CF4 | CH₂O-pyrrolidine-NMe | H, H |
| A3928 | C≡CC4H6-4-CF4 | CH₂O-pyrrolidine-NEt | H, H |
| A3929 | C≡CC4H6-4-CF4 | CH₂O-pyrrolidine-NnPr | H, H |
| A3930 | C≡CC4H6-4-CF4 | CH₂O-tetrahydropyran-O | H, H |
| A3931 | C≡CC4H6-4-CF4 | CH₂O-tetrahydrothiopyran-S | H, H |
| A3932 | C≡CC4H6-4-CF4 | CH₂O-tetrahydrothiopyran-SO₂ | H, H |
| A3933 | C≡CC4H6-4-CF4 | CH₂O-piperidine-NH | H, H |
| A3934 | C≡CC4H6-4-CF4 | CH₂O-piperidine-NMe | H, H |
| A3935 | C≡CC4H6-4-CF4 | CH₂O-piperidine-NEt | H, H |
| A3936 | C≡CC4H6-4-CF4 | CH₂O-piperidine-NnPr | H, H |
| A3937 | C≡CC4H6-4-CF4 | CH₂OCH₂-tetrahydrofuran-O | H, H |
| A3938 | C≡CC4H6-4-CF4 | CH₂OCH₂-tetrahydrothiophene-S | H, H |
| A3939 | C≡CC4H6-4-CF4 | CH₂OCH₂-tetrahydrothiophene-SO₂ | H, H |
| A3940 | C≡CC4H6-4-CF4 | CH₂OCH₂-pyrrolidine-NH | H, H |
| A3941 | C≡CC4H6-4-CF4 | CH₂OCH₂-pyrrolidine-NMe | H, H |
| A3942 | C≡CC4H6-4-CF4 | CH₂OCH₂-pyrrolidine-NnPr | H, H |
| A3943 | C≡CC4H6-4-CF4 | CH₂OCH₂-pyrrolidine-NEt | H, H |
| A3944 | C≡CC4H6-4-CF4 | CH₂OCH₂-tetrahydropyran-O | H, H |
| A3945 | C≡CC4H6-4-CF4 | CH₂OCH₂-tetrahydrothiopyran-S | H, H |
| A3946 | C≡CC4H6-4-CF4 | CH₂OCH₂-tetrahydrothiopyran-SO₂ | H, H |
| A3947 | C≡CC4H6-4-CF4 | CH₂OCH₂-piperidine-NH | H, H |
| A3948 | C≡CC4H6-4-CF4 | CH₂OCH₂-piperidine-NMe | H, H |
| A3949 | C≡CC4H6-4-CF4 | CH₂OCH₂-piperidine-NEt | H, H |

TABLE 60-continued

| Part A No. | R1 | R2 | R3, R4 |
|---|---|---|---|
| A3950 | C≡CC4H6-4-CF4 | CH₂O-(4-piperidinyl-N-nPr) | H, H |

TABLE 61

| Part A No. | R1 | R2 | R3, R4 |
|---|---|---|---|
| A3951 | C≡CC4H6-4-CF4 | CH₂O-CH₂-(morpholin-4-yl) | H, H |
| A3952 | C≡CC4H6-4-CF4 | CH₂O-CH₂-(thiomorpholin-4-yl) | H, H |
| A3953 | C≡CC4H6-4-CF4 | CH₂O-CH₂-(thiomorpholin-4-yl-S,S-dioxide) | H, H |
| A3954 | C≡CC4H6-4-CF4 | CH₂O-CH₂-(piperazin-4-yl-NH) | H, H |
| A3955 | C≡CC4H6-4-CF4 | CH₂O-CH₂-(piperazin-4-yl-NMe) | H, H |
| A3956 | C≡CC4H6-4-CF4 | CH₂O-CH₂-(piperazin-4-yl-NEt) | H, H |
| A3957 | C≡CC4H6-4-CF4 | CH₂O-CH₂-(piperazin-4-yl-NnPr) | H, H |
| A3958 | C≡CC4H6-4-CF4 | CH₂O-CH₂-(furan-2-yl) | H, H |
| A3959 | C≡CC4H6-4-CF4 | CH₂O-CH₂CH₂-(furan-2-yl) | H, H |
| A3960 | C≡CC4H6-4-CF4 | CH₂O-CH₂-(thiazol-2-yl) | H, H |
| A3961 | C≡CC4H6-4-CF4 | CH₂O-CH₂-(thiophen-2-yl) | H, H |
| A3962 | C≡CC4H6-4-CF4 | CH₂O-CH₂-(thiophen-3-yl) | H, H |
| A3963 | C≡CC4H6-4-CF4 | CH₂O-CH₂-(pyridin-3-yl) | H, H |
| A3964 | C≡CC4H6-4-CF4 | CH₂O-CH₂-(pyridin-4-yl) | H, H |
| A3965 | C≡CC4H6-4-CF4 | CH₂O-CH₂CH₂-NHSO₂Me | H, H |
| A3966 | C≡CC4H6-4-CF4 | CH₂O-CH₂CH₂-NHSO₂Et | H, H |
| A3967 | C≡CC4H6-4-CF4 | CH₂O-CH₂CH₂-NHSO₂nPr | H, H |
| A3968 | C≡CC4H6-4-CF4 | CH₂O-CH₂CH₂-NHSO₂Ph | H, H |
| A3969 | C≡CC4H6-4-CF4 | CH₂O-(CH₂)₃-NHSO₂Me | H, H |
| A3970 | C≡CC4H6-4-CF4 | CH₂O-(CH₂)₃-NHSO₂Et | H, H |
| A3971 | C≡CC4H6-4-CF4 | CH₂O-(CH₂)₃-NHSO₂nPr | H, H |
| A3972 | C≡CC4H6-4-CF4 | CH₂O-(CH₂)₃-NHSO₂Ph | H, H |
| A3973 | C≡CC4H6-4-CF4 | CH2ON=CHCH3 | H, H |
| A3974 | C≡CC4H6-4-CF4 | CH2ON=CH(CH3)2 | H, H |
| A3975 | C≡CC4H6-4-CF4 | CH₂O-N=cyclopentylidene | H, H |
| A3976 | C≡CC4H6-4-CF4 | CH₂O-N=cyclohexylidene | H, H |
| A3977 | 4-benzofuryl | CH=NOH | H, H |
| A3978 | 4-benzofuryl | CH=NOMe | H, H |
| A3979 | 4-benzofuryl | CH=NOEt | H, H |
| A3980 | 4-benzofuryl | CH=NOnPr | H, H |

TABLE 62

| Part A No. | R1 | R2 | R3, R4 |
|---|---|---|---|
| A3981 | 4-benzofuryl | CH=NOiPr | H, H |
| A3982 | 4-benzofuryl | CH=NOcPr | H, H |
| A3983 | 4-benzofuryl | CH=NOnBu | H, H |
| A3984 | 4-benzofuryl | CH=NOcBu | H, H |
| A3985 | 4-benzofuryl | CH=NOnPen | H, H |
| A3986 | 4-benzofuryl | CH=NOcPen | H, H |
| A3987 | 4-benzofuryl | CH=NOnHex | H, H |
| A3988 | 4-benzofuryl | CH=NOcHex | H, H |
| A3989 | 4-benzofuryl | CH=NOCH2iPr | H, H |
| A3990 | 4-benzofuryl | CH=NOCH2cPr | H, H |
| A3991 | 4-benzofuryl | CH=NOCH2cBu | H, H |

TABLE 62-continued

| Part A No. | R1 | R2 | R3, R4 |
|---|---|---|---|
| A3992 | 4-benzofuryl | CH=NOCH2cPen | H, H |
| A3993 | 4-benzofuryl | CH=NOCH2cHex | H, H |
| A3994 | 4-benzofuryl | CH=NO(CH2)2iPr | H, H |
| A3995 | 4-benzofuryl | CH=NO(CH2)2cPr | H, H |
| A3996 | 4-benzofuryl | CH=NO(CH2)2cBu | H, H |
| A3997 | 4-benzofuryl | CH=N0(CH2)2cPen | H, H |
| A3998 | 4-benzofuryl | CH=NO(CH2)2cHex | H, H |
| A3999 | 4-benzofuryl | CH=NO(CH2)3iPr | H, H |
| A4000 | 4-benzofuryl | CH=NO(CH2)3cPr | H, H |
| A4001 | 4-benzofuryl | CH=NO(CH2)3cBu | H, H |
| A4002 | 4-benzofuryl | CH=NO(CH2)3cPen | H, H |
| A4003 | 4-benzofuryl | CH=NO(CH2)3cHex | H, H |
| A4004 | 4-benzofuryl | 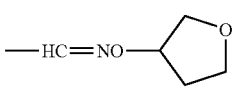 | H, H |
| A4005 | 4-benzofuryl | 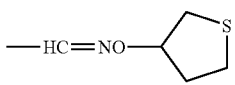 | H, H |
| A4006 | 4-benzofuryl | 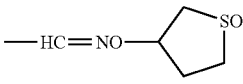 | H, H |
| A4007 | 4-benzofuryl | 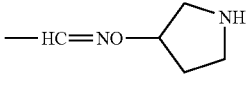 | H, H |
| A4008 | 4-benzofuryl | 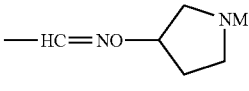 | H, H |
| A4009 | 4-benzofuryl | 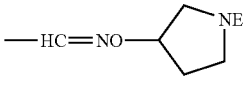 | H, H |
| A4010 | 4-benzofuryl | 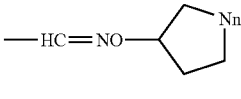 | H, H |
| A4011 | 4-benzofuryl | 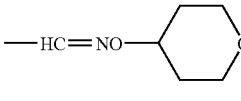 | H, H |
| A4012 | 4-benzofuryl | 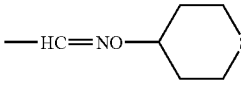 | H, H |
| A4013 | 4-benzofuryl | 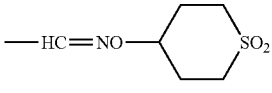 | H, H |
| A4014 | 4-benzofuryl | 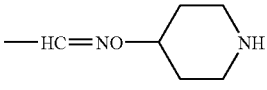 | H, H |
| A4015 | 4-benzofuryl | 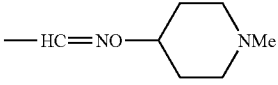 | H, H |
| A4016 | 4-benzofuryl | 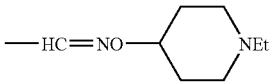 | H, H |
| A4017 | 4-benzofuryl | 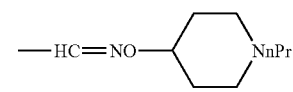 | H, H |

TABLE 63

| Part A No. | R1 | R2 | R3, R4 |
|---|---|---|---|
| A4018 | 4-benzofuryl | 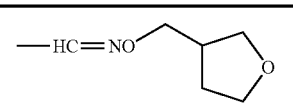 | H, H |
| A4019 | 4-benzofuryl | 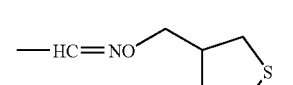 | H, H |
| A4020 | 4-benzofuryl | 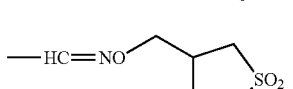 | H, H |
| A4021 | 4-benzofuryl | 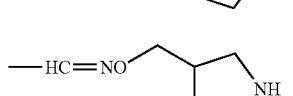 | H, H |
| A4022 | 4-benzofuryl | 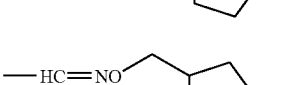 | H, H |
| A4023 | 4-benzofuryl | 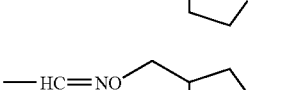 | H, H |
| A4024 | 4-benzofuryl | 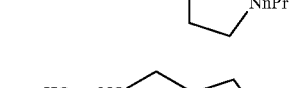 | H, H |
| A4025 | 4-benzofuryl |  | H, H |
| A4026 | 4-benzofuryl |  | H, H |
| A4027 | 4-benzofuryl | 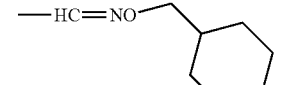 | H, H |
| A4028 | 4-benzofuryl | 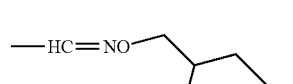 | H, H |

TABLE 63-continued

| Part A No. | R1 | R2 | R3, R4 |
|---|---|---|---|
| A4029 | 4-benzofuryl | —HC=NO-CH2-(piperidine-NMe) | H, H |
| A4030 | 4-benzofuryl | —HC=NO-CH2-(piperidine-NEt) | H, H |
| A4031 | 4-benzofuryl | —HC=NO-CH2-(piperidine-NnPr) | H, H |
| A4032 | 4-benzofuryl | —HC=NO-CH2-morpholine | H, H |
| A4033 | 4-benzofuryl | —HC=NO-CH2-thiomorpholine | H, H |
| A4034 | 4-benzofuryl | —HC=NO-CH2-thiomorpholine-SO2 | H, H |
| A4035 | 4-benzofuryl | —HC=NO-CH2-(piperazine-NH) | H, H |
| A4036 | 4-benzofuryl | —HC=NO-CH2-(piperazine-NMe) | H, H |
| A4037 | 4-benzofuryl | —HC=NO-CH2-(piperazine-NEt) | H, H |
| A4038 | 4-benzofuryl | —HC=NO-CH2-(piperazine-NnPr) | H, H |
| A4039 | 4-benzofuryl | —HC=NO-CH2-(2-furyl) | H, H |
| A4040 | 4-benzofuryl | —HC=NO-CH2-(3-furyl) | H, H |
| A4041 | 4-benzofuryl | —HC=NO-CH2-(2-thiazolyl) | H, H |

TABLE 64

| Part A No. | R1 | R2 | R3, R4 |
|---|---|---|---|
| A4042 | 4-benzofuryl | —HC=NO-CH2-(2-thienyl) | H, H |
| A4043 | 4-benzofuryl | —HC=NO-CH2-(3-thienyl) | H, H |
| A4044 | 4-benzofuryl | —HC=NO-CH2-(3-pyridyl) | H, H |
| A4045 | 4-benzofuryl | —HC=NO-CH2-(4-pyridyl) | H, H |
| A4046 | 4-benzofuryl | —HC=NO-(CH2)2-NHSO2Me | H, H |
| A4047 | 4-benzofuryl | —HC=NO-(CH2)2-NHSO2Et | H, H |
| A4048 | 4-benzofuryl | —HC=NO-(CH2)2-NHSO2nPr | H, H |
| A4049 | 4-benzofuryl | —HC=NO-(CH2)2-NHSO2Ph | H, H |
| A4050 | 4-benzofuryl | —HC=NO-(CH2)3-NHSO2Me | H, H |
| A4051 | 4-benzofuryl | —HC=NO-(CH2)3-NHSO2Et | H, H |
| A4052 | 4-benzofuryl | —HC=NO-(CH2)3-NHSO2nPr | H, H |
| A4053 | 4-benzofuryl | —HC=NO-(CH2)3-NHSO2Ph | H, H |
| A4054 | 4-benzofuryl | CH2OcPr | H, H |
| A4055 | 4-benzofuryl | CH2OcBu | H, H |
| A4056 | 4-benzofuryl | CH2OcPen | H, H |
| A4057 | 4-benzofuryl | CH2OcHex | H, H |
| A4058 | 4-benzofuryl | CH2OCH2cPr | H, H |
| A4059 | 4-benzofuryl | CH2OCH2cBu | H, H |
| A4060 | 4-benzofuryl | CH2OCH2cPen | H, H |
| A4061 | 4-benzofuryl | CH2OCH2cHex | H, H |
| A4062 | 4-benzofuryl | CH2O(CH2)2cPr | H, H |
| A4063 | 4-benzofuryl | CH2O(CH2)2cBu | H, H |
| A4064 | 4-benzofuryl | CH2O(CH2)2cPen | H, H |
| A4065 | 4-benzofuryl | CH2O(CH2)2cHex | H, H |
| A4066 | 4-benzofuryl | CH2O(CH2)3cPr | H, H |
| A4067 | 4-benzofuryl | CH2O(CH2)3cBu | H, H |
| A4068 | 4-benzofuryl | CH2O(CH2)3cPen | H, H |
| A4069 | 4-benzofuryl | CH2O(CH2)3cHex | H, H |
| A4070 | 4-benzofuryl | CH2O-(tetrahydrofuran-3-yl) | H, H |
| A4071 | 4-benzofuryl | CH2O-(tetrahydrothiophen-3-yl) | H, H |

TABLE 64-continued

| Part A No. | R1 | R2 | R3, R4 |
|---|---|---|---|
| A4072 | 4-benzofuryl | CH₂O-tetrahydrothiophene-SO₂ | H, H |
| A4073 | 4-benzofuryl | CH₂O-pyrrolidine-NH | H, H |
| A4074 | 4-benzofuryl | CH₂O-pyrrolidine-NMe | H, H |
| A4075 | 4-benzofuryl | CH₂O-pyrrolidine-NEt | H, H |
| A4076 | 4-benzofuryl | CH₂O-pyrrolidine-NnPr | H, H |
| A4077 | 4-benzofuryl | CH₂O-tetrahydropyran-O | H, H |

TABLE 65

| Part A No. | R1 | R2 | R3, R4 |
|---|---|---|---|
| A4078 | 4-benzofuryl | CH₂O-tetrahydrothiopyran-S | H, H |
| A4079 | 4-benzofuryl | CH₂O-tetrahydrothiopyran-SO₂ | H, H |
| A4080 | 4-benzofuryl | CH₂O-piperidine-NH | H, H |
| A4081 | 4-benzofuryl | CH₂O-piperidine-NMe | H, H |
| A4082 | 4-benzofuryl | CH₂O-piperidine-NEt | H, H |
| A4083 | 4-benzofuryl | CH₂O-piperidine-NnPr | H, H |
| A4084 | 4-benzofuryl | CH₂O-CH₂-tetrahydrofuran-O | H, H |
| A4085 | 4-benzofuryl | CH₂O-CH₂-tetrahydrothiophene-S | H, H |

TABLE 65-continued

| Part A No. | R1 | R2 | R3, R4 |
|---|---|---|---|
| A4086 | 4-benzofuryl | CH₂O-CH₂-tetrahydrothiophene-SO₂ | H, H |
| A4087 | 4-benzofuryl | CH₂O-CH₂-pyrrolidine-NH | H, H |
| A4088 | 4-benzofuryl | CH₂O-CH₂-pyrrolidine-NMe | H, H |
| A4089 | 4-benzofuryl | CH₂O-CH₂-pyrrolidine-NnPr | H, H |
| A4090 | 4-benzofuryl | CH₂O-CH₂-pyrrolidine-NEt | H, H |
| A4091 | 4-benzofuryl | CH₂O-CH₂-tetrahydropyran-O | H, H |
| A4092 | 4-benzofuryl | CH₂O-CH₂-tetrahydrothiopyran-S | H, H |
| A4093 | 4-benzofuryl | CH₂O-CH₂-tetrahydrothiopyran-SO₂ | H, H |
| A4094 | 4-benzofuryl | CH₂O-CH₂-piperidine-NH | H, H |
| A4095 | 4-benzofuryl | CH₂O-CH₂-piperidine-NMe | H, H |
| A4096 | 4-benzofuryl | CH₂O-CH₂-piperidine-NEt | H, H |
| A4097 | 4-benzofuryl | CH₂O-CH₂-piperidine-NnPr | H, H |
| A4098 | 4-benzofuryl | CH₂O-CH₂-morpholine | H, H |

TABLE 65-continued

| Part A No. | R1 | R2 | R3, R4 |
|---|---|---|---|
| A4099 | 4-benzofuryl | CH₂O-CH₂-N(thiomorpholine-S) | H, H |
| A4100 | 4-benzofuryl | CH₂O-CH₂-N(thiomorpholine-SO₂) | H, H |
| A4101 | 4-benzofuryl | CH₂O-CH₂-N(piperazine-NH) | H, H |

TABLE 66

| Part A No. | R1 | R2 | R3, R4 |
|---|---|---|---|
| A4102 | 4-benzofuryl | CH₂O-CH₂-N(piperazine-NMe) | H, H |
| A4103 | 4-benzofuryl | CH₂O-CH₂-N(piperazine-NEt) | H, H |
| A4104 | 4-benzofuryl | CH₂O-CH₂-N(piperazine-NnPr) | H, H |
| A4105 | 4-benzofuryl | CH₂O-CH₂-(2-furyl) | H, H |
| A4106 | 4-benzofuryl | CH₂O-CH₂CH₂-(2-furyl) | H, H |
| A4107 | 4-benzofuryl | CH₂O-CH₂-(2-thiazolyl) | H, H |
| A4108 | 4-benzofuryl | CH₂O-CH₂-(2-thienyl) | H, H |
| A4109 | 4-benzofuryl | CH₂O-CH₂-(3-thienyl) | H, H |
| A4110 | 4-benzofuryl | CH₂O-CH₂-(3-pyridyl) | H, H |
| A4111 | 4-benzofuryl | CH₂O-CH₂-(4-pyridyl) | H, H |

TABLE 66-continued

| Part A No. | R1 | R2 | R3, R4 |
|---|---|---|---|
| A4112 | 4-benzofuryl | CH₂O-CH₂CH₂-NHSO₂Me | H, H |
| A4113 | 4-benzofuryl | CH₂O-CH₂CH₂-NHSO₂Et | H, H |
| A4114 | 4-benzofuryl | CH₂O-CH₂CH₂-NHSO₂nPr | H, H |
| A4115 | 4-benzofuryl | CH₂O-CH₂CH₂-NHSO₂Ph | H, H |
| A4116 | 4-benzofuryl | CH₂O-(CH₂)₃-NHSO₂Me | H, H |
| A4117 | 4-benzofuryl | CH₂O-(CH₂)₃-NHSO₂Et | H, H |
| A4118 | 4-benzofuryl | CH₂O-(CH₂)₃-NHSO₂nPr | H, H |
| A4119 | 4-benzofuryl | CH₂O-(CH₂)₃-NHSO₂Ph | H, H |
| A4120 | 4-benzofuryl | CH2ON=CHCH3 | H, H |
| A4121 | 4-benzofuryl | CH2ON=CH(CH3)2 | H, H |
| A4122 | 4-benzofuryl | CH₂O-N=cyclopentylidene | H, H |
| A4123 | 4-benzofuryl | CH₂O-N=cyclohexylidene | H, H |
| A4124 | C≡CC4H6-4-CF | CH₂O-(tetrahydrothiophene-SO₂) | H, H |

2) A compound wherein the part (Part B) of the formula:

[Formula 16]

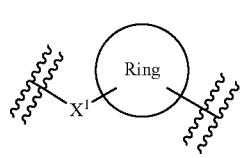

is the one of the followings.

TABLE 67

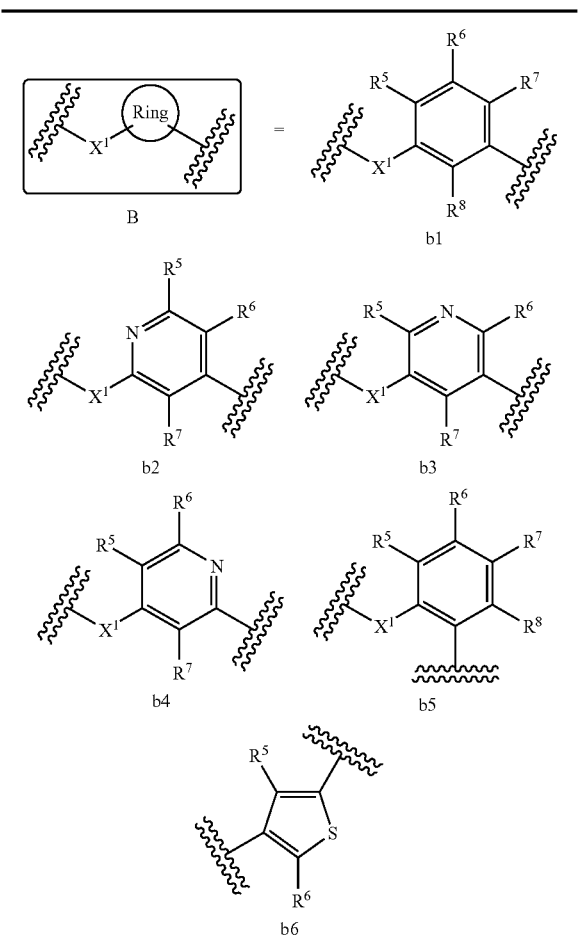

| Part B No. | Type | X1 | R5, R6, R7, R8 |
|---|---|---|---|
| B1 | b1 | S | H, H, H, H |
| B2 | b1 | S | H, Me, H, H |
| B3 | b1 | S | H, nPr, H, H |
| B4 | b1 | S | H, OCH2CF3, H, H |
| B5 | b1 | S | H, OH, H, H |
| B6 | b1 | S | H, OMe, H, H |
| B7 | b1 | S | H, SMe, H, H |
| B8 | b1 | S | Me, H, H, H |
| B9 | b1 | S | OMe, H, H, H |
| B10 | b1 | S | H, SPh, H, H |
| B11 | b1 | S | Me, Me, Me, Me |
| B12 | b1 | S | H, Me, H, Me |
| B13 | b1 | S | OCH2CF3, H, H, H |
| B14 | b1 | S | Cl, Cl, H, H |
| B15 | b1 | S | Cl, H, H, H |
| B16 | b1 | S | H, Cl, H, H |
| B17 | b1 | S | H, F, H, H |
| B18 | b1 | S | F, F, H, H |
| B19 | b1 | S | F, H, H, H |
| B20 | b1 | S | H, CH2CH=CH2, H, H |
| B21 | b1 | S | Et, H, H, H |
| B22 | b1 | S | nPr, H, H, H |
| B23 | b1 | S | CF3, H, H, H |
| B24 | b1 | S | CN, H, H, H |
| B25 | b1 | S | H, Et, H, H |
| B26 | b1 | S | H, CF3, H, H |
| B27 | b1 | S | H, CN, H, H |

TABLE 68

| Part B No. | Type | X1 | R5, R6, R7, R8 |
|---|---|---|---|
| B28 | b1 | S | H, H, H, Me |
| B29 | b1 | S | H, H, H, F |
| B30 | b1 | S | H, H, H, Cl |
| B31 | b1 | S | H, H, H, OMe |
| B32 | b1 | S | H, H, H, OH |
| B33 | b1 | S | H, H, Me, H |
| B34 | b1 | S | H, H, Et, H |
| B35 | b1 | S | H, H, nPr, H |
| B36 | b1 | S | H, H, F, H |
| B37 | b1 | S | H, H, Cl, H |
| B38 | b1 | S | H, H, Br, H |
| B39 | b1 | S | H, H, OMe, H |
| B40 | b1 | S | H, H, CF3, H |
| B41 | b1 | S | H, H, CN, H |
| B42 | b1 | S | H, H, C≡CH, H |
| B43 | b1 | S | H, H, CH=CH2, H |
| B44 | b1 | O | H, H, H, H |
| B45 | b1 | O | H, Me, H, H |
| B46 | b1 | O | H, nPr, H, H |
| B47 | b1 | O | H, OCH2CF3, H, H |
| B48 | b1 | O | H, OH, H, H |
| B49 | b1 | O | H, OMe, H, H |
| B50 | b1 | O | H, SMe, H, H |
| B51 | b1 | O | Me, H, H, H |
| B52 | b1 | O | OMe, H, H, H |
| B53 | b1 | O | Me, Me, H, H |
| B54 | b1 | O | Me, Me, Me, Me |
| B55 | b1 | O | H, OPh, H, H |
| B56 | b1 | O | OCH2CF3, H, H, H |
| B57 | b1 | O | Cl, Cl, H, H |
| B58 | b1 | O | Cl, H, H, H |
| B59 | b1 | O | H, Cl, H, H |
| B60 | b1 | O | H, F, H, H |
| B61 | b1 | O | F, F, H, H |
| B62 | b1 | O | F, H, H, H |
| B63 | b1 | O | H, CH2CH=CH2, H, H |
| B64 | b1 | O | Et, H, H, H |
| B65 | b1 | O | nPr, H, H, H |
| B66 | b1 | O | CF3, H, H, H |
| B67 | b1 | O | CN, H, H, H |
| B68 | b1 | O | H, Et, H, H |
| B69 | b1 | O | H, CF3, H, H |
| B70 | b1 | O | H, CN, H, H |
| B71 | b1 | O | H, H, H, Me |

TABLE 69

| Part B No. | Type | X1 | R5, R6, R7, R8 |
|---|---|---|---|
| B72 | b1 | O | H, H, H, F |
| B73 | b1 | O | H, H, H, Cl |
| B74 | b1 | O | H, H, H, OMe |
| B75 | b1 | O | H, H, H, OH |
| B76 | b1 | O | H, H, Me, H |
| B77 | b1 | O | H, H, Et, H |
| B78 | b1 | O | H, H, nPr, H |
| B79 | b1 | O | H, H, F, H |
| B80 | b1 | O | H, H, Cl, H |
| B81 | b1 | O | H, H, Br, H |
| B82 | b1 | O | H, H, OMe, H |
| B83 | b1 | O | H, H, CF3, H |
| B84 | b1 | O | H, H, CN, H |
| B85 | b1 | O | H, H, C≡CH, H |
| B86 | b1 | O | H, H, CH=CH2, H |
| B87 | b1 | CH2CO | H, H, H, H |
| B88 | b1 | CH2CO | H, Me, H, H |
| B89 | b1 | CH2CO | H, nPr, H, H |
| B90 | b1 | CH2CO | H, OCH2CF3, H, H |
| B91 | b1 | CH2CO | H, OH, H, H |
| B92 | b1 | CH2CO | H, OMe, H, H |
| B93 | b1 | CH2CO | H, SMe, H, H |
| B94 | b1 | CH2CO | Cl, H, H, H |
| B95 | b1 | CH2CO | OMe, H, H, H |
| B96 | b1 | CH2CO | Me, Me, H, H |

TABLE 69-continued

| Part B No. | Type | X1 | R5, R6, R7, R8 |
|---|---|---|---|
| B97 | b1 | CH2CO | Me, CH=CH2, Me, Me |
| B98 | b1 | CH2CO | H, Me, H, NHMe |
| B99 | b1 | CH2CO | OCH2CF3, H, H, H |
| B100 | b1 | CH2CO | Cl, Cl, H, H |
| B101 | b1 | CH2CO | Cl, H, H, H |
| B102 | b1 | CH2CO | H, F, H, H |
| B103 | b1 | CH2CO | H, CH2CH=CH2, H, H |
| B104 | b1 | NH | H, H, H, H |
| B105 | b1 | NH | H, Me, H, H |
| B106 | b1 | NH | H, nPr, H, H |
| B107 | b1 | NH | H, OCH2CF3, H, H |
| B108 | b1 | NH | H, OH, H, H |
| B109 | b1 | NH | H, OMe, H, H |
| B110 | b1 | NH | H, SMe, H, H |
| B111 | b1 | NH | Me, H, H, H |
| B112 | b1 | NH | OMe, H, H, H |
| B113 | b1 | NH | Me, C≡CH, H, H |
| B114 | b1 | NH | Me, Me, Me, Me |
| B115 | b1 | NH | H, Ac, H, H |

TABLE 70

| Part B No. | Type | X1 | R5, R6, R7, R8 |
|---|---|---|---|
| B116 | b1 | NH | OCH2CF3, H, H, H |
| B117 | b1 | NH | Cl, Cl, H, H |
| B118 | b1 | NH | Cl, H, H, H |
| B119 | b1 | NH | H, F, H, H |
| B120 | b1 | NH | H, CH2CH=CH2, H, H |
| B121 | b1 | NMe | H, H, H, H |
| B122 | b1 | NMe | H, Me, H, H |
| B123 | b1 | NMe | H, nPr, H, H |
| B124 | b1 | NMe | H, OCH2CF3, H, H |
| B125 | b1 | NMe | H, OH, H, H |
| B126 | b1 | NMe | H, OMe, H, H |
| B127 | b1 | NMe | H, SMe, H, H |
| B128 | b1 | NMe | Me, H, H, H |
| B129 | b1 | NMe | H, Ph, H, H |
| B130 | b1 | NMe | Me, Me, H, H |
| B131 | b1 | NMe | Me, Me, Me, Me |
| B132 | b1 | NMe | H, Me, H, Me |
| B133 | b1 | NMe | OCH2CF3, H, H, H |
| B134 | b1 | NMe | Cl, Cl, H, H |
| B135 | b1 | NMe | Cl, H, H, H |
| B136 | b1 | NMe | H, F, H, H |
| B137 | b1 | NMe | H, CH2CH=CH2, H, H |
| B138 | b1 | NEt | H, H, H, H |
| B139 | b1 | NEt | H, Me, H, H |
| B140 | b1 | NCH2Ph | H, nPr, H, H |
| B141 | b1 | NCH2Ph | H, H, H, H |
| B142 | b1 | NAc | H, OCH2CF3, H, H |
| B143 | b1 | NAc | H, H, H, H |
| B144 | b1 | NCOEt | H, OMe, H, H |
| B145 | b1 | NCOEt | H, H, H, H |
| B146 | b1 | NCOPh | Me, H, H, H |
| B147 | b1 | NCOPh | H, H, H, H |
| B148 | b1 | NSO2Me | H, Ph, H, H |
| B149 | b1 | NSO2Me | H, H, H, H |
| B150 | b1 | NSO2Et | Me, Me, H, H |
| B151 | b1 | NSO2Et | H, H, H, H |
| B152 | b1 | NSO2Ph | Me, Me, Me, Me |
| B153 | b1 | NSO2Ph | H, H, H, H |
| B154 | b1 | NSO2C6H4-p-Me | OCH2CF3, H, H, H |
| B155 | b1 | NSO2C6H4-p-Me | H, H, H, H |
| B156 | b1 | 4-piperadin-1-yl | H, H, H, H |
| B157 | b1 | 4-methylpiperadin-1-yl | H, H, H, H |
| B158 | b1 | ON=CH | H, H, H, H |
| B159 | b1 | CH2O | H, H, H, H |

TABLE 71

| Part B No. | Type | X1 | R5, R6, R7, R8 |
|---|---|---|---|
| B160 | b1 | CH2O | H, Me, H, H |
| B161 | b1 | CH2O | H, nPr, H, H |
| B162 | b1 | CH2O | H, OCH2CF3, H, H |
| B163 | b1 | CH2O | H, OH, H, H |
| B164 | b1 | CH2O | H, OMe, H, H |
| B165 | b1 | CH2O | H, Cl, H, H |
| B166 | b1 | CH2O | Me, H, H, H |
| B167 | b1 | CH2O | H, Ph, H, H |
| B168 | b1 | CH2O | Me, Me, H, H |
| B169 | b1 | CH2O | Me, Me, Me, Me |
| B170 | b1 | CH2O | H, Me, H, Me |
| B171 | b1 | CHEtO | OCH2CF3, H, H, H |
| B172 | b1 | CHEtO | H, H, H, H |
| B173 | b1 | OCH2 | H, H, H, H |
| B174 | b1 | OCH2 | H, Me, H, H |
| B175 | b1 | OCH2 | H, nPr, H, H |
| B176 | b1 | OCH2 | H, OCH2CF3, H, H |
| B177 | b1 | OCH2 | H, OH, H, H |
| B178 | b1 | OCH2 | H, OMe, H, H |
| B179 | b1 | OCH2 | H, SMe, H, H |
| B180 | b1 | OCH2 | Me, H, H, H |
| B181 | b1 | OCH2 | H, Ph, H, H |
| B182 | b1 | OCH2 | H, F, H, H |
| B183 | b1 | OCH2 | Me, Me, Me, Me |
| B184 | b1 | OCH2 | H, Me, H, Me |
| B185 | b1 | OCHMe | OCH2CF3, H, H, H |
| B186 | b1 | OCHMe | H, H, H, H |
| B187 | b2 | O | H, H, H |
| B188 | b2 | O | Me, H, H |
| B189 | b2 | O | H, Me, H |
| B190 | b2 | S | H, H, H |
| B191 | b2 | S | Me, H, H |
| B192 | b3 | O | H, H, H, |
| B193 | b3 | O | Me, H, H |
| B194 | b3 | O | H, Me, H |
| B195 | b3 | S | H, H, H, |
| B196 | b3 | S | Me, H, H |
| B197 | b3 | S | H, Me, H |
| B198 | b4 | O | H, H, H, |
| B199 | b4 | O | Me, H, H |
| B200 | b4 | O | H, Me, H |
| B201 | b4 | S | H, H, H, |
| B202 | b4 | S | Me, H, H |
| B203 | b4 | S | H, Me, H |

TABLE 72

| Part B No. | Type | X1 | R5, R6, R7, R8 |
|---|---|---|---|
| B204 | b5 | S | H, H, H, H |
| B205 | b5 | S | F, H, H, H |
| B206 | b5 | S | Cl, H, H, H |
| B207 | b5 | S | Me, H, H, H |
| B208 | b5 | S | Et, H, H, H |
| B209 | b5 | S | OMe, H, H, H |
| B210 | b5 | S | H, F, H, H |
| B211 | b5 | S | H, Cl, H, H |
| B212 | b5 | S | H, Me, H, H |
| B213 | b5 | S | H, Et, H, H |
| B214 | b5 | S | H, OMe, H, H |
| B215 | b5 | S | H, H, F, H |
| B216 | b5 | S | H, H, Cl, H |
| B217 | b5 | S | H, H, Me, H |
| B218 | b5 | S | H, H, Et, H |
| B219 | b5 | S | H, H, OMe, H |
| B220 | b5 | S | H, H, H, F |
| B221 | b5 | O | H, H, H, Cl |
| B222 | b5 | O | H, H, H, Me |
| B223 | b5 | O | H, H, H, Et |
| B224 | b5 | O | H, H, H, OMe |
| B225 | b5 | O | H, H, H, H |
| B226 | b5 | O | F, H, H, H |
| B227 | b5 | O | Cl, H, H, H |
| B228 | b5 | O | Me, H, H, H |

TABLE 72-continued

| Part B No. | Type | X1 | R5, R6, R7, R8 |
|---|---|---|---|
| B229 | b5 | O | Et, H, H, H |
| B230 | b5 | O | OMe, H, H, H |
| B231 | b5 | O | H, F, H, H |
| B232 | b5 | O | H, Cl, H, H |
| B233 | b5 | O | H, Me, H, H |
| B234 | b5 | O | H, Et, H, H |
| B235 | b5 | O | H, OMe, H, H |
| B236 | b5 | O | H, H, F, H |
| B237 | b5 | O | H, H, Cl, H |
| B238 | b5 | O | H, H, Me, H |
| B239 | b5 | O | H, H, Et, H |
| B240 | b5 | O | H, H, OMe, H |
| B241 | b5 | O | H, H, H, F |
| B242 | b5 | O | H, H, H, Cl |
| B243 | b5 | O | H, H, H, Me |
| B244 | b5 | O | H, H, H, Et |
| B245 | b5 | O | H, H, H, OMe |
| B246 | b5 | OCH2CO | H, H, H, H |
| B247 | b5 | OCH2 | H, H, H, H |

TABLE 73

| Part B No. | Type | X1 | R5, R6, R7, R8 |
|---|---|---|---|
| B248 | b5 | CH2O | H, H, H, H |
| B249 | b5 | NH | H, H, H, H |
| B250 | b5 | NMe | H, H, H, H |
| B251 | b5 | NEt | H, H, H, H |
| B252 | b5 | NCH2Ph | H, H, H, H |
| B253 | b5 | NAc | H, H, H, H |
| B254 | b5 | NCH2Ph | H, H, H, H |
| B255 | b5 | NCH2Et | H, H, H, H |
| B256 | b5 | NSO2Me | H, H, H, H |
| B257 | b5 | NSO2Et | H, H, H, H |
| B258 | b5 | NSO2Ph | H, H, H, H |
| B259 | b5 | NSO2C6H4-p-Me | H, H, H, H |
| B260 | b5 | 4-piperadin-1-yl | H, H, H, H |
| B261 | b5 | 4-methylpiperadin-1-yl | H, H, H, H |
| B262 | b5 | ON=CH | H, H, H, H |
| B263 | b6 | O | H, H |
| B264 | b6 | O | Me, H |
| B265 | b6 | O | H, Me |
| B266 | b6 | S | H, H |
| B267 | b6 | S | Me, H |
| B268 | b6 | S | H, Me |

3) A compound wherein the part (Part C) of the formula:

[Formula 17]

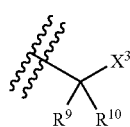

is one of the followings.

TABLE 74

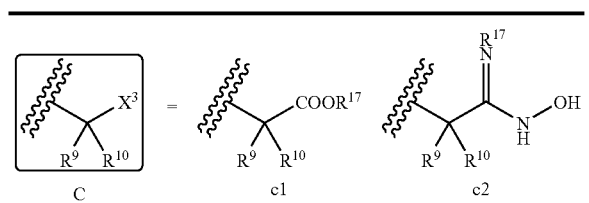

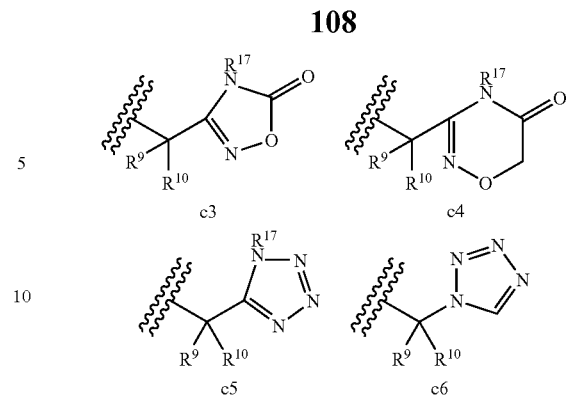

| Part C No. | Type | R9, R10 | R17 |
|---|---|---|---|
| C1 | c1 | H, H | H |
| C2 | c1 | H, H | Me |
| C3 | c1 | Me, H | H |
| C4 | c1 | Me, H | Me |
| C5 | c1 | Et, H | H |
| C6 | c1 | CH2OMe, H | Me |
| C7 | c1 | nPr, H | H |
| C8 | c1 | nPr, H | Me |
| C9 | c1 | Me, Me | H |
| C10 | c1 | Ph, Me | Me |
| C11 | c1 | CH2Ph, H | H |
| C12 | c1 | Et, H | Et |
| C13 | c1 | nPr, H | iPr |
| C14 | c1 | Me, Me | Me |
| C15 | c1 | Me, Me | tBu |
| C16 | c1 | Et, H | Me |
| C17 | c2 | H, H | H |
| C18 | c2 | H, H | Me |
| C19 | c2 | Me, H | H |
| C20 | c2 | Me, H | Me |
| C21 | c2 | Et, H | H |
| C22 | c2 | CH2OMe, H | Me |
| C23 | c2 | nPr, H | H |
| C24 | c2 | nPr, H | Me |
| C25 | c2 | Me, Me | H |
| C26 | c2 | Ph, Me | Me |
| C27 | c2 | CH2Ph, H | H |
| C28 | c2 | Et, H | Et |
| C29 | c2 | nPr, H | iPr |
| C30 | c2 | Me, Me | Me |
| C31 | c2 | Me, Me | tBu |
| C32 | c2 | Et, H | Me |
| C33 | c3 | H, H | H |

TABLE 75

| Part C No. | Type | R9, R10 | R17 |
|---|---|---|---|
| C34 | c3 | H, H | Me |
| C35 | c3 | Me, H | H |
| C36 | c3 | Me, H | Me |
| C37 | c3 | Et, H | H |
| C38 | c3 | CH2OMe, H | Me |
| C39 | c3 | nPr, H | H |
| C40 | c3 | nPr, H | Me |
| C41 | c3 | Me, Me | H |
| C42 | c3 | Ph, Me | Me |
| C43 | c3 | CH2Ph, H | H |
| C44 | c3 | Et, H | Et |
| C45 | c3 | nPr, H | iPr |
| C46 | c3 | Me, Me | Me |
| C47 | c3 | Me, Me | tBu |
| C48 | c3 | Et, H | Me |
| C49 | c4 | H, H | H |
| C50 | c4 | H, H | Me |
| C51 | c4 | Me, H | H |
| C52 | c4 | Me, H | Me |
| C53 | c4 | Et, H | H |
| C54 | c4 | CH2OMe, H | Me |
| C55 | c4 | nPr, H | H |

TABLE 75-continued

| Part C No. | Type | R9, R10 | R17 |
|---|---|---|---|
| C56 | c4 | nPr, H | Me |
| C57 | c4 | Me, Me | H |
| C58 | c4 | Ph, Me | Me |
| C59 | c4 | CH2Ph, H | H |
| C60 | c4 | Et, H | Et |
| C61 | c4 | nPr, H | iPr |
| C62 | c4 | Me, Me | Me |
| C63 | c4 | Me, Me | tBu |
| C64 | c4 | Et, H | Me |
| C65 | c5 | H, H | H |
| C66 | c5 | H, H | Me |
| C67 | c5 | Me, H | H |
| C68 | c5 | Me, H | Me |
| C69 | c5 | Et, H | H |
| C70 | c5 | CH2OMe, H | Me |
| C71 | c5 | nPr, H | H |
| C72 | c5 | nPr, H | Me |
| C73 | c5 | Me, Me | H |
| C74 | c5 | Ph, Me | Me |
| C75 | c5 | CH2Ph, H | H |
| C76 | C5 | Et, H | Et |
| C77 | c5 | nPr, H | iPr |
| C78 | c5 | Me, Me | Me |

TABLE 76

| Part C No. | Type | R9, R10 | R17 |
|---|---|---|---|
| C79 | c5 | Me, Me | tBu |
| C80 | c5 | Et, H | Me |
| C81 | c6 | H, H | H |
| C82 | c6 | H, H | Me |
| C83 | c6 | Me, H | H |
| C84 | c6 | Me, H | Me |
| C85 | c6 | Et, H | H |
| C86 | c6 | CH2OMe, H | Me |
| C87 | c6 | nPr, H | H |
| C88 | c6 | nPr, H | Me |
| C89 | c6 | Me, Me | H |
| C90 | c6 | Ph, Me | Me |
| C91 | c6 | CH2Ph, H | H |
| C92 | c6 | Et, H | Et |
| C93 | c6 | nPr, H | iPr |
| C94 | c6 | Me, Me | Me |
| C95 | c6 | Me, Me | tBu |
| C96 | c6 | Et, H | Me |

Concretely, a compound by the combination of Part A, B and C of Compound (I) is preferable.

A pharmaceutical composition for PPAR agonist of this invention can be effectively acted on all diseases concerning PPAR and especially for prevention and/or treatment of hyperlipidemia, dyslipidosis, disorder of lipid metabolism, Low HDL, High LDL, High VLDL, High TG, diabetes, hyperglycosemia, insulin resistance, obesity, bulimia, arteriosclerosis, atherosclerosis, hypertension, syndrome X, ischemic disease, inflammation, allergic disease (inflammatory bowel disease, rheumatoid arthritis, chronic pancreatitis, multiple sclerosis, glomerulosclerosis, psoriasis, eczema or the like), osteoporosis, sterility, cancer (breast cancer, colonic cancer, colon cancer, ovarian cancer, lung cancer or the like), Alzheimer's disease, parkinsonism or Basedow's disease. Especially, a compound having PPARδ selective agonistic activity in a compound of the present invention having PPAR agonistic activity can be good medicine. The reason is, for example, that it can be expected to have a high HDL increasing activity or that the side effect can be lightened.

When administering a compound of the present invention as a pharmaceutical composition for PPAR agonist, it can be administered orally or parenterally. For oral administration, the compound of the present invention can be used in any form of usual formulations, for example, tablets, granules, powders, capsules, pills, solutions, syrup, buccals, sublingual tablets or the like which are made by the usual process. For parenteral administration, the compound of the present invention can be used in any form of usual formulations, for example, injections such as intramuscular administration and intravenous administration, suppository, transdermal therapeutic agent, insufflation or the like. A compound of the present invention can be preferably used as an oral agent because it has high oral bioavailability.

The formulation according to the present invention may be manufactured by combining a curatively effective amount of a compound of the present invention with various pharmaceutically acceptable excipients such as binder, moistening agent, disintegrating agents, lubricant, diluent or the like, if necessary. When the formulation is injection, the compound of the present invention may be manufactured by sterilization treatment with an appropriate carrier.

For example, the excipient is lactose, saccharose, glucose, starch, calcium carbonate, crystalline cellulose or the like. The binder is methylcellulose, carboxy methylcellulose, hydroxy propylcellulose, gelatin, polyvinylpyrrolidone or the like. The disintegrating agent is carboxy methyl cellulose, carboxymethylcellulose sodium, starch, sodium alginate, powdered agar, sodium lauryl sulfate or the like. The lubricant is talc, magnesium stearate, macrogol or the like. As a basis for suppository, cocoa butter, macrogol, methylcellulose or the like can be used. When the present invention is manufactured as liquid medicine, emulsion injection or suspension injection, solubilizing agent, suspending agent, emulsifying agent, stabilizing agent, preservatives, isotonic agent or the like which is usually used can be appropriately added. In case of oral administration, sweetening agent, flavoring agent or the like can be added.

The dose as a pharmaceutical composition for PPAR agonist of a compound of the present invention is preferably established depending on age, body weight, kind of disease, conditions of the patient, the administration route or the like. In case of the oral administration for an adult, it is usually 0.05 to 100 mg/kg/day and preferably 0.1 to 10 mg/kg/day. In case of the parenteral administration, although it is very different depending on route of administration, it is usually 0.005 to 10 mg/kg/day and preferably 0.01 to 1 mg/kg/day. This can be separated and administrated at 1 to few times a day.

The following examples are provided to explain in more detail and do not restrict the present invention.

EXAMPLE

In the examples, the meaning of each abbreviation is as below.

| Me | methyl |
|---|---|
| Et | ethyl |
| nBu | n-butyl |
| tBu | tert-butyl |
| nPr | n-propyl |
| Ph | phenyl |
| Bn | benzyl |
| Ac | acetyl |
| Ms | methanesulfonyl |
| TMS | trimethylsilyl |
| PCC | pyridinium chlorochromate |
| CDI | 1,1'-carbonyldiimidazole |

-continued

| DBU | 1,8-diazabicyclo[5.4.0]undec-7-ene |
| DME | 1,2-dimethoxyethane |
| DPM | diphenylmethyl |
| TBS | 3-tert-butyldimethylsilyl |
| TFMP | 4-trifluoromethylphenyl |

Reference 1

(4-Chloro-3-hydroxyphenyl)acetic acid methyl ester

[Formula 18]

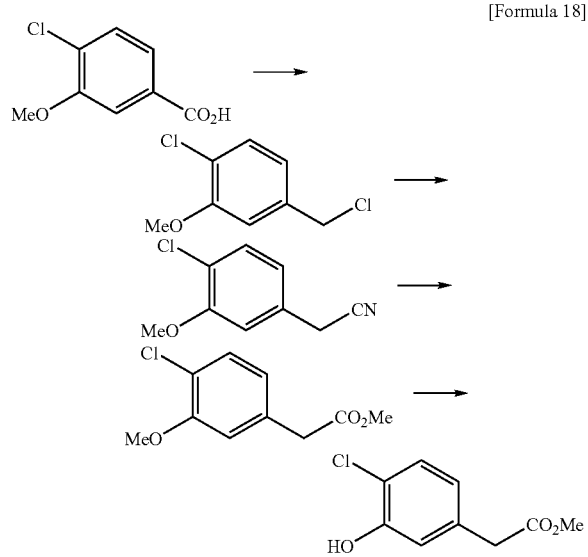

The First Step

1-Chloro-4-chloromethyl-2-methoxybenzene

To a suspension of lithium aluminum hydride (1.52 g) in tetrahydrofuran (100 ml) was added 4-chloro3-methoxybenzoic acid (5.16 g) under ice-cooling. The mixture was stirred at room temperature for 22 hours. The reaction solution was cooled with ice, and water (1.5 ml), 2N sodium hydroxide solution (1.5 ml) and water (4.6 ml) were added thereto. The mixture was stirred at room temperature for 1 hour. 2N sodium hydroxide solution (1.5 ml), anhydrous magnesium sulfate and the mixture of hexane and diethyl ether were added and stirred under ice-cooling for 30 min. The mixture was filtrated and the filtrate was condensed to give oil (4.61 g). This oil was dissolved in methylene chloride (40 ml), and thionyl chloride (5.0 ml) and pyridine (2.4 ml) were added thereto under ice-cooling. The mixture was stirred for 25 minutes. The reaction solution was condensed under reduced pressure. Then water was added thereto and the mixture was extracted with ethyl acetate. The organic layer was washed with brine and dried over magnesium sulphate. The solvent was evaporated under reduced pressure. The obtained residue was purified by silica gel column chromatography (eluting with the mixed solvent of ethyl acetate-hexane) to give a title compound (4.53 g). The yield was 86%.

$^1$H-NMR (CDCl$_3$) δ: 3.92 (3H, s), 4.55 (2H, s), 6.91 (1H, dd, J=1.8, 7.8 Hz), 6.96 (1H, d, J=1.8 Hz), 7.33 (1H, d, J=7.8 Hz).

The Second Process

4-Chloro-3-methoxyphenylacetonitrile

To a solution of 1-chloro-4-chloromethyl-2-methoxybenzene (4.52 g) in dimethylsulfoxide (70 ml) was added sodium cyanide (1.16 g). The mixture was stirred at room temperature for 2.5 hours. Water was added to the reaction solution and the mixture was extracted with ethyl acetate. The organic layer was washed with water and brine, and dried over magnesium sulphate. The solvent was evaporated under reduced pressure. The obtained residue was purified by silica gel column chromatography (eluting with the mixed solvent of ethyl acetate-hexane) to give a title compound (3.81 g). The yield was 89%.

$^1$H-NMR (CDCl$_3$) δ: 3.74 (2H, s), 3.93 (3H, s), 6.82-6.90 (2H, m), 7.36 (1H, d, J=7.8 Hz).

The Third Process (4-Chloro-3-methoxyphenyl)acetic acid methyl ester

Potassium hydroxide (5.86 g) was dissolved in water (25 ml) and the mixture was added to a solution of 4-chloro-3-methoxyphenylacetonitrile (3.80 g) in ethanol (80 ml) at room temperature. The reaction solution was refluxed for 1.5 hours. After cooling, concentrated hydrochloric acid (8.8 ml) and water (50 ml) were added to the reaction solution and the mixture was extracted with ethyl acetate. The organic layer was washed with brine, and dried over magnesium sulphate. The solvent was evaporated under reduced pressure. The obtained residue was dissolved in methanol (100 ml) and concentrated sulphuric acid was added thereto. The mixture was refluxed for 1.45 hours. After cooling, the reaction solvent was evaporated under reduced pressure and water was added thereto. The mixture was extracted with ethyl acetate. The organic layer was washed with brine, and dried over magnesium sulphate. The solvent was evaporated under reduced pressure to give a title compound (4.43 g). The yield was 99%.

$^1$H-NMR (CDCl$_3$) δ: 3.61 (2H, s), 3.71 (3H, s), 3.91 (3H, s), 6.81 (1H, dd, J=1.8, 8.1 Hz), 6.87 (1H, d, J=1.8 Hz), 7.30 (1H, d, J=8.1 Hz).

The Fourth Step (4-Chloro-3-hydroxyphenyl)acetic acid methyl ester

To a solution of (4-chloro-3-methoxyphenyl)acetic acid methyl ester (4.43 g) in methylene chloride (62 ml) was added 1.0 M boron tribromide methylene chloride solution (62 ml) under ice-cooling for 30 minutes. After the mixture was stirred for 30 minutes, water was added to the reaction solution and the mixture was extracted with ethyl acetate. The organic layer was washed with saturated sodium hydrogencarbonate solution, and dried over magnesium sulphate. The solvent was evaporated under reduced pressure. The obtained residue was purified by column chromatography on silica gel (eluting with the mixed solvent of ethyl acetate-hexane) to give a title compound (3.73 g). The yield was 90%.

$^1$H-NMR (CDCl$_3$) δ: 3.57 (2H, s), 3.70 (3H, s), 5.53 (1H, s), 6.79 (1H, dd, J=1.8, 8.1 Hz), 6.96 (1H, d, J=1.8 Hz), 726 (1H, d, J=8.1 Hz).

The following compounds were synthesized in a similar way as above.

(4-fluoro-3-hydroxyphenyl)acetic acid methyl ester $^1$H-NMR (CDCl$_3$) δ: 3.53 (3H, s), 3.60 (2H, s), 5.21 (1H, s), 6.83-7.15 (3H, m).

(3-hydroxy-4-methylphenyl)acetic acid methyl ester

¹H-NMR (CDCl₃) δ: 2.21 (3H, s), 3.55 (2H, s), 3.69 (3H, s), 5.22 (1H, s), 6.60-7.10 (3H, m).

(3-hydroxy-4-methoxyphenyl)acetic acid methyl ester

¹H-NMR (CDCl₃) δ: 3.68 (2H, s), 3.72 (3H, s), 5.39 (1H, s), 6.74-7.00 (3H, m).

(2-fluoro-3-hydroxy phenyl)acetic acid methyl ester

¹H-NMR (CDCl₃) δ: 2.19 (3H, s), 3.65 (2H, s), 3.70 (3H, s), 4.85 (1H, s), 6.67-7.06 (3H, m).

(3-hydroxy-2-methylphenyl)acetic acid methyl ester

¹H-NMR (CDCl₃) δ: 2.19 (3H, s), 3.65 (2H, s), 3.70 (3H, s), 4.85 (1H, s), 6.67-7.06 (3H, m).

(2-fluoro-5-hydroxy phenyl)acetic acid methyl ester

¹H-NMR (CDCl₃) δ: 3.62 (2H, s), 3.72 (3H, s), 6.66-6.95 (3H, m).

Reference 2

(5-Methyl-3-hydroxyphenyl)acetic acid methyl ester

[Formula 19]

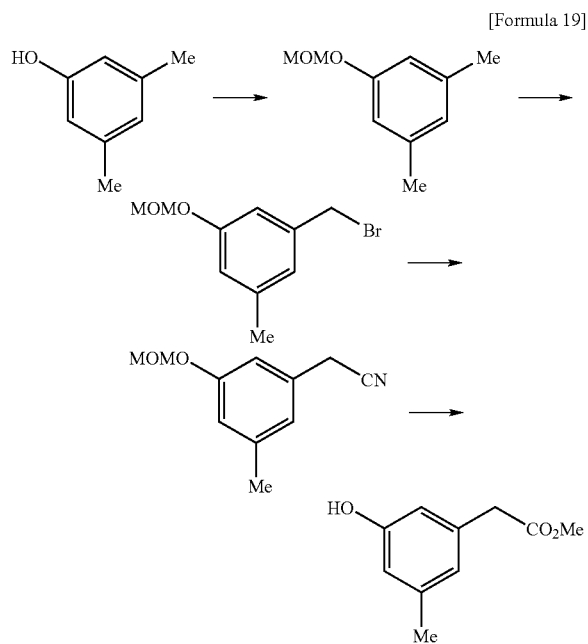

The First Step 3,5-Dimethyl-1-methoxymethoxybenzene

To a solution of 3,5-dimethylphenol (6.14 g) in tetrahydrofuran (60 ml) were added diisopropylethylamine (13.1 ml) and chloromethylmethylether (4.1 ml). The mixture was refluxed for 6 hours. After cooling, water was added to the reaction solution and the mixture was extracted with ethyl acetate. The organic layer was washed with brine, dried over magnesium sulphate and evaporated under reduced pressure. The obtained residue was purified by column chromatography on silica gel (eluting with the mixed solvent of ethyl acetate-hexane) to give a title compound (6.96 g). The yield was 83%.

¹H-NMR (CDCl₃) δ: 2.29 (6H, s), 3.48 (3H, s), 5.15 (2H, s), 6.66 (3H, s).

The Second Step

1-Bromomethyl-3-methoxymethoxy-5-methylbenzene

To a solution of 3,5-dimethyl-1-methoxymethoxybenzene (6.44 g) in carbon tetrachloride (60 ml) were added N-bromosuccinimide (7.24 g) and 2,2'-azobisisobutyronitrile (191 mg). The mixture was refluxed for 30 minutes. After cooling, the reaction solution was filtrated and the filtrate was evaporated under reduced pressure. The obtained residue was purified by column chromatography on silica gel (eluting with the mixed solvent of ethyl acetate-hexane) to give a title compound (6.94 g). The yield was 58%.

¹H-NMR (CDCl₃) δ: 2.32 (3H, s), 3.48 (3H, s), 4.42 (2H, s), 5.16 (2H, s), 6.63 (1H, s), 6.79 (2H, s).

The Third Step

3-Methoxymethoxy-5-methylphenylacetonitrile

To a solution of 1-bromomethyl-3-methoxymethoxy-5-methylbenzene (6.94 g) in dimethylsulfoxide (100 ml) was added sodium cyanide (1.18 g). The mixture was stirred at room temperature for 1 hour. Water was added to the reaction solution and the mixture was extracted with ethyl acetate. The organic layer was washed with water and brine, dried over magnesium sulphate, and evaporated under reduced pressure. The obtained residue was purified by column chromatography on silica gel (eluting with the mixed solvent of ethyl acetate-hexane) to give a title compound (4.00 g). The yield was 87%.

¹H-NMR (CDCl₃) δ: 2.34 (3H, s), 3.48 (3H, s), 3.68 (2H, s), 5.17 (2H, s), 6.77-6.85 (1H, m).

The Fourth Step (3-Hydroxy-5-methylphenyl)acetic acid methyl ester

Potassium hydroxide (5.87 g) was dissolved in water (20 ml) and the solution was added to a solution of 3-methoxymethoxy-5-methylphenylacetonitrile (4.00 g) in ethanol (40 ml) at room temperature. The reaction solution was refluxed for 2 hours. After cooling, 2N hydrochloric acid (55 ml) and water were added to the reaction solution and the mixture was extracted with ethyl acetate. The organic layer was washed with brine, dried over magnesium sulphate and evaporated under reduced pressure. The obtained residue was dissolved in methanol (100 ml) and concentrated sulphuric acid was added thereto. The mixture was refluxed for 1 hour. After cooling, the reaction solvent was evaporated under reduced pressure and water was added thereto. The mixture was extracted with ethyl acetate. The organic layer was washed with brine, dried over magnesium sulphate and evaporated under reduced pressure to give a title compound (3.18 g). The yield was 84%.

¹H-NMR (CDCl₃) δ: 2.29 (3H, s), 3.53 (2H, s), 3.70 (3H, s), 4.80 (1H, s), 6.57 (1H, s), 6.66 (2H, s).

The following compound was synthesized in a similar way as above.

(2-Chloro-5-hydroxyphenyl)acetic acid methyl ester

¹H-NMR (CDCl₃) δ: 3.72 (2H, s), 3.73 (3H, s), 5.19 (1H, s), 6.69 (1H, dd, J=3.0, 8.7 Hz), 6.77 (1H, d, J=3.0 Hz), 7.22 (1H, d, J=8.7 Hz).

Reference 3

(3-Hydroxy-5-methoxyphenyl)acetic acid methyl ester

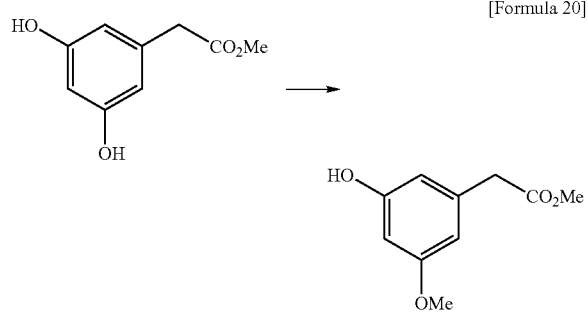

[Formula 20]

To a solution of (3,5-dihydroxyphenyl)acetic acid methyl ester (2.73 g) in dimethylformamide (20 ml) was added sodium hydride (659 mg) under ice-cooling. The mixture was stirred at room temperature for 30 minutes. Iodomethane (1.03 ml) was added thereto and the mixture was stirred at room temperature for 15 hours. 2N hydrochloric acid and water were added to the reaction solution and the mixture was extracted with ethyl acetate. The organic layer was washed successively with water and brine, and dried over magnesium sulphate. The solvent was evaporated under reduced pressure. The obtained residue was purified by column chromatography on silica gel (eluting with the mixed solvent of ethyl acetate-hexane) to give a title compound (1.18 g). The yield was 40%.

$^1$H-NMR (CDCl$_3$) δ: 3.53 (2H, s), 3.70 (3H, s), 3.77 (3H, s), 4.96 (1H, s), 6.30-6.43 (3H, m).

Reference 4

(3-Fluoro-5-hydroxyphenyl)acetic acid methyl ester

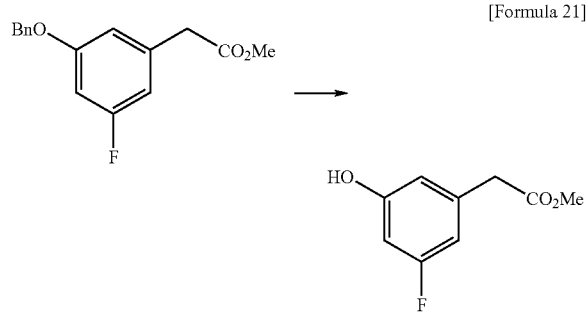

[Formula 21]

To a solution of (3-benzyloxy-5-fluorophenyl)acetic acid methyl ester (522 mg) described in J. Med. Chem., 2004, 47, 720-725 in methylene chloride (5 ml) was added aluminum chloride (761 mg) at room temperature. The mixture was stirred for 1 hour. 2N hydrochloric acid was added to the reaction solution and the mixture was extracted with methylene chloride. The organic layer was washed successively with water and brine, and dried over magnesium sulphate. The solvent was evaporated under reduced pressure. The obtained residue was purified by column chromatograph on silica gel (eluting with the mixed solvent of ethyl acetate-hexane) to give a title compound (135 mg). The yield was 39%.

$^1$H-NMR (CDCl$_3$) δ: 3.55 (2H, s), 3.71 (3H, s), 6.48 (1H, dt, J=2.4, 10.0 Hz), 6.57 (2H, dt, J=5.0, 9.9 Hz).

Reference 5

(4-Fluoro-3-mercaptophenyl)acetic acid methyl ester

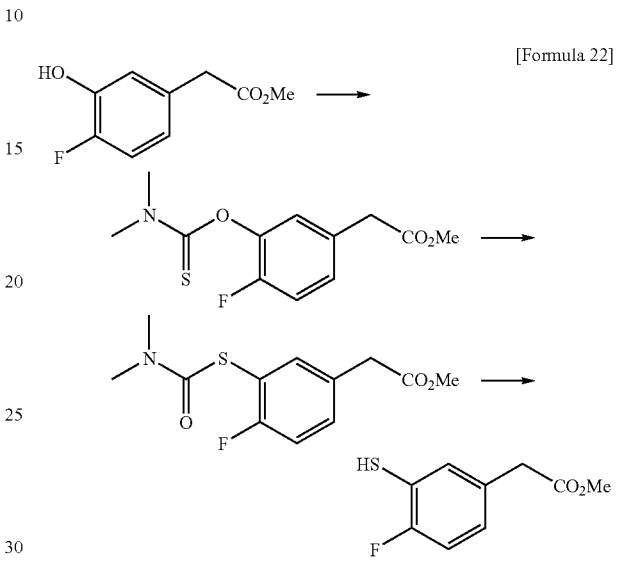

[Formula 22]

The First Step (3-Dimethylthiocarbamoyloxy-4-fluorophenyl)acetic acid methyl ester A mixture of (3-hydroxy-4-fluorophenyl)acetic acid methyl ester (1.36 g), N,N-dimethylthiocarbamoylchloride (1.10 g), triethylamine (1.54 ml), N,N-dimethylaminopyridine (90 mg) and dioxane (20 ml) was refluxed for 15 hours. After cooling, water and 2N hydrochloric acid were added to the reaction solution and the mixture was extracted with ethyl acetate. The organic layer was washed with water and brine, and dried over magnesium sulphate. The solvent was evaporated under reduced pressure. The obtained residue was purified by column chromatograph on silica gel (eluting with the mixed solvent of ethyl acetate-hexane) to give a title compound (1.95 g). The yield was 97%.

$^1$H-NMR (CDCl$_3$) δ: 3.36 (3H, s), 3.60 (3H, s), 3.62 (2H, s), 3.70 (3H, s), 7.05-7.16 (3H, m).

The Second Step (3-Dimethylcarbamoyl sulfanyl-4-fluorophenyl)acetic acid methyl ester A mixture of (3-dimethylthiocarbamoyloxy-4-fluorophenyl)acetic acid methyl ester (1.95 g) and SAS-296 (10 ml) was stirred at 270° C. for 1 hour. The reaction solution was cooled to room temperature, and then purified by column chromatography on silica gel (eluting with the mixed solvent of ethyl acetate-hexane) to give a title compound (1.74 g). The yield was 89%.

$^1$H-NMR (CDCl$_3$) δ: 2.95-3.20 (6H, m), 3.60 (2H, s), 3.70 (3H, s), 7.11 (1H, d, J=8.4 Hz), 7.30-7.39 (1H, m), 7.40 (1H, dd, J=2.4, 6.6 Hz).

The Third Step (4-Fluoro-3-mercaptophenyl)acetic acid methyl ester

To a solution of (3-dimethylcarbamoyl sulfanyl-4-fluorophenyl)acetic acid methyl ester (1.74 g) in methanol (20 ml) was added 1 N sodium methoxide (methanol solution) (7.7 ml). The mixture was stirred under heating for 2.5 hours. After cooling, the reaction solution was added to 2N hydrochloric acid-ice water and the mixture was extracted with ethyl acetate. The organic layer was washed with brine, and dried over magnesium sulphate. The solvent was evaporated under reduced pressure. The obtained residue was purified by column chromatograph on silica gel (eluting with the mixed solvent of ethyl acetate-hexane) to give a title compound (951 mg). The yield was 74%.

$^1$H-NMR (CDCl$_3$) δ: 3.54 (2H, s), 3.59 (1H, s), 3.70 (3H, s), 6.99-7.26 (3H, m).

The following compound was synthesized in a similar way as above.

3-Mercaptophenylacetic acid methyl ester $^1$H-NMR (CDCl$_3$) δ: 3.45 (1H, s), 3.57 (2H, s), 3.70 (3H, s), 7.04-7.24 (3H, m).

Reference 6

[Formula 23]

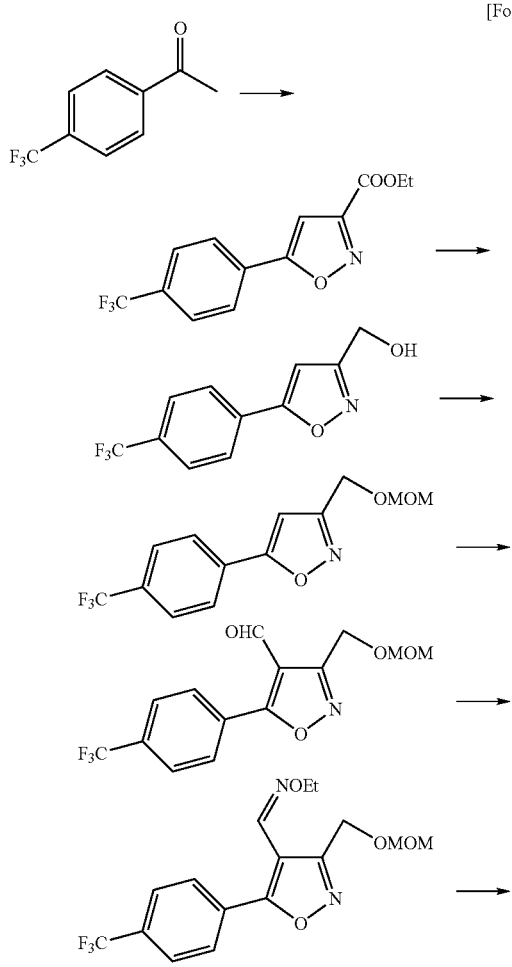

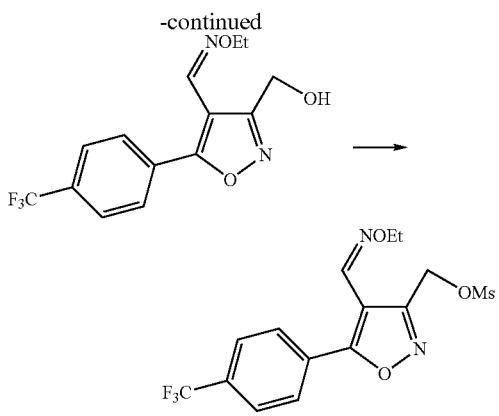

The First Step 5-(4-Trifluoromethylphenyl) isoxazole-3-carboxylic acid ethyl ester To dry ether (60 ml) was added lithium bis(trimethylsilyl) amide solution (15 ml). The mixture was cooled to −70° C. or less and a solution of 4-trifluoromethylacetophenone (2.82 g) in ether (15 ml) was added dropwise under −65° C. for 6 minutes. The mixture was stirred at room temperature for 17 hours. Ether (100 ml) was added to the reaction solution and the mixture was cooled with ice. The deposited crystal was filtrated to give a lithium salt of pyruvate (2.9 g) as the first crystal. The filtrate was condensed, diluted with ether and cooled with ice to give the second crystal (610 mg). To this lithium salt (3.5 g) were added ethanol (35 ml) and hydroxylamine hydrochloride (1.22 g). The mixture was refluxed for 20 hours. The solvent was evaporated and water was added thereto. The mixture was extracted with chloroform. The organic layer was dried over magnesium sulfate and evaporated under reduced pressure. The obtained residue was purified by column chromatograph on silica gel (eluting with ethyl acetate:hexane=1:1) to give a title compound (2.55 g) as a colorless crystal.

NMR (CDCl$_3$): 1.46 (3H, t, J=6.9 Hz), 4.49 (2H, q, J=6.9 Hz), 7.04 (1H, s), 7.77 (2H, d, J=8.7 Hz), 7.95 (2H, d, J=8.7 Hz).

The Second Step 5-(4-Trifluoromethylphenyl) isoxazole-3-yl]methanol 5-(4-Trifluoromethylphenyl)-isoxazole-3-carboxylic acid ethyl ester (1.0 g) was dissolved in methanol (15 ml). Sodium borohydride (358 mg) was added thereto under ice-cooling. After 5 minutes, the mixture was heated to room temperature and stirred for 2 hours. Hydrochloric acid (1M solution) was added to the reaction solution under 10° C. The solvent was evaporated under reduced pressure. Water was added to the residual solution and the mixture was extracted with chloroform. The organic layer was washed with brine, dried over anhydrous magnesium sulfate, and evaporated under reduced pressure. The obtained residue was purified by column chromatograph on silica gel (eluting with ethyl acetate:hexane=1:8) to give a title compound (820 mg) as a crystal.

mp; 111-113° C.

The Third Step

3-Methoxymethoxymethyl-5-(4-trifluoromethylphenyl) isoxazole

To a mixture of [5-(4-trifluoromethylphenyl) isoxazole-3-yl]methanol (21.9 g) and tetrahydrofuran (300 ml) was added sodium hydride (60%) (4.14 g) under ice-cooling. The mixture was stirred at room temperature for 1 hour. Chloromethylmethyl ether (9.42 g) was added to the reaction solution and the mixture was stirred at room temperature for 20 hours. The reaction solution was poured into ice water and the mixture was extracted with ethyl acetate. The organic layer was washed with water and brine, and dried over magnesium sulphate. The solvent was evaporated under reduced pressure. The residue was purified by column chromatograph on silica gel (eluting with ethyl acetate: n-hexane=1:4) to give a title compound (20.8 g).

NMR (CDCl$_3$): δ 3.44 (3H, s), 4.73 (2H, s), 4.76 (2H, s), 6.70 (1H, s), 7.72 (2H, d, J=8.7 Hz), 7.92 (2H, d, J=8.7 Hz)

The Fourth Step

3-Methoxymethoxymethyl-5-(4-trifluoromethylphenyl) isoxazole-4-carboxaldehyde

To a mixture of 3-methoxymethoxymethyl-5-(4-trifluoromethylphenyl) isoxazole (286 mg) and tetrahydrofuran (6 ml) was added n-butyllithium (1.6 M hexane solution) (1.56 ml) at −78° C. After stirring at −78° C. for 0.5 hour, N,N-dimethylformamide (257 mg) was added at once. After heating the reaction solution to room temperature, ice water was added thereto and the mixture was extracted with ethyl acetate. The organic layer was washed with water and brine, and dried over magnesium sulphate. The solvent was evaporated under reduced pressure. The residue was purified by column chromatograph on silica gel (eluting with ethyl acetate: n-hexane=1:5) to give a title compound (179 mg).

$^1$H-NMR (CDCl$_3$): δ 3.45 (3H, s), 4.81 (2H, s), 4.96 (2H, s), 7.84 (2H, d, J=8.4 Hz), 8.08 (2H, d, J=8.4 Hz), 10.14 (1H, s)

The Fifth Step

3-Methoxymethoxymethyl-5-(4-trifluoromethylphenyl) isoxazole-4-carbaldehyde ethyl oxime A mixture of 3-methoxymethoxymethyl-5-(4-trifluoromethylphenyl) isoxazole-4-carbaldehyde (12.4 g), ethoxyamine hydrochloride (4.79 g) and tetrahydrofuran (300 ml) was stirred at 60° C. for 3 hours. The solvent was evaporated under reduced pressure. Water was added to the residue and the mixture was extracted with ethyl acetate. The organic layer was washed with water and brine, and dried over magnesium sulphate. The solvent was evaporated under reduced pressure. The residue was purified by column chromatograph on silica gel eluting with ethyl acetate: n-hexane (5:95) to give a title compound (10.6 g).

NMR (CDCl$_3$): δ 1.33 (3H, t, J=7.2 Hz), 3.46 (3H, s), 4.23 (2H, q, J=7.2 Hz), 4.18 (2H, s), 4.89 (2H, s), 7.77 (2H, d, J=8.4 Hz), 7.88 (2H, d, J=8.4 Hz), 8.17 (1H, s).

The Sixth Step

3-Hydroxymethyl-5-(4-trifluoromethylphenyl) isoxazole-4-carbaldehyde ethyl oxime A mixture of 3-methoxymethoxymethyl-5-(4-trifluoromethylphenyl) isoxazole-4-carbaldehyde ethyl oxime (10.6 g), 6N hydrochloric acid (20 ml) and methanol (172 ml) was refluxed for 4.5 hours. The solvent was evaporated and water was added thereto. The mixture was extracted with ethyl acetate. The obtained residue was recrystallized from ethyl acetate/n-hexane to give a title compound (7.97 g).

TLC Rf 0.27(ethyl acetate/n-hexane, 1/4)

The Seventh Step

Methanesulfonic acid 4-(ethoxyiminomethyl)-5-(4-trifluoromethylphenyl) isoxazole-3-yl methyl ester A mixture of 3-hydroxymethyl-5-(4-trifluoromethylphenyl) isoxazole-4-carbaldehyde ethyl oxime (7.90 g), methanesulfonic chloride (2.37 ml), triethylamine (4.23 g) and methylene chloride (200 ml) was stirred at 0° C. for 1 hour. The reaction solution was poured into ice water and the mixture was extracted with chloroform to give a title compound (9.72 g).

NMR (CDCl$_3$) δ 1.34 (3H, t, J=7.2 Hz), 3.18 (3H, s), 4.26 (2H, q, J=7.2 Hz), 5.58 (2H, s), 7.80-7.81 (4H, m), 8.17 (1H, s).

Reference 7

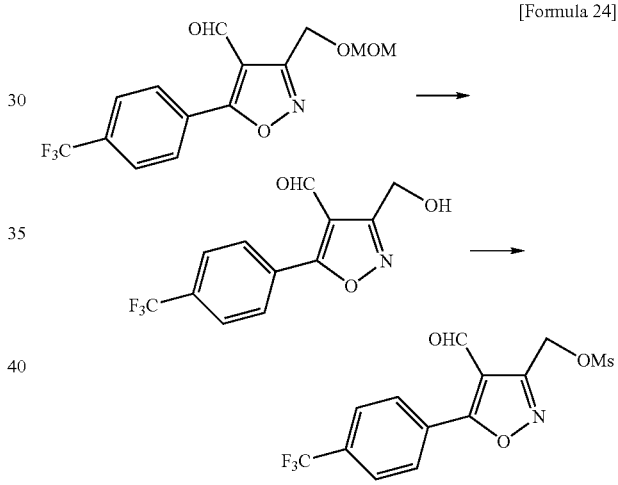

[Formula 24]

The First Step

3-Hydroxy methyl-5-(4-trifluoromethylphenyl) isoxazole-4-carbaldehyde

A mixture of 3-methoxymethoxymethyl-5-(4-trifluoromethylphenyl) isoxazole-4-carbaldehyde (41.8 g), 6N hydrochloric acid (60 ml) and methanol (300 ml) was refluxed for 3 hours. The solvent was evaporated and water was added thereto. The mixture was extracted with ethyl acetate. The obtained crude product was purified by column chromatograph on silica gel to give a title compound (21.1 g).

TLC Rf 0.25(ethyl acetate/n-hexane, 1/2)

The Second Step

Methanesulfonic acid 4-formyl-5-(4-trifluoromethylphenyl) isoxazole-3-yl methyl ester 3-Hydroxymethyl-5-(4-trifluoromethylphenyl) isoxazole-4-carboxaldehyde (21.0 g), methanesulfonyl chloride (6.6 ml) and triethylamine (13 ml) were dissolved in methylene chloride (300 ml) and the mixture was stirred at 0° C. for 5 hours. Water and 2N hydrochloric acid were added thereto and the mixture was extracted with chloroform. The obtained crude product was recrystallized from ethyl acetate/diisopropylether to give a title compound (25.8 g).

TLC Rf 0.37 (toluene/ethyl acetate, 6/1)

Example 1

{3-[4-(Ethoxyiminomethyl-5-(4-trifluoromethylphenyl) isoxazole-3-yl methoxy]phenyl}acetic acid

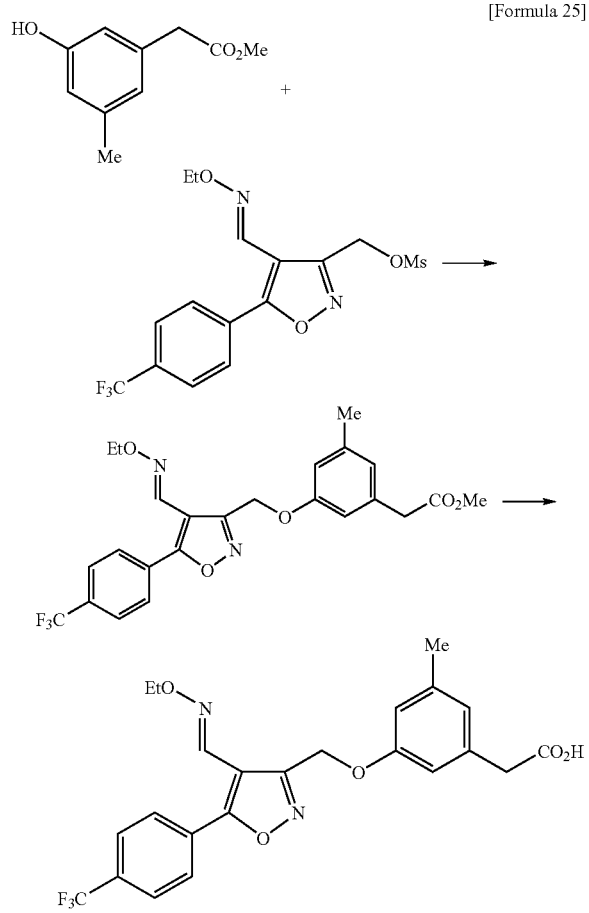

[Formula 25]

The First Step

{3-[4-(Ethoxyiminomethyl-5-(4-trifluoromethylphenyl) isoxazole-3-yl methoxy]phenyl}acetic acid methyl ester To a solution of (5-methyl-3-hydroxyphenyl)acetic acid methyl ester (100 mg) in acetonitrile (2 ml) were added methanesulfonic acid 4-(ethoxyiminomethyl)-5-(4-trifluoromethylphenyl) isoxazole-3-yl methyl ester (218 mg) and cesium carbonate (217 mg). The mixture was stirred at 60° C. for 30 minutes. The reaction solution was filtrated and the filtrate was evaporated under reduced pressure. The obtained residue was purified by column chromatograph on silica gel (eluting with the mixed solvent of ethyl acetate-hexane) to give a title compound (264 mg). The yield was 100%.

$^1$H-NMR (CDCl$_3$) δ: 1.24 (3H, t, J=6.6 Hz), 2.32 (3H, s), 3.57 (2H, s), 3.69 (3H, s), 4.10 (2H, q, J=6.6 Hz), 5.33 (2H, s), 6.74 (1H, s), 6.76 (2H, s), 7.77 (2H, d, J=8.4 Hz), 7.90 (2H, d, J=8.4 Hz), 8.19 (1H, s).

The Second Step

{3-[4-(Ethoxyiminomethyl-5-(4-trifluoromethylphenyl) isoxazole-3-yl methoxy]phenyl}acetic acid To a solution of {3-[4-(ethoxyiminomethyl-5-(4-trifluoromethylphenyl) isoxazole-3-yl methoxy]phenyl}acetic acid methyl ester (263 mg) in tetrahydrofuran (2.5 ml)-methanol (2.5 ml) was added 2N sodium hydroxide solution (0.55 ml). The mixture was stirred at room temperature for 1 hour. Hydrochloric acid (2N solution, 0.6 ml) and water (2 ml) were added to the reaction solution and the mixture was stirred under ice-cooling. Water (8 ml) was added thereto. The precipitate was collected, washed with water and dried to give a title compound (217 mg). The yield was 85%.

$^1$H-NMR (CDCl$_3$) δ: 1.23 (3H, t, J=7.0 Hz), 2.33 (3H, s), 3.60 (2H, s), 4.09 (2H, q, J=7.0 Hz), 5.33 (2H, s), 6.75 (1H, s), 6.77 (2H, s), 7.77 (2H, d, J=8.4 Hz), 7.90 (2H, d, J=8.4 Hz), 8.19 (1H, s).

Example 2

{3-[4-(2-Fluoroethoxyiminomethyl)-5-(4-trifluoromethylphenyl) isoxazole-3-yl methoxy]phenyl}acetic acid

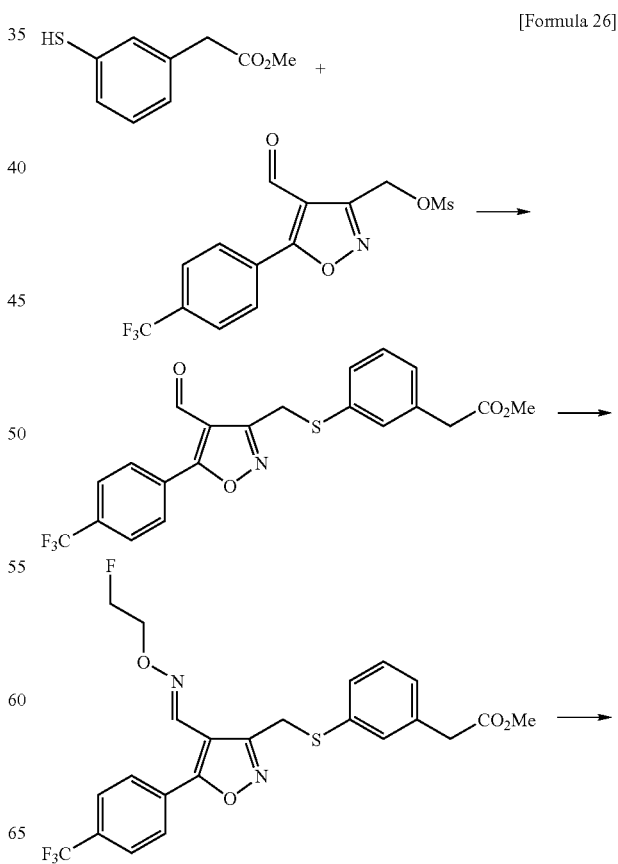

[Formula 26]

-continued

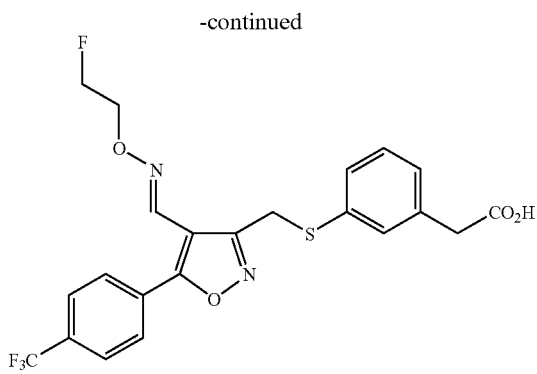

The First Step

{3-[4-Formyl-5-(4-trifluoromethylphenyl) isoxazole-3-yl methyl sulfanyl]phenyl}acetic acid methyl ester To a solution of (3-mercaptophenyl)acetic acid methyl ester (8.00 g) in acetonitrile (200 ml) were added methanesulfonic acid 4-formyl-5-(4-trifluoromethylphenyl) isoxazole-3-yl methyl ester (5.42 g) and cesium carbonate (9.70 g). The mixture was stirred at room temperature for 17 hours. The reaction solution was evaporated under reduced pressure and 2N hydrochloric acid (140 ml) was added thereto. The mixture was extracted with ethyl acetate. The organic layer was washed successively with water and brine and dried over magnesium sulphate. The solvent was evaporated under reduced pressure. The obtained residue was purified by column chromatograph on silica gel (eluting with the mixed solvent of ethyl acetate-hexane) to give a title compound (1.86 g). The yield was 19%.

$^1$H-NMR (CDCl$_3$) δ: 3.59 (2H, s), 3.68 (3H, s), 4.40 (2H, s), 7.14-7.38 (4H, m), 7.84 (2H, d, J=8.4 Hz), 8.01 (2H, d, J=8.4 Hz), 10.12 (1H, s).

The Second Step

{3-[4-(2-Fluoroethoxyiminomethyl)-5-(4-trifluoromethylphenyl) isoxazole-3-yl methyl sulfanyl] phenyl}acetic acid methyl ester A solution of {3-[4-formyl-5-(4-trifluoromethylphenyl) isoxazole-3-yl methyl sulfanyl]phenyl}acetic acid methyl ester (269 mg) and O-(2-fluoroethyl)-hydroxylamine hydrochloride (143 mg) in tetrahydrofuran (10 ml) was stirred at room temperature for 24 hours. The saturated sodium hydrogencarbonate solution was added to the reaction solution and the mixture was extracted with ethyl acetate. The organic layer was washed successively with water and brine and dried over magnesium sulphate. The solvent was evaporated under reduced pressure. The obtained residue was purified by column chromatograph on silica gel (eluting with the mixed solvent of ethyl acetate-hexane) to give a title compound (249 mg). The yield was 81%.

$^1$H-NMR (CDCl$_3$) δ: 3.59 (2H, s), 3.69 (3H, s), 4.32-4.80 (4H, m), 4.37 (2H, s), 7.12-7.37 (4H, m), 7.77 (2H, d, J=8.4 Hz), 7.82 (2H, d, J=8.4 Hz), 8.26 (1H, s).

The Third Step

{3-[4-(2-Fluoroethoxyiminomethyl)-5-(4-trifluoromethylphenyl) isoxazole-3-yl methyl sulfanyl] phenyl}acetic acid To a solution of {3-[4-(2-fluoroethoxyiminomethyl)-5-(4-trifluoromethylphenyl) isoxazole-3-yl methylsulfanyl]phenyl}acetic acid methyl ester (247 mg) in tetrahydrofuran (10 ml)-methanol (5 ml) was added 4N lithium hydroxide solution (0.37 ml) under ice-cooling. The mixture was stirred under ice-cooling for 1 hour and at room temperature for 1 hour. Citric acid solution (0.5 M) was added to the reaction solution and the mixture was extracted with ethyl acetate. The organic layer was washed successively with water and brine, and dried over magnesium sulphate. The solvent was evaporated under reduced pressure. The obtained residue was recrystallized from hexane to give a title compound (220 mg). The yield was 92%.

$^1$H-NMR (CDCl$_3$) δ: 3.62 (2H, s), 4.32-4.79 (4H, m), 4.37 (2H, s), 7.12-7.38 (4H, m), 7.76 (2H, d, J=8.1 Hz), 7.81 (2H, d, J=8.1 Hz), 8.25 (1H, s).

The present invention includes the following compounds synthesized in a similar way as above.

TABLE 77

| No | R1 | R2 | R3, R4 | X1 | Y | 1H-NMR(CDCl3 or DMSO-d6) δ |
|---|---|---|---|---|---|---|
| X-1 | 4-CF3-phenyl | Me | H, H | O | 3-CH2CO2H-phenyl | 2.32(3H, s), 3.65(2H, s), 5.19(2H, s), 6.92-7.32(4H, m), 7.75(2H, d, J = 8.4 Hz), 7.84(2H, d, J = 8.4 Hz) |
| X-2 | 4-CF3-phenyl | CH2OEt | H, H | O | 3-CH2CO2H-phenyl | 1.22(3H, t, J = 6.9 Hz), 3.58(2H, q, J = 6.9 Hz), 3.65(2H, s), 4.55(2H, s), 5.25(2H, s), 6.90-7.32(4H, m), 7.76(2H, d, J = 8.7 Hz), 7.94(2H, d, J = 8.7 Hz) |

TABLE 77-continued

| No | R1 | R2 | R3, R4 | X1 | Y | 1H-NMR(CDCl3 or DMSO-d6) δ |
|---|---|---|---|---|---|---|
| X-3 | 4-CF3-C6H4 | CH2OCH2cPr | H, H | O | 3-Me-C6H4-CH2-CO2H | 0.10-0.15(2H, m), 0.39-0.45(2H, m), 0.94-1.05(1H, m), 3.31(2H, d, J = 6.9 Hz), 3.55(2H, s), 4.57(2H, s), 5.28(2H, s), 6.90(1H, d, J = 7.8 Hz), 6.97-6.99(2H, m), 7.24-7.30(1H, m), 7.97(2H, d, J = 8.4 Hz), 8.06(2H, d, J = 8.24 Hz), 12.33(1H, s) |
| X-4 | 4-CF3-C6H4 | CH=NOEt | H, H | O | 3-Me-C6H4-CH2-CO2H | 1.21(3H, t, J = 7.1 Hz), 3.64(2H, s), 4.07(2H, q, J = 7.1 Hz), 5.35(2H, s), 6.90-7.31(4H, m), 7.77(2H, d, J = 8.4 Hz), 7.90(2H, d, J = 8.4 Hz), 8.19(1H, s) |
| X-5 | 4-CF3-C6H4 | Me | H, H | S | 3-Me-C6H4-CH2-CO2H | 2.51(3H, s), 3.62(2H, s), 4.15(2H, s), 7.12-7.36(4H, m), 7.73(2H, d, J = 8.1 Hz), 7.80(2H, d, J = 8.1 Hz) |
| X-6 | 4-CF3-C6H4 | CH=NOCH2CH2F | H,H | S | 3-Me-C6H4-CH2-CO2H | 3.62(2H, s), 4.32-4.79(4H, m), 4.37(2H, s), 7.12-7.38(4H, m), 7.76(2H, d, J = 8.1 Hz), 7.81(2H, d, J = 8.1 Hz), 8.25(1H, s) |
| X-7 | 4-CF3-C6H4 | CH=NOEt | H, H | O | 4-F-3-Me-C6H3-CH2-CO2H | 1.22(3H, t, J = 7.1 Hz), 3.62(2H, s), 4.07(2H, q, J = 7.1 Hz), 5.42(2H, s), 6.86-7.10(3H, m), 7.77(2H, d, J = 8.4 Hz), 7.88(2H, d, J = 8.4 Hz), 8.19(1H, s) |
| X-8 | 4-CF3-C6H4 | CH=NOEt | H, H | S | 4-F-3-Me-C6H3-CH2-CO2H | 1.34(3H, t, J = 6.9 Hz), 3.59(2H, s), 4.27(2H, q, J = 6.9 Hz), 4.35(2H, s), 7.03(1H, t, J = 8.7 Hz), 7.14-7.22(3H, m), 7.38(1H, dd, J = 2.4, 6.9 Hz), 7.75(2H, d, J = 8.4 Hz), 7.81(2H, d, J = 8.4 Hz), 8.17(1H, s) |
| X-9 | 4-CF3-C6H4 | CH=NOEt | H, H | O | 4-Cl-3-Me-C6H3-CH2-CO2H | 8.22(s, 1H), 7.90(d, 2H, J = 8.4 Hz), 7.77(d, 2H, J = 8.4 Hz), 7.34(d, 1H, J = 8.1 Hz), 7.04(d, 1H, J = 1.8 Hz), 6.88(dd, 1H, J = 8.1, 1.8 Hz), 5.42(s, H), 4.07(q, 2H, J = 6.9 Hz), 3.64(s, 2H), 1.22(t, 3H, J = 6.9 Hz) |
| X-10 | 4-CF3-C6H4 | CH=NOEt | H, H | O | 4-MeO-3-Me-C6H3-CH2-CO2H | 1.24(3H, t, J = 7.0 Hz), 3.59(2H, s), 4.10(2H, q, J = 7.0 Hz), 5.39(2H, s), 6.85-7.00(3H, m), 7.76(2H, d, J = 8.4 Hz), 7.92(2H, d, J = 8.4 Hz), 8.24(1H, s) |
| X-11 | 4-CF3-C6H4 | CH=NOEt | H, H | O | 3,5-diMe-C6H3-CH2-CO2H | 1.23(3H, t, J = 7.0 Hz), 2.33(3H, s), 3.60(2H, s), 4.09(2H, q, J = 7.0 Hz), 5.33(2H, s), 6.75(1H, s), 6.77(2H, s), 7.77(2H, d, J = 8.4 Hz), 7.90(2H, d, J = 8.4 Hz), 8.19(1H, s) |
| X-12 | 4-CF3-C6H4 | CH=NOEt | H, H | O | 3-OMe-5-Me-C6H3-CH2-CO2H | 2.32(3H, s), 3.61(2H, s), 3.79(3H, s), 5.16(2H, s), 6.48-6.60(4H, m), 7.75(2H, d, J = 8.4 Hz), 7.84(2H, d, J = 8.4 Hz) |

TABLE 77-continued

General structure: isoxazole with R1 at 5-position, R2 at 4-position, 3-position bearing CR3R4-X1-Y

| No | R1 | R2 | R3, R4 | X1 | Y | 1H-NMR(CDCl3 or DMSO-d6) δ |
|---|---|---|---|---|---|---|
| X-13 | 4-(F3C)C6H4- | CH=NOEt | H, H | O | 2-Cl, 5-Me-C6H3-CH2-CO2H | 8.18(s, 1H), 7.87(d, 2H, J = 8.7 Hz), 7.78(d, 2H, J = 8.7 Hz), 7.32(d, 1H, J = 9.0 Hz), 6.99(d, 1H, 2.7 Hz), 6.92(dd, 1H, J = 9.0, 2.7 Hz), 5.34(s, 2H), 4.09(q, 2H, J = 6.9 Hz), 3.79(s, 2H), 1.23(t, 3H, 6.9 Hz) |

TABLE 78

General structure: isoxazole with R1 at 5-position, R2 at 4-position, 3-position bearing CR3R4-X1-Y

| No | R1 | R2 | R3, R4 | X1 | Y | 1H-NMR(CDCl3 or DMSO-d6) δ |
|---|---|---|---|---|---|---|
| X-14 | 4-(F3C)C6H4- | CH=NOEt | H, H | O | 2-Me, 3-Me-C6H3-CH2-CO2H | 1.21(3H, t, J = 7.2 Hz), 2.21 (3H, s), 3.70(2H, s), 4.06(2H, q, J =7.2 Hz), 5.35(2H, s), 6.35-7.20(3H, m), 7.77(2H, d, J = 8.4 Hz), 7.91(2H, d, J = 8.4 Hz), 8.19(1H, s) |
| Y-1 | 4-(F3C)C6H4- | Me | H, H | —ON=CH— | 3-Me-C6H4-CH2-CO2H | 2.33(3H, s), 3.67(2H, s), 5.31 (2H, s), 7.29-7.37(2H, m), 7.48-7.52(2H, m), 7.74(2H, d, J = 8.4 Hz), 7.84(2H, d, J = 8.4 Hz), 8.11(1H, s) |
| X-82 | 4-(F3C)C6H4- | CH=NOnPr | H, H | S | 3-Cl, 5-Me-C6H3-CH2-CO2H | 0.91(3H, t, J = 7.2 Hz), 1.68 (2H, m), 3.59(2H, s), 4.06(2H, t, J = 6.8 Hz), 4.53(2H, s), 7.21 (1H, s), 7.25(1H, s), 7.43(1H, s), 7.93(2H, d, J = 8.4 Hz), 8.03(2H, d, J = 8.3 Hz), 8.36(1 Hz, s), 12.55(1H, brs) |
| X-97 | 4-Cl-C6H4- | CH=NOCH2CH2F | H, H | S | 3-Me-C6H4-CH2-CO2H | 3.55(2H, s), 4.28(1H, t, J = 3.0 Hz), 4.36(1H, t, J = 3.0 Hz), 4.57(2H, s), 4.61(1H, t, J = 3.0 Hz), 4.73(1H, t, J = 3.0 Hz), 7.12-7.13(2H, m), 7.27-7.30 (2H, m), 7.64(2H, d, J = 6.3 Hz), 7.83(2H, d, J = 6.3 Hz), 8.38(1H, s), 12.30(1H, br) |
| X-104 | 4-Cl-C6H4- | CH=NOCH2CH2F | H, H | O | 4-Me, 3-Me-C6H3-CH2-CO2H | 2.10(3H, s), 3.52(2H, s), 4.27 (1H, t, J = 3.0 Hz), 4.08(1H, t, J = 3.0 Hz), 4.15(1H, t, J = 3.0 Hz), 4.54(1H, t, J = 3.0 Hz), 5.33(2H, s), 6.78(1H, d, J = 6.0 Hz), 7.00(1H, s), 7.08(1H, d, J = 6.0 Hz), 7.66(2H, d, J = 6.3 Hz), 7.89(2H, d, J = 6.3 Hz), 8.37(1H, s), 12.30(1H, br) |

TABLE 78-continued

[Structure: isoxazole with R1 at 5-position, R2 at 4-position, and C(R3)(R4)-X1-Y at 3-position]

| No | R1 | R2 | R3, R4 | X1 | Y | 1H-NMR(CDCl3 or DMSO-d6) δ |
|---|---|---|---|---|---|---|
| X-111 | 4-Cl-C6H4 | CH=NOCH2CH2F | H, H | S | 4-methyl-3-methylphenyl-CH2CO2H | 2.24(3H, s), 3.51(2H, s), 4.27 (1H, t, J = 3.0 Hz), 4.35(1H, t, J = 3.0 Hz), 4.39(2H, s), 4.59 (1H, t, J = 3.0 Hz), 4.71(1H, t, J = 3.0 Hz), 7.04(1H, d, J = 6.0 Hz), 7.16(1H, d, J = 6.0 Hz), 7.34(1H, s), 7.64(2H, d, J = 6.3 Hz), 7.83(2H, d, J = 6.3 Hz), 8.37(1H, s), 12.30(1H, br) |
| X-184 | 4-F3CO-C6H4 | CH2OCH2cPr | H, H | O | 4-Cl-3-methylphenyl-CH2CO2H | 0.098(2H, m), 0.40(2H, m), 0.97(1H, m), 3.30(2H, d, J = 4.4 Hz), 3.61(2H, s), 4.61(2H, s), 5.36(2H, s), 6.94(1H, d, J = 8.2 Hz), 7.30(1H, s), 7.40(1H, d, J = 8.2 Hz), 7.60(2H, d, J = 8.2 Hz), 7.98(2H, d, J = 8.2 Hz), 12.44(1H, brs) |
| X-186 | 4-F3CO-C6H4 | CH=NOEt | H, H | O | 4-Cl-3-methylphenyl-CH2CO2H | 1.21(3H, t, J = 7.2 Hz), 3.64 (2H, S), 4.05(2H, q, J = 7.2 Hz), 5.41(2H, s), 6.87(1H, dd, J = 1.5 Hz, 7.8 Hz), 7.03(1H, d, J = 1.5 Hz), 7.34(1H, d, J = 7.8 Hz), 7.35(2H, d, J = 8.7 Hz), 7.81(2H, d, J = 8.7 Hz), 8.20 (1H, s) |
| X-208 | 4-F3CO-C6H4 | CH=NOnPr | H, H | S | 3,5-dimethylphenyl-CH2CO2H | 0.91(3H, t, J = 7.2 Hz), 1.68 (2H, m), 3.59(2H, s), 4.05(2H, t, J = 6.8 Hz), 4.51(2H, s), 7.20 (1H, s), 7.24(1H, s), 7.42(1H, s), 7.56(2H, d, J = 8.4 Hz), 7.95(2H, d, J = 8.8 Hz), 8.32 (1 Hz, s), 12.50(1H, brs) |
| X-216 | 4-F3CO-C6H4 | CH=NOCH2CH2F | H, H | O | 3-Cl-5-methylphenyl-CH2CO2H | 3.61(2H, s), 4.16(1H, t, J = 4.1 Hz), 4.26(1H, t, J = 4.1 Hz), 4.46(1H, t, J = 4.1 Hz), 4.61 (1H, t, J = 4.1 Hz), 5.31(2H, s), 6.97-6.84(3H, m), 7.37(2H, d, J = 8.7 Hz), 7.77(2H, d, J = 8.7 Hz), 8.24(1H, s) |

TABLE 79

[Structure: isoxazole with R1 at 5-position, R2 at 4-position, and C(R3)(R4)-X1-Y at 3-position]

| No | R1 | R2 | R3, R4 | X1 | Y | |
|---|---|---|---|---|---|---|
| X-224 | 4-F3C-C6H4 | CH=NOEt | H, H | S | 1-methyl-5-methyl-pyrazol-3-yl-CH2CO2H | (1H-NMR, acetone-d6) 8.10(s, 1H), 7.87 (d, 2H, J = 9.0 Hz), 7.75(d, 2H, J = 8.1 Hz), 6.16 (s, 1H), 4.08(s, 2H), 4.02(q, 2H, J = 7.2 Hz), 3.54(s, 3H), 3.35(s, 2H), 1.12(t, 3H, 7.2 Hz) |

TABLE 79-continued

| No | R1 | R2 | R3, R4 | X1 | Y | |
|---|---|---|---|---|---|---|
| X-225 | 4-CF3-C6H4 | CH2OcBu | H, H | S | 3-methylphenyl-CH2COOH | (1H-NMR, DMSO-d6) 1.43-1.52(1H, m), 1.60-1.70(1H, m), 1.82-1.92(2H, m), 2.10-2.15(2H, m), 3.55(2H, s), 3.99-4.10(1H, m), 4.36(2H, s), 4.44(2H, s), 7.14(1H, d, J = 5.4 Hz), 7.27-7.35(3H, m), 7.94-8.01(4H, m), 12.35(1H, br) |
| X-226 | 4-CF3-C6H4 | CH2OcBu | H, H | O | 4-Cl-3-methylphenyl-CH2CO2H | (1H-NMR, DMSO-d6) 1.37-1.46(1H, m), 1.53-1.60(1H, m), 1.75-1.85(2H, m), 1.93-2.08(2H, m), 3.61(2H, s), 3.98-4.05(1H, m), 4.52(2H, s), 5.36(2H, s), 6.93(1H, d, J = 6.3 Hz), 7.30(1H, s), 7.39-7.41(1H, d, J = 6.3 Hz), 7.97(2H, d, J = 6.3 Hz), 8.05(2H, d, J = 6.3 Hz), 12.41(1H, br) |
| X-227 | 4-CF3-C6H4 | CH2OcBu | H, H | S | 3,5-dimethylphenyl-CH2CO2H | (1H-NMR, DMSO-d6) 1.40-1.52(1H, m), 1.60-1.70(1H, m), 1.82-1.92(2H, m), 2.10-2.15(2H, m), 2.26(3H, s), 2.50(2H, s), 3.55(2H, s), 3.99-4.06(1H, m), 4.34(2H, s), 4.43(2H, s), 6.95(1H, s), 7.11(1H, s), 7.16(1H, s), 7.95(2H, d, J = 6.3 Hz), 7.99(2H, d, J = 6.3 Hz), 12.35(1H, br) |
| X-228 | 4-CF3O-C6H4 | CH2OcBu | H, H | S | 3-Cl-5-methylphenyl-CH2CO2H | (1H-NMR, DMSO-d6) 1.40-2.20(6H, m), 3.58(2H, s), 3.97-4.12(1H, m), 4.42(2H, s), 4.42(2H, s), 7.18-7.47(3H, m), 7.58(2H, d, J = 8.7 Hz), 7.90(2H, d, J = 8.7 Hz) |
| X-229 | 4-CF3-C6H4 | CH2OcBu | H, H | S | 3-Cl-5-methylphenyl-CH2CO2H | (1H-NMR, CDCl3) 1.50-2.30(6H, m), 3.60(2H, s), 3.98-4.10(1H, m), 4.25(2H, s), 4.44(2H, s), 7.12-7.35(3H, m), 7.75(2H, d, J = 8.4 Hz), 7.86(2H, d, J = 8.4 Hz) |
| X-230 | 4-CF3-C6H4 | CH2OCH2cPr | H,H | O | 3-methylphenyl-CF2CO2H | (1H-NMR, CDCl3) 0.15-0.20(2H, m), 0.50-0.56(2H, m), 1.06(1H, m), 3.38(2H, d, J = 7.2 Hz), 4.59(2H, s), 5.28(2H, s), 7.14(1H, d, J = 8.1 Hz), 7.26-7.27(2H, m), 7.39(1H, t, J = 8.1 Hz), 7.76(2H, d, J = 8.1 Hz), 7.93(2H, d, J = 8.1 Hz) |
| X-231 | 4-CF3-C6H4 | CH=NOEt | H, H | S | pyridyl-CF2CO2H | (1H-NMR, CDCl3) 1.35(3H, t, J = 7.2 Hz), 4.24(2H, q, J = 7.2H), 4.41(2H, s), 7.39(1H, t, J = 7.8 Hz), 7.48(1H, d, J = 7.8 Hz), 7.59(1H, d, J = 7.8 Hz), 7.63(1H, s), 7.75(2H, d, J = 8.4 Hz), 7.80(2H, d, J = 8.4 Hz), 8.19(1H, s) |
| X-232 | 4-CF3O-C6H4 | CH2OcBu | H, H | O | 4-Cl-3-methylphenyl-CH2CO2H | (1H-NMR, DMSO-d6) 1.35-1.61(2H, m), 1.76-1.85(2H, m), 2.00-2.09(2H, m), 3.59(2H, s), 3.96-4.05(1H, m), 4.49(2H, s), 5.34(2H, s), 6.93(1H, dd, J = 8.1 Hz, 1.5 Hz), 7.29(1H, d, J = 1.5 Hz), 7.40(1H, d, J = 8.1 Hz), 7.61(2H, d, J = 8.4 Hz), 7.96(2H, d, J = 8.4 Hz), 12.45(1H, s) |
| X-233 | 4-CF3O-C6H4 | CH2OcBu | H, H | S | 3-methylphenyl-CH2COOH | (1H-NMR, DMSO-d6) 1.41-1.68(2H, m), 1.80-1.93(2H, m), 2.08-2.16(2H, m), 3.55(2H, s), 3.97-4.07(1H, m), 4.34(2H, s), 4.41(2H, s), 7.13(1H, d, J = 7.2 Hz), 7.26-7.34(3H, m), 7.58(2H, d, J = 8.4 Hz), 7.90(2H, d, J = 8.4 Hz), 12.35(1H, s) |

TABLE 80

| No | R1 | R2 | R3, R4 | X1 | Y | |
|---|---|---|---|---|---|---|
| X-234 | 4-F3CO-C6H4- | CH2OcBu | H, H | S | 4-Cl-3-Me-C6H3-CH2-CO2H | (1H-NMR, DMSO-d6) 1.41-1.68(2H, m), 1.81-1.94(2H, m), 2.08-2.16(2H, m), 3.58(2H, s), 3.99-4.09(1H, m), 4.40(2H, s), 4.43(2H, s), 7.15(1H, d, J = 8.1 Hz), 7.43(1H, d, J = 8.1 hZ), 7.49(1H, s), 7.59(2H, d, J = 9.0 Hz), 7.91(2H, d, J = 9.0 Hz), 12.43(1H, s) |
| X-235 | 4-F3CO-C6H4- | CH2OcBu | H, H | O | 3-Me-C6H4-CH2-COOH | (1H-NMR, DMSO-d6) 1.37-1.64(2H, m), 1.75-1.84(2H, m), 2.04-2.11(2H, m), 3.55(2H, s), 3.96-4.05(1H, m), 4.44(2H, s), 5.26(2H, s), 6.89-6.97(3H, m), 7.27(1H, t, J = 7.8 Hz), 7.61(2H, d, J = 9.0 Hz), 7.95(2H, d, J = 9.0 Hz), 12.33(1H, s) |
| X-236 | 4-F3CO-C6H4- | CH2OcBu | H, H | S | 3,4-diMe-C6H3-CH2-CO2H | (1H-NMR, DMSO-d6) 1.41-1.68(2H, m), 1.80-1.93(2H, m), 2.07-2.16(2H, m), 2.27(3H, s), 3.51(2H, s), 3.97-4.06(1H, m), 4.28(2H, s), 4.38(2H, s), 7.06(1H, d, J = 7.8 Hz), 7.17(1H, d, J = 7.8 Hz), 7.37(1H, s), 7.59(2H, d, J = 8.7 Hz), 7.90(2H, d, J = 8.7 Hz), 12.33(1H, s) |
| X-237 | 4-F3CO-C6H4- | CH2OcBu | H, H | O | 3,4-diMe-C6H3-CH2-CO2H | (1H-NMR, DMSO-d6) 1.36-1.63(2H, m), 1.77-1.83(2H, m), 2.06-2.14(2H, m), 3.53(2H, s), 3.97-4.02(1H, m), 4.45(2H, s), 5.24(2H, s), 6.80(1H, d, J = 7.8 Hz), 7.06(1H, s), 7.10(1H, d, J = 7.8 Hz), 7.62(2H, d, J = 8.4 Hz), 7.96(2H, d, J = 8.4 Hz), 12.28(1H, s) |
| Z-1 | 2-benzofuranyl | CH2OCH2cPr | H, H | S | 3,5-diMe-C6H3-CH2-CO2H | (1H NMR, CDCl3) 7.65(1H, dt, J = 7.8, 0.6), 7.54(1H, dd, J = 8.1, 0.6), 7.38(1H, dt, 7.2, 1.2), 7.29(1H, dt, J = 7.8, 1.2), 7.14(2H, d, J = 9.6), 6.94(1H, s), 5.86(2H, s), 4.27(2H, s), 3.55(2H, s), 3.37(2H, d, J = 6.9), 2.30(3H, s), 1.3-1.8(1H, m), 0.55(2H, dt, J = 6.0, 4.5), 0.22(2H, dt, J = 6, 4.8) |

TABLE 81

| No | R1 | R2 | X1 | R3, R4 | Y | m/z |
|---|---|---|---|---|---|---|
| X-15 | 4-F3C-C6H4- | CH=NOCH2CH2Cl | S | H, H | 3-Me-C6H4-CH2-CO2H | 497[M − H]− |
| X-16 | 4-F3C-C6H4- | CH=N-O-CH2CH2-N(morpholinyl-SO2) | S | H, H | 3-Me-C6H4-CH2-CO2H | 597[M + H]− |
| X-17 | 4-F3C-C6H4- | CH=NOEt | O | H, H | 3,4-diMe-C6H3-CH2-CO2H | 463[M + H]+ |

TABLE 81-continued
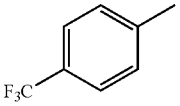
| No | R1 | R2 | X1 | R3, R4 | Y | m/z |
|---|---|---|---|---|---|---|
| X-18 | 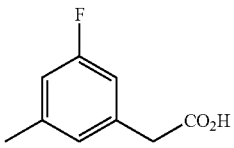 | CH=NOEt | O | H, H | 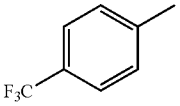 | 467(M + 1) |
| X-19 | 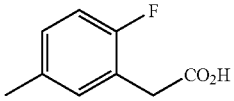 | CH=NOEt | O | H, H | 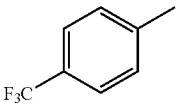 | 467(M + 1) |
| X-20 | 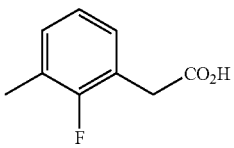 | CH=NOEt | O | H, H | 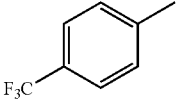 | 467[M + H]+ |
| X-21 | 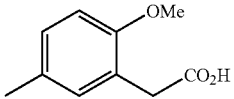 | CH=NOEt | O | H, H | 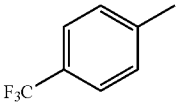 | 479(M + 1) |
TABLE 82
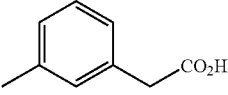
| No | R1 | R2 | R3, R4 | X1 | Y | TLC Rf |
|---|---|---|---|---|---|---|
| X-22 | 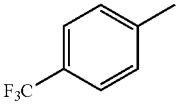 | CH2OCH2cPr | H, H | S | 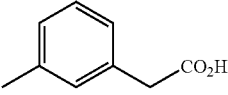 | 0.58 (AcOEt) |
| X-23 | 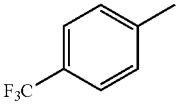 | CH2ON=C(CH3)2 | H, H | S | 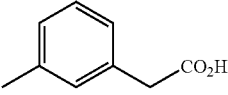 | 0.54 (AcOEt) |

TABLE 83

| No | R1 | R2 | R3, R4 | X1 | Y | mp |
|---|---|---|---|---|---|---|
| X-24 | 4-CF3-phenyl (2-methyl) | CH2OEt | H, H | S | 3-methylphenyl-CH2CO2H | 94-95 |
| X-25 | 4-CF3-phenyl (2-methyl) | CH=NOEt | H, H | S | 3-methylphenyl-CH2CO2H | 131-133 |
| X-81 | 4-CF3-phenyl | CH=NOEt | H, H | S | 3-chloro-5-methylphenyl-CH2CO2H | 132-134 |
| X-173 | 4-CF3O-phenyl | CH=NOnPr | H, H | O | 3,4-dimethylphenyl-CH2CO2H | 128-130 |
| X-221 | 4-CF3O-phenyl | CH=NOEt | H, H | S | 3-chloro-5-methylphenyl-CH2CO2H | 113-115 |
| X-223 | 4-CF3O-phenyl | CH=NOCH2CH2F | H, H | S | 3-chloro-5-methylphenyl-CH2CO2H | 120-122 |
| Z-2 | benzofuran-2-yl | CH=NOEt | H, H | S | 3,5-dimethylphenyl-CH2CO2H | 158-160 |
| Z-3 | benzofuran-2-yl | CH=NOEt | H, H | S | 3-methylphenyl-CH2CO2H | 143-146 |

TABLE 84

| No | R1 | R2 | R3, R4 | X1 | Y |
|---|---|---|---|---|---|
| X-26 | 4-(F₃C)C₆H₄ | CH=NOMe | H, H | O | 3-Me-C₆H₄-CH₂CO₂H |
| X-27 | 4-(F₃C)C₆H₄ | CH=NOnPr | H, H | O | 3-Me-C₆H₄-CH₂CO₂H |
| X-28 | 4-(F₃C)C₆H₄ | CH=NOCH2CH2F | H, H | O | 3-Me-C₆H₄-CH₂CO₂H |
| X-29 | 4-(F₃C)C₆H₄ | CH=NOMe | H, H | S | 3-Me-C₆H₄-CH₂CO₂H |
| X-30 | 4-(F₃C)C₆H₄ | CH=NOnPr | H, H | S | 3-Me-C₆H₄-CH₂CO₂H |
| X-31 | 4-(F₃C)C₆H₄ | Me | H, H | O | 3,4-diMe-C₆H₃-CH₂CO₂H |
| X-32 | 4-(F₃C)C₆H₄ | CH2OEt | H, H | O | 3,4-diMe-C₆H₃-CH₂CO₂H |
| X-33 | 4-(F₃C)C₆H₄ | CH2OCH2cPr | H, H | O | 3,4-diMe-C₆H₃-CH₂CO₂H |
| X-34 | 4-(F₃C)C₆H₄ | CH=NOMe | H, H | O | 3,4-diMe-C₆H₃-CH₂CO₂H |
| X-35 | 4-(F₃C)C₆H₄ | CH=NOnPr | H, H | O | 3,4-diMe-C₆H₃-CH₂CO₂H |
| X-36 | 4-(F₃C)C₆H₄ | CH=NOCH2CH2F | H, H | O | 3,4-diMe-C₆H₃-CH₂CO₂H |

TABLE 84-continued

| No | R1 | R2 | R3, R4 | X1 | Y |
|---|---|---|---|---|---|
| X-37 | 4-F$_3$C-C$_6$H$_4$- | Me | H, H | S | 3-Me-4-Me-C$_6$H$_3$-CH$_2$CO$_2$H |
| X-38 | 4-F$_3$C-C$_6$H$_4$- | CH2OEt | H, H | S | 3-Me-4-Me-C$_6$H$_3$-CH$_2$CO$_2$H |
| X-39 | 4-F$_3$C-C$_6$H$_4$- | CH2OCH2cPr | H, H | S | 3-Me-4-Me-C$_6$H$_3$-CH$_2$CO$_2$H |
| X-40 | 4-F$_3$C-C$_6$H$_4$- | CH=NOMe | H, H | S | 3-Me-4-Me-C$_6$H$_3$-CH$_2$CO$_2$H |
| X-41 | 4-F$_3$C-C$_6$H$_4$- | CH=NOEt | H, H | S | 3-Me-4-Me-C$_6$H$_3$-CH$_2$CO$_2$H |
| X-42 | 4-F$_3$C-C$_6$H$_4$- | CH=NOnPr | H, H | S | 3-Me-4-Me-C$_6$H$_3$-CH$_2$CO$_2$H |
| X-43 | 4-F$_3$C-C$_6$H$_4$- | CH=NOCH2CH2F | H, H | S | 3-Me-4-Me-C$_6$H$_3$-CH$_2$CO$_2$H |
| X-44 | 4-F$_3$C-C$_6$H$_4$- | Me | H, H | O | 3-Me-4-Cl-C$_6$H$_3$-CH$_2$CO$_2$H |
| X-45 | 4-F$_3$C-C$_6$H$_4$- | CH2OEt | H, H | O | 3-Me-4-Cl-C$_6$H$_3$-CH$_2$CO$_2$H |
| X-46 | 4-F$_3$C-C$_6$H$_4$- | CH2OCH2cPr | H, H | O | 3-Me-4-Cl-C$_6$H$_3$-CH$_2$CO$_2$H |
| X-47 | 4-F$_3$C-C$_6$H$_4$- | CH=NOMe | H, H | O | 3-Me-4-Cl-C$_6$H$_3$-CH$_2$CO$_2$H |

TABLE 85
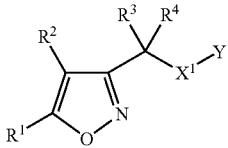
| No | R1 | R2 | R3, R4 | X1 | Y |
|---|---|---|---|---|---|
| X-48 | 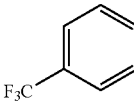 | CH=NOnPr | H, H | O | 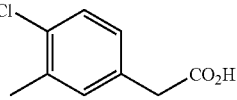 |
| X-49 | 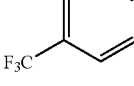 | CH=NOCH2CH2F | H, H | O | 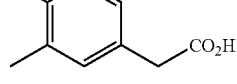 |
| X-50 | 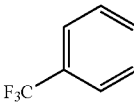 | Me | H, H | S | 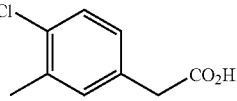 |
| X-51 | 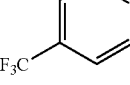 | CH2OEt | H, H | S | 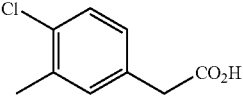 |
| X-52 | 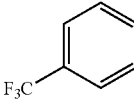 | CH2OCH2cPr | H, H | S | 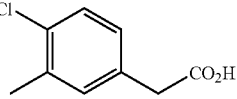 |
| X-53 | 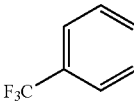 | CH=NOMe | H, H | S | 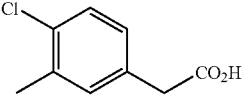 |
| X-54 | 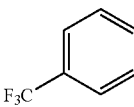 | CH=NOEt | H, H | S | 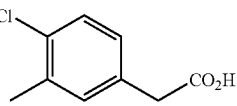 |
| X-55 | 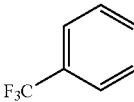 | CH=NOnPr | H, H | S | 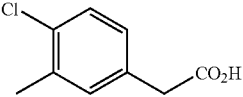 |
| X-56 | 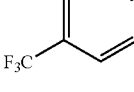 | CH=NOCH2CH2F | H, H | S | 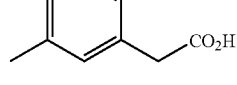 |
| X-57 | 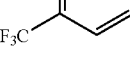 | Me | H, H | O | 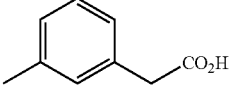 |
| X-58 | 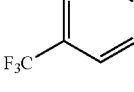 | CH2OEt | H, H | O | 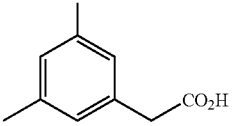 |

TABLE 85-continued
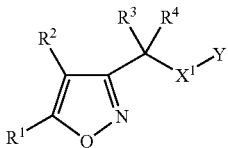
| No | R1 | R2 | R3, R4 | X1 | Y |
|---|---|---|---|---|---|
| X-59 |  | CH2OCH2cPr | H, H | O | 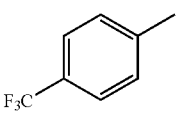 |
| X-60 | 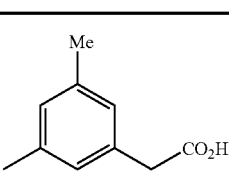 | CH=NOMe | H, H | O |  |
| X-61 | 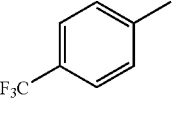 | CH=NOnPr | H, H | O | 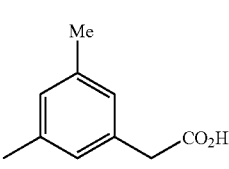 |
| X-62 |  | CH=NOCH2CH2F | H, H | O | 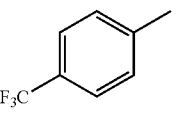 |
| X-63 | 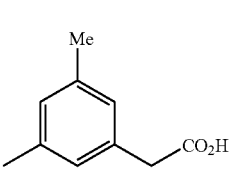 | Me | H, H | S |  |
| X-64 | 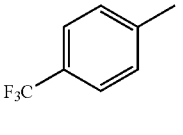 | CH2OEt | H, H | S | 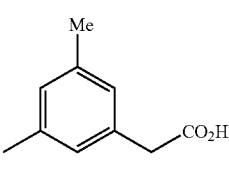 |
| X-65 |  | CH2OCH2cPr | H, H | S | 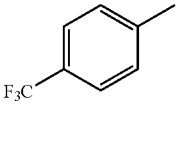 |
| X-66 | 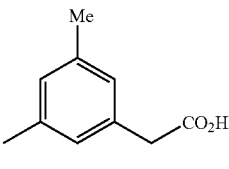 | CH=NOMe | H, H | S |  |

TABLE 86

| No | R1 | R2 | R3, R4 | X1 | Y |
|---|---|---|---|---|---|
| X-67 | 4-F₃C-C₆H₄- | CH=NOEt | H, H | S | 3,5-diMe-C₆H₃-CH₂-CO₂H (Me at 3, CH₂CO₂H at 1, Me at 5) |
| X-68 | 4-F₃C-C₆H₄- | CH=NOnPr | H, H | S | 3,5-diMe-C₆H₃-CH₂-CO₂H |
| X-69 | 4-F₃C-C₆H₄- | CH=NOCH2CH2F | H, H | S | 3,5-diMe-C₆H₃-CH₂-CO₂H |
| X-70 | 4-F₃C-C₆H₄- | Me | H, H | O | 3-Cl-5-Me-C₆H₃-CH₂-CO₂H |
| X-71 | 4-F₃C-C₆H₄- | CH2OEt | H, H | O | 3-Cl-5-Me-C₆H₃-CH₂-CO₂H |
| X-72 | 4-F₃C-C₆H₄- | CH2OCH2cPr | H, H | O | 3-Cl-5-Me-C₆H₃-CH₂-CO₂H |
| X-73 | 4-F₃C-C₆H₄- | CH=NOMe | H, H | O | 3-Cl-5-Me-C₆H₃-CH₂-CO₂H |
| X-74 | 4-F₃C-C₆H₄- | CH=NOEt | H, H | O | 3-Cl-5-Me-C₆H₃-CH₂-CO₂H |
| X-75 | 4-F₃C-C₆H₄- | CH=NOnPr | H, H | O | 3-Cl-5-Me-C₆H₃-CH₂-CO₂H |

TABLE 86-continued
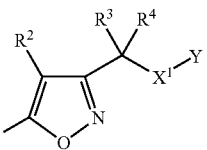
| No | R1 | R2 | R3, R4 | X1 | Y |
|---|---|---|---|---|---|
| X-76 | 4-F₃C-C₆H₄- | CH=NOCH2CH2F | H, H | O | 3-Cl-5-(CH₂CO₂H)-C₆H₃- |
| X-77 | 4-F₃C-C₆H₄- | Me | H, H | S | 3-Cl-5-(CH₂CO₂H)-C₆H₃- |
| X-78 | 4-F₃C-C₆H₄- | CH2OEt | H, H | S | 3-Cl-5-(CH₂CO₂H)-C₆H₃- |
| X-79 | 4-F₃C-C₆H₄- | CH2OCH2cPr | H, H | S | 3-Cl-5-(CH₂CO₂H)-C₆H₃- |
| X-80 | 4-F₃C-C₆H₄- | CH=NOMe | H, H | S | 3-Cl-5-(CH₂CO₂H)-C₆H₃- |
| X-83 | 4-F₃C-C₆H₄- | CH=NOCH2CH2F | H, H | S | 3-Cl-5-(CH₂CO₂H)-C₆H₃- |
| X-84 | 4-Cl-C₆H₄- | Me | H, H | O | 3-(CH₂CO₂H)-C₆H₄- |

TABLE 87
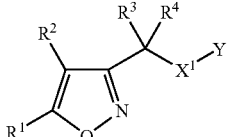
| No | R1 | R2 | R3, R4 | X1 | Y |
|---|---|---|---|---|---|
| X-85 | 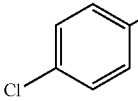 | CH2OEt | H, H | O | 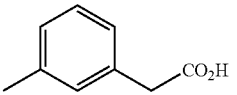 |
| X-86 | 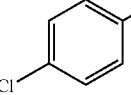 | CH2OCH2cPr | H, H | O | 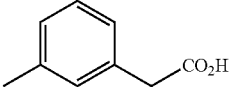 |
| X-87 | 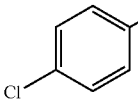 | CH=NOMe | H, H | O | 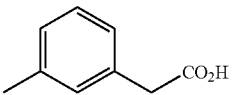 |
| X-88 | 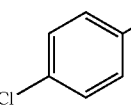 | CH=NOEt | H, H | O | 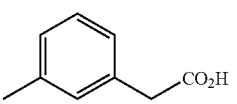 |
| X-89 | 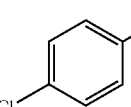 | CH=NOnPr | H, H | O | 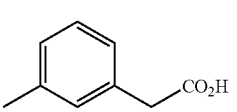 |
| X-90 | 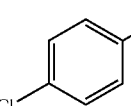 | CH=NOCH2CH2F | H, H | O | 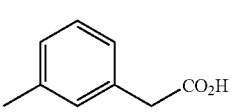 |
| X-91 | 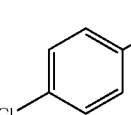 | Me | H, H | S | 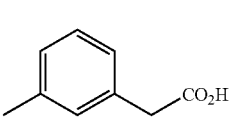 |
| X-92 | 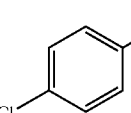 | CH2OEt | H, H | S | 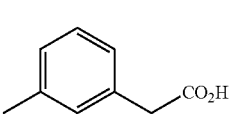 |
| X-93 | 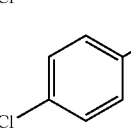 | CH2OCH2cPr | H, H | S | 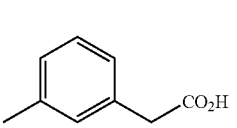 |
| X-94 | 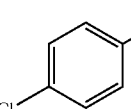 | CH=NOMe | H, H | S | 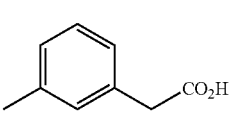 |
| X-95 | 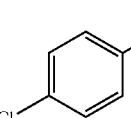 | CH=NOEt | H, H | S |  |
| X-96 | 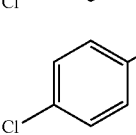 | CH=NOnPr | H, H | S | 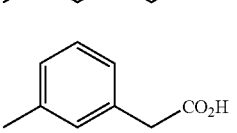 |

TABLE 87-continued

| No | R1 | R2 | R3, R4 | X1 | Y |
|---|---|---|---|---|---|
| X-98 | 4-Cl-C6H4 | Me | H, H | O | 3-Me-4-Me-C6H3-CH2-CO2H |
| X-99 | 4-Cl-C6H4 | CH2OEt | H, H | O | 3-Me-4-Me-C6H3-CH2-CO2H |
| X-100 | 4-Cl-C6H4 | CH2OCH2cPr | H, H | O | 3-Me-4-Me-C6H3-CH2-CO2H |
| X-101 | 4-Cl-C6H4 | CH=NOMe | H, H | O | 3-Me-4-Me-C6H3-CH2-CO2H |
| X-102 | 4-Cl-C6H4 | CH=NOEt | H, H | O | 3-Me-4-Me-C6H3-CH2-CO2H |
| X-103 | 4-Cl-C6H4 | CH=NOnPr | H, H | O | 3-Me-4-Me-C6H3-CH2-CO2H |
| X-105 | 4-Cl-C6H4 | Me | H, H | S | 3-Me-4-Me-C6H3-CH2-CO2H |
| X-106 | 4-Cl-C6H4 | CH2OEt | H, H | S | 3-Me-4-Me-C6H3-CH2-CO2H |
| X-107 | 4-Cl-C6H4 | CH2OCH2cPr | H, H | S | 3-Me-4-Me-C6H3-CH2-CO2H |
| X-108 | 4-Cl-C6H4 | CH=NOMe | H, H | S | 3-Me-4-Me-C6H3-CH2-CO2H |

TABLE 88
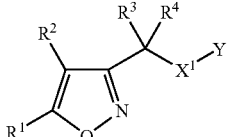
| No | R1 | R2 | R3, R4 | X1 | Y |
|----|----|----|--------|----|---|
| X-109 | 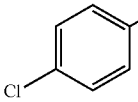 | CH=NOEt | H, H | S | 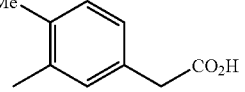 |
| X-110 | 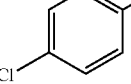 | CH=NOnPr | H, H | S | 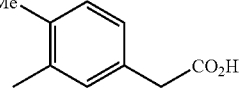 |
| X-112 | 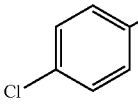 | Me | H, H | O | 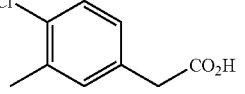 |
| X-113 | 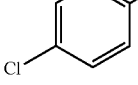 | CH2OEt | H, H | O | 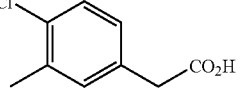 |
| X-114 | 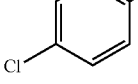 | CH2OCH2cPr | H, H | O | 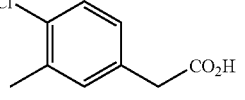 |
| X-115 | 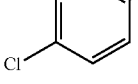 | CH=NOMe | H, H | O | 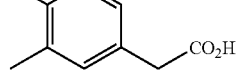 |
| X-116 | 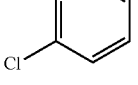 | CH=NOEt | H, H | O | 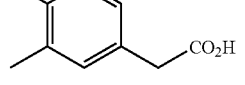 |
| X-117 | 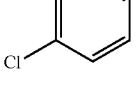 | CH=NOnPr | H, H | O | 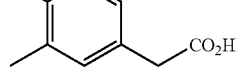 |
| X-118 | 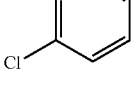 | CH=NOCH2CH2F | H, H | O | 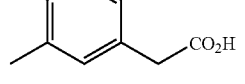 |
| X-119 | 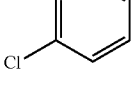 | Me | H, H | S | 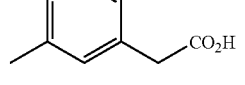 |
| X-120 | 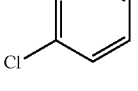 | CH2OEt | H, H | S | 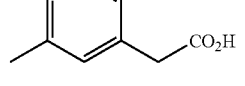 |
| X-121 | 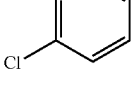 | CH2OCH2cPr | H, H | S | 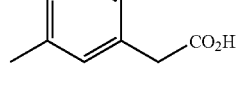 |

TABLE 88-continued
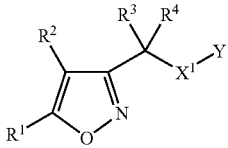
| No | R1 | R2 | R3, R4 | X1 | Y |
|---|---|---|---|---|---|
| X-122 | 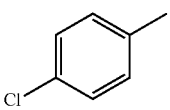 | CH=NOMe | H, H | S | 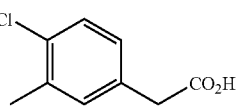 |
| X-123 | 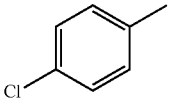 | CH=NOEt | H, H | S | 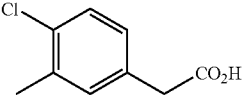 |
| X-124 | 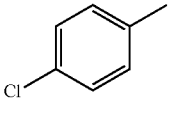 | CH=NOnPr | H, H | S | 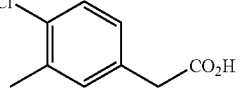 |
| X-125 | 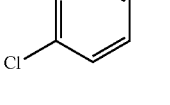 | CH=NOCH2CH2F | H, H | S | 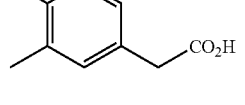 |
| X-126 | 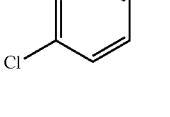 | Me | H, H | O | 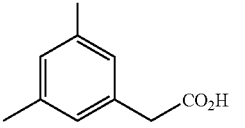 |
| X-127 | 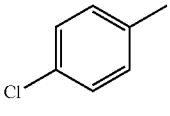 | CH2OEt | H, H | O | 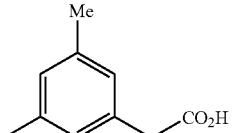 |
| X-128 | 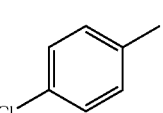 | CH2OCH2cPr | H, H | O | 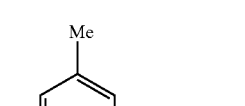 |
| X-129 | 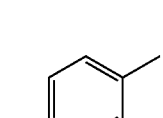 | CH=NOMe | H, H | O | 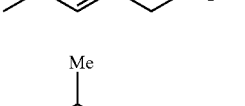 |
| X-130 | 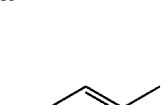 | CH=NOEt | H, H | O | 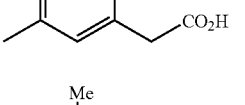 |

TABLE 89

| No | R1 | R2 | R3, R4 | X1 | Y |
|---|---|---|---|---|---|
| X-131 | 4-Cl-C6H4 | CH=NOnPr | H, H | O | 3,5-diMe-C6H3-CH2-CO2H |
| X-132 | 4-Cl-C6H4 | CH=NOCH2CH2F | H, H | O | 3,5-diMe-C6H3-CH2-CO2H |
| X-133 | 4-Cl-C6H4 | Me | H, H | S | 3,5-diMe-C6H3-CH2-CO2H |
| X-134 | 4-Cl-C6H4 | CH2OEt | H, H | S | 3,5-diMe-C6H3-CH2-CO2H |
| X-135 | 4-Cl-C6H4 | CH2OCH2cPr | H, H | S | 3,5-diMe-C6H3-CH2-CO2H |
| X-136 | 4-Cl-C6H4 | CH=NOMe | H, H | S | 3,5-diMe-C6H3-CH2-CO2H |
| X-137 | 4-Cl-C6H4 | CH=NOEt | H, H | S | 3,5-diMe-C6H3-CH2-CO2H |
| X-138 | 4-Cl-C6H4 | CH=NOnPr | H, H | S | 3,5-diMe-C6H3-CH2-CO2H |
| X-139 | 4-Cl-C6H4 | CH=NOCH2CH2F | H, H | S | 3,5-diMe-C6H3-CH2-CO2H |

TABLE 89-continued

| No | R1 | R2 | R3, R4 | X1 | Y |
|---|---|---|---|---|---|
| X-140 | 4-Cl-C6H4 | Me | H, H | O | 3-Cl-5-Me-C6H3-CH2-CO2H |
| X-141 | 4-Cl-C6H4 | CH2OEt | H, H | O | 3-Cl-5-Me-C6H3-CH2-CO2H |
| X-142 | 4-Cl-C6H4 | CH2OCH2cPr | H, H | O | 3-Cl-5-Me-C6H3-CH2-CO2H |
| X-143 | 4-Cl-C6H4 | CH=NOMe | H, H | O | 3-Cl-5-Me-C6H3-CH2-CO2H |
| X-144 | 4-Cl-C6H4 | CH=NOEt | H, H | O | 3-Cl-5-Me-C6H3-CH2-CO2H |
| X-145 | 4-Cl-C6H4 | CH=NOnPr | H, H | O | 3-Cl-5-Me-C6H3-CH2-CO2H |
| X-146 | 4-Cl-C6H4 | CH=NOCH2CH2F | H, H | O | 3-Cl-5-Me-C6H3-CH2-CO2H |
| X-147 | 4-Cl-C6H4 | Me | H, H | S | 3-Cl-5-Me-C6H3-CH2-CO2H |

TABLE 89-continued
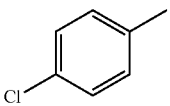
| No | R1 | R2 | R3, R4 | X1 | Y |
|---|---|---|---|---|---|
| X-148 | 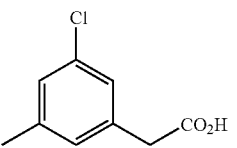 | CH2OEt | H, H | S | 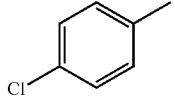 |
TABLE 90
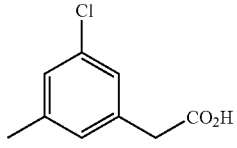
| No | R1 | R2 | R3, R4 | X1 | Y |
|---|---|---|---|---|---|
| X-149 | 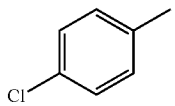 | CH2OCH2cPr | H, H | S | 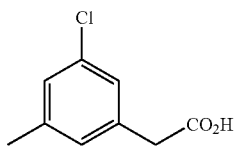 |
| X-150 | 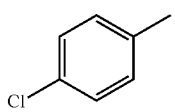 | CH=NOMe | H, H | S | 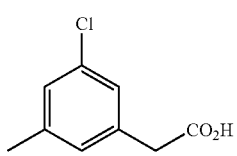 |
| X-151 | 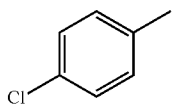 | CH=NOEt | H, H | S | 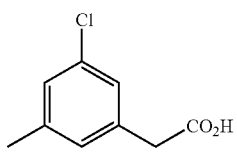 |
| X-152 | 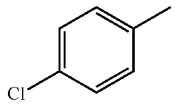 | CH=NOnPr | H, H | S | 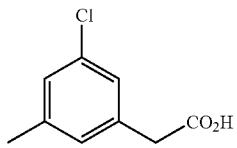 |
| X-153 | 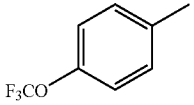 | CH=NOCH2CH2F | H, H | S | 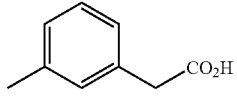 |
| X-154 |  | Me | H, H | O |  |

TABLE 90-continued

| No | R1 | R2 | R3, R4 | X1 | Y |
|---|---|---|---|---|---|
| X-155 | 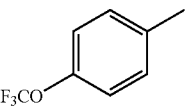 4-F₃CO-C₆H₄ | CH2OEt | H, H | O | 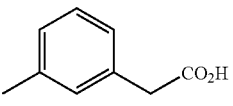 3-(CH2CO2H)-C₆H₄ |
| X-156 | 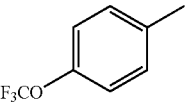 4-F₃CO-C₆H₄ | CH2OCH2cPr | H, H | O | 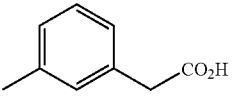 3-(CH2CO2H)-C₆H₄ |
| X-157 | 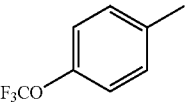 4-F₃CO-C₆H₄ | CH=NOMe | H, H | O | 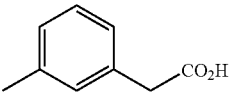 3-(CH2CO2H)-C₆H₄ |
| X-158 | 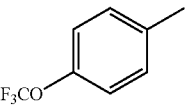 4-F₃CO-C₆H₄ | CH=NOEt | H, H | O | 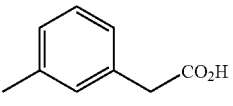 3-(CH2CO2H)-C₆H₄ |
| X-159 | 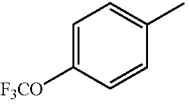 4-F₃CO-C₆H₄ | CH=NOnPr | H, H | O | 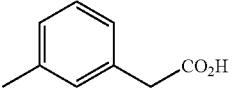 3-(CH2CO2H)-C₆H₄ |
| X-160 | 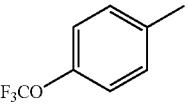 4-F₃CO-C₆H₄ | CH=NOCH2CH2F | H, H | O | 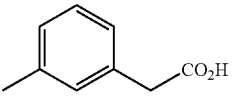 3-(CH2CO2H)-C₆H₄ |
| X-161 | 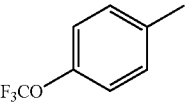 4-F₃CO-C₆H₄ | Me | H, H | S | 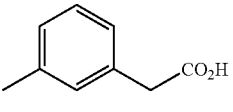 3-(CH2CO2H)-C₆H₄ |
| X-162 | 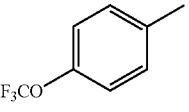 4-F₃CO-C₆H₄ | CH2OEt | H, H | S | 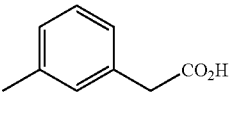 3-(CH2CO2H)-C₆H₄ |
| X-163 | 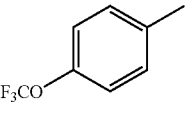 4-F₃CO-C₆H₄ | CH2OCH2cPr | H, H | S | 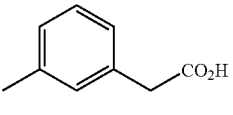 3-(CH2CO2H)-C₆H₄ |
| X-164 | 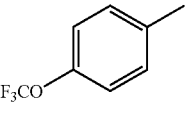 4-F₃CO-C₆H₄ | CH=NOMe | H, H | S | 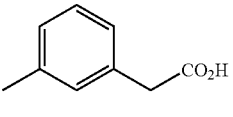 3-(CH2CO2H)-C₆H₄ |
| X-165 | 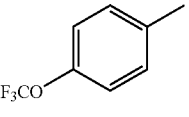 4-F₃CO-C₆H₄ | CH=NOEt | H, H | S | 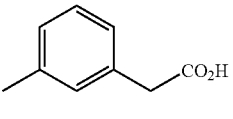 3-(CH2CO2H)-C₆H₄ |

TABLE 90-continued

| No | R1 | R2 | R3, R4 | X1 | Y |
|---|---|---|---|---|---|
| X-166 | 4-F$_3$CO-C$_6$H$_4$ | CH=NOnPr | H, H | S | 3-Me-C$_6$H$_4$-CH$_2$CO$_2$H |
| X-167 | 4-F$_3$CO-C$_6$H$_4$ | CH=NOCH2CH2F | H, H | S | 3-Me-C$_6$H$_4$-CH$_2$CO$_2$H |
| X-168 | 4-F$_3$CO-C$_6$H$_4$ | Me | H, H | O | 3,4-diMe-C$_6$H$_3$-CH$_2$CO$_2$H |
| X-169 | 4-F$_3$CO-C$_6$H$_4$ | CH2OEt | H, H | O | 3,4-diMe-C$_6$H$_3$-CH$_2$CO$_2$H |
| X-170 | 4-F$_3$CO-C$_6$H$_4$ | CH2OCH2cPr | H, H | O | 3,4-diMe-C$_6$H$_3$-CH$_2$CO$_2$H |

TABLE 91

| No | R1 | R2 | R3, R4 | X1 | Y |
|---|---|---|---|---|---|
| X-171 | 4-F$_3$CO-C$_6$H$_4$ | CH=NOMe | H, H | O | 3,4-diMe-C$_6$H$_3$-CH$_2$CO$_2$H |
| X-172 | 4-F$_3$CO-C$_6$H$_4$ | CH=NOEt | H, H | O | 3,4-diMe-C$_6$H$_3$-CH$_2$CO$_2$H |
| X-174 | 4-F$_3$CO-C$_6$H$_4$ | CH=NOCH2CH2F | H, H | O | 3,4-diMe-C$_6$H$_3$-CH$_2$CO$_2$H |
| X-175 | 4-F$_3$CO-C$_6$H$_4$ | Me | H, H | S | 3,4-diMe-C$_6$H$_3$-CH$_2$CO$_2$H |

TABLE 91-continued
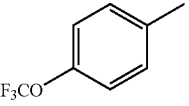
| No | R1 | R2 | R3, R4 | X1 | Y |
|---|---|---|---|---|---|
| X-176 | 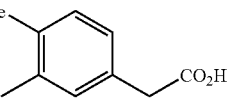 | CH2OEt | H, H | S | 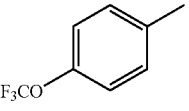 |
| X-177 | 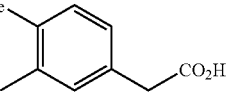 | CH2OCH2cPr | H, H | S | 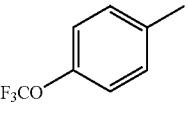 |
| X-178 | 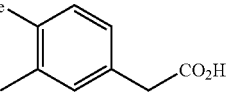 | CH=NOMe | H, H | S | 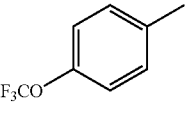 |
| X-179 | 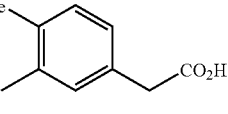 | CH=NOEt | H, H | S | 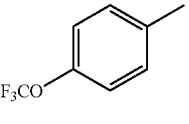 |
| X-180 | 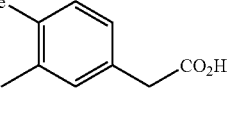 | CH=NOnPr | H, H | S | 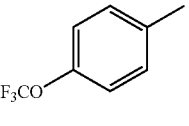 |
| X-181 | 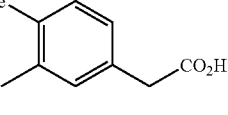 | CH=NOCH2CH2F | H, H | S | 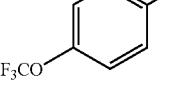 |
| X-182 | 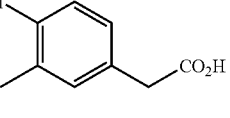 | Me | H, H | O | 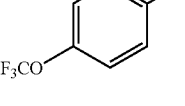 |
| X-183 | 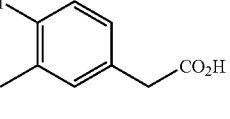 | CH2OEt | H, H | O | 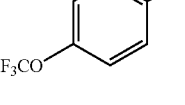 |
| X-185 | 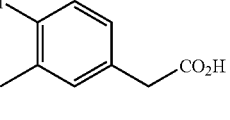 | CH=NOMe | H, H | O | 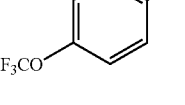 |
| X-187 | 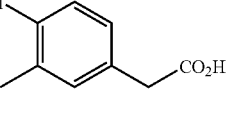 | CH=NOnPr | H, H | O | 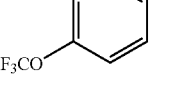 |
| X-188 | 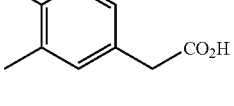 | CH=NOCH2CH2F | H, H | O | |

TABLE 91-continued
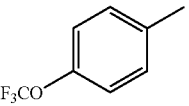
| No | R1 | R2 | R3, R4 | X1 | Y |
|---|---|---|---|---|---|
| X-189 | 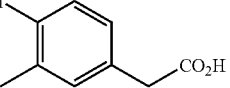 | Me | H, H | S | 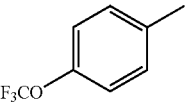 |
| X-190 | 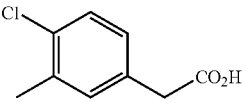 | CH2OEt | H, H | S | 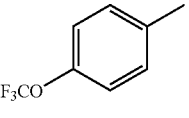 |
| X-191 | 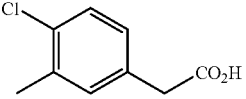 | CH2OCH2cPr | H, H | S | 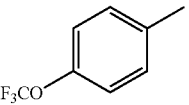 |
| X-192 | 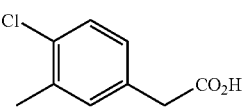 | CH=NOMe | H, H | S | 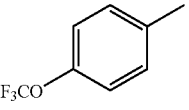 |
| X-193 | 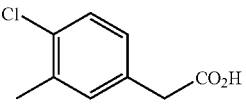 | CH=NOEt | H, H | S | 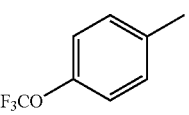 |
| X-194 | 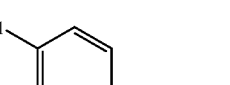 | CH=NOnPr | H, H | S | 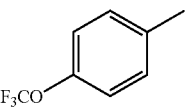 |
| X-195 | 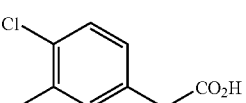 | CH=NOCH2CH2F | H, H | S | 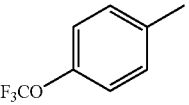 |
TABLE 92
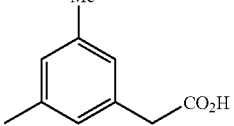
| No | R1 | R2 | R3, R4 | X1 | Y |
|---|---|---|---|---|---|
| X-196 | 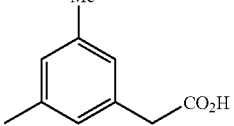 | Me | H, H | O | 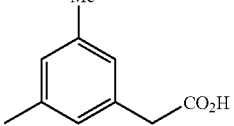 |

TABLE 92-continued

| No | R1 | R2 | R3, R4 | X1 | Y |
|---|---|---|---|---|---|
| X-197 | 4-F₃CO-C₆H₄- | CH2OEt | H, H | O | 3,5-diMe-C₆H₃-CH₂CO₂H |
| X-198 | 4-F₃CO-C₆H₄- | CH2OCH2cPr | H, H | O | 3,5-diMe-C₆H₃-CH₂CO₂H |
| X-199 | 4-F₃CO-C₆H₄- | CH=NOMe | H, H | O | 3,5-diMe-C₆H₃-CH₂CO₂H |
| X-200 | 4-F₃CO-C₆H₄- | CH=NOEt | H, H | O | 3,5-diMe-C₆H₃-CH₂CO₂H |
| X-201 | 4-F₃CO-C₆H₄- | CH=NOnPr | H, H | O | 3,5-diMe-C₆H₃-CH₂CO₂H |
| X-202 | 4-F₃CO-C₆H₄- | CH=NOCH2CH2F | H, H | O | 3,5-diMe-C₆H₃-CH₂CO₂H |
| X-203 | 4-F₃CO-C₆H₄- | Me | H, H | S | 3,5-diMe-C₆H₃-CH₂CO₂H |
| X-204 | 4-F₃CO-C₆H₄- | CH2OEt | H, H | S | 3,5-diMe-C₆H₃-CH₂CO₂H |
| X-205 | 4-F₃CO-C₆H₄- | CH2OCH2cPr | H, H | S | 3,5-diMe-C₆H₃-CH₂CO₂H |

TABLE 92-continued
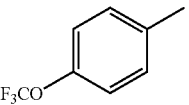
| No | R1 | R2 | R3, R4 | X1 | Y |
|---|---|---|---|---|---|
| X-206 | 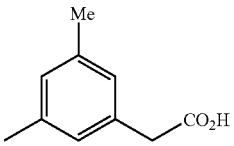 | CH=NOMe | H, H | S | 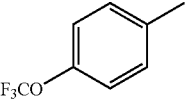 |
| X-207 | 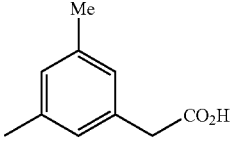 | CH=NOEt | H, H | S | 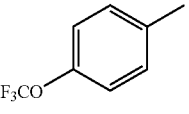 |
| X-209 | 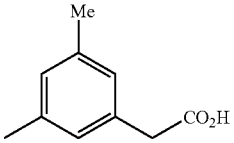 | CH=NOCH2CH2F | H, H | S | 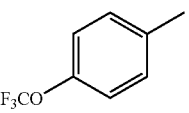 |
| X-210 | 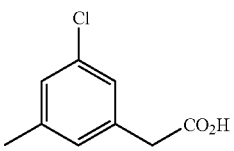 | Me | H, H | O | 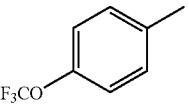 |
| X-211 | 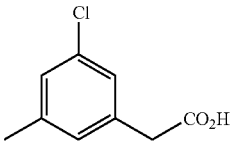 | CH2OEt | H, H | O | 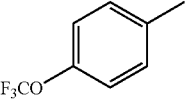 |
| X-212 | 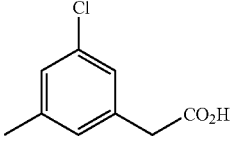 | CH2OCH2cPr | H, H | O | 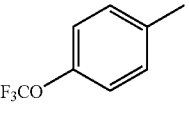 |
| X-213 | 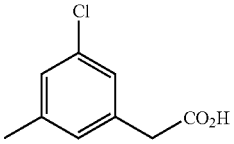 | CH=NOMe | H, H | O | 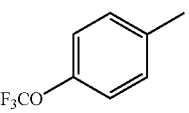 |
| X-214 | 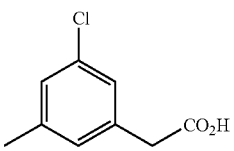 | CH=NOEt | H, H | O | |

TABLE 93

[Structure: isoxazole with R1 at 5-position, R2 at 4-position, and at 3-position a CR3R4-X1-Y group]

| No | R1 | R2 | R3, R4 | X1 | Y |
|---|---|---|---|---|---|
| X-215 | 4-(F3CO)C6H4- | CH=NOnPr | H, H | O | 3-Cl-5-Me-C6H3-CH2-CO2H |
| X-217 | 4-(F3CO)C6H4- | Me | H, H | S | 3-Cl-5-Me-C6H3-CH2-CO2H |
| X-218 | 4-(F3CO)C6H4- | CH2OEt | H, H | S | 3-Cl-5-Me-C6H3-CH2-CO2H |
| X-219 | 4-(F3CO)C6H4- | CH2OCH2cPr | H, H | S | 3-Cl-5-Me-C6H3-CH2-CO2H |
| X-220 | 4-(F3CO)C6H4- | CH=NOMe | H, H | S | 3-Cl-5-Me-C6H3-CH2-CO2H |
| X-222 | 4-(F3CO)C6H4- | CH=NOnPr | H, H | S | 3-Cl-5-Me-C6H3-CH2-CO2H |

TABLE 94

[Structure: isoxazole with R1 at 5-position, R2 at 4-position, and at 3-position a CR3R4-X1-Y group]

| No | R1 | R2 | R3, R4 | X1 | Y |
|---|---|---|---|---|---|
| Y-2 | 4-(F3C)C6H4- | CH2OEt | H, H | —ON=CH— | 3-Me-C6H4-CH2-CO2H |

TABLE 94-continued

| No | R1 | R2 | R3, R4 | X1 | Y |
|---|---|---|---|---|---|
| Y-3 | 4-F₃C-C₆H₄- | CH2OCH2cPr | H, H | —ON=CH— | 3-(CH₃)-C₆H₄-CH₂-CO₂H |
| Y-4 | 4-F₃C-C₆H₄- | CH=NOMe | H, H | —ON=CH— | 3-(CH₃)-C₆H₄-CH₂-CO₂H |
| Y-5 | 4-F₃C-C₆H₄- | CH=NOEt | H, H | —ON=CH— | 3-(CH₃)-C₆H₄-CH₂-CO₂H |
| Y-6 | 4-F₃C-C₆H₄- | CH=NOnPr | H, H | —ON=CH— | 3-(CH₃)-C₆H₄-CH₂-CO₂H |
| Y-7 | 4-F₃C-C₆H₄- | CH=NOCH2CH2F | H, H | —ON=CH— | 3-(CH₃)-C₆H₄-CH₂-CO₂H |
| Y-8 | 4-F₃C-C₆H₄- | Me | H, H | —ON=CH— | 3,4-di(CH₃)-C₆H₃-CH₂-CO₂H |
| Y-9 | 4-F₃C-C₆H₄- | CH2OEt | H, H | —ON=CH— | 3,4-di(CH₃)-C₆H₃-CH₂-CO₂H |
| Y-10 | 4-F₃C-C₆H₄- | CH2OCH2cPr | H, H | —ON=CH— | 3,4-di(CH₃)-C₆H₃-CH₂-CO₂H |
| Y-11 | 4-F₃C-C₆H₄- | CH=NOMe | H, H | —ON=CH— | 3,4-di(CH₃)-C₆H₃-CH₂-CO₂H |
| Y-12 | 4-F₃C-C₆H₄- | CH=NOEt | H, H | —ON=CH— | 3,4-di(CH₃)-C₆H₃-CH₂-CO₂H |
| Y-13 | 4-F₃C-C₆H₄- | CH=NOnPr | H, H | —ON=CH— | 3,4-di(CH₃)-C₆H₃-CH₂-CO₂H |

TABLE 94-continued

| No | R1 | R2 | R3, R4 | X1 | Y |
|---|---|---|---|---|---|
| Y-14 | 4-F₃C-C₆H₄- | CH=NOCH2CH2F | H, H | —ON=CH— | 4-Me-3-Me-C₆H₃-CH₂CO₂H |
| Y-15 | 4-F₃C-C₆H₄- | CH=NOEt | H, H | —ON=CH— | 4-F-3-Me-C₆H₃-CH₂CO₂H |
| Y-16 | 4-F₃C-C₆H₄- | Me | H, H | —ON=CH— | 4-Cl-3-Me-C₆H₃-CH₂CO₂H |
| Y-17 | 4-F₃C-C₆H₄- | CH2OEt | H, H | —ON=CH— | 4-Cl-3-Me-C₆H₃-CH₂CO₂H |
| Y-18 | 4-F₃C-C₆H₄- | CH2OCH2cPr | H, H | —ON=CH— | 4-Cl-3-Me-C₆H₃-CH₂CO₂H |
| Y-19 | 4-F₃C-C₆H₄- | CH=NOMe | H, H | —ON=CH— | 4-Cl-3-Me-C₆H₃-CH₂CO₂H |
| Y-20 | 4-F₃C-C₆H₄- | CH=NOEt | H, H | —ON=CH— | 4-Cl-3-Me-C₆H₃-CH₂CO₂H |
| Y-21 | 4-F₃C-C₆H₄- | CH=NOnPr | H, H | —ON=CH— | 4-Cl-3-Me-C₆H₃-CH₂CO₂H |
| Y-22 | 4-F₃C-C₆H₄- | CH=NOCH2CH2F | H, H | —ON=CH— | 4-Cl-3-Me-C₆H₃-CH₂CO₂H |
| Y-23 | 4-F₃C-C₆H₄- | CH=NOEt | H, H | —ON=CH— | 4-MeO-3-Me-C₆H₃-CH₂CO₂H |

TABLE 95
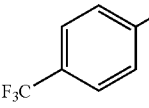
| No | R1 | R2 | X1 | R3, R4 | Y |
|---|---|---|---|---|---|
| Y-24 | 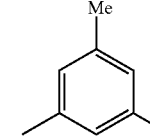 | Me | —ON=CH— | H, H | 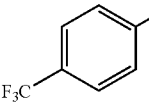 |
| Y-25 | 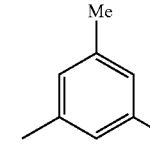 | CH2OEt | —ON=CH— | H, H | 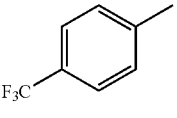 |
| Y-26 | 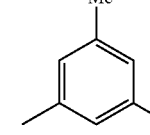 | CH2OCH2cPr | —ON=CH— | H, H | 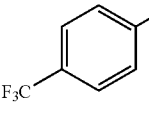 |
| Y-27 | 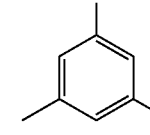 | CH=NOMe | —ON=CH— | H, H | 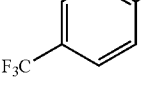 |
| Y-28 | 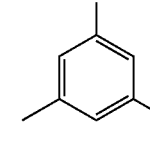 | CH=NOEt | —ON=CH— | H, H | 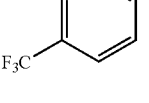 |
| Y-29 | 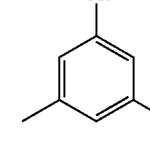 | CH=NOnPr | —ON=CH— | H, H | 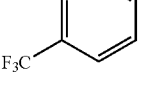 |
| Y-30 | 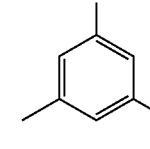 | CH=NOCH2CH2F | —ON=CH— | H, H | 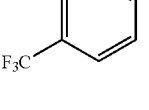 |
| Y-31 | 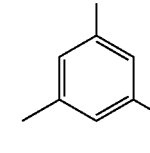 | CH=NOEt | —ON=CH— | H, H | 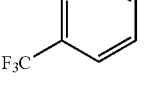 |
| Y-32 | 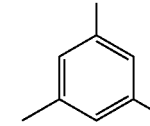 | Me | —ON=CH— | H, H | (Cl, CO2H aryl) |

TABLE 95-continued
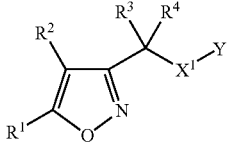
| No | R1 | R2 | X1 | R3, R4 | Y |
|---|---|---|---|---|---|
| Y-33 | 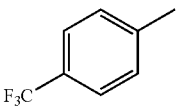 | CH2OEt | —ON=CH— | H, H | 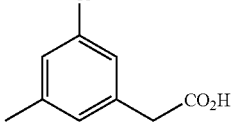 |
| Y-34 | 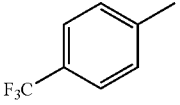 | CH2OCH2cPr | —ON=CH— | H, H | 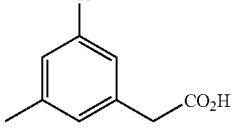 |
| Y-35 | 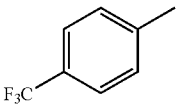 | CH=NOMe | —ON=CH— | H, H | 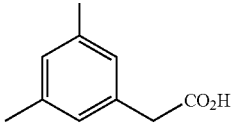 |
| Y-36 | 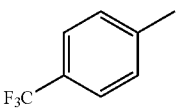 | CH=NOEt | —ON=CH— | H, H | 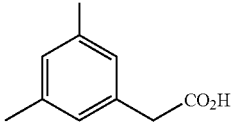 |
| Y-37 | 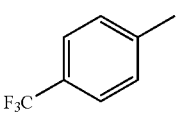 | CH=NOnPr | —ON=CH— | H, H | 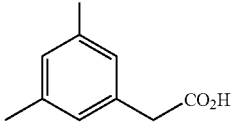 |
| Y-38 | 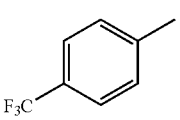 | CH=NOCH2CH2F | —ON=CH— | H, H | 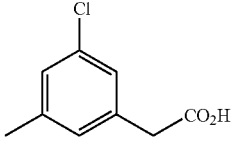 |
| Y-39 | 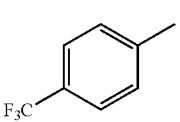 | CH=NOEt | —ON=CH— | H, H | 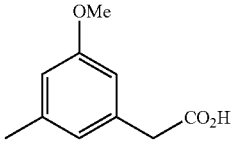 |
| Y-40 | 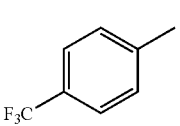 | CH=NOEt | —ON=CH— | H, H | 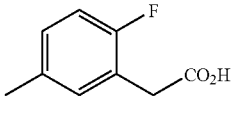 |

TABLE 96

| No | R1 | R2 | R3, R4 | X1 | Y |
|---|---|---|---|---|---|
| Y-41 | 4-F₃C-C₆H₄- | CH=NOEt | H, H | —ON=CH— | 2-Cl, 5-Me-C₆H₃-CH₂CO₂H |
| Y-42 | 4-F₃C-C₆H₄- | CH=NOEt | H, H | —ON=CH— | 2-Me, 3-Me-C₆H₃-CH₂CO₂H |
| Y-43 | 4-F₃C-C₆H₄- | CH=NOEt | H, H | —ON=CH— | 2-F, 3-Me-C₆H₃-CH₂CO₂H |
| Y-44 | 4-F₃C-C₆H₄- | CH=NOEt | H, H | —ON=CH— | 2-OMe, 5-Me-C₆H₃-CH₂CO₂H |
| Y-45 | 4-Cl-C₆H₄- | Me | H, H | —ON=CH— | 3-Me-C₆H₄-CH₂CO₂H |
| Y-46 | 4-Cl-C₆H₄- | CH2OEt | H, H | —ON=CH— | 3-Me-C₆H₄-CH₂CO₂H |
| Y-47 | 4-Cl-C₆H₄- | CH2OCH2cPr | H, H | —ON=CH— | 3-Me-C₆H₄-CH₂CO₂H |
| Y-48 | 4-Cl-C₆H₄- | CH=NOMe | H, H | —ON=CH— | 3-Me-C₆H₄-CH₂CO₂H |
| Y-49 | 4-Cl-C₆H₄- | CH=NOEt | H, H | —ON=CH— | 3-Me-C₆H₄-CH₂CO₂H |
| Y-50 | 4-Cl-C₆H₄- | CH=NOnPr | H, H | —ON=CH— | 3-Me-C₆H₄-CH₂CO₂H |
| Y-51 | 4-Cl-C₆H₄- | CH=NOCH2CH2F | H, H | —ON=CH— | 3-Me-C₆H₄-CH₂CO₂H |

TABLE 96-continued
| No | R1 | R2 | R3, R4 | X1 | Y | |
|---|---|---|---|---|---|---|
| Y-52 | 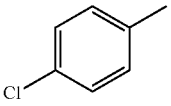 | Me | H, H | —ON=CH— | 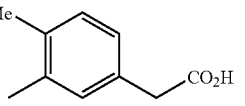 | |
| Y-53 | 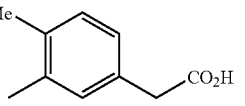 | CH2OEt | H, H | —ON=CH— | 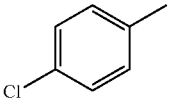 | |
| Y-54 | 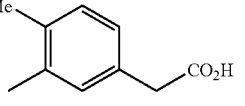 | CH2OCH2cPr | H, H | —ON=CH— | 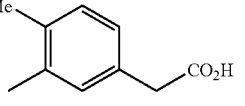 | |
| Y-55 | 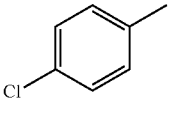 | CH=NOMe | H, H | —ON=CH— | 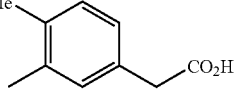 | |
| Y-56 | 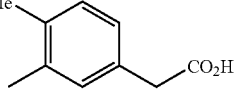 | CH=NOEt | H, H | —ON=CH— | 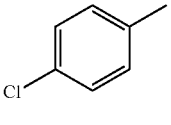 | |
| Y-57 | 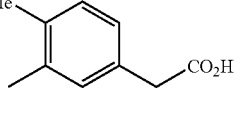 | CH=NOnPr | H, H | —ON=CH— | 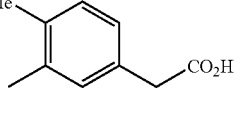 | |
| Y-58 | 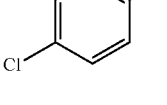 | CH=NOCH2CH2F | H, H | —ON=CH— | 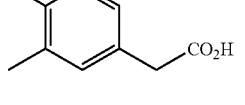 | |
| Y-59 | 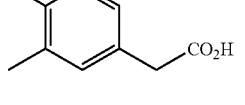 | Me | H, H | —ON=CH— | 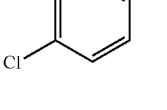 | |
| Y-60 | 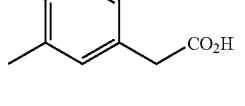 | CH2OEt | H, H | —ON=CH— | 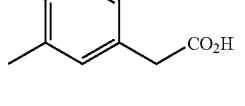 | |
| Y-61 | 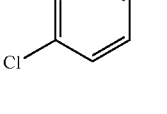 | CH2OCH2cPr | H, H | —ON=CH— | 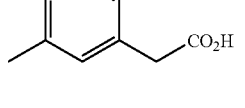 | |

TABLE 97
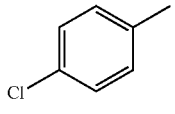
| No | R1 | R2 | R3, R4 | X1 | Y |
|---|---|---|---|---|---|
| Y-62 | 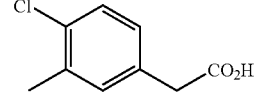 | CH=NOMe | H, H | —ON=CH— | 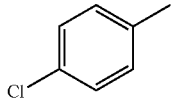 |
| Y-63 | 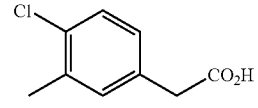 | CH=NOEt | H, H | —ON=CH— | 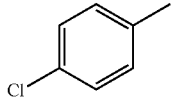 |
| Y-64 | 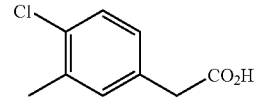 | CH=NOnPr | H, H | —ON=CH— | 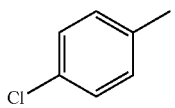 |
| Y-65 | 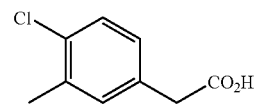 | CH=NOCH2CH2F | H, H | —ON=CH— | 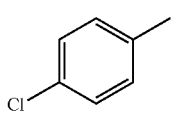 |
| Y-66 | 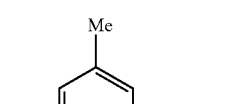 | Me | H, H | —ON=CH— | 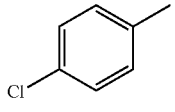 |
| Y-67 | 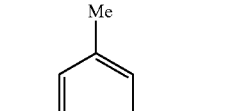 | CH2OEt | H, H | —ON=CH— | 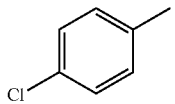 |
| Y-68 | 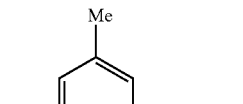 | CH2OCH2cPr | H, H | —ON=CH— | 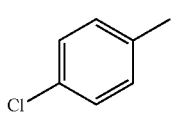 |
| Y-69 | 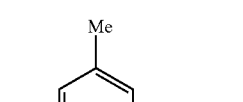 | CH=NOMe | H, H | —ON=CH— | 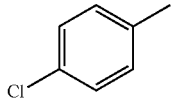 |
| Y-70 | 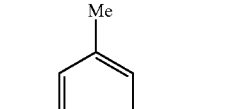 | CH=NOEt | H, H | —ON=CH— | 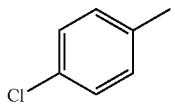 |
| Y-71 | 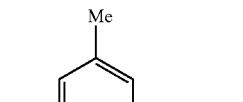 | CH=NOnPr | H, H | —ON=CH— | |

TABLE 97-continued
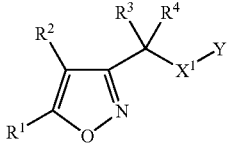
| No | R1 | R2 | R3, R4 | X1 | Y |
|---|---|---|---|---|---|
| Y-72 | 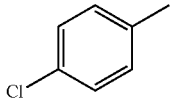 | CH=NOCH2CH2F | H, H | —ON=CH— | 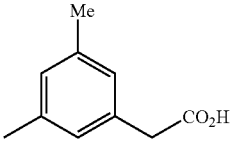 |
| Y-73 | 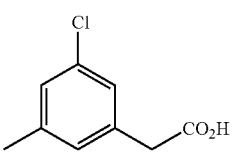 | Me | H, H | —ON=CH— | 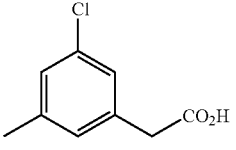 |
| Y-74 | 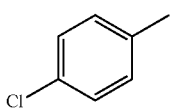 | CH2OEt | H, H | —ON=CH— | 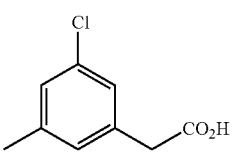 |
| Y-75 | 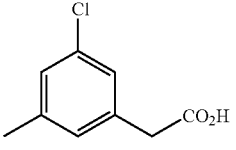 | CH2OCH2cPr | H, H | —ON=CH— | 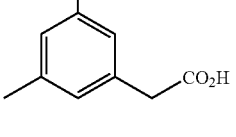 |
| Y-76 | 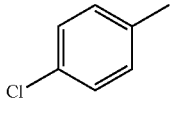 | CH=NOMe | H, H | —ON=CH— | 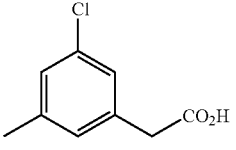 |
| Y-77 | 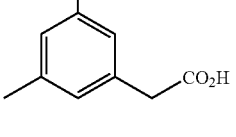 | CH=NOEt | H, H | —ON=CH— | 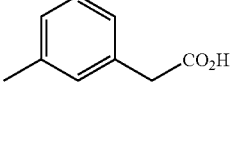 |
| Y-78 | 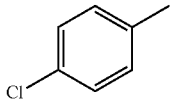 | CH=NOnPr | H, H | —ON=CH— | 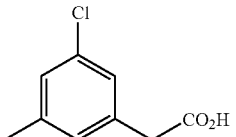 |

TABLE 98

| No | R1 | R2 | R3, R4 | X1 | Y |
|---|---|---|---|---|---|
| Y-79 | 4-Cl-C6H4 | CH=NOCH2CH2F | H, H | —ON=CH— | 3-Cl-5-Me-C6H3-CH2-CO2H |
| Y-80 | 4-F3CO-C6H4 | Me | H, H | —ON=CH— | 3-Me-C6H4-CH2-CO2H |
| Y-81 | 4-F3CO-C6H4 | CH2OEt | H, H | —ON=CH— | 3-Me-C6H4-CH2-CO2H |
| Y-82 | 4-F3CO-C6H4 | CH2OCH2cPr | H, H | —ON=CH— | 3-Me-C6H4-CH2-CO2H |
| Y-83 | 4-F3CO-C6H4 | CH=NOMe | H, H | —ON=CH— | 3-Me-C6H4-CH2-CO2H |
| Y-84 | 4-F3CO-C6H4 | CH=NOEt | H, H | —ON=CH— | 3-Me-C6H4-CH2-CO2H |
| Y-85 | 4-F3CO-C6H4 | CH=NOnPr | H, H | —ON=CH— | 3-Me-C6H4-CH2-CO2H |
| Y-86 | 4-F3CO-C6H4 | CH=NOCH2CH2F | H, H | —ON=CH— | 3-Me-C6H4-CH2-CO2H |
| Y-87 | 4-F3CO-C6H4 | Me | H, H | —ON=CH— | 3,4-diMe-C6H3-CH2-CO2H |
| Y-88 | 4-F3CO-C6H4 | CH2OEt | H, H | —ON=CH— | 3,4-diMe-C6H3-CH2-CO2H |
| Y-89 | 4-F3CO-C6H4 | CH2OCH2cPr | H, H | —ON=CH— | 3,4-diMe-C6H3-CH2-CO2H |

TABLE 98-continued
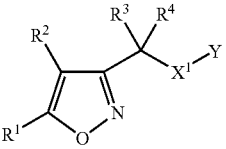
| No | R1 | R2 | R3, R4 | X1 | Y |
|---|---|---|---|---|---|
| Y-90 | 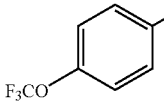 | CH=NOMe | H, H | —ON=CH— | 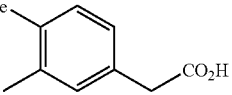 |
| Y-91 | 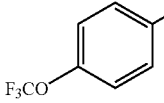 | CH=NOEt | H, H | —ON=CH— | 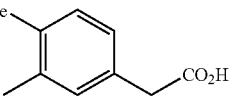 |
| Y-92 | 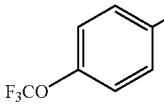 | CH=NOnPr | H, H | —ON=CH— | 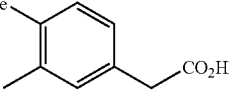 |
| Y-93 | 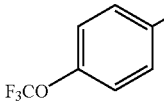 | CH=NOCH2CH2F | H, H | —ON=CH— | 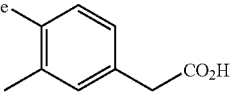 |
| Y-94 | 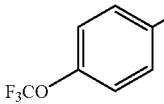 | Me | H, H | —ON=CH— | 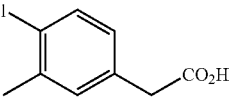 |
| Y-95 | 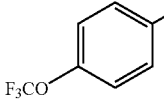 | CH2OEt | H, H | —ON=CH— | 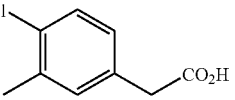 |
| Y-96 | 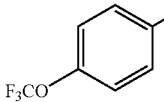 | CH2OCH2cPr | H, H | —ON=CH— | 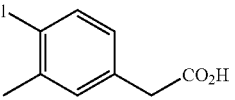 |
| Y-97 | 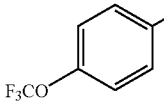 | CH=NOMe | H, H | —ON=CH— | 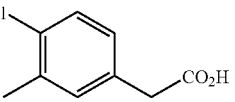 |
| Y-98 | 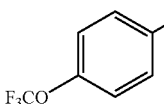 | CH=NOEt | H, H | —ON=CH— | 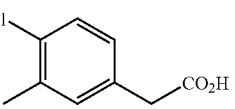 |
| Y-99 | 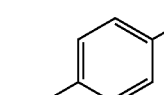 | CH=NOnPr | H, H | —ON=CH— | 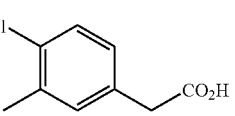 |

TABLE 99

| No | R1 | R2 | R3, R4 | X1 | Y |
|---|---|---|---|---|---|
| Y-100 | 4-F3CO-C6H4- | CH=NOCH2CH2F | H, H | —ON=CH— | 4-Cl-3-Me-C6H3-CH2-CO2H |
| Y-101 | 4-F3CO-C6H4- | Me | H, H | —ON=CH— | 3,5-Me2-C6H3-CH2-CO2H |
| Y-102 | 4-F3CO-C6H4- | CH2OEt | H, H | —ON=CH— | 3,5-Me2-C6H3-CH2-CO2H |
| Y-103 | 4-F3CO-C6H4- | CH2OCH2cPr | H, H | —ON=CH— | 3,5-Me2-C6H3-CH2-CO2H |
| Y-104 | 4-F3CO-C6H4- | CH=NOMe | H, H | —ON=CH— | 3,5-Me2-C6H3-CH2-CO2H |
| Y-105 | 4-F3CO-C6H4- | CH=NOEt | H, H | —ON=CH— | 3,5-Me2-C6H3-CH2-CO2H |
| Y-106 | 4-F3CO-C6H4- | CH=NOnPr | H, H | —ON=CH— | 3,5-Me2-C6H3-CH2-CO2H |
| Y-107 | 4-F3CO-C6H4- | CH=NOCH2CH2F | H, H | —ON=CH— | 3,5-Me2-C6H3-CH2-CO2H |
| Y-108 | 4-F3CO-C6H4- | Me | H, H | —ON=CH— | 3-Cl-5-Me-C6H3-CH2-CO2H |

TABLE 99-continued

| No | R1 | R2 | R3, R4 | X1 | Y |
|---|---|---|---|---|---|
| Y-109 | 4-F3CO-C6H4 | CH2OEt | H, H | —ON=CH— | 3-Cl-5-Me-C6H3-CH2-CO2H |
| Y-110 | 4-F3CO-C6H4 | CH2OCH2cPr | H, H | —ON=CH— | 3-Cl-5-Me-C6H3-CH2-CO2H |
| Y-111 | 4-F3CO-C6H4 | CH=NOMe | H, H | —ON=CH— | 3-Cl-5-Me-C6H3-CH2-CO2H |
| Y-112 | 4-F3CO-C6H4 | CH=NOEt | H, H | —ON=CH— | 3-Cl-5-Me-C6H3-CH2-CO2H |
| Y-113 | 4-F3CO-C6H4 | CH=NOnPr | H, H | —ON=CH— | 3-Cl-5-Me-C6H3-CH2-CO2H |
| Y-114 | 4-F3CO-C6H4 | CH=NOCH2CH2F | H, H | —ON=CH— | 3-Cl-5-Me-C6H3-CH2-CO2H |

Test Example 1 Test for Transcriptional Activity of PPARδ and α

A chimeric transcription factor assay, which is commonly used to detect nuclear receptor activity, was employed to measure PPAR transcriptional activity. Specifically, two plasmids, one that expresses the fusion protein of DNA binding domain of yeast transcription factor GAL4 and a ligand binding domain of a receptor, and a reporter plasmid were transiently transfected to CHO cells. The activity of the promoter containing a recognition sequence of GAL4 coded on the reporter plasmid was used as a parameter to estimate the activity of the receptor.

Plasmid: The ligand binding domain of human PPARδ (hPPARδ) or α (hPPARα) (δ: aa 139-C-end; α: aa 167-C-end) is obtained by PCR amplification using Human Universal Quick-Clone cDNA (CLONTECH). Each amplified cDNA was subcloned into pCR2.1-TOPO vector (Invitrogen) and the identity of the cDNA clones was confirmed by the DNA sequence. Then, each obtained cDNA fragment was subcloned into pBIND vector (Promega) to construct a plasmid expressing the fusion protein with DNA binding domain of yeast transcription factor GAL4. pG5luc vector (Promega) was used as a reporter plasmid.

Cell culturing and transfection: CHO cells were cultured in 10% FBS-αMEM. With a 96-well plate (Costar), CHO cells, that were dispersed with trypsin treatment, 20000 cells per well and the two plasmids obtained by the above procedure, 25 ng per well, were transfected with FuGene Reagent (Roche) by following the instruction of the manufacture.

Measurement of the transcriptional activity: CHO cells 100 μl per well, which were transfected as above, were dispensed into the wells in which a test compound dissolved in DMSO 0.5 μl was spotted in advance. After the cells and a test compound were cultured together for 24 hours in a CO₂ incubator, the luciferase activity was measured by adding luciferase substrates, PicaGene LT2.0 (Toyo ink) 100 μl per well. LUMINOUS CT-9000D (DIA-IATRON) is used to measure the activity.

As to PPARδ, the concentration of a test compound which shows ½ of maximum luciferase activity was calculated using an Excel program to obtain the EC50 value for PPARδ activity of a test compound. The result is shown in Table 100.

TABLE 100

| No. | $EC_{50}$ (nM) hPPARδ |
|---|---|
| A reference compound  | 37 |
| X-6 | 9.8 |
| X-8 | 9.8 |
| X-25 | 12 |

Test Example 2 Test for Inhibition of Cyp2C9 Enzyme

The test for inhibition of CYP2C9 enzyme was carried out with human liver microsomes and hydration activity of 4-position of tolbutamide that is a typical reaction of CYP2C9 as a parameter.

The reaction condition was as below: A substrate, 5 μM Tolbutamide ($^{14}$C labeled compound); the reaction time, 30 minutes; the reaction temperature, 37° C.; the protein concentration, 0.25 mg/ml (human liver microsomes, 15 pol, Lot. 210296, XenoTech).

To the HEPES Buffer (pH 7.4), was added the protein (human liver microsomes), a drug solution and a substrate with the composition as the above. NADPH, which is a coenzyme of the reaction, was added thereto to start the reaction. After reacting for the fixed hours, 2N hydrochloric acid solution was added thereto and the reaction was stopped by removing protein. The remaining substrate drug and the generating metabolite were extracted with chloroform. The solvent was removed and the residue was redissolved in methanol. This solution was spotted on TLC, developed with chloroform:methanol:acetic acid=90:10:1, contacted on the imaging plate for about 14-20 hours and analyzed by BAS2000. As to the generation activity of the metabolite, Tolbutamide 4-potition hydration body, the activity in case that the solvent dissolving a drug was added to the reaction assay was used as a control (100%). The residual activity (%) in case that the test drug solution was added to the reaction was calculated to confirm the compounds of the present invention had little effect on inhibition of CYP2C9 enzyme.

Test Example 3 Test for Metabolic Stability

Test for Metabolic Stability in Hepatic Microsomes: To trishydrochloric acid buffer (pH 7.4), were added NADPH (the final concentration was 1 mM in case of oxidative metabolism), Hepatic Microsomes (the final concentration was 0.5 mg protein/ml) and each compound (the final concentration was 2 μM). The mixture was reacted at 37° C. for 0 and 30 minutes. In case of conjugated glucuronic acid, UDPGA (the final concentration is 5 mM) was added instead of NADPH. The reaction was stopped by adding acetonitrile/methanol=1/1 (v/v) which is 2 parts by volume based on 1 part by volume of the reaction solution and then compounds in the centrifugal supernatant were measured by HPLC. By comparing the values between 0 and 30 minutes the disappearance volume of the compounds by the metabolic reaction was calculated to confirm metabolic stability of the compounds of the present invention.

Test Example 4 Test for Solubility

The compounds of the present invention and test solvents (JP-2 solution, and JP-2 solution containing 20 mM sodium taurocholate) were stirred at 37° C. for 3 hours. The mixture was filtrated with a 0.45 μm filter and the concentration of the filtrate was measured with HPLC method to confirm solubility of compounds of the present invention.

Test Example 5 Test for Toxicity

The compounds of the present invention (30 to 300 mg/kg/day) were administered to rats. After administration, number of deaths, conditions, food intake and body weight of rats were checked and histopathological examination and the like were performed.

Additionally, as a hematological examination, after few days from administration, the blood was collected and PT, APTT and Fbg were measured after blood treatment. The activities of extrinsic blood coagulation factors (F-III, F-V, F-VII, F-X) and intrinsic blood coagulation factors (F-VIII, F-IX, F-XI, F-XII) were measured. The coagulation times of extrinsic or intrinsic blood coagulation factors were measured by a method for measurement of PT (extrinsic) or APTT (intrinsic) after adding plasma which is deficient a factor of each measuring object (Dade Boehringer Marburg) to plasma of rat and preincubating. Plasma of control rats was mixed and calibration curve was made with diluent which the plasma was sequentially double-diluted with Owren's Veronal Buffer as a reference material. Activity percentage was calculated with coagulation time measured by a method for coagulation time with factor deficient plasma and calibration curve and activities of each coagulation factor were evaluated by activity percentage compared to plasma of intact rat.

As the above, toxicities of compounds of the present invention were confirmed.

The invention claimed is:

1. A compound of the formula (I):

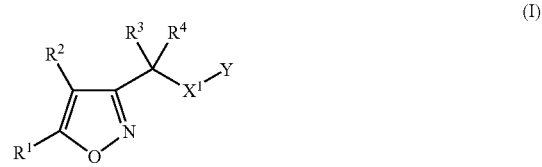

or a pharmaceutically acceptable salt thereof,
wherein:
Y is a group of the formula:

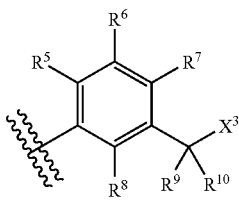

wherein $R^5$, $R^6$, $R^7$ and $R^8$ are each independently hydrogen, halogen, hydroxy, cyano, optionally substituted lower alkyl, optionally substituted lower alkenyl, optionally substituted lower alkynyl, optionally substituted lower alkoxy, optionally substituted lower alkylthio, optionally substituted acyl, optionally substituted amino, optionally substituted aryl, optionally substituted aryloxy, optionally substituted arylthio or optionally substituted heterocycle, $R^9$ and $R^{10}$ are each independently hydrogen, halogen, cyano, optionally substituted lower alkyl, optionally substituted lower alkoxy, optionally substituted amino or optionally substituted aryl, $X^3$ is $COOR^{17}$ or $C(=NR^{17})NR^{18}OR^{19}$, wherein $R^{17}$, $R^{18}$ and $R^{19}$ are each independently hydrogen or optionally substituted lower alkyl, $R^1$ is optionally substituted aryl or optionally substituted heterocycle, $R^2$ is optionally substituted lower alkyl, $R^3$ and $R^4$ are each independently hydrogen, halogen, optionally substituted lower alkyl, optionally substituted lower alkenyl, optionally substituted lower alkynyl, optionally substituted aryl or optionally substituted heterocycle, and $X^1$ is O, S or $-ON=CR^{14}-$ wherein $R^{14}$ is hydrogen or optionally substituted lower alkyl.

2. The compound or pharmaceutically acceptable salt thereof according to claim 1, wherein $R^3$ and $R^4$ are hydrogen.

3. The compound or pharmaceutically acceptable salt thereof according to claim 1, wherein $R^5$, $R^6$, $R^7$ and $R^8$ are each independently hydrogen, halogen, optionally substituted lower akyl or optionally substituted lower alkoxy.

4. The compound or pharmaceutically acceptable salt thereof according to claim 1, wherein $R^9$ and $R^{10}$ are each independently hydrogen or halogen.

5. The compound or pharmaceutically acceptable salt thereof according to claim 1, wherein $X^3$ is $COOR^{17}$ wherein $R^{17}$ is hydrogen or optionally substituted lower alkyl.

6. The compound or pharmaceutically acceptable salt thereof according to claim 1, wherein $R^1$ is optionally substituted aryl or heterocycle, the substituent(s) of the aryl of $R^1$ is/are selected from the group consisting of halogen, optionally substituted lower alkyl and optionally substituted lower alkoxy, $R^2$ is optionally substituted lower alkyl, the substituent(s) of the lower alkyl of $R^2$ is/are selected from the group consisting of optionally substituted lower alkoxy, lower alkylamino, optionally substituted imino, optionally substituted iminooxy, lower alkylsulfonyl, cycloalkyloxy, optionally substituted aryl and optionally substituted heterocycle, $R^3$ and $R^4$ are hydrogen, $R^5$, $R^6$, $R^7$ and $R^8$ are each independently, hydrogen, halogen, lower alkyl or lower alkoxy, $R^9$ and $R^{10}$ are each independently hydrogen or halogen, $X^1$ is O, S or $-ON=CR^{14}-$ wherein $R^{14}$ is hydrogen, and $X^3$ is $COOR^{17}$ wherein $R^{17}$ is hydrogen or lower alkyl.

7. A pharmaceutical composition comprising the compound or pharmaceutically acceptable salt thereof according to claim 1 as an active ingredient, and a pharmaceutically acceptable excipient and/or carrier.

8. A pharmaceutical composition comprising the compound or pharmaceutically acceptable salt thereof according to claim 2 as an active ingredient, and a pharmaceutically acceptable excipient and/or carrier.

9. A pharmaceutical composition comprising the compound or pharmaceutically acceptable salt thereof according to claim 3 as an active ingredient, and a pharmaceutically acceptable excipient and/or carrier.

10. A pharmaceutical composition comprising the compound or pharmaceutically acceptable salt thereof according to claim 4 as an active ingredient, and a pharmaceutically acceptable excipient and/or carrier.

11. A pharmaceutical composition comprising the compound or pharmaceutically acceptable salt thereof according to claim 5 as an active ingredient, and a pharmaceutically acceptable excipient and/or carrier.

12. A pharmaceutical composition comprising the compound or pharmaceutically acceptable salt thereof according to claim 6 as an active ingredient, and a pharmaceutically acceptable excipient and/or carrier.

13. A method of treating hyperlipidemia, obesity, arteriosclerosis, atherosclerosis or hyperglycemia comprising administering an effective amount of the compound or pharmaceutically acceptable salt thereof according to claim 1 to a patient in need thereof.

14. A method of treating hyperlipidemia, obesity, arteriosclerosis, atherosclerosis or hyperglycemia comprising administering an effective amount of the compound or pharmaceutically acceptable salt thereof according to claim 2 to a patient in need thereof.

15. A method of treating hyperlipidemia, obesity, arteriosclerosis, atherosclerosis or hyperglycemia comprising administering an effective amount of the compound or pharmaceutically acceptable salt thereof according to claim 3 to a patient in need thereof.

16. A method of treating hyperlipidemia, obesity, arteriosclerosis, atherosclerosis or hyperglycemia comprising administering an effective amount of the compound or pharmaceutically acceptable salt thereof according to claim 4 to a patient in need thereof.

17. A method of treating hyperlipidemia, obesity, arteriosclerosis, atherosclerosis or hyperglycemia comprising administering an effective amount of the compound or pharmaceutically acceptable salt thereof according to claim 5 to a patient in need thereof.

18. A method of treating hyperlipidemia, obesity, arteriosclerosis, atherosclerosis or hyperglycemia comprising administering an effective amount of the compound or pharmaceutically acceptable salt thereof according to claim 6 to a patient in need thereof.

* * * * *